(12) United States Patent
Sueoka et al.

(10) Patent No.: US 6,288,061 B1
(45) Date of Patent: Sep. 11, 2001

(54) IMIDAZOLE DERIVATIVES

(75) Inventors: Hiroyuki Sueoka, Fukuoka; Jouji Yasuoka, Osaka; Akira Nishiyama, Iruma; Masatoshi Kiuchi, Hirakata; Katsuya Yamamoto, Fukuoka; Kunio Sugahara, Iruma; Syuji Ehara, Miyazaki; Kei Sakata, Hirakata, all of (JP)

(73) Assignee: Welfide Corporation, Osaka (JP)

( * ) Notice: Subject to any disclaimer, the term of this patent is extended or adjusted under 35 U.S.C. 154(b) by 0 days.

(21) Appl. No.: 09/598,216

(22) Filed: Jun. 21, 2000

Related U.S. Application Data

(63) Continuation-in-part of application No. PCT/JP98/05930, filed on Dec. 24, 1998.

(30) Foreign Application Priority Data

Dec. 26, 1997 (JP) .................................................. 9-359671
Jun. 21, 1999 (JP) ................................................ 11-174074
Feb. 17, 2000 (JP) ................................................ 12-045165

(51) Int. Cl.$^7$ ................ A61K 31/4178; A61K 31/5386; C07D 265/30; C07D 239/60; C07D 277/44
(52) U.S. Cl. ...................... 514/235.8; 514/371; 514/275; 514/363; 544/71; 544/297; 548/195; 548/128
(58) Field of Search ................................. 514/371, 235.8, 514/275, 363; 548/195, 128; 544/71, 297

(56) References Cited

U.S. PATENT DOCUMENTS 5,286,860 * 2/1994 Blum et al. ........................ 544/230

FOREIGN PATENT DOCUMENTS 63-10767 1/1988 (JP) .

OTHER PUBLICATIONS

Ying, et al., Expression of IL–4 and IL–5 mRNA and Protein Product by CD4$^+$ and CD8$^+$ T Cells, Eosinophils, and Mast Cells in Bronchial Biopsies Obtained from Atopic and Nonatopic (Intrinsic) Asthmatics, J. Immunol., vol. 158, pp. 3539–3544, 1997.

Kay, et al., "Messenger RNA Expression of the Cytokine Gene Cluster, Interleukin 3(IL–3), IL–4, IL–5, and Granulocyte/Macrophage Colony–stimulating Factor, in Allergen–induced Late–phase Cutaneous Reactions in Atopic Subjects", J. Exp. Med., vol. 173, pp. 775–778, 1991.

Kopf et al., "Disruption of the murine IL–4 gene blocks Th2 cytokine responses", Nature, vol. 362, pp. 245–247, 1993.

Foster, et al., "Interleukin 5 Deficiency Abolishes Eosinophilia, Airways Hyperreactivity, and Lung Damage in a Mouse Asthma Model", J. Exp. Med., vol. 183, pp. 195–201, 1996.

Mauser, et al., "Effects of an Antibody to Interleukin–5 in a Monkey Model of Asthma", Am. J. Respir. Crit. Care Med., vol. 152, pp. 467–472, 1995.

* cited by examiner

*Primary Examiner*—Deborah C. Lambkin
*Assistant Examiner*—Sonya N. Wright
(74) *Attorney, Agent, or Firm*—Wenderoth, Lind & Ponack, L.L.P.

(57) ABSTRACT

The present invention relates to the imidazole derivative of the following formula (I)

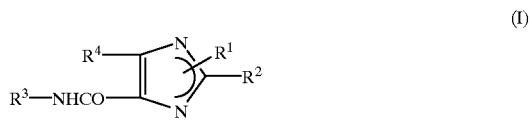

wherein $R^1$ is hydrogen, optionally substituted alkyl and the like, $R^2$ is hydrogen, optionally substituted alkyl and the like, $R^3$ is optionally substituted heteroaryl, $R^4$ is optionally substituted cycloalkyl, optionally substituted phenyl and the like, provided that when $R^1$ is hydrogen, and $R^2$ and $R^4$ are the same or different and each is phenyl or phenyl substituted by halogen atom, lower alkyl or lower alkoxy, $R^3$ is benzothiazolyl or thiazolyl substituted by phenyl, the imidazole derivative of the following formula (XII)

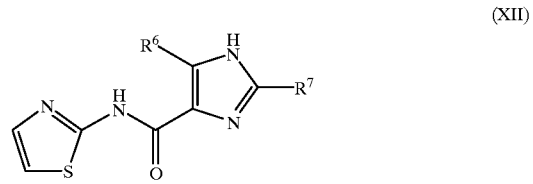

wherein $R^6$ is optionally substituted phenyl or optionally substituted heteroaryl and $R^7$ is substituted phenyl, and pharmaceutically acceptable salts thereof. The compounds of the formulas (I) and (XII) and pharmaceutically acceptable salts thereof of the present invention inhibit IL-4 and IL-5 production by Th2 cells and are effective for the prophylaxis and treatment of allergic diseases such as atopic dermatitis, bronchial asthma, allergic rhinitis and the like.

17 Claims, 5 Drawing Sheets

IMIDAZOLE DERIVATIVES

This is a continuation-in-part of PCT/JP98/05930 filed Dec. 24, 1998.

TECHNICAL FIELD OF THE INVENTION

The present invention relates to a novel imidazole derivative and a pharmaceutically acceptable salt thereof, that show an inhibitory effect on the production of interleukin-4 (hereinafter IL-4) and interleukin-5 (hereinafter IL-5) by type 2 helper T cell (hereinafter to be abbreviated as Th2 cell), and that are useful for the prophylaxis and treatment of allergic diseases.

BACKGROUND OF THE INVENTION

Helper T cells are divided into Th1 cells and Th2 cells based on the cytokines they produce. The Th1 cells produce cytokines such as interleukin-2 (hereinafter IL-2), interferon-γ (hereinafter IFN-γ) and the like and mainly regulate cellular immunity. The Th2 cells produce cytokines such as IL-4, IL-5, interleukin-10 (hereinafter IL-10) and the like and mainly regulate humoral immunity. Immune responses are regulated on the balance between the Th1 cells and Th2 cells. The IFN-γ produced by Th1 cells promotes differentiation into Th1 cells but inhibits differentiation into Th2 cells. The IL-4 produced by Th2 cells promotes differentiation into Th2 cells but inhibits differentiation into Th1 cells.

In recent years, the onset of various immune diseases has been clarified to be triggered by a failure to balance Th1 cells and Th2 cells. Reports have been documented that Th2 cells are dominant in allergic diseases and systemic autoimmune diseases and Th1 cells are dominant in organ-specific autoimmune diseases. of the cytokines produced by Th2 cells, IL-4 shows class switching to immunoglobulin E (IgE) and induction of differentiation into Th2 cells, and IL-5 shows activation of eosinophil and induction of infiltration, and is involved particularly deeply in the formation of an allergic disease state. In fact, many studies have reported that large amounts of IL-4 and IL-5 were found in bronchoalveolar lavage fluid of patients with asthma and mRNAs of IL-4 and IL-5 were found in rash from patients with atopic dermatitis (Am. J. Respir. Cell Mol. Biol., Vol. 12, pp.477–487, 1995, J. Immunol., Vol. 158, pp. 3539–3544 and J. Exp. Med., Vol. 173, pp. 775–778, 1991).

Also, there is a report that various allergic reactions are less easily induced in mice defective in IL-4 or IL-5 gene (Nature, Vol. 362, pp. 245–247, 1993 and J. Exp. Med., Vol. 183, pp. 195–201, 1996). In addition, infiltration of eosinophils could be reportedly inhibited strongly by the administration of an anti-IL-5 antibody in various animal models inclusive of airway inflammation model monkey (Am. J. Respir. Crit. Care Med., Vol. 152, pp. 467–472, 1995).

It has been elucidated using animal models of allergic diseases that IL-4 or IL-5 is involved in the onset of these diseases.

Therefore, a pharmaceutical agent that inhibits production of IL-4 and IL-5 in allergic patients, that improves a shift toward Th2 cells and that inhibits eosinophilic inflammation is considered to make a useful anti-allergy drug.

While JP-B-7-53716 discloses a certain imidazole derivative having an antiphlogistic effect and analgesic effect, but this publication is silent on an inhibitory effect and the like on the production of IL-4 or IL-5 by Th2 cells.

With regard to suplatast tosilate (IPD-1151T) recently developed, a clinical achievement report has been documented that it has a specific inhibitory effect on the production of IL-4 and IL-5 by Th2 cells, and is effective against asthma and atopic dermatitis (Journal of Clinical Therapeutics & Medicines, Vol. 8, No. 7, 1992). However, the inhibitory effect provided by IPD-1151T on the production of IL-4 and IL-5 is not very potent, and it is not clear if a clinical dose is sufficient to express an inhibitory effect on the production of IL-4 and IL-5.

At present, steroidal agents have been widely used for the treatment of allergic diseases and show high clinical effects. Steroidal agents exhibit an IL-5 production inhibitory effect among the broad range of effects, and the IL-5 production inhibitory effect is considered to be the mechanism of inhibition of eosinophilic inflammation. Due to the broad range of effects provided by steroidal agents, however, side effects pose serious problems.

Recent reports show that immunosuppressants such as cyclosporin A and tacrolimus also inhibit production of IL-5, and are effective against eosinophilic inflammation. These drugs, nevertheless, are associated with side effects to kidney, side effects of immunosuppression, induction of infections and the like, due to the wide inhibition they provide with respect to the production of cytokines of not only IL-5 but also IL-2.

Therefore, creation of a therapeutic agent for allergic diseases having an equally potent anti-allergic action as steroidal agents and causing less side effects is awaited.

A compound having a specific IL-4 and IL-5 production inhibitory effect is expected to make a pharmaceutical agent with less side effect as compared to conventional drugs and to be useful for the prophylaxis and treatment of allergic diseases such as atopic dermatitis, bronchial asthma and allergic rhinitis, because it improves the shift toward Th2 cells and suppresses eosinophilic inflammation in allergic patients.

It is therefore an object of the present invention to provide a drug that specifically inhibits production of particularly IL-4 and IL-5 that are deeply involved in the formation of a disease state of allergy, from among the cytokines produced by Th2 cells.

SUMMARY OF THE INVENTION

The present inventors have found that the novel imidazole compounds of the following formulas (I) and (XII) andpharmacologically acceptable salts thereof have a superior IL-4 and IL-5 production inhibitory effect and are useful as pharmaceutical agents for the prophylaxis and treatment of allergic diseases.

The present invention relates to an imidazole derivative of the formula (I)

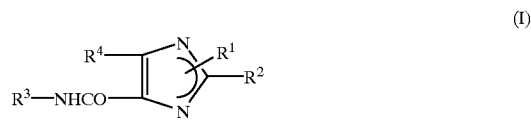

wherein
- $R^1$ is hydrogen, optionally substituted alkyl, optionally substituted aralkyl or morpholinoalkyl;
- $R^2$ is hydrogen, optionally substituted alkyl, optionally substituted cycloalkyl, optionally substituted phenyl, optionally substituted naphthyl, optionally substituted quinolyl, optionally substituted isoquinolyl, optionally substituted pyridyl or optionally substituted aralkyl;

$R^3$ is optionally substituted heteroaryl; and $R^4$ is optionally substituted cycloalkyl, optionally substituted phenyl, optionally substituted naphthyl or optionally substituted heteroaryl; provided that when $R^1$ is hydrogen, $R^2$ is phenyl or phenyl substituted by halogen atom, lower alkyl or lower alkoxy, and $R^4$ is phenyl or phenyl substituted by halogen atom, lower alkyl or lower alkoxy, and $R^3$ is benzothiazolyl or thiazolyl substituted by phenyl, a pharmaceutically acceptable salt thereof, a pharmaceutical composition containing the imidazole derivative, and a pharmaceutical use thereof (particularly for selective inhibition of production of interleukin 4 and interleukin 5, and prophylaxis and/or treatment of allergy).

In the formula (I), when $R^1$ is hydrogen and $R^2$ is phenyl or phenyl substituted by halogen atom, lower alkyl or lower alkoxy, $R^4$ is preferably a group other than phenyl and phenyl substituted by halogen atom, lower alkyl or lower alkoxy.

More preferably, $R^1$ is hydrogen, $R^2$ is phenyl substituted by one of nitro, amino, monoalkylamino, dialkylamino, acylamino, dialkylaminoalkylamino, acyloxyalkylcarbonylamino, dialkylaminoalkoxy, acyloxyalkoxy, hydroxyalkoxy and saturated 5- or 6-membered heteromonocyclic group having 1 or 2 nitrogen atoms and optionally substituted by lower alkyl having 1 to 6 carbon atoms and optionally having an oxygen atom, $R^3$ is optionally substituted heteroaryl, and $R^4$ is optionally substituted phenyl.

Still more preferably, $R^1$ is hydrogen, $R^2$ is optionally substituted naphthyl, $R^3$ is optionally substituted heteroaryl and $R^4$ is optionally substituted phenyl.

Preferable compounds include 5-(4-methylphenyl)-2-(1-naphthyl)-N-(2-thiazolyl) imidazole-4-carboxamide, 5-(4-methoxyphenyl)-2-(4-nitrophenyl)-N-(2-thiazolyl) imidazole-4-carboxamide, 5-(4-methoxyphenyl)-2-(4-methylaminophenyl)-N-(2-thiazolyl)-imidazole-4-carboxamide, 2-(4-butylaminophenyl)-5-(4-methoxyphenyl)-N-(2-thiazolyl)-imidazole-4-carboxamide, 2-(3-dimethylaminophenyl)-5-(4-methoxyphenyl)-N-(2-thiazolyl)-imidazole-4-carboxamide, 2-(4-butylaminophenyl)-5-(4-chlorophenyl)-N-(2-thiazolyl)-imidazole-4-carboxamide, 5-(4-chlorophenyl)-2-(4-methylaminophenyl)-N-(2-thiazolyl)-imidazole- 4-carboxamide, 5-(4-chlorophenyl)-2-(4-nitrophenyl)-N-(2-thiazolyl) imidazole-4-carboxamide, 5-(4-chlorophenyl)-2-(4-(1-pyrrolidinyl)phenyl)-N-(2-thiazolyl)-imidazole-4-carboxamide, 5-(4-chlorophenyl)-2-(4-(2-dimethylaminoethyloxy) phenyl)-N-(2-thiazolyl)imidazole-4-carboxamide, 5-(4-chlorophenyl)-2-(4-(3-dimethylaminopropyloxy) phenyl)-N-(2-thiazolyl)imidazole-4-carboxamide and 5-(4-chlorophenyl)-2-(4-(2-hydroxyethyloxy)phenyl)-N-(2-thiazolyl)imidazole-4-carboxamide.

Another aspect of the present invention relates to an imidazole derivative of the following formula (XII)

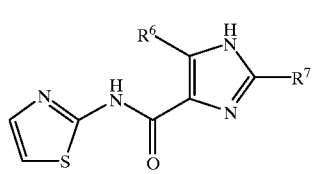
(XII)

wherein $R^6$ is optionally substituted phenyl or optionally substituted heteroaryl, $R^7$ is phenyl substituted by a substituent or the same or different 2 substituents selected from the group consisting of cyano, substituted alkyl, optionally substituted saturated 6- or 7-membered heteromonocyclic group having 1 or 2 nitrogen atoms and optionally having oxygen atom or sulfur atom, an optionally substituted spiro ring comprising the same or different two saturated 6- or 7-membered heteromonocyclic groups having 1 to 3 nitrogen atoms and optionally having oxygen atom or sulfur atom, and a group of the formula (XIII)

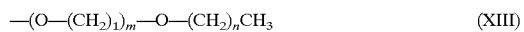
(XIII)

wherein l and m are each an integer of 1 to 4, n is an integer of 0 to 3, and alkyl chain is optionally substituted, a pharmaceutically acceptable salt thereof, a pharmaceutical composition containing the imidazole derivative, and a pharmaceutical use thereof (particularly for selective inhibition of interleukin-4 and interleukin-5 production, and prophylaxis and/or treatment of allergy).

$R^6$ is preferably phenyl substituted by a member selected from the group consisting of halogen atom and methyl.

$R^7$ is preferably phenyl substituted by a member selected from the group consisting of substituted alkyl, optionally substituted saturated 6- or 7-membered heteromonocyclic group having 1 or 2 nitrogen atoms and optionally having oxygen atom or sulfur atom, an optionally substituted spiro ring comprising the same or different two saturated 6- or 7-membered heteromonocyclic groups having 1 to 3 nitrogen atoms and optionally having oxygen atom or sulfur atom, and a group of the formula (XIV)

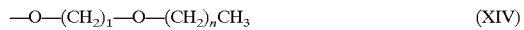
(XIV)

wherein l is an integer of 1 to 4, n is an integer of 0 to 3, and alkyl chain is optionally substituted.

More preferably, $R^7$ is phenyl substituted by a member selected from the group consisting of trifluoromethyl, morpholino, morpholinomethyl, 4-(dimethylaminomethyl) piperidin-1-yl and a group of the formula (XIV)

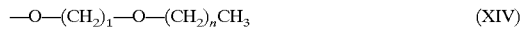
(XIV)

wherein l is an integer of 1 to 4 and n is an integer of 0 to 3.

Of the compounds of the formula (XII), the following compounds are preferable.

5-(4-chlorophenyl)-2-(4-morpholinophenyl)-N-(2-thiazolyl)-imidazole-4-carboxamide, 5-(4-fluorophenyl)-2-(4-morpholinophenyl)-N-(2-thiazolyl)-imidazole-4-carboxamide, 5-(4-chlorophenyl)-2-[4-(morpholinomethyl)phenyl]-N-(2-thiazolyl)imidazole-4-carboxamide, 5-(4-chlorophenyl)-2-[4-(2-methoxyethoxy)phenyl]-N-(2-thiazolyl)-imidazole-4-carboxamide, 5-(4-fluorophenyl)-2-[4-(2-methoxyethoxy)phenyl]-N-(2-thiazolyl)-imidazole-4-carboxamide, 5-(4-methylphenyl)-N-(2-thiazolyl)-2-(4-trifluoromethylphenyl)-imidazole-4-carboxamide, 5-(4-fluorophenyl)-N-(2-thiazolyl)-2-(4-trifluoromethylphenyl)-imidazole-4-carboxamide, 5-(4-chlorophenyl)-N-(2-thiazolyl)-2-(4-trifluoromethylphenyl)-imidazole-4-carboxamide, 5-(4-chlorophenyl)-2-{4-[4-(dimethylaminomethyl)piperidin-1-yl]phenyl}-N-(2-thiazolyl)imidazole-4-carboxamide, and 5-(4-chlorophenyl)-2-[4-(4-methyl-1-oxa-4,9-diazaspiro[5,5]-undecan-9-yl)phenyl]-N-(2-thiazolyl)imidazole-4-carboxamide.

By the concurrent use of the imidazole derivative of the above formula (XII) with a steroidal agent, the effect of prophylaxis and/or treatment of allergy can be potentiated.

DETAILED DESCRIPTION OF THE INVENTION

Figure 1:
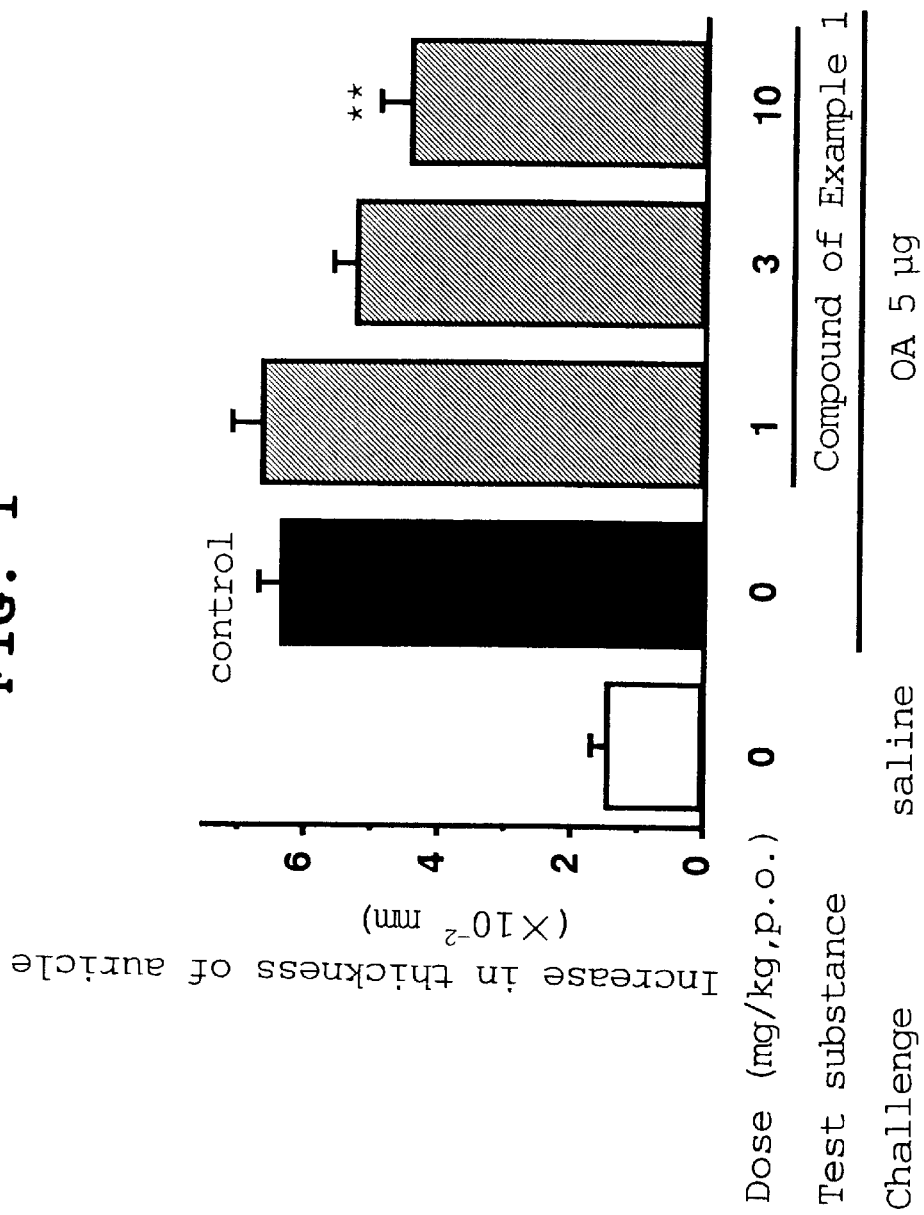
FIG. 1 is a graph showing the effect of the compound of Example 1 on ovalbumin (OA)-induced mouse biphasic ear edema model in Experimental Example 2, wherein each value shows mean±standard error (n=23–28). The significant difference test was performed by Dunnett's multiple comparison test, wherein ** shows P<0.01, indicating significant difference from control.

The substituents of the compound of the formula (I) of the present invention are defined as follows.

The alkyl of "optionally substituted alkyl" at $R^1$ and $R^2$ is linear or branched chain alkyl having 1 to 20 carbon atoms, such as methyl, ethyl, propyl, isopropyl, butyl, isobutyl, tert-butyl, pentyl, isopentyl, hexyl, isohexyl, heptyl, octyl, nonyl, decyl, dodecyl, tetradecyl, hexadecyl, octadecyl, icosyl and the like, with preference given to alkyl having 1 to 6 carbon atoms.

The substituent of the "optionally substituted alkyl" is exemplified by aralkyloxy (aralkyloxy wherein alkoxy having 1 to 6 carbon atoms is substituted by phenyl, such as benzyloxy, phenylethoxy, phenylpropyloxy, phenylbutoxy and the like); hydroxy; lower alkoxy (alkoxy having 1 to 6 carbon atoms such as methoxy, ethoxy, propyloxy, isopropyloxy, butoxy and the like); hydroxyalkoxy (hydroxyalkoxy wherein lower alkoxy having 1 to 6 carbon atoms is substituted by hydroxy, such as hydroxyethoxy, hydroxypropyloxy, hydroxyisopropyloxy, hydroxybutoxy, hydroxyisobutoxy, hydroxypentyloxy and the like); alkoxyalkoxy (alkoxyalkoxy wherein lower alkoxy having 1 to 6 carbon atoms is substituted by alkoxy having 1 to 6 carbon atoms, such as methoxymethoxy, methoxyethoxy, methoxypropyloxy, ethoxypropyloxy, propyloxyethoxy, isopropyloxybutoxy, butoxyisopropyloxy and the like); aminoalkoxy (aminoalkoxy wherein lower alkoxy having 1 to 6 carbon atoms is substituted by amino, such as aminoethoxy, aminopropyloxy, aminoisopropyloxy, aminobutoxy, aminoisobutoxy and the like); monoalkylaminoalkoxy (monoalkylaminoalkoxy wherein lower alkoxy having 1 to 6 carbon atoms is substituted by alkylamino having 1 to 6 carbon atoms, such as methylaminoethoxy, ethylaminoethoxy, ethylaminoisobutoxy, propylaminoethoxy, isopropylaminobutoxy and the like); dialkylaminoalkoxy (dialkylaminoalkoxy wherein lower alkoxy having 1 to 6 carbon atoms is substituted by alkylamino having 1 to 6 carbon atoms, such as dimethylaminoethoxy, diethylaminopropyloxy, diisopropylaminoethoxy, dibutylaminoisopropyloxy and the like); mercaptoalkoxy (mercaptoalkoxy wherein lower alkoxy having 1 to 6 carbon atoms is substituted by mercapto, such as mercaptoethoxy, mercaptopropyloxy, mercaptoisopropyloxy, mercaptobutoxy and the like); alkylthioalkoxy (alkylthioalkoxy wherein lower alkoxy having 1 to 6 carbon atoms is substituted by alkylthio having 1 to 6 carbon atoms, such as methylthioethoxy, ethylthioethoxy, ethylthiopropyloxy, propylthioisopropyloxy, isopropylthiobutoxy and the like); acyloxyalkoxy (acyloxyalkoxy wherein lower alkoxy having 1 to 6 carbon atoms is substituted by aliphatic acyloxy having 2 to 6 carbon atoms, such as acetyloxyethoxy, propionyloxyethoxy, isobutyryloxypropyloxy, acetyloxypropyloxy, butyryloxypropyloxy and the like); cyanoalkoxy (cyanoalkoxy wherein lower alkoxy having 1 to 6 carbon atoms is substituted by cyano, such as cyanoethoxy, cyanopropyloxy, cyanoisopropyloxy, cyanobutoxy, cyanoisobutoxy and the like); nitroalkoxy (nitroalkoxy wherein lower alkoxy having 1 to 6 carbon atoms is substituted by nitro, such as nitroethoxy, nitropropyloxy, nitrobutoxy, nitroisobutoxy and the like); haloalkoxy (haloalkoxy wherein lower alkoxy having 1 to 6 carbon atoms is substituted by halogen atom (e.g., fluorine, chlorine, bromine, iodine), such as chloromethoxy, bromomethoxy, fluoromethoxy, trifluoromethoxy, dichloroethoxy, dibromoethoxy, pentafluoroethoxy, chloropropyloxy, dichlorobutoxy and the like); mercapto; alkylthio (alkylthio wherein the alkyl moiety is alkyl having 1 to 6 carbon atoms, such as methylthio, ethylthio, propylthio, isopropylthio, butylthio, isobutylthio and the like); amino; monoalkylamino (monoalkylamino wherein the alkyl moiety is alkyl having 1 to 6 carbon atoms, such as methylamino, ethylamino, propylamino, butylamino and the like); dialkylamino (dialkylamino wherein the alkyl moiety is alkyl having 1 to 6 carbon atoms, such as dimethylamino, diethylamino, dipropylamino, diisopropylamino, dibutylamino and the like); dialkylaminoalkylamino (dialkylaminoalkylamino wherein the alkyl moiety is alkyl having 1 to 6 carbon atoms, such as dimethylaminoethylamino, dimethylaminopropylamino and the like); carbamoyl; monoalkylcarbamoyl (monoalkylcarbamoyl wherein the alkyl moiety is alkyl having 1 to 6 carbon atoms, such as methylcarbamoyl, ethylcarbamoyl, propylcarbamoyl, butylcarbamoyl and the like); dialkylcarbamoyl (dialkylcarbamoyl wherein the alkyl moiety is alkyl having 1 to 6 carbon atoms, such as dimethylcarbamoyl, diethylcarbamoyl, dipropylcarbamoyl, dibutylcarbamoyl and the like); acylamino (aliphatic acylamino having 2 to 6 carbon atoms, such as acetylamino, propionylamino and the like, and benzoylamino); nitro; cyano; alkylsulfonyl (alkylsulfonyl wherein the alkyl moiety is alkyl having 1 to 6 carbon atoms, such as methylsulfonyl, ethylsulfonyl and the like); alkylsulfinyl (alkylsulfinyl wherein the alkyl moiety is alkyl having 1 to 6 carbon atoms, such as methylsulfinyl, ethylsulfinyl and the like); sulfamoyl; monoalkylsulfamoyl (monoalkylsulfamoyl wherein the alkyl moiety is alkyl having 1 to 6 carbon atoms, such as methylsulfamoyl, ethylsulfamoyl and the like); dialkylsulfamoyl (dialkylsulfamoyl wherein the alkyl moiety is alkyl having 1 to 6 carbon atoms, such as dimethylsulfamoyl, diethylsulfamoyl and the like); cycloalkyl (cycloalkyl having 3 to 7 carbon atoms, such as cyclopropyl, cyclobutyl, cyclopentyl, cyclohexyl and the like); halogen atom (e.g., fluorine, chlorine, bromine, iodine); carboxyl; alkoxycarbonyl (alkoxycarbonyl wherein the alkoxy moiety is alkoxy having 1 to 6 carbon atoms, such as methoxycarbonyl, ethoxycarbonyl, propyloxycarbonyl, butoxycarbonyl and the like); acyl (aliphatic acyl having 1 to 6 carbon atoms such as formyl, acetyl, propionyl and the like and benzoyl); acyloxy (aliphatic acyloxy having 1 to 6 carbon atoms such as formyloxy, acetyloxy, propionyloxy and the like and benzoyloxy); and the like, with preference given to hydroxy, amino, monoalkylamino, dialkylamino, nitro, lower alkoxy, halogen atom, aralkyloxy and the like.

The "optionally substituted alkyl" may be substituted by 1 to 3 substituents, wherein the substituents may be the same or different.

The aralkyl of the "optionally substituted aralkyl" at $R^1$ and $R^2$ is that wherein alkyl having 1 to 6 carbon atoms is substituted by phenyl, such as benzyl, phenylethyl, phenylpropyl, phenylbutyl and the like.

The substituent on the phenyl ring of the "optionally substituted aralkyl" may be lower alkyl (e.g., alkyl having 1 to 6 carbon atoms such as methyl, ethyl, propyl, isopropyl, butyl, isobutyl, tert-butyl, pentyl, isopentyl, hexyl and the like); hydroxyalkyl (e.g., hydroxyalkyl wherein lower alkyl having 1 to 6 carbon atoms is substituted by hydroxy, such as hydroxymethyl, hydroxyethyl, hydroxylpropyl, hydroxyisopropyl, hydroxylbutyl, hydroxylisobutyl, hydroxylpentyl and the like); alkoxyalkyl (alkoxyalkyl wherein lower alkyl having 1 to 6 carbon atoms is substituted by alkoxy having 1 to 6 carbon atoms, such as methoxyethyl, methoxypropyl, ethoxypropyl, propyloxyethyl, isopropyloxybutyl, butoxybutyl and the like); aminoalkyl (aminoalkyl wherein lower alkyl having 1 to 6 carbon atoms is substituted by amino, such as aminomethyl, aminoethyl, aminopropyl, aminoisopropyl, aminobutyl, aminoisobutyl and the like); monoalkylaminoalkyl (monoalkylaminoalkyl wherein lower alkyl having 1 to 6 carbon atoms is substituted by alkylamino having 1 to 6 carbon atoms, such as methylaminomethyl, methylaminoethyl, ethylaminoethyl, ethylaminoisobutyl, propylaminoethyl, isopropylaminobutyl and the like); dialkylaminoalkyl (dialkylaminoalkyl wherein lower alkyl having 1 to 6 carbon atoms is substituted by alkylamino having 1 to 6 carbon atoms, such as dimethylaminomethyl, dimethylaminoethyl, diethylaminopropyl, diisopropylaminoethyl, dibutylaminoisopropyl and the like); mercaptoalkyl (mercaptoalkyl wherein lower alkyl having 1 to 6 carbon atoms is substituted by mercapto, such as mercaptomethyl, mercaptoethyl, mercaptoisopropyl and the like); alkylthioalkyl (alkylthioalkyl wherein lower alkyl having 1 to 6 carbon atoms is substituted by alkylthio having 1 to 6 carbon atoms, such as methylthiomethyl, methylthioethyl, ethylthioethyl, ethylthiopropyl, propylthioisopropyl, isopropylthiobutyl and the like); acyloxyalkyl (acyloxyalkyl wherein lower alkyl having 1 to 6 carbon atoms is substituted by aliphatic acyloxy having 2 to 6 carbon atoms, such as acetyloxymethyl, acetyloxyethyl, propionyloxymethyl, propionyloxyethyl, isobutyloxymethyl, acetyloxypropyl, butyloxypropyl and the like); acyloxyacyl (acyloxyacyl wherein aliphatic acyl having 2 to 5 carbon atoms is substituted by aliphatic acyl having 2 to 5 carbon atoms, such as acetyloxyacetyl, acetyloxypropionyl, acetyloxybutyryl, propionyloxyacetyl, propionyloxypropionyl and the like); alkoxycarbonylalkyl (alkoxycarbonylalkyl wherein lower alkyl having 1 to 6 carbon atoms is substituted by alkoxycarbonyl having 1 to 5 carbon atoms in the alkoxy moiety, such as methoxycarbonylmethyl, ethoxycarbonylmethyl, propoxycarbonylmethyl, butoxycarbonylmethyl, methoxycarbonylethyl, methoxycarbonylpropyl and the like); acyloxyalkylcarbonylamino (acyloxyalkylcarbonylamino wherein aliphatic acylamino having 2 to 6 carbon atoms is substituted by aliphatic acyloxy having 2 to 6 carbon atoms, such as acetoxymethylcarbonylamino, acetoxyethylcarbonylamino, propionyloxymethylcarbonylamino, propionyloxyethylcarbonylamino and the like); cyanoalkyl (cyanoalkyl wherein lower alkyl having 1 to 6 carbon atoms is substituted by cyano, such as cyanomethyl, cyanoethyl, cyanopropyl, cyanoisopropyl, cyanobutyl, cyanoisobutyl and the like); nitroalkyl (nitroalkyl wherein lower alkyl having 1 to 6 carbon atoms is substituted by nitro, such as nitromethyl, nitroethyl, nitropropyl, nitrobutyl, nitroisobutyl and the like); haloalkyl (haloalkyl wherein alkyl having 1 to 6 carbon atoms is substituted by halogen (e.g., fluorine, chlorine, bromine, iodine), such as chloromethyl, bromomethyl, fluoromethyl, trifluoromethyl, dichloroethyl, dibromoethyl, pentafluoroethyl, chloropropyl, dichlorobutyl and the like); phenyl; aralkyl (aralkyl wherein alkyl having 1 to 6 carbon atoms is substituted by phenyl, such as benzyl, phenylethyl, phenylpropyl, phenylbutyl and the like); aralkyloxy (aralkyloxy wherein alkyl having 1 to 6 carbon atoms is substituted by phenyl optionally substituted by halogen (e.g., fluorine, chlorine, bromine, iodine), such as benzyloxy, phenylethyloxy, phenylpropyloxy, phenylbutyloxy, chlorobenzyloxy and the like); hydroxy; lower alkoxy (alkoxy having 1 to 6 carbon atoms such as methoxy, ethoxy, propyloxy, isopropyloxy, butoxy and the like); hydroxyalkoxy (hydroxyalkoxy wherein lower alkoxy having 1 to 6 carbon atoms is substituted by hydroxy, such as hydroxyethoxy, hydroxypropyloxy, hydroxyisopropyloxy, hydroxybutoxy, hydroxyisobutoxy, hydroxypentyloxy and the like); alkoxyalkoxy (alkoxyalkoxy wherein alkoxy having 1 to 6 carbon atoms is substituted by lower alkoxy having 1 to 6 carbon atoms, such as methoxymethoxy, methoxyethoxy, methoxypropyloxy, ethoxypropyloxy, propyloxyethoxy, isopropyloxybutoxy, butoxyisopropyloxy and the like); aminoalkoxy (aminoalkoxy wherein lower alkoxy having 1 to 6 carbon atoms is substituted by amino, such as aminoethoxy, aminopropyloxy, aminoisopropyloxy, aminobutoxy, aminoisobutoxy and the like); monoalkylaminoalkoxy (monoalkylaminoalkoxy wherein lower alkoxy having 1 to 6 carbon atoms is substituted by alkylamino having 1 to 6 carbon atoms, such as methylaminoethoxy, ethylaminoethoxy, ethylaminoisobutoxy, propylaminoethoxy, isopropylaminobutoxy and the like); dialkylaminoalkoxy (dialkylaminoalkoxy wherein lower alkoxy having 1 to 6 carbon atoms is substituted by alkylamino having 1 to 6 carbon atoms, such as dimethylaminoethoxy, dimethylaminopropyloxy, diethylaminopropyloxy, diisopropylaminoethoxy, dibutylaminoisopropyloxy and the like); mercaptoalkoxy (mercaptoalkoxy wherein lower alkoxy having 1 to 6 carbon atoms is substituted by mercapto, such as mercaptoethoxy, mercaptopropyloxy, mercaptoisopropyloxy, mercaptobutoxy and the like); alkylthioalkoxy (alkylthioalkoxy wherein lower alkoxy having 1 to 6 carbon atoms is substituted by alkylthio having 1 to 6 carbon atoms, such as methylthioethoxy, ethylthioethoxy, ethylthiopropyloxy, propylthioisopropyloxy, isopropylthiobutoxy and the like); acyloxyalkoxy (acyloxyalkoxy wherein lower alkoxy having 1 to 6 carbon atoms is substituted by aliphatic acyloxy having 2 to 6 carbon atoms, such as acetyloxyethoxy, propionyloxyethoxy, isobutyryloxypropyloxy, acetyloxypropyloxy, butyryloxypropyloxy and the like); cyanoalkoxy (cyanoalkoxy wherein lower alkoxy having 1 to 6 carbon atoms is substituted by cyano, such as cyanoethoxy, cyanopropyloxy, cyanoisopropyloxy, cyanobutoxy, cyanoisobutoxy and the like); nitroalkoxy (nitroalkoxy wherein lower alkoxy having 1 to 6 carbon atoms is substituted by nitro, such as nitroethoxy, nitropropyloxy, nitrobutoxy, nitroisobutoxy and the like); haloalkoxy (haloalkoxy wherein lower alkoxy having 1 to 6 carbon atoms is substituted by halogen atom (e.g., fluorine, chlorine, bromine, iodine), such as chloromethoxy, bromomethoxy, fluoromethoxy, trifluoromethoxy, dichloroethoxy, dibromoethoxy, pentafluoroethoxy, chloropropyloxy, dichlorobutoxy and the like); mercapto; alkylthio (alkylthio wherein the alkyl moiety is alkyl having 1 to 6 carbon atoms, such as methylthio, ethylthio, propylthio, isopropylthio, butylthio, isobutylthio and the like); amino; monoalkylamino (monoalkylamino wherein the alkyl moiety is alkyl having 1 to 6 carbon atoms, such as methylamino, ethylamino, propylamino, butylamino, isopentylamino and the like); dialkylamino (dialkylamino wherein the alkyl moiety is alkyl having 1 to 6 carbon atoms, such as dimethylamino, diethylamino, dipropylamino, diisopropylamino, dibutylamino and the like); dialkylaminoalkylamino (dialkylaminoalkylamino wherein the alkyl moiety is alkyl having 1 to 6 carbon atoms, such as dimethylaminoethylamino, dimethylaminopropylamino and the like); carbamoyl; monoalkylcarbamoyl (monoalkylcarbamoyl wherein the alkyl moiety is alkyl having 1 to 6 carbon atoms, such as methylcarbamoyl, ethylcarbamoyl, propylcarbamoyl, butylcarbamoyl and the like); dialkylcarbamoyl (dialkylcarbamoyl wherein the alkyl moiety is alkyl having 1 to 6 carbon atoms, such as dimethylcarbamoyl, diethylcarbamoyl, dipropylcarbamoyl, dibutylcarbamoyl and the like); acylamino (acylamino wherein the acyl moiety is aliphatic acyl having 1 to 6 carbon atoms, such as acetylamino, propionylamino and the like, and benzoylamino); nitro; cyano; alkylsulfonyl (alkylsulfonyl wherein the alkyl moiety is alkyl having 1 to 6 carbon atoms, such as methylsulfonyl, ethylsulfonyl and the like); alkylsulfinyl (alkylsulfinyl wherein the alkyl moiety is alkyl having 1 to 6 carbon atoms, such as methylsulfinyl, ethylsulfinyl and the like); alkylsulfinyloxyalkyl (alkylsulfinyloxyalkyl wherein the alkyl moiety is alkyl having 1 to 6 carbon atoms, such as methylsulfinyloxymethyl, methylsulfinyloxyethyl, methylsulfinyloxypropyl, ethylsulfinyloxymethyl, ethylsulfinyloxyethyl, ethylsulfinyloxypropyl and the like); sulfamoyl; monoalkylsulfamoyl (monoalkylsulfamoyl wherein the alkyl moiety is alkyl having 1 to 6 carbon atoms, such as methylsulfamoyl, ethylsulfamoyl and the like); dialkylsulfamoyl (dialkylsulfamoyl wherein the alkyl moiety is alkyl having 1 to 6 carbon atoms, such as dimethylsulfamoyl, diethylsulfamoyl and the like); cycloalkyl (cycloalkyl having 3 to 7 carbon atoms, such as cyclopropyl, cyclobutyl, cyclopentyl, cyclohexyl and the like); cycloalkylalkyl (cycloalkylalkyl wherein alkyl having 1 to 6 carbon atoms is substituted by cycloalkyl having 3 to 7 carbon atoms, such as cyclopropylmethyl, cyclobutylmethyl, cyclopentylmethyl, cyclohexylmethyl and the like); halogen atom (e.g., fluorine, chlorine, bromine, iodine); carboxyl; alkoxycarbonyl (alkoxycarbonyl wherein the alkoxy moiety is alkoxy having 1 to 6 carbon atoms, such as methoxycarbonyl, ethoxycarbonyl, propyloxycarbonyl, butoxycarbonyl and the like); acyl (aliphatic acyl having 1 to 6 carbon atoms such as formyl, acetyl, propionyl and the like and benzoyl); acyloxy (acyloxy wherein the acyl moiety is aliphatic acyl having 1 to 6 carbon atoms, such as formyloxy, acetyloxy, propionyloxy and the like, and benzoyl); saturated 5- or 6-membered heteromonocyclic group having 1 or 2 nitrogen atoms and optionally substituted by lower alkyl having 1 to 6 carbon atoms (e.g., alkyl such as methyl, ethyl, propyl, isopropyl, butyl, isobutyl, tert-butyl, pentyl, isopentyl, hexyl and the like), and optionally having oxygen atom, which is exemplified by pyrrolidinyl, imidazolidinyl, pyrazolidinyl, piperidyl, piperazinyl, morpholinyl, morpholino and the like; nitrogen-containing heteromonocyclic alkyl optionally substituted by lower alkyl having 1 to 6 carbon atoms (e.g., alkyl such as methyl, ethyl, propyl, isopropyl, butyl, isobutyl, tert-butyl, pentyl, isopentyl, hexyl and the like), wherein the nitrogen-containing heteromonocyclic group is saturated 5- or 6-membered heteromonocyclic group having 1 or 2 nitrogen atoms and optionally having an oxygen atom, which group being exemplified by pyrrolidinyl, imidazolidinyl, pyrazolidinyl, piperidyl, piperazinyl, morpholinyl, morpholino and the like, and wherein the alkyl moiety is alkyl having 1 to 6 carbon atoms, which nitrogen-containing heteromonocyclic alkyl being exemplified by piperazinylmethyl, pyrrolidinylmethyl, piperidinomethyl, morpholinylmethyl, morpholinomethyl and the like); and the like. Preferred are hydroxy, amino, monoalkylamino, dialkylamino, nitro, lower alkyl, lower alkoxy, haloalkyl, halogen atom, aralkyl, aralkyloxy optionally substituted by halogen, hydroxyalkyl, hydroxyalkoxy, dialkylaminoalkyl, acyloxyalkyl, alkoxycarbonylalkyl, acyloxyalkylcarbonylamino, phenyl, acyloxyalkoxy, dialkylaminoalkoxy, acylamino, alkylsulfinyloxyalkyl, saturated 5- or 6-membered heteromonocyclic group having 1 or 2 nitrogen atoms and optionally having an oxygen atom, nitrogen-containing heteromonocyclic alkyl optionally substituted by lower alkyl having 1 to 6 carbon atoms and the like.

The phenyl ring of the "optionally substituted aralkyl" may be substituted by 1 to 3 substituents, wherein the substituents may be the same or different.

The substituent of the alkyl moiety of the "optionally substituted aralkyl" may be phenyl, aralkyloxy (aralkyloxy wherein alkoxy having 1 to 6 carbon atoms is substituted by phenyl, such as benzyloxy, phenylethoxy, phenylpropyloxy, phenylbutoxy and the like); hydroxy; lower alkoxy (alkoxy having 1 to 6 carbon atoms such as methoxy, ethoxy, propyloxy, isopropyloxy, butoxy and the like); hydroxyalkoxy (hydroxyalkoxy wherein lower alkoxy having 1 to 6 carbon atoms is substituted by hydroxy, such as hydroxyethoxy, hydroxypropyloxy, hydroxyisopropyloxy, hydroxybutoxy, hydroxyisobutoxy, hydroxypentyloxy and the like); alkoxyalkoxy (alkoxyalkoxy wherein lower alkoxy having 1 to 6 carbon atoms is substituted by alkoxy having 1 to 6 carbon atoms, such as methoxymethoxy, methoxyethoxy, methoxypropyloxy, ethoxypropyloxy, propyloxyethoxy, isopropyloxybutoxy, butoxyisopropyloxy and the like); aminoalkoxy (aminoalkoxy wherein lower alkoxy having 1 to 6 carbon atoms is substituted by amino, such as aminoethoxy, aminopropyloxy, aminoisopropyloxy, aminobutoxy, aminoisobutoxy and the like); monoalkylaminoalkoxy (monoalkylaminoalkoxy wherein lower alkoxy having 1 to 6 carbon atoms is substituted by alkylamino having 1 to 6 carbon atoms, such as methylaminoethoxy, ethylaminoethoxy, ethylaminoisobutoxy, propylaminoethoxy, isopropylaminobutoxy and the like); dialkylaminoalkoxy (dialkylaminoalkoxy wherein lower alkoxy having 1 to 6 carbon atoms is substituted by alkylamino having 1 to 6 carbon atoms, such as dimethylaminoethoxy, diethylaminopropyloxy, diisopropylaminoethoxy, dibutylaminoisopropyloxy and the like); mercaptoalkoxy (mercaptoalkoxy wherein lower alkoxy having 1 to 6 carbon atoms is substituted by mercapto, such as mercaptoethoxy, mercaptopropyloxy, mercaptoisopropyloxy, mercaptobutoxy and the like); alkylthioalkoxy (alkylthioalkoxy wherein lower alkoxy having 1 to 6 carbon atoms is substituted by alkylthio having 1 to 6 carbon atoms, such as methylthioethoxy, ethylthioethoxy, ethylthiopropyloxy, propylthioisopropyloxy, isopropylthiobutoxy and the like); acyloxyalkoxy (acyloxyalkoxy wherein lower alkoxy having 1 to 6 carbon atoms is substituted by aliphatic acyloxy having 2 to 6 carbon atoms, such as acetyloxyethoxy, propionyloxyethoxy, isobutyryloxypropyloxy, acetyloxypropyloxy, butyryloxypropyloxy and the like); cyanoalkoxy (cyanoalkoxy wherein lower alkoxy having 1 to 6 carbon atoms is substituted by cyano, such as cyanoethoxy, cyanopropyloxy, cyanoisopropyloxy, cyanobutoxy, cyanoisobutoxy and the like); nitroalkoxy (nitroalkoxy wherein lower alkoxy having 1 to 6 carbon atoms is substituted by nitro, such as nitroethoxy, nitropropyloxy, nitrobutoxy, nitroisobutoxy and the like); haloalkoxy (haloalkoxy wherein lower alkoxy having 1 to 6 carbon atoms is substituted by halogen atom (e.g., fluorine, chlorine, bromine, iodine), such as chloromethoxy, bromomethoxy, fluoromethoxy, trifluoromethoxy, dichloroethoxy, dibromoethoxy, pentafluoroethoxy, chloropropyloxy, dichlorobutoxy and the like); mercapto; alkylthio (alkylthio wherein the alkyl moiety is alkyl having 1 to 6 carbon atoms, such as methylthio, ethylthio, propylthio, isopropylthio, butylthio, isobutylthio and the like); amino; monoalkylamino (monoalkylamino wherein the alkyl moiety is alkyl having 1 to 6 carbon atoms, such as methylamino, ethylamino, propylamino, butylamino and the like); dialkylamino (dialkylamino wherein the alkyl moiety is alkyl having 1 to 6 carbon atoms, such as dimethylamino, diethylamino, dipropylamino, diisopropylamino, dibutylamino and the like); dialkylaminoalkylamino (dialkylaminoalkylamino wherein the alkyl moiety is alkyl having 1 to 6 carbon atoms, such as dimethylaminoethylamino, dimethylaminopropylamino and the like); carbamoyl; monoalkylcarbamoyl (monoalkylcarbamoyl wherein the alkyl moiety is alkyl having 1 to 6 carbon atoms, such as methylcarbamoyl, ethylcarbamoyl, propylcarbamoyl, butylcarbamoyl and the like); dialkylcarbamoyl (dialkylcarbamoyl wherein the alkyl moiety is alkyl having 1 to 6 carbon atoms, such as dimethylcarbamoyl, diethylcarbamoyl, dipropylcarbamoyl, dibutylcarbamoyl and the like); acylamino (aliphatic acylamino having 2 to 6 carbon atoms such as acetylamino, propionylamino and the like and benzoylamino); nitro; cyano; alkylsulfonyl (alkylsulfonyl wherein the alkyl moiety is alkyl having 1 to 6 carbon atoms, such as methylsulfonyl, ethylsulfonyl and the like); alkylsulfinyl (alkylsulfinyl wherein the alkyl moiety is alkyl having 1 to 6 carbon atoms, such as methylsulfinyl, ethylsulfinyl and the like); sulfamoyl; monoalkylsulfamoyl (monoalkylsulfamoyl wherein the alkyl moiety is alkyl having 1 to 6 carbon atoms, such as methylsulfamoyl, ethylsulfamoyl and the like); dialkylsulfamoyl (dialkylsulfamoyl wherein the alkyl moiety is alkyl having 1 to 6 carbon atoms, such as dimethylsulfamoyl, diethylsulfamoyl and the like); cycloalkyl (cycloalkyl having 3 to 7 carbon atoms, such as cyclopropyl, cyclobutyl, cyclopentyl, cyclohexyl and the like); halogen atom (e.g., fluorine, chlorine, bromine, iodine); carboxyl; alkoxycarbonyl (alkoxycarbonyl wherein the alkoxy moiety has 1 to 6 carbon atoms, such as methoxycarbonyl, ethoxycarbonyl, propyloxycarbonyl, butoxycarbonyl and the like); acyl (aliphatic acyl having 1 to 6 carbon atoms such as formyl, acetyl, propionyl and the like and benzoyl); acyloxy (aliphatic acyloxy having 1 to 6 carbon atoms such as formyloxy, acetyloxy, propionyloxy and the like and benzoyloxy); and the like, with preference given to hydroxy, amino, monoalkylamino, dialkylamino, nitro, lower alkyl, lower alkoxy, haloalkyl, halogen atom, aralkyl, aralkyloxy and the like.

The substituent of the alkyl moiety of the "optionally substituted aralkyl" may be substituted by 1 to 3 substituents, wherein the substituents may be the same or different.

The "morpholinoalkyl" at $R^1$ is that wherein alkyl having 1 to 6 carbon atoms is substituted by morpholino, such as morpholinomethyl, morpholinoethyl, morpholinopropyl, morpholinobutyl and the like.

The cycloalkyl of the "optionally substituted cycloalkyl" at $R^2$ and $R^4$ is cycloalkyl having 3 to 7 carbon atoms, such as cyclopropyl, cyclobutyl, cyclopentyl, cyclohexyl and the like.

The substituent of the "optionally substituted cycloalkyl" is the same as that on the phenyl ring of the "optionally substituted aralkyl".

The cycloalkyl of the "optionally substituted cycloalkyl" may be substituted by 1 to 3 substituents, wherein the substituents may be the same-or different.

The heteroaryl of the "optionally substituted heteroaryl" at $R^3$ and $R^4$ is thiazolyl, thiazolinyl, oxazolyl, imidazolyl, thiadiazolyl, pyridyl, pyrimidinyl, pyrazinyl, pyridazinyl, benzothiazolyl, benzoxazolyl, benzimidazolyl, quinolyl, isoquinolyl and the like.

The substituent of the "optionally substituted heteroaryl" is the same as that on the phenyl ring of the "optionally substituted aralkyl".

The heteroaryl of the "optionally substituted heteroaryl" may be substituted by 1 to 3 substituents, wherein the substituents may be the same or different.

The substituents of the "optionally substituted phenyl", and "optionally substituted naphthyl" at $R^2$ and $R^4$, and "optionally substituted quinolyl", "optionally substituted isoquinolyl" and "optionally substituted pyridyl", at $R^2$ are the same as those on the phenyl ring of the "optionally substituted aralkyl".

The phenyl and each hetero ring of the "optionally substituted phenyl", "optionally substituted naphthyl", "optionally substituted quinolyl", "optionally substituted isoquinolyl" and "optionally substituted pyridyl" may be substituted by 1 to 3 substituents, wherein the substituents may be the same or different.

In the proviso, the "halogen atom", "lower alkyl" and "lower alkoxy" at $R^2$ and $R^4$ are the same as "halogen atom", "lower alkyl" and "lower alkoxy" that can substitute on the phenyl ring of the aforementioned "optionally substituted aralkyl".

Preferable examples of the substituent of the "optionally substituted heteroaryl" at $R^3$ include thiazolyl, thiazolinyl, thiadiazolyl, benzothiazolyl, pyrimidinyl and imidazolyl. Preferable examples of the substituent that can substitute heteroaryl include lower alkyl, alkoxycarbonylalkyl and phenyl.

Preferable examples of the substituent of the "optionally substituted heteroaryl" at $R^4$ include pyridyl and pyrimidinyl. Preferable examples of the substituent that can substitute heteroaryl include lower alkyl and lower alkoxyl.

Preferable examples of the substituent of the "optionally substituted phenyl" at $R^2$ include lower alkyl, aralkyloxy optionally substituted by halogen, hydroxy, lower alkoxy, amino, monoalkylamino, dialkylamino, acylamino, nitro, halogen atom, acyloxyalkylcarbonylamino, dialkylaminoalkoxy, acyloxyalkoxy, hydroxyalkoxy and saturated 5- or 6-membered heteromonocyclic group having 1 or 2 nitrogen atoms and optionally having oxygen atom.

Preferable examples of the substituent of the "optionally substituted naphthyl" at $R^2$ include monoalkylamino, dialkylamino, nitro, lower alkyl and lower alkoxy.

Preferable examples of the substituent of the "optionally substituted phenyl" at $R^4$ include lower alkyl, hydroxyalkyl, dialkylaminoalkyl, acyloxyalkyl, haloalkyl, hydroxy, lower alkoxy, amino, monoalkylamino, dialkylamino, nitro, halogen atom, alkylsulfinyloxyalkyl, saturated 5- or 6-membered heteromonocyclic group having 1 or 2 nitrogen atoms and optionally having oxygen atom, and nitrogen-containing heteromonocyclic alkyl optionally substituted by lower alkyl having 1 to 6 carbon atoms.

The pharmaceutically acceptable salt of the compound of the formula (I) of the present invention includes salts with inorganic acid such as hydrochloric acid, hydrobromic acid, hydroiodic acid, sulfuric acid, nitric acid, phosphoric acid and the like, and salts with organic acid such as acetic acid, propionic acid, succinic acid, glycolic acid, lactic acid, malic acid, tartaric acid, fumaric acid, maleic acid, citric acid, benzoic acid, methanesulfonic acid, benzenesulfonic acid, p-toluenesulfonic acid and the like. In addition, salts with metal hydroxide such as lithium hydroxide, sodium hydroxide, potassium hydroxide, calcium hydroxide, magnesium hydroxide and the like, and salts with organic base such as triethylamine, pyridine and the like can be exemplified. The compound of the formula (I) of the present invention and a pharmaceutically acceptable salt thereof may exist as hydrates or solvates, which are encompassed in the present invention.

When the compound of the present invention contains an asymmetric carbon, the compound can be obtained in the form of a racemic mixture or an optically active compound. When at least two asymmetric carbons are contained, the compound can be obtained as individual diastereomers or a mixture thereof.

The present invention encompasses these mixtures, isomers and stereoisomers.

The novel imidazole compound of the formula (I) of the present invention can be obtained by, for example, the following method. However, the production methods of the compound of the present invention are not limited to these.

Production Method 1

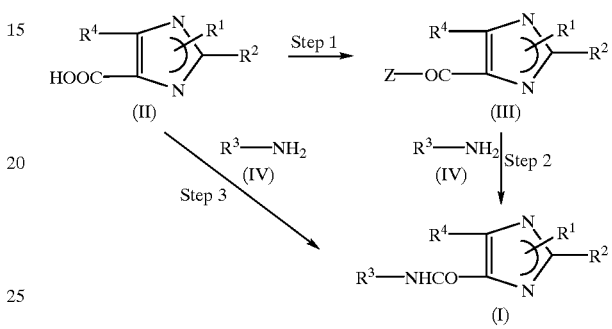

In the above formulas, $R^1$, $R^2$, $R^3$ and $R^4$ are as defined above, and Z is halogen atom such as chlorine, bromine and the like; azido; N-hydroxybenzotriazolyl; p-nitrophenyloxy; p-chlorophenyloxy; alkoxy such as methoxy, ethoxy and the like; acyloxy such as acetyloxy, pivaloyloxy and the like; isobutyloxycarbonyloxy; methoxycarbonyloxy; ethoxycarbonyloxy and the like.

A compound of the formula (II) is reacted with thionyl chloride, isobutyl chloroformate, methyl chloroformate, ethyl chloroformate and the like in an inert solvent according to a conventional method to give a reactive intermediate (III), which is further reacted with a compound of the formula (IV) in an inert organic solvent in the presence or absence of a salt, preferably in the presence of a salt, to give compound (I) (Step 1 and Step 2).

Alternatively, a compound of the formula (II) is reacted, without conversion to a reactive derivative thereof, with a compound of the formula (IV) using a suitable condensing agent and the like in an inert solvent in the presence or absence of a salt, preferably in the presence of a salt, to give compound (I) (Step 3).

The salt to be used for the method of the present invention includes pyridine, picoline, lutidine, collidine, N-methylpiperidine, N-methylpyrrolidine, N-methylmorpholine, N,N-dimethylaminopyridine, triethylamine, diisopropylethylamine, potassium carbonate, sodium carbonate and the like, preferably pyridine, N,N-dimethylaminopyridine, triethylamine, diisopropylethylamine and potassium carbonate. The inert organic solvent to be used for the method of the present invention can be any as long as the reaction is not inhibited, preferably ether, benzene, toluene, ethyl acetate, tetrahydrofuran, dioxane, chloroform, methylene chloride, dimethyl sulfoxide, N,N-dimethylformamide, 1,3-dimethyl-2-imidazolidinone, pyridine and the like, particularly preferably toluene, tetrahydrofuran, dioxane, chloroform, methylene chloride, N,N-dimethylformamide, 1,3-dimethyl-2-imidazolidinone, pyridine and the like.

The reaction proceeds at from −30° C. to the refluxing temperature of the solvent to be used, preferably from room temperature to the refluxing temperature of the solvent to be used, particularly preferably at the refluxing temperature of the solvent to be used.

Preferable examples of the condensing agent include N,N'-dicyclohexylcarbodiimide, 1,1-carbonyldiimidazole, 1-hydroxybenzotriazole, 1-hydroxy-7-azabenzotriazole, 1-ethyl-3-(3-(dimethylamino)propyl)carbodiimide hydrochloride, benzotriazol-1-yloxy-tris(dimethylamino) phosphonium hexafluorophosphate, 4,4'-dichloro-α-methylbenzhydrol and the like.

Production Method 2

In the formula (I), a compound having lower alkoxy or aralkyloxy as a substituent can be produced by reacting a compound of the formula (I), wherein the corresponding substituent is hydroxy, with the corresponding lower alkyl alcohol or phenyl lower alkyl alcohol in the presence of triphenylphosphine and diethyl azodicarboxylate.

Production Method 3

In the formula (I), a compound having hydroxy, hydroxyalkyl, amino or aminoalkyl as substituents can be also produced by hydrolysis of a compound of the formula (I) wherein the corresponding substituent is acyloxy, acyloxyalkyl, acylamino or acylaminoalkyl under basic or acidic conditions.

In the formula (I), a compound having hydroxy, hydroxyalkyl, amino or aminoalkyl as substituents can be also produced by hydrogenation of a compound of the formula (I), wherein the corresponding substituent is benzyloxy, benzyloxyalkyl, benzylamino or benzylaminoalkyl, in the presence of a catalyst such as palladium and the like, or by reacting the compound with hydrobromic acid in a solvent such as acetic acid and the like, or by treating the compound in thioanisole and trifluoroacetic acid.

Production Method 4

In the formula (I), a compound having amino or aminoalkyl as a substituent can be produced by reducing a compound of the formula (I), wherein the corresponding substituent is nitro or nitroalkyl, using iron powder and an acid such as hydrochloric acid, acetic acid, sulfuric acid and the like, or by hydrogenation in the presence of a catalyst such as palladium and the like, or by refluxing under heating in a solution of tin(II) chloride 6 hydrate in 6 M hydrochloric acid.

Production Method 5

In the formula (I), a compound having dialkylamino or monoalkylamino as a substituent can be also produced by alkylating a compound of the formula (I) wherein the corresponding substituent is amino. The method of alkylation may comprise the use of alkyl halide, alkyl p-toluenesulfonate and the like and, where necessary, a base such as triethylamine, pyridine, potassium carbonate, sodium carbonate, sodium hydrogencarbonate and the like, a reaction with formalin, alkyl aldehyde and the like and a metal hydrogen complex compound such as sodium borohydride, sodium cyanoborohydride and the like, reductive alkylation comprising catalytic reduction and the like.

The aforementioned compound of the formula (II) used as the starting material in the present invention can be produced by, for example, hydrolysis under alkaline or acidic conditions of the compounds of the formulas (VII) and (XI) obtained by the following Methods 1 to 4.

Method 1

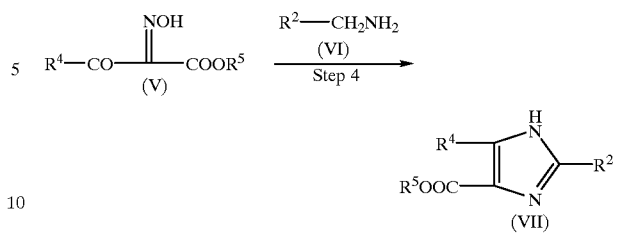

wherein $R^2$ and $R^4$ are as defined above, and $R^5$ is lower alkyl.

By reacting a compound of the formula (V) and a compound of the formula (VI), a compound of the formula (VII) can be produced (Step 4).

As the reaction solvent, for example, toluene, benzene, xylene, pyridine, picoline, dioxane, hexane, petroleum ether, acetonitrile, acetic acid, tetrahydrofuran and the like can be used.

The reaction proceeds at from −30° C. to the refluxing temperature of the solvent to be used, preferably from room temperature to the refluxing temperature of the solvent to be used, particularly preferably at the refluxing temperature of the solvent to be used.

Method 2

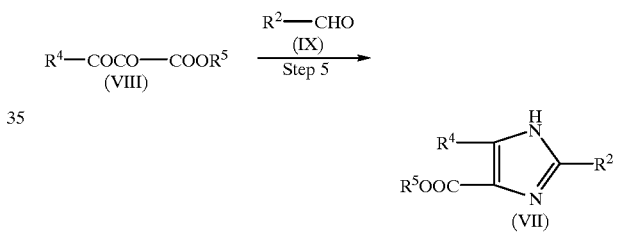

wherein $R^2$ and $R^4$ are as defined above, and R' is lower alkyl.

A compound of the formula (VIII) reported by Harry H. Wasserman, Tetrahedron Letter, Vol. 33, No. 40, pp. 6003–6006, 1992 and the like is reacted with a compound of the formula (IX) in the presence of an ammonium salt such as ammonium lower alkanecarboxylate (e.g., ammonium acetate, ammonium formate and the like) and an ammonium salt of inorganic acid (e.g., ammonium carbonate and the like), in an acidic solution of lower alkanecarboxylic acid, such as formic acid, acetic acid, propionic acid and the like, to give a compound of the formula (VII) (Step 5).

As the reaction solvent, for example, toluene, benzene, xylene, pyridine, picoline, dioxane, hexane, petroleum ether, acetic acid and the like can be used. Alternatively, the reaction may be carried out without solvent.

The reaction advantageously proceeds at from 0° C. to the refluxing temperature of the solvent to be used.

Method 3

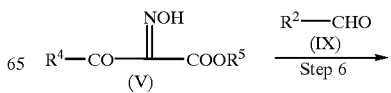

-continued

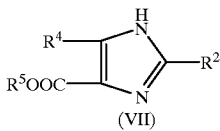

wherein $R^2$ and $R^4$ are as defined above, and $R^5$ is lower alkyl.

A compound of the formula (V) is reacted with a compound of the formula (IX) in the presence of an ammonium salt, such as ammonium lower alkanecarboxylate (e.g., ammonium acetate, ammonium formate and the like) and an ammonium salt of inorganic acid (e.g., ammonium carbonate and the like), to give a compound of the formula (VII) (Step 6).

As the reaction solvent, for example, acetic acid, toluene, pyridine, ethyl acetate and the like can be used.

The reaction preferably proceeds at from 0° C. to the refluxing temperature of the solvent to be used, particularly preferably at the refluxing temperature of the solvent to be used.

Method 4

A compound of the formula (II) wherein $R^1$ is other than hydrogen can be synthesized by the following Step.

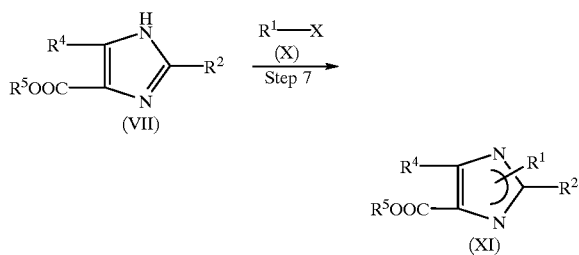

wherein $R^1$, $R^2$, and $R^4$ are as defined above, $R^5$ is lower alkyl, and X is halogen atom.

A compound of the formula (XI) can be produced by reacting a compound of the formula (VII) with a compound of the formula (X) in the presence or absence of a base, such as sodium hydroxide, potassium hydroxide, sodium hydride and the like, in an inert organic solvent (Step 7).

Examples of the inert organic solvent include toluene, tetrahydrofuran, dioxane, chloroform, methylene chloride, N,N-dimethylformamide and the like.

The reaction proceeds at from −30° C. to the refluxing temperature of the solvent to be used, preferably from room temperature to the refluxing temperature of the solvent to be used, particularly preferably at the refluxing temperature of the solvent to be used.

The pharmaceutically acceptable salt of the compound of the formula (I) of the present invention can be converted to the aforementioned acid addition salt by treating with an inorganic acid (hydrochloric acid, hydrobromic acid, hydroiodic acid, sulfuric acid, nitric acid, phosphoric acid and the like), or an organic acid (e.g., acetic acid, propionic acid, succinic acid, glycolic acid, lactic acid, malic acid, tartaric acid, fumaric acid, maleic acid, citric acid, benzoic acid, methanesulfonic acid, benzenesulfonic acid, p-toluenesulfonic acid and the like) according to a conventional method. For crystallization, the compound can be converted to oxalate. In addition, by the treatment with lithium hydroxide, sodium hydroxide, potassium hydroxide, calcium hydroxide, magnesium hydroxide and the like, the corresponding metal salt can be obtained, which, upon treatment with triethylamine, pyridine and the like, can be converted to a salt with organic base. When the obtained crystal of the inventive compound is anhydrous, the inventive compound is treated with water, water-containing solvent or other solvent to give hydrate or solvate.

The compound of the present invention thus obtained can be purified and isolated by a conventional method such as recrystallization, column chromatography and the like. When the obtained product is a racemic modification, a desired optically active compound can be resolved by fractional recrystallization of a salt with an optically active acid or by passing through a column packed with an optically active carrier. Each diastereomer can be separated by a means such as fractional crystallization and chromatography. The compound of the present invention can be also obtained by using an optically active starting compound and the like. A stereoisomer can be isolated by recrystallization, column chromatography and the like.

The substituents of the compound of the following formula (XII) of the present invention are defined as follows.

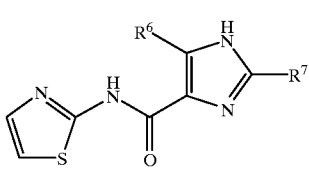

The substituent of the "optionally substituted phenyl" at $R^6$ include halogen atom (fluorine, chlorine, bromine, iodine); lower alkyl (linear or branched chain alkyl having 1 to 6 carbon atoms such as methyl, ethyl, propyl, isopropyl, butyl, isobutyl, tert-butyl, pentyl, isopentyl, hexyl and the like); haloalkyl (haloalkyl wherein linear or branched chain alkyl having 1 to 6 carbon atoms is substituted by halogen (fluorine, chlorine, bromine, iodine), such as chloromethyl, bromomethyl, fluoromethyl, trifluoromethyl, dichloroethyl, dibromoethyl, pentaf luoroethyl, chloropropyl, dichlorobutyl and the like); hydroxyalkyl (hydroxyalkyl wherein linear or branched chain alkyl having 1 to 6 carbon atoms is substituted by hydroxy, such as hydroxymethyl, hydroxyethyl, hydroxypropyl, hydroxyisopropyl, hydroxybutyl, hydroxyisobutyl, hydroxypentyl and the like); and the like, preferably halogen atom, lower alkyl and the like.

The "optionally substituted phenyl" may be substituted by 1 or 2 substituents, wherein the substituents may be the same or different.

The substituent of the "optionally substituted heteroaryl" at $R^6$ is the same as that of the "optionally substituted phenyl", which may be substituted by 1 or 2 substituents, wherein the substituents may be the same or different. Preferable substituents are lower alkyl, halogen atom (fluorine atom, chlorine atom, bromine atom, iodine atom) and the like.

The heteroaryl of the "optionally substituted heteroaryl" is pyridine or thiophene.

The substituent of the "optionally substituted saturated 6- or 7-membered heteromonocyclic group having 1 or 2 nitrogen atoms and optionally having oxygen atom or sulfur atom" as the substituent of phenyl at $R^7$ is exemplified by lower alkyl (linear or branched chain alkyl having 1 to 6, preferably 1 to 4, carbon atoms such as methyl, ethyl, propyl, isopropyl, butyl, isobutyl, tert-butyl, pentyl, isopentyl, hexyl and the like); haloalkyl (haloalkyl wherein linear or branched chain alkyl having 1 to 4 carbon atoms is substituted by halogen (fluorine, chlorine, bromine, iodine), such as chloromethyl, bromomethyl, fluoromethyl, trifluoromethyl, dichloroethyl, dibromoethyl, pentafluoroethyl, chloropropyl, dichlorobutyl and the like); hydroxy; hydroxyalkyl (hydroxyalkyl wherein linear or branched chain lower alkyl having 1 to 6, preferably 1 to 4, carbon atoms is substituted by hydroxy, such as hydroxymethyl, hydroxyethyl, hydroxypropyl, hydroxyisopropyl, hydroxybutyl, hydroxyisobutyl, hydroxypentyl and the like); amino; monoalkylamino (monoalkylamino wherein the alkyl moiety is linear or branched chain alkyl having 1 to 6 carbon atoms, such as methylamino, ethylamino, propylamino, butylamino and the like); dialkylamino (dialkylamino wherein the alkyl moiety is linear or branched chain alkyl having 1 to 6 carbon atoms, such as dimethylamino, diethylamino, dipropylamino, diisopropylamino, dibutylamino and the like); optionally substituted saturated 6- or 7-membered heteromonocyclic group having 1 or 2 nitrogen atoms and optionally having oxygen atom or sulfur atom wherein the substituent is exemplified by linear or branched chain lower alkyl having 1 to 4 carbon atoms, such as pyrrolidine, morpholine, thiomorpholine, piperidine, piperazine, homopiperazine, homopiperidine, methylpiperidine, dimethylpiperidine and the like); aminoalkyl (aminoalkyl wherein the alkyl moiety is linear or branched chain alkyl having 1 to 6 carbon atoms, such as aminomethyl, aminoethyl, aminopropyl, aminobutyl and the like); monoalkylaminoalkyl (monoalkylaminoalkyl wherein the alkyl moiety on nitrogen is linear or branched chain alkyl having 1 to 6 carbon atoms and a methylene chain length of 1 to 6, such as methylaminomethyl, methylaminoethyl, methylaminopropyl, methylaminoethyl and the like); dialkylaminoalkyl (dialkylaminoalkyl wherein the alkyl moiety on nitrogen is linear or branched chain alkyl having 1 to 6 carbon atoms and a methylene chain length of 1 to 6, such as dimethylaminomethyl, dimethylaminoethyl, diethylaminomethyl, dipropylaminomethyl, diisopropylaminomethyl, dimethylaminopropyl and the like); acyloxyalkyl (acyloxyalkyl wherein alkyl is substituted by linear or branched chain aliphatic acyloxy having 2 to 6 carbon atoms, such as acetyloxy, propionyloxy and the like, or benzoyloxy, wherein the alkyl moiety is linear or branched chain alkyl having 1 to 6 carbon atoms), such as acetyloxymethyl, acetyloxyethyl, propionyloxymethyl, propionyloxyethyl, benzoyloxymethyl, benzoyloxyethyl; and the like.

The "optionally substituted saturated 6- or 7-membered heteromonocyclic group having 1 or 2 nitrogen atoms and optionally having oxygen atom or sulfur atom" may be substituted by 1 to 4 substituents, wherein the substituents may be the same or different.

Preferable substituent includes lower alkyl, hydroxyalkyl, optionally substituted saturated 5-, 6-or 7-membered heteromonocyclic group having 1 or 2 nitrogen atoms and optionally having oxygen atom or sulfur atom, dialkylaminoalkyl, acyloxyalkyl and the like.

The "saturated 6- or 7-membered heteromonocyclic group having 1 or 2 nitrogen atoms and optionally having oxygen atom or sulfur atom" of the "optionally substituted saturated 6- or 7-membered heteromonocyclic group having 1 or 2 nitrogen atoms and optionally having oxygen atom or sulfur atom" is exemplified by morpholine, piperidine, piperazine, homopiperazine, homopiperidine, thiomorpholine and the like, with preference given to morpholine and , piperidine.

The alkyl of the "substituted alkyl" as the substituent of phenyl at $R^7$ is linear or branched chain alkyl having 1 to 6 carbon atoms, which is exemplified by methyl, ethyl, propyl, isopropyl, butyl, isobutyl, tert-butyl, pentyl, isopentyl, hexyl, isohexyl and the like, preferably alkyl having 1 to 3 carbon atoms.

The substituent of the "substituted alkyl" is exemplified by halogen atom (e.g., fluorine, chlorine, bromine, iodine); hydroxy; acyloxy (linear or branched chain aliphatic acyloxy having 2 to 6 carbon atoms, such as acetyloxy, propionyloxy and the like, and benzoyloxy); lower alkoxy (linear or branched chain alkoxy having 1 to 6 carbon atoms, such as methoxy, ethoxy, propyloxy, isopropyloxy, butoxy and the like); haloalkoxy (haloalkoxy wherein linear or branched chain lower alkoxy having 1 to 6 carbon atoms is substituted by halogen atom (e.g., fluorine, chlorine, bromine, iodine), such as chloromethoxy, bromomethoxy, fluoromethoxy, trifluoromethoxy, dichloroethoxy, dibromoethoxy, pentafluoroethoxy, chloropropyloxy, dichlorobutoxy and the like); alkylthio (alkylthio wherein the alkyl moiety is linear or branched chain alkyl having 1 to 6 carbon atoms, such as methylthio, ethylthio, propylthio, isopropylthio, butylthio, isobutylthio and the like); amino; monoalkylamino (monoalkylamino wherein the alkyl moiety is linear or branched chain alkyl having 1 to 6 carbon atoms, such as methylamino, ethylamino, propylamino, butylamino and the like); dialkylamino (dialkylamino wherein the alkyl moiety is linear or branched chain alkyl having 1 to 6 carbon atoms, such as dimethylamino, diethylamino, dipropylamino, diisopropylamino, dibutylamino and the like); optionally substituted saturated 6- or 7-membered heteromonocyclic group having 1 or 2 nitrogen atoms and optionally having oxygen atom or sulfur atom wherein the substituent thereof is as defined above, which group may be morpholino, 4-methylpiperidino, 4-dimethylaminopiperidin-1-yl and the like; acylamino (linear or branched chain aliphatic acylamino having 2 to 6 carbon atoms, such as acetylamino, propionylamino and the like, and benzoylamino); carboxyl; alkoxycarbonyl (alkoxycarbonyl wherein the alkoxy moiety is linear or branched chain alkyl having 1 to 6 carbon atoms, such as methoxycarbonyl, ethoxycarbonyl, propyloxycarbonyl, butoxycarbonyl and the like); phthalimidoalkyl (e.g., phthalimidoethyl and phthalimidopropyl) and the like, with preference given to halogen atom, hydroxy, lower alkoxy, acyloxy, amino, dialkylamino, optionally substituted saturated 6- or 7-membered heteromonocyclic group having 1 or 2 nitrogen atoms and optionally having oxygen atom or sulfur atom, phthalimidoethyl and the like, more preference given to halogen atom, hydroxy, lower alkoxy and the like.

The "substituted alkyl" may be substituted by 1 to 3 substituents, wherein the substituents may be the same or different.

Preferable "substituted alkyl" is trifluoromethyl, morpholinomethyl, aminomethyl, dimethylaminomethyl, dimethylaminoethyl, hydroxymethyl, hydroxyethyl and the like.

The substituent of the alkyl chain moiety of the formulas (II) and (III) as the substituent of phenyl at $R^7$ is exemplified by the substituent of the "substituted alkyl" and lower alkyl (linear or branched chain alkyl having 1 to 6 carbon atoms such as methyl, ethyl, propyl, isopropyl, butyl, isobutyl, tert-butyl, pentyl, isopentyl, hexyl and the like). This alkyl chain moiety may be substituted by 1 or 2 substituents, wherein the substituents may be the same or different.

In the formulas (II) and (III), the alkoxy moiety has 1 to 4 carbon atoms. The groups of the formulas (II) and (III) are 2-methoxyethoxy, 2-ethoxyethoxy, 2-isopropoxyethoxy, 4-methoxybutoxy, 2-(2,2,2-trifluoroethoxy)ethoxy, 3-methoxypropoxy, 2-(2-morpholinoethoxy)ethoxy, 2-(2-hydroxyethoxy)ethoxy, 2-(2-methoxyethoxy)ethoxy, 2-(2-ethoxyethoxy)ethoxy, 3-(2-methoxyethoxy)propoxy, 3-(2-hydroxyethoxy)propoxy, 3-(3-methoxypropoxy)propoxy, 2-(2-dimethylaminoethoxy)ethoxy, 2-(3-dimethylaminopropoxy)ethoxy, 2-(2-(2-methoxyethoxy)ethoxy)ethoxy, 2-(2-(2-hydroxyethoxy)ethoxy)ethoxy, 2-(2-(2-ethoxyethoxy)ethoxy)-ethoxy, 3-(2-(2-methoxyethoxy)ethoxy)propoxy, 3-(2-(2-hydroxyethoxy)ethoxy)propoxy, 2-(2-(2-dimethylaminoethoxy)-ethoxy)ethoxy and the like.

The groups of the formulas (II) and (III) are preferably 2-methoxyethoxy, 2-ethoxyethoxy, 2-isopropoxyethoxy, 4-inethoxybutoxy, 3-methoxypropoxy, 2-(2-methoxyethoxy)ethoxy or 2-(2-(2-methoxyethoxy)ethoxy) ethoxy, and more preferably 2-methoxyethoxy.

The spiro ring of the "optionally substituted spiro ring comprising the same or different two saturated 6- or 7-membered heteromonocyclic groups having 1 to 3 nitrogen atoms and optionally having oxygen atom or sulfur atom" as the substituent of phenyl at $R^7$ is exemplified by 4,8-(or 4,9-)diazaspiro[5,5]undecane, 1,4,9-(or 1,4,8-)triazaspiro[5,5]undecane, 1-(2-, 3- or 5-)oxa-4,8-diazaspiro[5,5]undecane, 1-(2-, 3- or 5-)oxa-4,9-diazaspiro[5,5]undecane, 1-(2-, 3- or 4-)thia-5,9-diazaspiro[5,5]undecane, 1-(2-, 3- or 5-)thia-4,9-diazaspiro[5,5]undecane, and the like. The number of nitrogen atom that the heteromonocyclic group constituting the spiro ring contains is preferably 1 or 2.

The spiro ring may be substituted by 1 or 2 substituents, wherein the substituents may be the same or different.

This substituent is lower alkyl (linear or branched chain alkyl having 1 to 6 carbon atoms such as methyl, ethyl, propyl, isopropyl, butyl, isobutyl, tert-butyl, pentyl, isopentyl, hexyl and the like), oxo and the like, preferably methyl and oxo.

Preferable examples of the "optionally substituted spiro ring comprising the same or different two saturated 6- or 7-membered heteromonocyclic groups having 1 to 3 nitrogen atoms and optionally having oxygen atom or sulfur atom" include 4-methyl-1-oxa-4,9-diazaspiro[5,5]undecane, 1-oxa-4,9-diazaspiro[5,5]undecane, 1-oxa-3-oxo-4,9-diazaspiro[5,5]undecane, 2,3-dioxo-1,4,9-triazaspiro[5,5]undecane, 1,4-dimethyl-1,4,9-triazaspiro[5,5]-undecane, 1,4,9-triazaspiro[5,5]undecane, 4-methyl-1-oxa-4,8-diazaspiro[5,5]undecane, 4-oxo-1-thia-5,9-diazaspiro[5,5]undecane, 4-methyl-1-thia-4,9-diazaspiro[5,5]undecane, and the like, preferably 4-methyl-1-oxa-4,9-diazaspiro[5,5]undecane, 1-oxa-4,9-diazaspiro[5,5]undecane and the like.

The pharmaceutically acceptable salt of the compound of the formula (XII) of the present invention includes salts with inorganic acid such as hydrochloric acid, hydrobromic acid, hydroiodic acid, sulfuric acid, nitric acid, phosphoric acid and the like, and salts with organic acid such as acetic acid, propionic acid, succinic acid, glycolic acid, lactic acid, malic acid, tartaric acid, fumaric acid, maleic acid, citric acid, benzoic acid, methanesulfonic acid, benzenesulfonic acid, p-toluenesulfonic acid and the like. In addition, salts with metal hydroxide such as lithium hydroxide, sodium hydroxide, potassium hydroxide, calcium hydroxide, magnesium hydroxide and the like, and salts with organic base such as triethylamine, pyridine and the like can be exemplified.

When the compound of the formula (XII) of the present invention and a pharmaceutically acceptable salt thereof contain an asymmetric carbon, a racemic mixture or an optically active compound can be obtained. The racemate can be resolved into each optically active compound by a method known per se. When the compound of the formula (XII) of the present invention and a pharmaceutically acceptable salt thereof contain additional asymmetric carbon, the compounds can be obtained as individual diastereomers or a mixture thereof, which can be each separated by a method known per se. The compound of the formula (XII) of the present invention and a pharmaceutically acceptable salt thereof can show polymorphism and can exist as at least one tautomer or also as a solvate (e.g., ketone solvate, hydrate etc.). The present invention encompasses all of the aforementioned stereoisomers, optical isomers, polymorphs, tautomers, solvates, optional mixtures thereof and the like.

The novel imidazole compound of the formula (XII) of the present invention can be obtained by, for example, the following method. However, the production methods of the compound of the present invention present are not limited to these.

Production Method 6

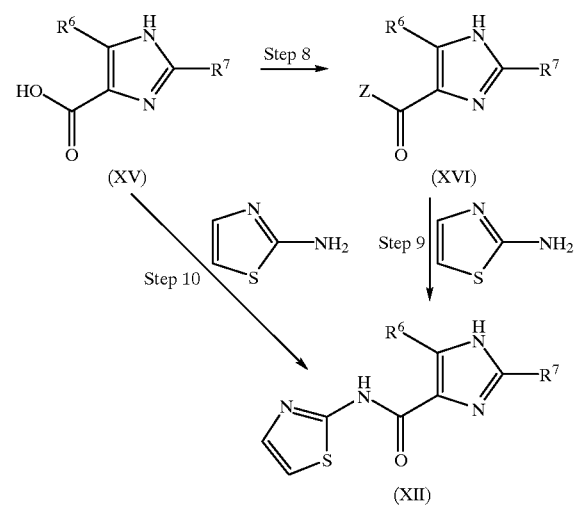

wherein $R^6$ and $R^7$ are as defined above, and Z is halogen atom such as chlorine, bromine and the like; azide; N-hydroxybenzotriazolyl; p-nitrophenyloxy; p-chlorophenyloxy; alkoxy such as methoxy, ethoxy and the like; acyloxy such as acetyloxy, pivaloyloxy and the like; isobutyloxycarbonyloxy; methoxycarbonyloxy; ethoxycarbonyloxy and the like.

A compound of the formula (XV) is reacted with thionyl chloride, isobutyl chloroformate, methyl chloroformate, ethyl chloroformate and the like in an inert solvent according to a conventional method to give a reactive intermediate (XVI), which is further reacted with 2-aminothiazole in an inert organic solvent in the presence or absence of a base, preferably in the presence of a base, to give compound (XII) (Step 8 and Step 9).

Alternatively, a compound of the formula (XV) is reacted, without converting to a reactive derivative thereof, with 2-aminothiazole using a suitable condensing agent and the like in an inert solvent in the presence or absence of a base, preferably in the presence of a base, to give compound (XII) (Step 10).

The salt to be used for the method of the present invention include pyridine, picoline, lutidine, collidine, N-methylpiperidine, N-methylpyrrolidine, N-methylmorpholine, N,N-dimethylaminopyridine, triethylamine, diisopropylethylamine, potassium carbonate, sodium carbonate and the like, preferably pyridine, N,N- dimethylamino-pyridine, triethylamine, diisopropylethylamine and potassium carbonate.

The inert organic solvent to be used for the method of the present invention can be any as long as the reaction is not inhibited. Preferably, ether, benzene, toluene, ethyl acetate, tetrahydrofuran, dioxane, chloroform, methylene chloride, dimethyl sulfoxide, N,N-dimethylformamide, 1,3-dimethyl-2-imidazolidinone, pyridine and the like, particularly preferably toluene, tetrahydrofuran, dioxane, chloroform, methylene chloride, N,N-dimethylformamide, 1,3-dimethyl-2-imidazolidinone, pyridine and the like can be used.

The reaction proceeds at from −30° C. to the refluxing temperature of the solvent to be used, preferably from room temperature to the refluxing temperature of the solvent to be used, particularly preferably at the refluxing temperature of the solvent to be used.

The reaction is carried out for 1 to 30 hours, preferably 1 to 3 hours.

Preferable examples of the condensing agent include N,N'-dicyclohexylcarbodiimide, 2-chloro-1,3-dimethylimidazolinium chloride, 1,1-carbonyldiimidazole, 1-hydroxybenzotriazole, 1-hydroxy-7-azabenzotriazole, 1-ethyl-3-(3-(dimethylamino)propyl)-carbodiimide hydrochloride, benzotriazol-1-yloxy-tris-(dimethylamino)phosphonium hexafluorophosphate, 4,4'-dichloro-α-methylbenzhydrol and the like.

Production Method 7

In the formula (XII), a compound having lower alkoxy or aralkyloxy as a substituent can be produced by reacting a compound of the formula (XII) whereinthecorresponding-substituent ishydroxywith the corresponding lower alkyl alcohol or phenyl lower alkyl alcohol in the presence of triphenylphosphine and diethyl azodicarboxylate.

Production Method 8

In the formula (XII), a compound having hydroxy, hydroxyalkyl, amino or aminoalkyl as a substituent can be also produced by hydrolysis of a compound of the formula (XII) wherein the corresponding substituent is acyloxy, acyloxyalkyl, acylamino or acylaminoalkyl under basic or acidic conditions.

In the formula (XII), a compound having hydroxy, hydroxyalkyl, amino or aminoalkyl as a substituent can be also produced by hydrogenation of a compound of the formula (XII) wherein the corresponding substituent is benzyloxy, benzyloxyalkyl, benzylamino or benzylaminoalkyl in the presence of a catalyst such as palladium and the like, or by reacting the compound with hydrobromic acid in a solvent such as acetic acid and the like, or by treating the compound in thioanisole and trifluoroacetic acid.

Production Method 9

In the formula (XII), a compound having amino and aminoalkyl as substituents can be produced by reducing a compound of the formula (XII) wherein the corresponding substituents are nitro and nitroalkyl using iron powder and an acid such as hydrochloric acid, acetic acid, sulfuric acid and the like, or by hydrogenation in the presence of a catalyst such as palladium and the like, or by refluxing under heating in a solution of tin(II) chloride 6 hydrate in 6 M hydrochloric acid. The compound can be also produced by reducing a compound of the formula (XII) wherein the corresponding substituent is cyano or amide with a reducing agent such as lithium aluminum hydride and the like.

Production Method 10

In the formula (XII), a compound having dialkylamino or monoalkylamino as a substituent can be also produced by alkylating a compound of the formula (XII) wherein the corresponding substituent is amino. Themethodof alkylation may comprise the use of alkyl halide, alkyl p-toluenesulfonate and the like and, where necessary, a base such triethylamine, pyridine, potassium carbonate, sodium carbonate, sodium hydrogencarbonate and the like, a reaction of formalin, alkyl aldehyde and the like and a metal hydrogen complex compound such as sodium borohydride, sodium cyanoborohydride and the like, or reductive alkylation comprising catalytic reduction and the like.

The aforementioned compound of the formula (XV) used as the starting material in the present invention can be produced by, for example, hydrolysis under alkaline or acidic conditions of the compound of the formula (XIX) obtained by the following Methods 5 to 7.

Method 5

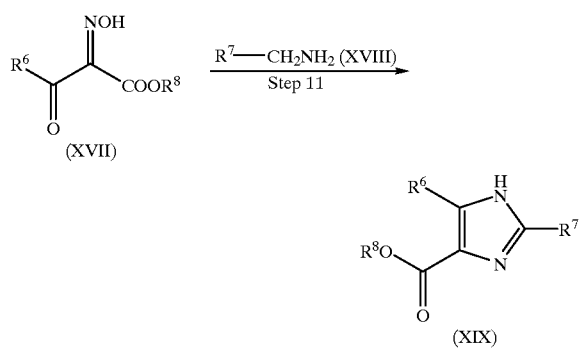

wherein $R^6$ and $R^7$ are as defined above, and $R^8$ is lower alkyl.

By reacting a compound of the formula (XVII) and a compound of the formula (XVIII), a compound of the formula (XIX) can be produced (Step 11).

As the reaction solvent, for example, toluene, benzene, xylene, pyridine, picoline, dioxane, hexane, petroleum ether, acetonitrile, acetic acid, tetrahydrofuran and the like can be used.

The reaction proceeds at from −30° C. to the refluxing temperature of the solvent to be used, preferably from room temperature to the refluxing temperature of the solvent to be used, particularly preferably at the refluxing temperature of the solvent to be used.

The reaction is carried out for 1 to 30 hours, preferably 10 to 15 hours.

Method 6

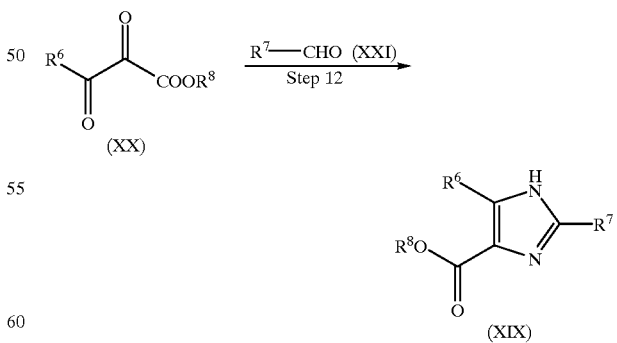

wherein $R^6$ and $R^7$ are as defined above, and $R^8$ is lower alkyl.

A compound of the formula (XX) reported by Harry H. Wasserman, Tetrahedron Letter, Vol. 33, No. 40, pp. 6003–6006, 1992 and the like is reacted with a compound of the formula (XXI) in the presence of an ammonium salt such as ammonium lower alkanecarboxylate (e.g., ammonium acetate, ammonium formate and the like) and an ammonium salt of inorganic acid (e.g., ammonium carbonate and the like), in an acidic solution of lower alkanecarboxylic acid such as formic acid, acetic acid, propionic acid and the like to give a compound of the formula (XIX) (Step 12).

As the reaction solvent, for example, toluene, benzene, xylene, pyridine, picoline, dioxane, hexane, petroleum ether, acetic acid and the like can be used. The reaction may also proceed without solvent.

The reaction preferably proceeds at from 0° C. to the refluxing temperature of the solvent to be used.

The reaction is carried out for 1 to 30 hours, preferably 12 to 15 hours.

Method 7

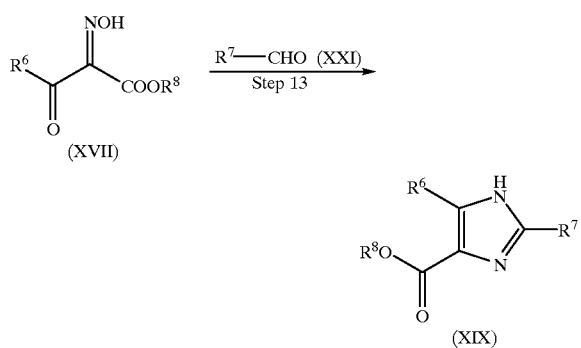

wherein $R^6$ and $R^7$ are as defined above, and $R^8$ is lower alkyl.

A compound of the formula (XVII) is reacted with a compound of the formula (XXI) in the presence of an ammonium salt such as ammonium lower alkanecarboxylate (e.g., ammonium acetate, ammonium formate and the like) and an ammonium salt of inorganic acid (e.g., ammonium carbonate and the like) to give a compound of the formula (XIX) (Step 13).

As the reaction solvent, for example, acetic acid, toluene, pyridine, ethyl acetate and the like can be used.

The reaction preferably proceeds at from 0° C. to the refluxing temperature of the solvent to be used, particularly preferably at the refluxing temperature of the solvent to be used.

The reaction is carried out for 1 to 30 hours, preferably 12 to 15 hours.

The pharmaceutically acceptable salt of the compound of the formula (XII) of the present invention can be converted to the aforementioned acid addition salt by treating with an inorganic acid (hydrochloric acid, hydrobromic acid, hydroiodic acid, sulfuric acid, nitric acid, phosphoric acid and the like), or an organic acid (e.g., acetic acid, propionic acid, succinic acid, glycolic acid, lactic acid, malic acid, tartaric acid, fumaric acid, maleic acid, citric acid, benzoic acid, methanesulfonic acid, benzenesulfonic acid, p-toluenesulfonic acid and the like) according to a conventional method. For crystallization, the compound can be converted to oxalate. In addition, by the treatment with lithium hydroxide, sodium hydroxide, potassium hydroxide, calcium hydroxide, magnesium hydroxide and the like, the corresponding metal salt can be obtained, and by the treatment with triethylamine, pyridine and the like, the compound can be converted to a salt with organic base. When the obtained crystal of the inventive compound is anhydrous, the inventive compound is treated with water, water-containing solvent or other solvent to give hydrate or solvate.

The inventive compound thus obtained can be purified and isolated by a conventional method such as recrystallization, column chromatography and the like. When the obtained product is a racemic modification, a desired optically active compound can be resolved by fractional recrystallization with an optically active acid or by passing through a column packed with an optically active carrier. Each diastereomer can be separated by a means such as fractional crystallization, chromatography and the like. The compound of the present invention can be also obtained by using an optically active starting compound and the like. A stereoisomer can be isolated by recrystallization, column chromatography and the like.

When the novel imidazole derivative and a pharmaceutically acceptable salt thereof of the present invention are used as pharmaceutical agents, a pharmaceutical composition or preparation (tablet, pill, capsule, granule, powder, syrup, emulsion, elixir, suspension, solution, injection, instillation, ointment, paste, liniment, lotion, plaster, poultice, eye drop, eye ointment, suppository, fomentation, inhalent, spray, aerosol, embrocation, nasal drop, cream, tape, patch etc.) obtained by admixing the inventive compound with a pharmaceutically acceptable carrier (e.g., excipient, binder, disintegrant, corrective, corrigent, emulsion, diluent, solubilizer etc.) can be administered orally or parenterally. The pharmaceutical composition can be formulated into a preparation according to a conventional method.

For example, ingredients for pharmaceutical preparations such as excipient (e.g., lactose, D-mannitol, starch, crystalline cellulose and the like), binder (e.g., hydroxypropylcellulose, hydroxylpropylmethylcellulose, polyvinylpyrrolidone and the like), disintegrant (e.g., carboxymethylcellulose, potassium carboxymethylcellulose and the like), lubricant (e.g., magnesium stearate, talc and the like), coating agent (e.g., hydroxylpropylmethylcellulose, sucrose and the like), base (polyethylene glycol, hard fat and the like) and the like are used. For injection, ingredients for pharmaceutical preparations such as solubilizer or dissolution auxiliary (distilled water for injection, physiological saline, propylene glycol and the like), pH adjusting agent (inorganic acid, organic acid or inorganic base), stabilizer and the like, that are aqueous or capable of forming an injection when in use, are used.

The compounds of the formula (I) and the formula (XII) of the present invention and pharmaceutically acceptable salts thereof inhibit production of IL-4 or IL-5 by Th2 cells and are effective for the prophylaxis and/or treatment of allergic diseases such as atopic dermatitis, bronchial asthma, allergic rhinitis and the like.

While the dose of the compound of the present invention to a patient to be treated varies depending on the kind and condition of the disease, the compound to be administered and administration route, age, sex and body weight of the patient, and the like, it is generally about 1.0–1000 mg by oral administration, and about 1.0–500 mg by parenteral administration to an adult per day.

The imidazole derivative and a pharmaceutically acceptable salt thereof according to the present invention provide, when used concurrently with a preparation (preferably external preparation) containing conventional steroid (hydrocortisone butyrate, dexamethasone acetate, methylprednisolone acetate and the like), a stronger anti-allergic effect, and can be effectively used for the prophylaxis and/or treatment of allergy. By utilizing the effect provided by the concurrent use, the amount of the steroidal agent can be reduced.

EXAMPLES

The present invention is explained in more detail in the following by referring to Starting Material Synthetic Examples, Examples and Experimental Examples. These Examples do not limit the present invention in any way.

Starting Material Synthetic Example 1

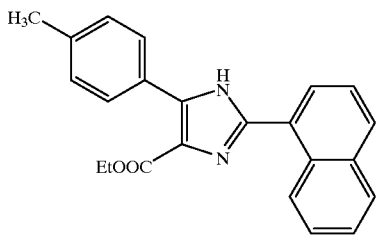

Ethyl 2-hydroxyimino-3-(4-methylphenyl)-3-oxopropionate (13.7 g) and 1-naphthalenemethylamine (11.0 g) were dissolved in xylene (137 ml), andrefluxed underheating for 9 hr whiledehydrating with Dean-stark trap. Water was added to the reaction mixture, and the mixture was extracted with ethyl acetate. The organic layer was washed with water and dried. The solvent was concentrated under reduced pressure and isopropyl alcohol was added to the obtained residue to allow crystallization. The crystals were collected by filtration to give ethyl 5-(4-methylphenyl)-2-(1-naphthyl)-imidazole-4-carboxylate (2.5 g), melting point 190–192° C.

Starting Material Synthetic Example 2

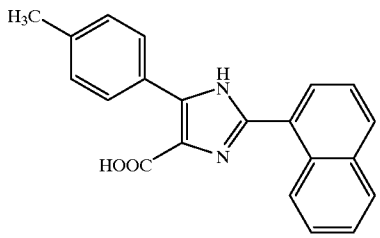

Ethyl 5-(4-methylphenyl)-2-(1-naphthyl)imidazole-4-carboxylate (4.5 g) was dissolved in ethyl alcohol (90 ml) and 1 M sodium hydroxide solution (38 ml) was added. The reaction mixture was refluxed under heating for 12 hr, and the mixture was concentrated under reduced pressure. To the obtained residue were added water and ethyl acetate, and the mixture was partitioned. The aqueous layer was filtered, and aqueous citric acid was added to the filtrate. The precipitated crystals were collected by filtration to give 5-(4-methylphenyl)-2-(1-naphthyl)imidazole-4-carboxylic acid (3.3 g), melting point 165° C. (decomposition).

Starting Material Synthetic Example 3

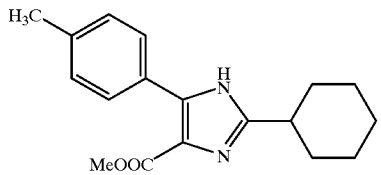

To a suspension of ammonium acetate (10.0 g) in acetic acid (10 ml) was added methyl 3-(4-methylphenyl)-2,3-dioxopropionate (2.0 g) at room temperature, and the mixture was stirred for 10 min. Cyclohexanecarbaldehyde (1.6 g) was added, and the mixture was heated to 40–50° C. on a hot water bath and stirred for 2 hr. To the reaction mixture was added water and the solvent was concentrated under reduced pressure. The obtained residue was purified by silica gel column chromatography to give methyl 2-cyclohexyl-5-(4-methylphenyl)imidazole-4-carboxylate (920 mg), melting point 210–213° C.

$^1$H-NMR400 MHz (CDCl$_3$, ppm) δ: 1.26–2.12(1H,m), 2.81(10H,m), 2.38(3H,s), 3.83(3H,s), 7.21(2H,d), 7.79(2H, d).

Starting Material Synthetic Example 4

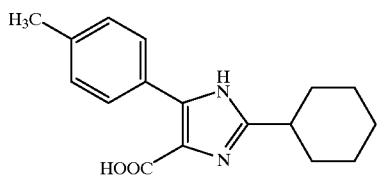

Methyl 2-cyclohexyl-5-(4-methylphenyl)imidazole-4-carboxylate (900 mg) was dissolved in ethyl alcohol (20 ml). Lithium hydroxide hydrate (1.1 g) and water (10 ml) were added, and the mixture was refluxed under heating for 2.5 hr and concentrated under reduced pressure. To the obtained residue were added water and ethyl acetate, and the mixture was partitioned. The aqueous layer was filtered, and aqueous citric acid was added to the filtrate. The precipitated crystals were collected by filtration to give 2-cyclohexyl-5-(4-methylphenyl)imidazole-4-carboxylic acid (390 mg), melting point 205–206° C.

$^1$H-NMR 400 MHz (CDCl$_3$, DMSO-D$_6$, ppm) δ: 1.25–2.05(10H,m), 2.36(3H,s), 2.78(1H,m), 7.20(2H,d), 7.84(2H,m).

Starting Material Synthetic Example 5

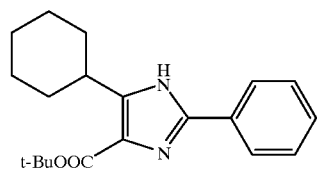

tert-Butyl 3-cyclohexyl-2-hydroxyimino-3-oxopropionate (2.6 g) and benzylamine (2.1 g) were dissolved in benzene (50 ml), and the mixture was refluxed under heating for 16 hr. The solvent was concentrated under reduced pressure. The obtained residue was purified by silica gel chromatography (chloroform:ethyl acetate=8:1) to give tert-butyl 5-cyclohexyl-2-phenylimidazole-4-carboxylate (0.90 g), melting point 222–223° C.

Starting Material Synthetic Example 6

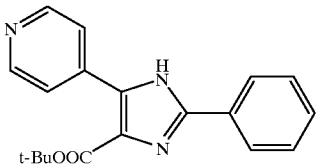

tert-Butyl 2-hydroxyimino-3-oxo-3-(4-pyridyl) propionate (2.8 g) and benzylamine (2.4 g) were dissolved in acetonitrile (80 ml), and the mixture was reacted and treated in the same manner as in Starting Material Synthetic Example 5 to give tert-butyl 2-phenyl-5-(4-pyridyl) imidazole-4-carboxylate (1.4 g), melting point 205–206° C.

Starting Material Synthetic Example 7

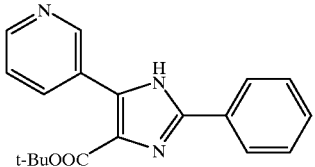

tert-Butyl 2-hydroxyimino-3-oxo-3-(3-pyridyl) propionate (4.1 g), benzylamine (3.5 g) and acetonitrile (80 ml) were reacted and treated in the same manner as in Starting Material Synthetic Example 5 to give tert-butyl 2-phenyl-5-(3-pyridyl)imidazole-4-carboxylate (2.2 g), melting point 196–197° C.

Starting Material Synthetic Example 8

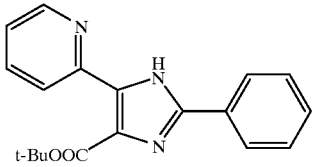

tert-Butyl 2-hydroxyimino-3-oxo-3-(2-pyridyl) propionate (6.0 g) and benzylamine (5.7 g) were dissolved in acetonitrile (100 ml), and the mixture was reacted and treated in the same manner as in Starting Material Synthetic Example 5 to give tert-butyl 2-phenyl-5-(2-pyridyl) imidazole-4-carboxylate (1.8 g), melting point 211–213° C.

Starting Material Synthetic Example 9

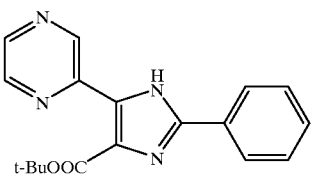

tert-Butyl 2-hydroxyimino-3-oxo-3-(2-pyrazinyl) propionate (4.1 g) and benzylamine (4.0 g) were dissolved in acetonitrile (100 ml), and the mixture was reacted and treated in the same manner as in Starting Material Synthetic Example 5 to give tert-butyl 2-phenyl-5-(2-pyrazinyl) imidazole-4-carboxylate (1.0 g), melting point 196–197° C.

Starting Material Synthetic Example 10

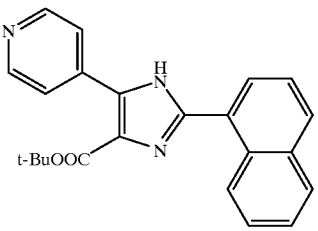

tert-Butyl 2-hydroxyimino-3-oxo-3-(4-pyridyl) propionate (5.0 g) and 1-naphthylmethylamine (3.5 g) were dissolved in toluene (60 ml). The mixture was refluxed under heating for 3 hr while dehydrating with Dean-stark trap. After cooling, the precipitated crystals were collected by filtration and dried to give tert-butyl 2-(1-naphthyl)-5-(4-pyridyl)imidazole-4-carboxylate (1.3 g), melting point 184–190° C.

Starting Material Synthetic Example 11

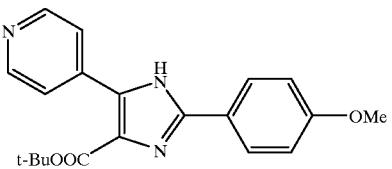

tert-Butyl 2-hydroxyimino-3-oxo-3-(4-pyridyl) propionate (3.0 g) and 4-methoxybenzylamine (1.7 g) were dissolved in toluene (80 ml), and the mixture was reacted and treated in the same manner as in Starting Material Synthetic Example 10 to give tert-butyl 2-(4-methoxyphenyl)-5-(4-pyridyl)imidazole-4-carboxylate (1.4 g), melting point 211–212° C.

Starting Material Synthetic Example 12

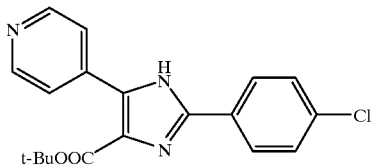

tert-Butyl 2-hydroxyimino-3-oxo-3-(4-pyridyl) propionate (3.9 g) and 4-chlorobenzylamine (3.0 g) were dissolved in toluene (80 ml), and the mixture was reacted and treated in the same manner as in Starting Material Synthetic Example 10 to give tert-butyl 2-(4-chlorophenyl)-5-(4-pyridyl)imidazole-4-carboxylate (1.9 g), melting point 206–207° C.

Starting Material Synthetic Example 13

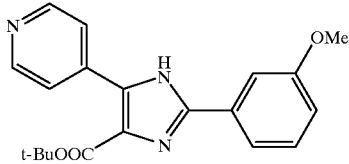

tert-Butyl 2-hydroxyimino-3-oxo-3-(4-pyridyl) propionate (3.2 g) and 3-methoxybenzylamine (2.1 g) were dissolved in toluene (120 ml), and the mixture was reacted and treated in the same manner as in Starting Material Synthetic Example 10 to give tert-butyl 2-(3-methoxyphenyl)-5-(4-pyridyl)imidazole-4-carboxylate (1.4 g), melting point 197–199° C.

Starting Material Synthetic Example 14

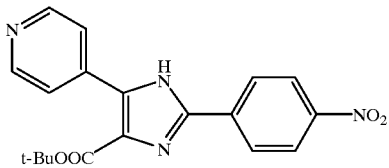

tert-Butyl 2-hydroxyimino-3-oxo-3-(4-pyridyl) propionate (3.0 g) and 4-nitrobenzylamine (2.2 g) were dissolved in toluene (40 ml), and the mixture was reacted and treated in the same manner as in Starting Material Synthetic Example 10 to give tert-butyl 2-(4-nitrophenyl)-5-(4-pyridyl)imidazole-4-carboxylate (0.7 g), melting point not less than 280° C.

$^1$H-NMR 400 MHz (CDCl$_3$, ppm) δ: 1.58(9H,s), 7.92(2H, d), 8.15(2H,d), 8.36(2H,d), 8.70(2H,d).

Starting Material Synthetic Example 15

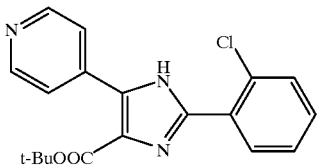

tert-Butyl 2-hydroxyimino-3-oxo-3-(4-pyridyl) propionate (3.0 g) and 2-chlorophenylbenzylamine (2.9 g) were dissolved in toluene (80 ml), and the mixture was reacted and treated in the same manner as in Starting Material Synthetic Example 10 to give tert-butyl 2-(2-chlorophenyl)-5-(4-pyridyl)imidazole-4-carboxylate (1.3 g), melting point 223–224° C. (decomposition).

Starting Material Synthetic Example 16

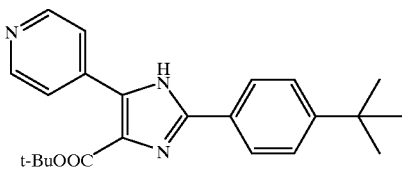

tert-Butyl 2-hydroxyimino-3-oxo-3-(4-pyridyl) propionate (6.0 g) and 4-tert-butylphenylbenzylamine (4.0 g) were dissolved in toluene (60 ml). The mixture was refluxed under heating for 3 hr while dehydrating with Dean-stark trap. After cooling, the precipitated crystals were collected by filtration and dissolved in ethyl acetate. 1 M hydrochloric acid-ether solution (3 ml) was added and the precipitated crystals were collected by filtration to give tert-butyl 2-(4-tert-butylphenyl)-5-(4-pyridyl)imidazole-4-carboxylate hydrochloride (3.2 g).

$^1$H-NMR 400 MHz (CD$_3$OD, ppm) δ: 1.37(9H,s), 1.63 (9H,s), 7.58(2H,d), 8.02(2H,d), 8.76(2H,d), 8.85(2H,d).

Starting Material Synthetic Example 17

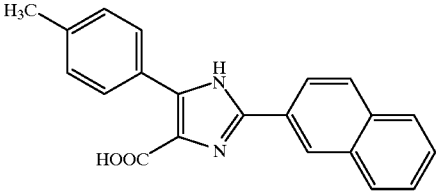

Ethyl 2-hydroxyimino-3-(4-methylphenyl)-3-oxopropionate(12.8 g) and 2-aminomethylnaphthalene (10.3 g) were reacted and treated in the same manner as in Starting Material Synthetic Example 1 to give ethyl 5-(4-methylphenyl)-2-(2-naphthyl)imidazole-4-carboxylate (4.8 9g). 0.5 g therefrom was dissolved in ethyl alcohol (10 ml), and the mixture was reacted and treated in the same manner as in Starting Material Synthetic Example 2 to give 5-(4-methylphenyl)-2-(2-naphthyl)imidazole-4-carboxylic acid (0.26 g), melting point 227° C. (decomposition).

Starting Material Synthetic Example 18

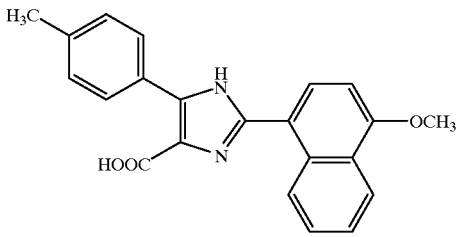

Ethyl 2-hydroxyimino-3-(4-methylphenyl)-3-oxopropionate (16.0 g) and 1-(aminomethyl)-4-methoxynaphthalene (15.3 g) were reacted and treated in the same manner as in Starting Material Synthetic Example 1 to give ethyl 2-(4-methoxy-1-naphthyl)-5-(4-methylphenyl)-imidazole-4-carboxylate (22.2 g), which was dissolved in ethyl alcohol (450 ml), and the mixture was reacted and treated in the same manner as in Starting Material Synthetic Example 2 to give 2-(4-methoxy-1-naphthyl)-5-(4-methylphenyl)imidazole-4-carboxylic acid (12.1 g), melting point 226° C. (decomposition).

Starting Material Synthetic Example 19

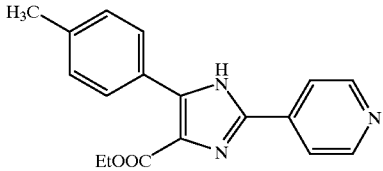

Ethyl 2-hydroxyimino-3-(4-methylphenyl)-3-oxopropionate (10.5 g) and 4-aminomethylpyridine (5.8 g) were dissolved in xylene (100 ml), and the mixture was reacted and treated in the same manner as in Starting Material Synthetic Example 1 to give ethyl 5-(4-methylphenyl)-2-(4-pyridyl)imidazole-4-carboxylate (54.2 g), melting point 182–185° C.

Starting Material Synthetic Example 20

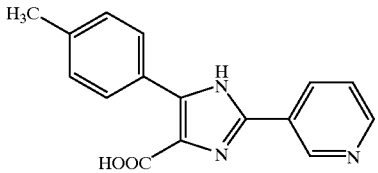

Ethyl 2-hydroxyimino-3-(4-methylphenyl)-3-oxopropionate (10.0 g) and 3-aminomethylpyridine (5.3 ml) were reacted and treated in the same manner as in Starting Material Synthetic Example 1 to give ethyl 5-(4-methylphenyl)-2-(3-pyridyl)imidazole-4-carboxylate (4.0 g). 0.5 g therefrom was dissolved in ethyl alcohol (10 ml), and the mixture was reacted and treated in the same manner as in Starting Material Synthetic Example 2 to give 5-(4-methylphenyl)-2-(3-pyridyl)-imidazole-4-carboxylic acid (0.39 g), melting point 140–142° C.

Starting Material Synthetic Example 21

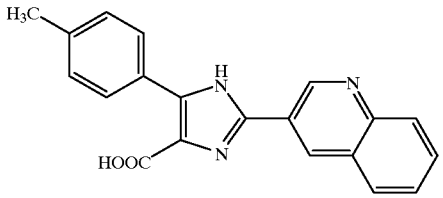

Ethyl 2-hydroxyimino-3-(4-methylphenyl)-3-oxopropionate (10.6 g) and 3-aminomethylquinoline (8.5 g) were reacted and treated in the same manner as in Starting Material Synthetic Example 1 to give ethyl 5-(4-methylphenyl)-2-(3-quinolyl)imidazole-4-carboxylate (7.0 g). 6.7 g therefrom was dissolved in ethyl alcohol (135 ml), and the mixture was reacted and treated in the same manner as in Starting Material Synthetic Example 2 to give 5-(4-methylphenyl)-2-(3-quinolyl)imidazole-4-carboxylic acid (2.5 g), melting point 224° C. (decomposition).

Starting Material Synthetic Example 22

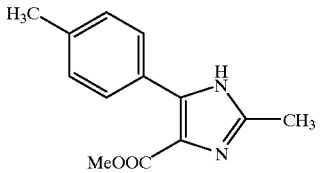

Ammonium acetate (15.0 g), acetic acid (20 ml), methyl 3-(4-methylphenyl)-2,3-dioxopropionate (3.0 g) and acetoaldehyde (1.1 g) were reacted and treated in the same manner as in Starting Material Synthetic Example 3 to give methyl 2-methyl-5-(4-methylphenyl)-imidazole-4-carboxylate (1.6 g).

$^1$H-NMR 400 MHz (CDCl$_3$, ppm) δ: 2.36(3H,s), 2.45(3H, s), 3.38(3H,s), 7.21(2H,d), 7.67(2H,d).

Starting Material Synthetic Example 23

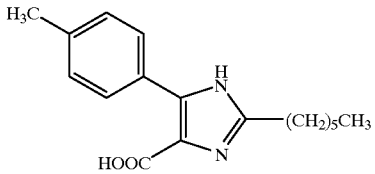

Ammonium acetate (10.0 g), acetic acid (10 ml), methyl 3-(4-methylphenyl)-2,3-dioxopropionate (2.0 g) and heptylaldehyde (1.7 g) were reacted and treated in the same manner as in Starting Material Synthetic Example 3 to give methyl 2-hexyl-5-(4-methylphenyl)-imidazole-4-carboxylate (1.2 g), which was dissolved in ethyl alcohol (20 ml). Thereto were added lithium hydroxide hydrate (420 mg) and water (10 ml), and the mixture was reacted and treated in the same manner as in Starting Material Synthetic Example 4 to give 2-hexyl-5-(4-methylphenyl)imidazole-4-carboxyic acid (700 mg), melting point 215–218° C.

Starting Material Synthetic Example 24

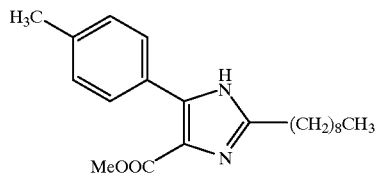

Ammonium acetate (10.0 g), acetic acid (10 ml), methyl 3-(4-methylphenyl)-2,3-dioxopropionate (2.0 g) and decylaldehyde (2.3 g) were reacted and treated in the same manner as in Starting Material Synthetic Example 3 to give methyl 5-(4-methylphenyl)-2-nonylimidazole-4-carboxylate (800 mg).

$^1$H-NMR 400 MHz (CDCl$_3$, ppm) δ: 0.88(3H,s), 1.26 (12H,m), 1.75(2H,m), 2.38(3H,s), 2.76(2H,t), 3.84(3H,s), 7.22(2H,d), 7.71(2H,d).

Starting Material Synthetic Example 25

Ammonium acetate (10.0 g), acetic acid (15 ml), methyl 3-(4-methylphenyl)-2,3-dioxopropionate (2.0 g) and pivalaldehyde (1.3 g) were reacted and treated in the same manner as in Starting Material Synthetic Example 3 to give methyl 2-tert-butyl-5-(4-methylphenyl)imidazole-4-carboxylate (630 mg).

$^1$H-NMR 400 MHz (CDCl$_3$, ppm) δ: 1.44(9H,s), 2.40(3H, s), 3.83(3H,s), 7.21(2H,d), 7.81(2H,d).

Starting Material Synthetic Example 26

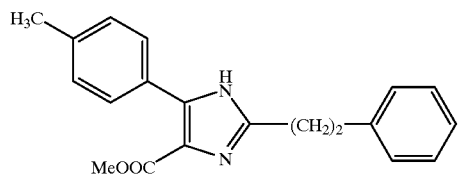

Ammonium acetate (15.0 g), acetic acid (30 ml), methyl 3-(4-methylphenyl)-2,3-dioxopropionate (3.0 g) and hydrocinnamaldehyde (2.9 ml) were reacted and treated in the same manner as in Starting Material Synthetic Example 3 to give methyl 5-(4-methylphenyl)-2-(2-phenylethyl) imidazole-4-carboxylate (1.6 g).

$^1$H-NMR 400 MHz (CDCl$_3$, ppm) δ: 2.38(3H,s), 3.09(4H, m), 3.81(3H,s), 7.19–7.32(10H,m).

Starting Material Synthetic Example 27

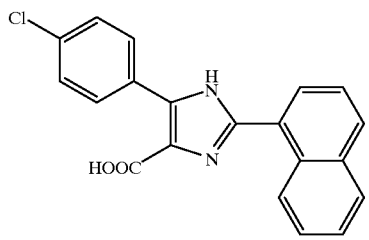

Ethyl 3-(4-chlorophenyl)-2-hydroxyimino-3-oxopropionate (10.0 g) and 1-aminomethylnaphthalene (7.0 g) were reacted and treated in the same manner as in Starting Material Synthetic Example 1 to give ethyl 5-(4-chlorophenyl)-2-(1-naphthyl)imidazole-4-carboxylate (6.6 g). 6.0 g therefrom was dissolved in ethyl alcohol (120 ml), and 1 M sodium hydroxide solution (45 ml) was added. The reaction mixture was reacted and treated in the same manner as in Starting Material Synthetic Example 2 to give 5-(4-chlorophenyl)-2-(1-naphthyl)-imidazole-4-carboxyic acid (4.1 g), melting point 210° C. (decomposition).

Starting Material Synthetic Example 28

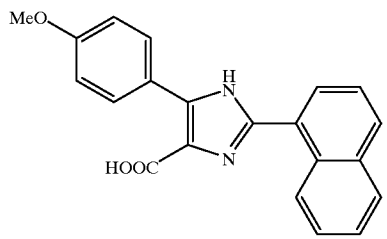

Ethyl 2-hydroxyimino-3-(4-methoxyphenyl)-3-oxopropionate (10.0 g) and 1-aminomethylnaphthalene (7.5 g) were reacted and treated in the same manner as in Starting Material Synthetic Example 1 to give ethyl 5-(4-methoxyphenyl)-2-(1-naphthyl)imidazole-4-carboxylate (5.2 g). 5.0 g therefrom was dissolved in ethyl alcohol (300 ml), and 1 M sodium hydroxide solution (50 ml) was added. The mixture was reacted and treated in the same manner as in Starting Material Synthetic Example 2 to give 5-(4-methoxyphenyl)-2-(1-naphthyl)imidazole-4-carboxyic acid (3.9 g), melting point 178° C. (decomposition).

Starting Material Synthetic Example 29

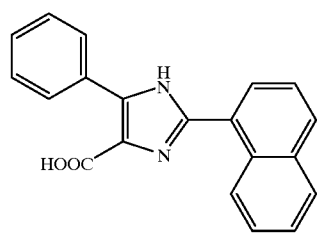

Ethyl 2-hydroxyimino-3-phenyl-3-oxopropionate (10.0 g) and 1-aminomethylnaphthalene (7.8 g) were reacted and treated in the same manner as in Starting Material Synthetic Example 1 to give ethyl 2-(1-naphthyl)-5-phenylimidazole- 4-carboxylate (6.4 g). 6.0 g therefrom was dissolved in ethyl alcohol (120 ml) and 1 M sodium hydroxide solution (45 ml) was added. The mixture was reacted and treated in the same manner as in Starting Material Synthetic Example 2 to give 2-(1-naphthyl)-5-phenylimidazole-4carboxyic acid (4.1 g), melting point 172° C. (decomposition).

Starting Material Synthetic Example 30

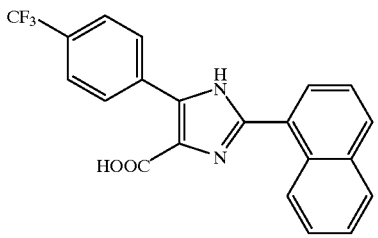

Ethyl 2-hydroxyimino-3-(4-trifluoromethylphenyl)-3-oxopropionate (15.0 g) and 1-aminomethylnaphthalene (9.6 g) were reacted and treated in the same manner as in Starting Material Synthetic Example 1 to give ethyl 2-(1-naphthyl)-5-(4-trifluoromethyl-phenyl)imidazole-4-carboxylate (6.4 g). 5.0 g therefrom was dissolved in ethyl alcohol (100 ml) and 1 M sodium hydroxide solution (30 ml) was added. The mixture was reacted and treated in the same manner as in Starting Material Synthetic Example 2 to give 2-(1-naphthyl)-5-(4-trifluoromethylphenyl)imidazole-4-carboxyic acid (3.4 g), melting point 166° C. (decomposition).

Starting Material Synthetic Example 31

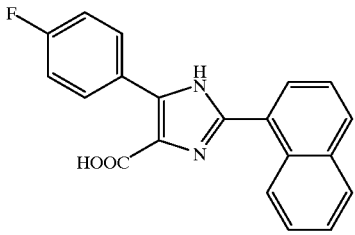

Ethyl 2-hydroxyimino-3-(4-fluorophenyl)-3-oxopropionate (10.0 g) and 1-aminomethylnaphthalene (8.3 g) were reacted and treated in the same manner as in Starting Material Synthetic Example 1 to give ethyl 5-(4-fluorophenyl)-2-(1-naphthyl)imidazole-4-carboxylate (3.3 g). 3.0 g therefrom was dissolved in ethyl alcohol (100 ml) and 1 M sodium hydroxide solution (20 ml) was added. The mixture was reacted and treated in the same manner as in Starting Material Synthetic Example 2 to give 5-(4-fluorophenyl)-2-(1-naphthyl)imidazole-4-carboxyic acid (2.4 g), melting point 175° C. (decomposition).

Starting Material Synthetic Example 32

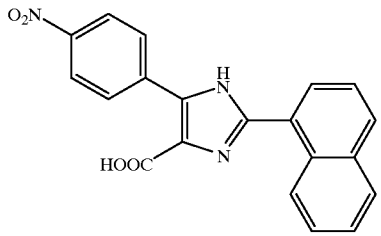

Ethyl 2-hydroxyimino-3-(4-nitrophenyl)-3-oxopropionate (10.0 g) and 1-aminomethylnaphthalene (6.4 g) were reacted and treated in the same manner as in Starting Material Synthetic Example 1 to give ethyl 2-(1-naphthyl)-5-(4-nitrophenyl)imidazole-4-carboxylate (3.6 g). 3.0 g therefrom was dissolved in ethyl alcohol (100 ml) and 1 M sodium hydroxide solution (20 ml) was added. The mixture was reacted and treated in the same manner as in Starting Material Synthetic Example 2 to give 2-(1-naphthyl)-5-(4-nitrophenyl)imidazole-4-carboxylic acid (3.4 g), melting point 161° C. (decomposition).

Starting Material Synthetic Example 33

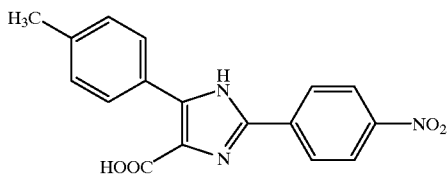

Ethyl 2-hydroxyimino-3-(4-methylphenyl)-3-oxopropionate (50.0 g) and 4-nitrobenzylamine (50.0 g) were reacted and treated in the same manner as in Starting Material Synthetic Example 1 to give ethyl 5-(4-methylphenyl)-2-(4-nitrophenyl)imidazole-4-carboxylate (58.0 g), which was dissolved in ethyl alcohol (1200 ml). Thereto was added 1 M sodium hydroxide solution (300 ml) and the mixture was reacted and treated in the same manner as in Starting Material Synthetic Example 2 to give 5-(4-methylphenyl)-2-(4-nitrophenyl)imidazole-4-carboxyic acid (37.6 g), melting point 212° C. (decomposition).

Starting Material Synthetic Example 34

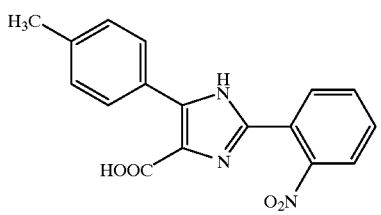

Ethyl 2-hydroxyimino-3-(4-methylphenyl)-3-oxopropionate (12.8 g) and 2-nitrobenzylamine (8.6 g) were reacted and treated in the same manner as in Starting Material Synthetic Example 1 to give ethyl 5-(4-methylphenyl)-2-(2-nitrophenyl)imidazole-4-carboxylate (3.5g). 3.0 g therefrom was dissolved in ethyl alcohol (100 ml) and 1 M sodium hydroxide solution (20 ml) was added. The mixture was reacted and treated in the same manner as in Starting Material Synthetic Example 2 to give 5-(4-methylphenyl)-2-(2-nitrophenyl)imidazole-4-carboxyic acid (2.4 g), melting point 144° C. (decomposition).

Starting Material Synthetic Example 35

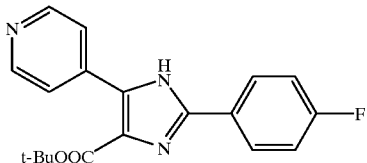

tert-Butyl 2-hydroxyimino-3-oxo-3-(4-pyridyl) propionate and 4-fluorobenzylamine were dissolved in acetonitrile (80 ml). The mixture was reacted and treated in the same manner as in Starting Material Synthetic Example 5 to give tert-butyl 2-(4-fluorophenyl)-5-(4-pyridyl) imidazole-4-carboxylate.

Starting Material Synthetic Example 36

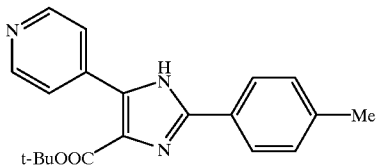

tert-Butyl 2-hydroxyimino-3-oxo-3-(4-pyridyl) propionate and 4-methylbenzylamine were dissolved in acetonitrile (80 ml). The mixture was reacted and treated in the same manner as in Starting Material Synthetic Example 5 to give tert-butyl 2-(4-methylphenyl)-5-(4-pyridyl) imidazole-4-carboxylate.

Starting Material Synthetic Example 37

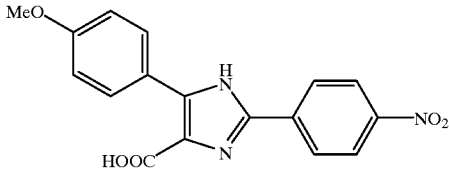

Ethyl 2-hydroxyimino-3-(4-methoxyphenyl)-3-oxopropionate (105.2 g) and 4-nitrobenzylamine (76.4 g) were reacted and treated in the same manner as in Starting Material Synthetic Example 1 to give ethyl 5-(4-methoxyphenyl)-2-(4-nitrophenyl)imidazole-4-carboxylate (55.1 g), which was dissolved in ethyl alcohol. 1 M Sodium hydroxide solution was added and the mixture was reacted and treated in the same manner as in Starting Material Synthetic Example 2 to give 5-(4-methoxyphenyl)-2-(4-nitrophenyl)imidazole-4-carboxylic acid (40.3 g), melting point 205–208° C. (decomposition).

Starting Material Synthetic Example 38

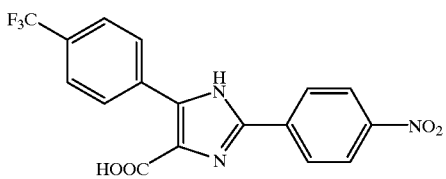

Ethyl 2-hydroxyimino-3-oxo-3-(4-trifluoromethylphenyl)-propionate (24.6 g) and 4-nitrobenzylamine (14.0 g) were reacted and treated in the same manner as in Starting Material Synthetic Example 1 to give ethyl 2-(4-nitrophenyl)-5-(4-trifluoromethylphenyl)-imidazole-4-carboxylate (10.6 g). 9.0 g therefrom was dissolved in ethyl alcohol. 1 M Sodium hydroxide solution was added and the mixture was reacted and treated in the same manner as in Starting Material Synthetic Example 2 to give 2-(4-nitrophenyl)-5-(4-trifluoromethylphenyl)imidazole-4-carboxylic acid (8.2 g), melting point 172-174° C. (decomposition).

Starting Material Synthetic Example 39

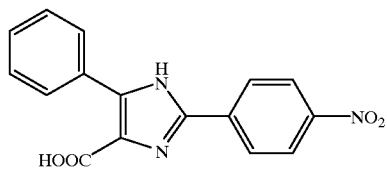

Ethyl 2-hydroxyimino-3-phenyl-3-oxopropionate (36.1 g) and 4-nitrobenzylamine (27.9 g) were reacted and treated in the same manner as in Starting Material Synthetic Example 1 to give ethyl 2-(4-nitrophenyl)-5-phenylimidazole-4-carboxylate (19.2 g). 18.0 g therefrom was dissolved in ethyl alcohol. 1 M Sodium hydroxide solution was added and the mixture was reacted and treated in the same manner as in Starting Material Synthetic Example 2 to give 2-(4-nitrophenyl)-5-phenylimidazole-4-carboxylic acid (12.8 g), melting point 175–178° C. (decomposition).

Starting Material Synthetic Example 40

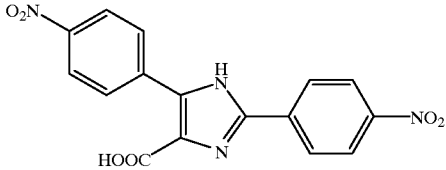

Ethyl 2-hydroxyimino-3-(4-nitrophenyl)-3-oxopropionate and 4-nitrobenzylamine are reacted and treated in the same manner as in Starting Material Synthetic Example 1 to give ethyl 2,5-bis(4-nitrophenyl)imidazole-4-carboxylate, which is dissolved in ethyl alcohol. 1 M Sodium hydroxide solution is added and the mixture is reacted and treated in the same manner as in Starting Material Synthetic Example 2 to give 2,5-bis(4-nitrophenyl) imidazole-4-carboxylic acid.

Starting Material Synthetic Example 41

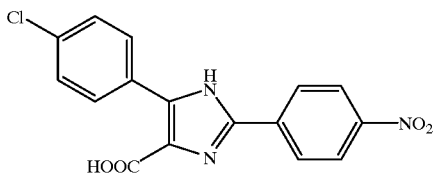

Ethyl 3-(4-chlorophenyl)-2-hydroxyimino-3-oxopropionate and 4-nitrobenzylamine are reacted and treated in the same manner as in Starting Material Synthetic Example 1 to give ethyl 5-(4-chlorophenyl)-2-(4-nitrophenyl)imidazole-4-carboxylate, which is dissolved in ethyl alcohol. 1 M Sodium hydroxide solution is added and the mixture is reacted and treated in the same manner as in Starting Material Synthetic Example 2 to give 5-(4-chlorophenyl)-2-(4-nitrophenyl)imidazole-4-carboxylic acid.

Starting Material Synthetic Example 42

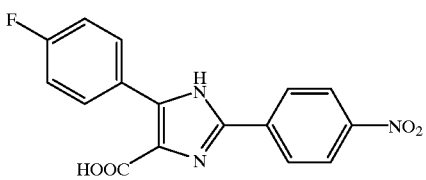

Ethyl 3-(4-fluorophenyl)-2-hydroxyimino-3-oxopropionate (33.5 g) and 4-nitrobenzylamine (23.7 g) were reacted and treated in the same manner as in Starting Material Synthetic Example 1 to give ethyl 5-(4-fluorophenyl)-2-(4-nitrophenyl)imidazole-4-carboxylate (12.1 g),whichwasdissolvedinethylalcohol. 1MSodiumhydroxidesolution was added and the mixture was reacted and treated in the same manner as in.Starting Material Synthetic Example 2 to give 5-(4-fluorophenyl)-2-(4-nitrophenyl) imidazole-4-carboxylic acid (10.3 g), melting point 173–178° C. (decomposition).

Starting Material Synthetic Example 43

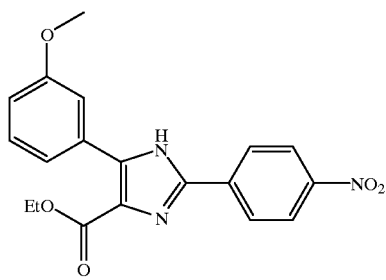

Ethyl 2-hydroxyimino-3-(3-methoxyphenyl)-3-oxopropionate (84.5 g) and 4-nitrobenzylamine (61.4 g) were reacted and treated in the same manner as in Starting Material Synthetic Example 1 to give ethyl 5-(3-methoxyphenyl)-2-(4-nitrophenyl)imidazole-4-carboxylate (39.0 g), melting point 194–196° C.

Starting Material Synthetic Example 44

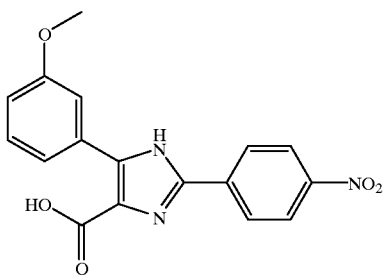

Ethyl 5-(3-methoxyphenyl)-2-(4-nitrophenyl)imidazole-4-carboxylate (45.1 g) was dissolved in ethanol. 1 M Sodium hydroxide solution was added and the mixture was reacted and treated in the same manner as in Starting Material Synthetic Example 2 to give 5-(3-methoxyphenyl)-2-(4-nitrophenyl)imidazole-4-carboxylic acid (42.1 g), melting point 116–118° C. (decomposition).

Starting Material Synthetic Example 45

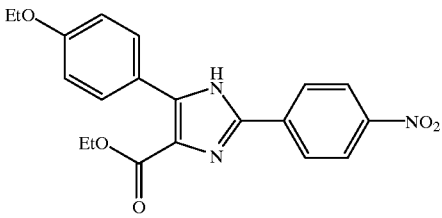

Ethyl 2-hydroxyimino-3-(4-ethoxyphenyl)-3-oxopropionate (84.5 g) and 4-nitrobenzylamine (87.1 g) were reacted and treated in the same manner as in Starting Material Synthetic Example 1 to give ethyl 5-(4-ethoxyphenyl)-2-(4-nitrophenyl)imidazole-4-carboxylate (28.1 g), melting point 214-217° C.

Starting Material Synthetic Example 46

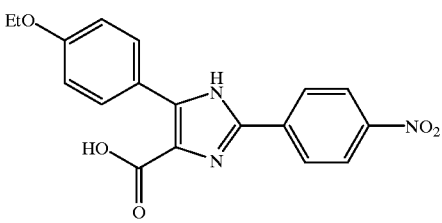

Ethyl 5-(4-ethoxyphenyl)-2-(4-nitrophenyl)imidazole-4-carboxylate (27.6 g) was dissolved in ethanol. 1 M Sodium hydroxide solution was added and the mixture was reacted and treated in the same manner as in Starting Material Synthetic Example 2 to give 5-(4-ethoxyphenyl)-2-(4-nitrophenyl) imidazole-4-carboxylic acid (30.7 g), melting point 148–152° C.

Starting Material Synthetic Example 47

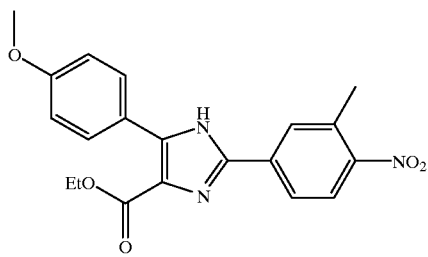

Ethyl 2-hydroxyimino-3-(4-methoxyphenyl)-3-oxopropionate (121.6 g) and 3-methyl-4-nitrobenzylamine (105.4 g) were reacted in the same manner as in Starting Material Synthetic Example 1. After the reaction, the solvent was evaporated under reduced pressure and the residue was subjected to silica gel column chromatography to give ethyl 5-(4-methoxyphenyl)-2-(3-methyl-4-nitrophenyl)imidazole-4-carboxylate (41.5 g), melting point 187–191° C.

Starting Material Synthetic Example 48

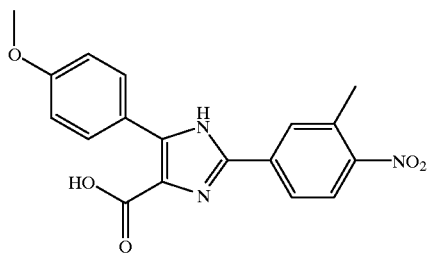

Ethyl 5-(4-methoxyphenyl)-2-(3-methyl-4-nitrophenyl)-imidazole-4-carboxylate (29 g) was dissolved in ethanol and 2 M sodium hydroxide solution was added. The mixture was reacted and treated in the same manner as in Starting Material Synthetic Example 2 to give 5-(4-methoxyphenyl)-2-(3-methyl-4-nitrophenyl)imidazole-4-carboxylic acid (20.9 g), melting point 229–230° C.

Starting Material Synthetic Example 49

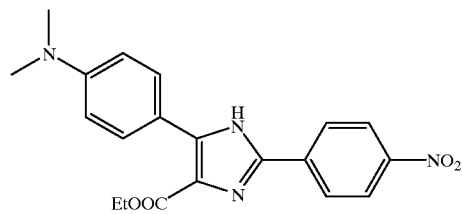

Ethyl 3-(4-dimethylaminophenyl)-2-hydroxyimino-3-oxopropionate (3.8 g) and 4-nitrobenzylamine (2.8 g) were reacted and treated in the same manner as in Starting Material Synthetic Example 1 to give ethyl 5-(4-dimethylaminophenyl)-2-(4-nitrophenyl)-imidazole-4-carboxylate (1.8 g), melting point 240–242° C.

Starting Material Synthetic Example 50

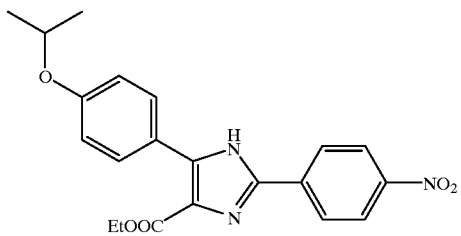

Ethyl 2-hydroxyimino-3-(4-isopropoxyphenyl)-3-oxopropionate (15.0 g) and 4-nitrobenzylamine (11.2 g) were reacted and treated in the same manner as in Starting Material Synthetic Example 1 to give ethyl 5-(4-isopropoxyphenyl)-2-(4-nitrophenyl)imidazole-4-carboxylate (4.2 g).

Starting Material Synthetic Example 51

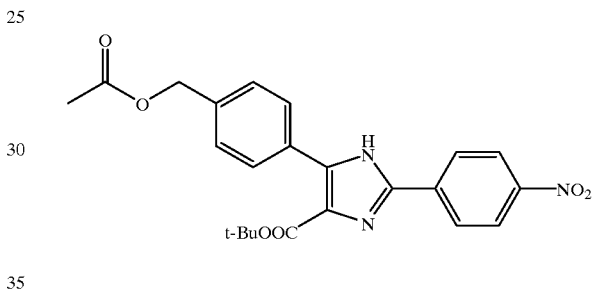

tert-Butyl 3-(4-acetoxymethylphenyl)-2-hydroxyimino-3-oxopropionate (33.9 g) and 4-nitrobenzylamine (19.3 g) were reacted and treated in the same manner as in Starting Material Synthetic Example 1 to give tert-butyl 5-(4-acetoxymethylphenyl)-2-(4-nitrophenyl)-imidazole-4-carboxylate (7.07 g), melting point 178–180° C. (decomposition).

Starting Material Synthetic Example 52

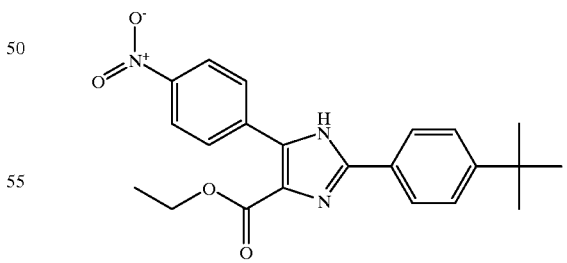

Ethyl 2-hydroxyimino-3-(4-nitrophenyl)-3-oxopropionate (47.8 g) and 4-tert-butylbenzylamine (35.4 g) were reacted and treated in the same manner as in Starting Material Synthetic Example 10 to give ethyl 2-(4-tert-butylphenyl)-5-(4-nitrophenyl)imidazole-4-carboxylate (22.5 g), melting point 190–191° C.

Starting Material Synthetic Example 53

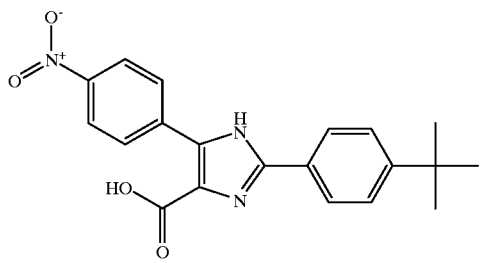

Ethyl 2-(4-tert-butylphenyl)-5-(4-nitrophenyl)imidazole-4-carboxylate (22.5 g), ethyl alcohol (1.2 L) and 1 M aqueous sodium hydroxide solution (225 ml) were reacted and treated in the same manner as in Starting Material Synthetic Example 2 to give 2-(4-tert-butylphenyl)-5-(4-nitrophenyl)imidazole-4-carboxylic acid (18.4 g), melting point 223° C. (decomposition).

Starting Material Synthetic Example 54

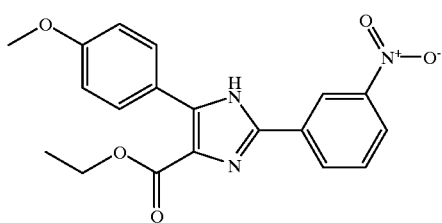

Ethyl 2-hydroxyimino-3-(4-methoxyphenyl)-3-oxopropionate (20.0 g) and 3-nitrobenzylamine (15.0 g) were reacted and treated in the same manner as in Starting Material Synthetic Example 10 to give ethyl 5-(4-methoxyphenyl)-2-(3-nitrophenyl)imidazole-4-carboxylate (13.3 g), melting point 208–210° C.

Starting Material Synthetic Example 55

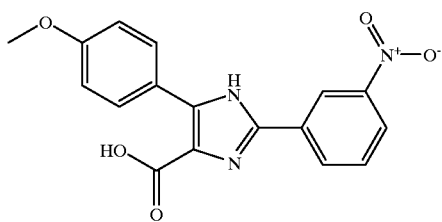

Ethyl 5-(4-methoxyphenyl)-2-(3-nitrophenyl)imidazole-4-carboxylate (13.3 g), ethyl alcohol (266 ml) and 1M aqueous sodium hydroxide solution (127 ml) were reacted and treated in the same manner as in Starting Material Synthetic Example 2 to give 5-(4-methoxyphenyl)-2-(3-nitrophenyl)imidazole-4-carboxyic acid (9.5 g), melting point 234–235° C.

Starting Material Synthetic Example 56

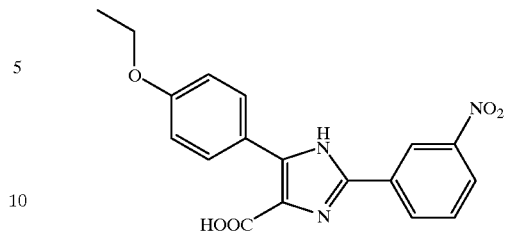

Ethyl 5-(4-ethoxyphenyl)-2-(3-nitrophenyl)imidazole-4-carboxylate obtained by reacting and treating ethyl 2-hydroxyimino-3-(4-ethoxyphenyl)-3-oxopropionate and 3-nitrobenzylamine in the same manner as in Starting Material Synthetic Example 1 is dissolved in ethyl alcohol and 1 M aqueous sodium hydroxide solution is added. The mixture is reacted and treated in the same manner as in Starting Material Synthetic Example 2 to give 5-(4-ethoxyphenyl)-2-(3-nitrophenyl)imidazole-4-carboxylic acid.

Starting Material Synthetic Example 57

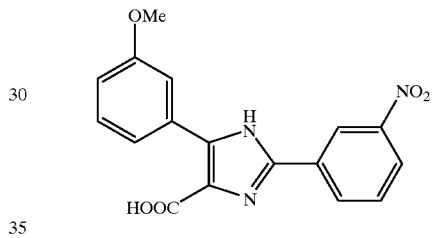

Ethyl 5-(3-methoxyphenyl)-2-(3-nitrophenyl)imidazole-4-carboxylate obtained by reacting and treating ethyl 2-hydroxyimino-3-(3-methoxyphenyl)-3-oxopropionate and 3-nitrobenzylamine in the same manner as in Starting Material Synthetic Example 1 is dissolved in ethyl alcohol and 1 M aqueous sodium hydroxide solution is added. The mixture is reacted and treated in the same manner as in Starting Material Synthetic Example 2 to give 5-(3-methoxyphenyl)-2-(3-nitrophenyl)imidazole-4-carboxylic acid.

Starting Material Synthetic Example 58

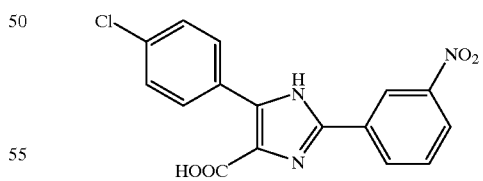

Ethyl 5-(4-chlorophenyl)-2-(3-nitrophenyl)imidazole-4-carboxylate obtained by reacting and treating ethyl 2-hydroxyimino-3-(4-chlorophenyl)-3-oxopropionate and 3-nitrobenzylamine in the same manner as in Starting Material Synthetic Example 1 is dissolved in ethyl alcohol and 1 M aqueous sodium hydroxide solution is added. The mixture is reacted and treated in the same manner as in Starting Material Synthetic Example 2 to give 5-(4-chlorophenyl)-2-(3-nitrophenyl)imidazole-4-carboxylic acid.

Starting Material Synthetic Example 59

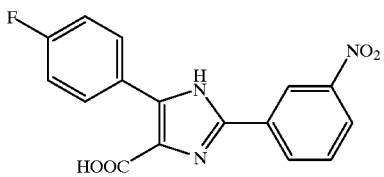

Ethyl 5-(4-fluorophenyl)-2-(3-nitrophenyl)imidazole-4-carboxylate obtained by reacting and treating ethyl 2-hydroxyimino-3-(4-fluorophenyl)-3-oxopropionate and 3-nitrobenzylamine in the same manner as in Starting Material Synthetic Example 1 is dissolved in ethyl alcohol and 1 M aqueous sodium hydroxide solution is added. The mixture is reacted and treated in the same manner as in Starting Material Synthetic Example 2 to give 5-(4-fluorophenyl)-2-(3-nitrophenyl)imidazole-4-carboxylic acid.

Starting Material Synthetic Example 60

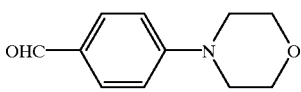

N-Phenylmorpholine (77.2 g) was dissolved in DMF (150 ml) and phosphorus oxychloride (67.1 ml) was dropwise added in an ice bath. After the dropwise addition, the mixture was stirred at 60° C. for 22 hr. Ice water was added portionwise to the reaction mixture in an ice bath and the mixture was neutralized with a saturated aqueous hydrogencarbonate solution. The mixture was extracted with ethyl acetate and the organic layer was dried over anhydrous magnesium sulfate. The solvent was evaporated under reduced pressure. Isopropyl ether was added to the residue, and the precipitated crystals were collected by filtration to give the objective 4-morpholinobenzaldehyde (70.7 g), melting point 55° C.

Starting Material Synthetic Example 61

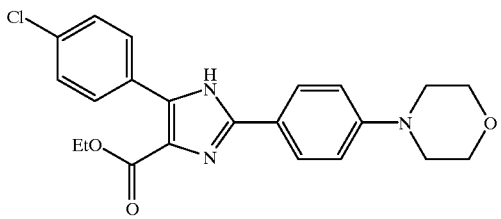

Ethyl 3-(4-chlorophenyl)-2-hydroxyimino-3-oxopropionate (200 g), 4-morpholinobenzaldehyde (244.4 g) and ammonium acetate (603 g) were refluxed under heating for 15 hr in acetic acid, and the solvent was evaporated under reduced pressure. The residue was dissolved in chloroform (2 L), and the solution was neutralized with a saturated aqueous hydrogencarbonate solution and extracted with chloroform. The organic layer was dried over anhydrous magnesium sulfate and, after drying, the solvent was evaporated under reduced pressure and crude crystals were obtained from ethyl acetate. The crude crystals were subjected to silica gel column chromatography to give the objective ethyl 5-(4-chlorophenyl)-2-(4-morpholinophenyl)imidazole-4-carboxylate (78 g), melting point 215° C.

Starting Material Synthetic Example 62

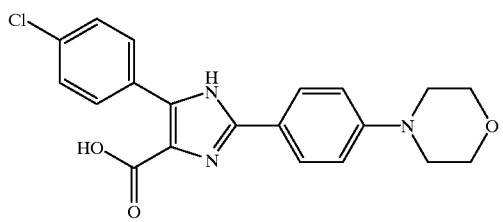

Ethyl 5-(4-chlorophenyl)-2-(4-morpholinophenyl)imidazole-4-carboxylate (53.7 g) was dissolved in ethanol (540 ml) and 3N aqueous sodium hydroxide solution (217 ml), and the mixture was refluxed under heating for 5 hr and concentrated under reduced pressure. Water (100 ml) was added and the mixture was washed with toluene. The aqueous layer was neutralized with 10% aqueous citric acid solution and the precipitated crystals were collected by filtration to give the objective 5-(4-chlorophenyl)-2-(4-morpholinophenyl)imidazole-4-carboxyic acid (49.4 g), melting point 205° C. (decomposition).

Starting Material Synthetic Example 63

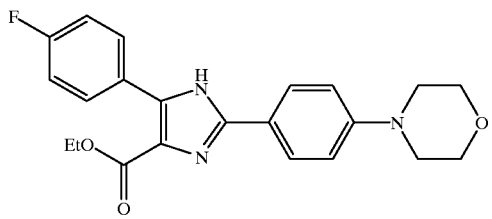

In the same manner as in Starting Material Synthetic Example 61, ethyl 5-(4-fluorophenyl)-2-(4-morpholinophenyl)imidazole-4-carboxylate (8.6 g) was obtained from ethyl 3-(4-fluorophenyl)-2-hydroxyimino-3-oxopropionate (20.8 g), 4-morpholinobenzaldehyde (25 g) and ammonium acetate (67 g), melting point 193° C.

$^1$H-NMR 270 MHz (DMSO-$d_6$, ppm) δ: 9.89(1H, s), 7.84–7.98(4H, m), 6.93–7.13(4H, m), 4.34(2H, q), 3.87(4H, t), 3.25(4H, t), 1.33(3H, t).

Starting Material Synthetic Example 64

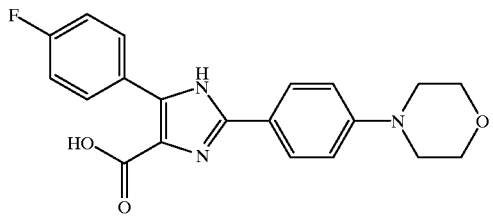

In the same manner as in Starting Material Synthetic Example 62, 5-(4-fluorophenyl)-2-(4-morpholinophenyl)imidazole-4-carboxyic acid (8.0 g) was obtained from ethyl 5-(4-fluorophenyl)-2-(4-morpholinophenyl)imidazole-4-carboxylate (8.6 g).

$^1$H-NMR 270 MHz (DMSO-$d_6$, ppm) δ: 12.8(1H, s), 6.99–8.04(9H, m), 3.75(4H, t), 3.20(4H, t).

Starting Material Synthetic Example 65

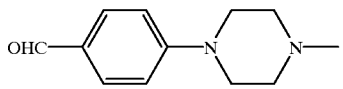

In the same manner as in Starting Material Synthetic Example 60, the objective 4-(4-methylpiperazin-1-yl)benzaldehyde (12.6 g) was obtained from 4-methyl-1-phenylpiperazine (16.5 g), melting point 50° C.

Starting Material Synthetic Example 66

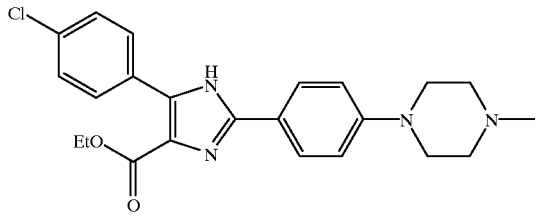

In the same manner as in Starting Material Synthetic Example 61, ethyl 5-(4-chlorophenyl)-2-[4-(4-methylpiperazin-1-yl)phenyl]imidazole-4-carboxylate (3.7 g) was obtained from ethyl 3-(4-chlorophenyl)-2-hydroxyimino-3-oxopropionate (6.4 g), 4-(4-methylpiperazin-1-yl)benzaldehyde (7.7 g) and ammonium acetate (19.4 g), melting point 190–192° C.

Starting Material Synthetic Example 67

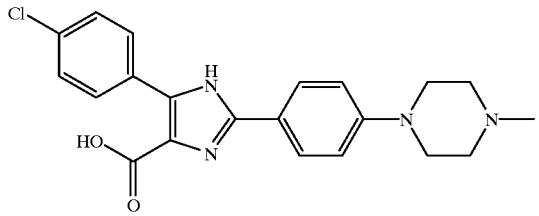

In the same manner as in Starting Material Synthetic Example 62, 5-(4-chlorophenyl)-2-[4-(4-methylpiperazin-1-yl)phenyl]-imidazole-4-carboxyic acid (3.5 g) was obtained from ethyl 5-(4-chlorophenyl)-2-[4-(4-methylpiperazin-1-yl)phenyl]imidazole-4 -carboxylate (3.7 g), melting point 214–218° C. (decomposition).

Starting Material Synthetic Example 68

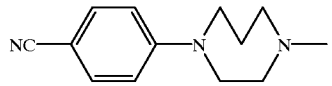

4-Fluorobenzonitrile (25.5 g), 4-methylhomopiperazine (26.2 ml) and potassium carbonate (28 g) were heated in DMSO for 15 hr. After heating, the reaction mixture was poured into water (1 L). The precipitated crystals were collected by filtration to give the objective 4-(4-methylhomopiperazin-1-yl)benzonitrile (34.6 g), melting point 82–84° C.

Starting Material Synthetic Example 69

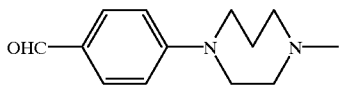

4-(4-Methylhomopiperazin-1-yl)benzonitrile (15 g) was dissolved in formic acid (225 ml) and Raney nickel (15.5 g) was added. The mixture was refluxed under heating for 2.5 hr. After the reaction, the catalyst was filtered off and the mixture was concentrated under reduced pressure. The residue was neutralized with saturated aqueous potassium carbonate solution and extracted with chloroform. The organic layer was dried over anhydrous magnesium sulfate. The solvent was concentrated under reduced pressure to give the objective 4-(4-methylhomopiperazin-1-yl)benzaldehyde as an oil (16.1 g).

$^1$H-NMR 270 MHz (CDCl$_3$, ppm) δ: 9.71(1H, s), 7.71 (2H, d), 6.71(2H, d), 3.48–3.65(4H, m), 2.66–2.73(2H, m), 2.52–2.57(2H, m), 2.37(3H, s), 1.97–2.06(2H, m).

Starting Material Synthetic Example 70

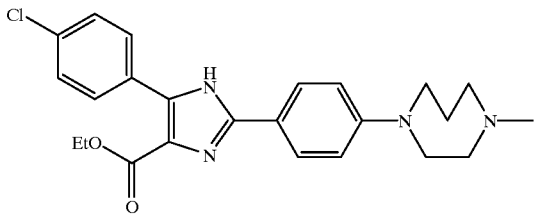

In the same manner as in Starting Material Synthetic Example 61, ethyl 5-(4-chlorophenyl)-2-[4-(4-methylhomopiperazin-1-yl)phenyl]imidazole-4-carboxylate (5.3 g) was obtained from ethyl 3-(4-chlorophenyl)-2-hydroxyimino-3-oxopropionate (10.5 g), 4-(4-methylhomopiperazin-1-yl)benzaldehyde (16.2 g) and ammonium acetate (31.7 g), melting point 205–207° C.

Starting Material Synthetic Example 71

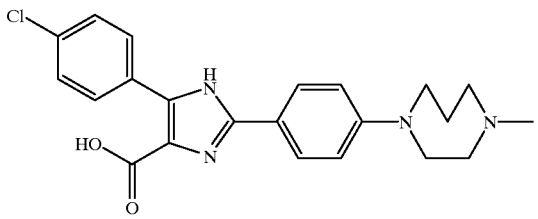

In the same manner as in Starting Material Synthetic Example 62, 5-(4-chlorophenyl)-2-[4-(4-methylhomopiperazin-1-yl)phenyl]-imidazole-4-carboxyic acid (5.0 g), melting point 177–180° C. (decomposition), was obtained from ethyl 5-(4-chlorophenyl)-2-[4-(4-methylhomopiperazin-1-yl)phenyl]imidazole-4-carboxylate (5.3 g).

Starting Material Synthetic Example 72

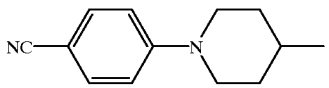

In the same manner as in Starting Material Synthetic Example 68, the objective 4-(4-methylpiperidin-1-yl) benzonitrile (24.5 g), melting point 53° C., was obtained from 4-fluorobenzonitrile (20 g) and 4-methylpiperidine (16.4 g).

Starting Material Synthetic Example 73

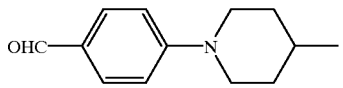

In the same manner as in Starting Material Synthetic Example 69, the objective 4-(4-methylpiperidin-1-yl) benzaldehyde was obtained as an oil (13.8 g) from 4-(4-methylpiperidin-1-yl)benzonitrile (15 g) and, without purification, used in the next Starting Material Synthetic Example 74.

Starting Material Synthetic Example 74

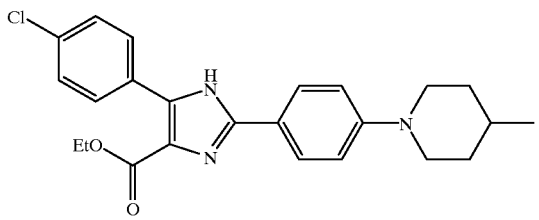

In the same manner as in Starting Material Synthetic Example 61, ethyl 5-(4-chlorophenyl)-2-[4-(4-methylpiperidin-1-yl)phenyl]imidazole-4-carboxylate (4.9 g), melting point 188–190° C., was obtained from ethyl 3-(4-chlorophenyl)-2-hydroxyimino-3-oxopropionate (8.7 g), unpurified 4-(4-methylpiperidin-1-yl)benzaldehyde (13.9 g) obtained in Starting Material Synthetic Example 73 and ammonium acetate (52.6 g).

Starting Material Synthetic Example 75

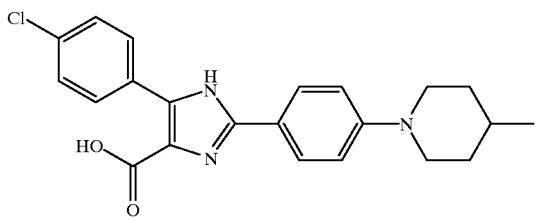

In the same manner as in Starting Material Synthetic Example 62, 5-(4-chlorophenyl)-2-[4-(4-methylpiperidin-1-yl)phenyl]-imidazole-4-carboxyic acid (4.6 g), melting point 188–192° C. (decomposition), was obtained from ethyl 5-(4-chlorophenyl)-2-[4-(4-methylpiperidin-1-yl)phenyl] imidazole-4-carboxylate (4.9 g).

Starting Material Synthetic Example 76

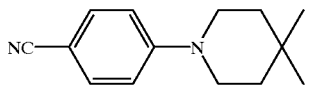

In the same manner as in Starting Material Synthetic Example 68, the objective 4-(4,4-dimethylpiperidin-1-yl) benzonitrile (34.7 g), melting point 115–117° C., was obtained from 4-fluorobenzonitrile (23 g) and 4,4-dimethylpiperidine hydrochloride (28.5 g).

Starting Material Synthetic Example 77

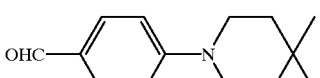

In the same manner as in Starting Material Synthetic Example 69, the objective 4-(4,4-dimethylpiperidin-1-yl) benzaldehyde (13.1 g), melting point 48° C., was obtained as an oil from 4-(4,4-dimethylpiperidin-1-yl)benzonitrile (18 g).

Starting Material Synthetic Example 78

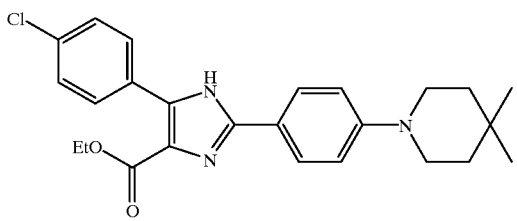

In the same manner as in Starting Material Synthetic Example 61, ethyl 5-(4-chlorophenyl)-2-[4-(4,4-dimethylpiperidin-1-yl)phenyl]imidazole-4-carboxylate (5.6 g), melting point 205° C., was obtained from ethyl 3-(4-chlorophenyl)-2-hydroxyimino-3-oxopropionate (10.3 g), 4-(4,4-dimethylpiperidin-1-yl)benzaldehyde (13.1 g) and ammonium acetate (31 g).

Starting Material Synthetic Example 79

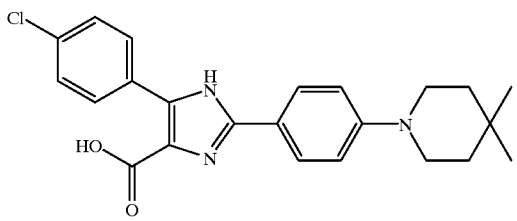

In the same manner as in Starting Material Synthetic Example 62, 5-(4-chlorophenyl)-2-[4-(4,4-dimethylpiperidin-1-yl)phenyl]-imidazole-4-carboxyic acid (5.4 g), melting point 188-192° C. (decomposition), was obtained from ethyl 5-(4-chlorophenyl)-2-[4-(4,4-dimethylpiperidin-1-yl)phenyl]imidazole-4-carboxylate (5.6 g).

Starting Material Synthetic Example 80

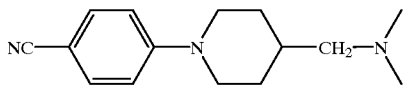

In the same manner as in Starting Material Synthetic Example 68, the objective 4-[4-(dimethylaminomethyl)piperidin-1-yl]-benzonitrile (35.5 g), melting point 84–86° C., was obtained from 4-fluorobenzonitrile (27 g) and 4-(dimethylaminomethyl)piperidine (32 g).

Starting Material Synthetic Example 81

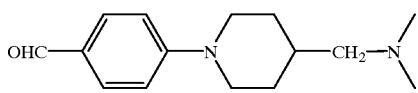

In the same manner as in Starting Material Synthetic Example 69, the objective 4-[4-(dimethylaminomethyl)piperidin-1-yl]benzaldehyde (34 g) was obtained as an oil from 4-[4-(dimethylaminomethyl)piperidin-1-yl]benzonitrile (35.5 g).

Starting Material Synthetic Example 82

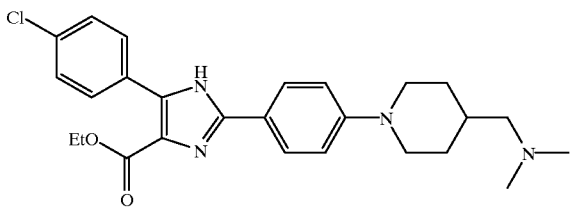

In the same manner as in Starting Material Synthetic Example 61, ethyl 5-(4-chlorophenyl)-2-{4-[4-(dimethylaminomethyl)-piperidin-1-yl]phenyl}imidazole-4-carboxylate (7.2 g), melting point 203-204° C., was obtained from ethyl 3-(4-chlorophenyl)-2-hydroxyimino-3-oxopropionate (22 g), 4-[4-(dimethylaminomethyl)-piperidin-1-yl]benzaldehyde (34 g) and ammonium acetate (66.5 g).

Starting Material Synthetic Example 83

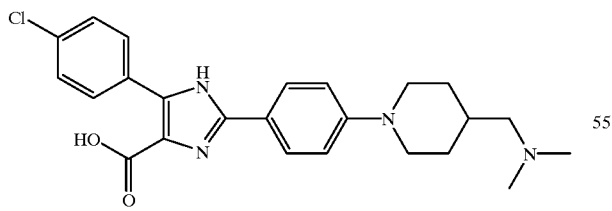

In the same manner as in Starting Material Synthetic Example 62, 5-(4-chlorophenyl)-2-{4-[4-(dimethylaminomethyl)piperidin-1-yl]phenyl}imidazole-4-carboxyic acid (6.2 g), melting point 243–245° C. (decomposition), was obtained from ethyl 5-(4-chlorophenyl)-2-{4-[4-(dimethylaminomethyl)piperidin-1-yl]phenyl}imidazole-4-carboxylate (7.2 g).

Starting Material Synthetic Example 84

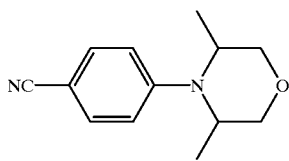

In the same manner as in Starting Material Synthetic Example 68, the objective 4-(3,5-dimethylmorpholin-4-yl)benzonitrile (34.8 g), melting point 75–78° C., was obtained from 4-fluorobenzonitrile (24.2 g) and 3,5-dimethylmorpholine (23 g).

Starting Material Synthetic Example 85

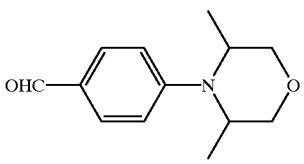

In the same manner as in Starting Material Synthetic Example 69, the objective 4-(3,5-dimethylmorpholin-4-yl)benzaldehyde (32.9 g) was obtained as an oil from 4-(3,5-dimethylmorpholin-4-yl)benzonitrile (34.8 g).

$^1$H-NMR 270 MHz (CDCl$_3$, ppm) δ: 9.78(1H, s), 7.73–7.78(2H, m), 6.89–6.93(2H, m), 3.63–3.81(4H, m), 2.52–2.62(2H, m), 1.27(6H, dd)

Starting Material Synthetic Example 86

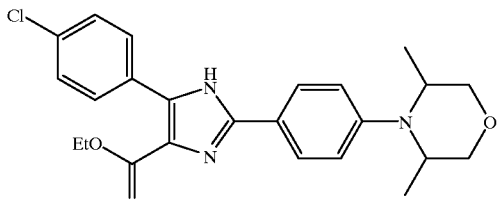

In the same manner as in Starting Material Synthetic Example 61, ethyl 5-(4-chlorophenyl)-2-[4-(3,5-dimethylmorpholin-4-yl)phenyl]imidazole-4-carboxylate (4.3 g), melting point 178–180° C., was obtained from ethyl 3-(4-chlorophenyl)-2-hydroxyimino-3-oxopropionate (25.5 g), 4-(3,5-dimethylmorpholin-4-yl)benzaldehyde (32.8 g) and ammonium acetate (77 g).

Starting Material Synthetic Example 87

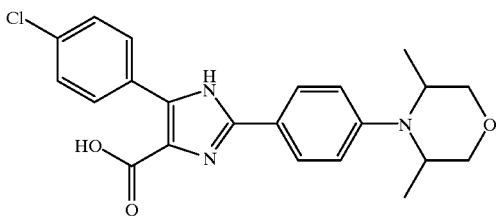

In the same manner as in Starting Material Synthetic Example 62, 5-(4-chlorophenyl)-2-[4-(3,5-dimethylmorpholin-4-yl)phenyl]imidazole-4-carboxyic acid (5 g), melting point 175° C. (decomposition), was obtained from ethyl 5-(4-chlorophenyl)-2-[4-(3,5-dimethylmorpholin-4-yl)phenyl] imidazole-4-carboxylate (5.5 g)).

Starting Material Synthetic Example 88

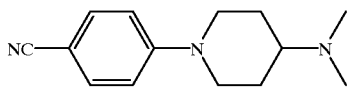

In the same manner as in Starting Material Synthetic Example 68, the objective 4-[4-(dimethylamino)piperidin-1-yl]benzonitrile (14 g) was obtained as an oil from 4-fluorobenzonitrile (39 g) and 4-dimethylaminopiperidine (41 g).

$^1$H-NMR 270 MHz (CDCl$_3$, ppm) δ: 7.46(2H, d), 6.85 (2H, d), 3.89–3.84(2H, m), 2.88–2.87(2H, m), 2.30(6H, s), 1.95–1.80(2H, m), 1.770–1.42(2H, m).

Starting Material Synthetic Example 89

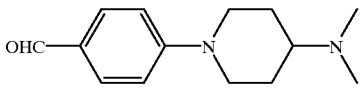

In the same manner as in Starting Material Synthetic Example 69, the objective 4-[4-(dimethylamino)piperidin-1-yl]benzaldehyde (8.3 g) was obtained as an oil from 4-[4-(dimethylamino)piperidin-1-yl]benzonitrile (14 g).

1H-NMR 270 MHz (CDCl$_3$, ppm) δ: 9.75(1H, s), 7.72 (2H, d), 6.90(2H, d), 3.98–3.87(2H, m), 2.96–2.97(2H, m), 2.30(6H, s), 1.95–1.90(2H, m), 1.64–1.49(2H, m).

Starting Material Synthetic Example 90

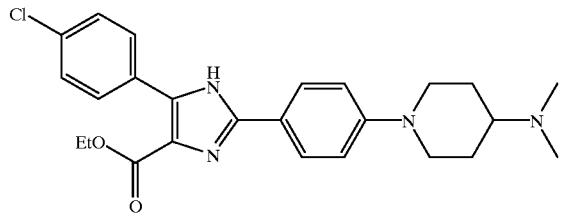

In the same manner as in Starting Material Synthetic Example 61, ethyl 5-(4-chlorophenyl)-2-[4-[4-(dimethylamino)piperidin-1-yl]phenyl]imidazole-4-carboxylate (2.5 g), melting point 173–174° C., was obtained from ethyl 3-(4-chlorophenyl)-2-hydroxyimino-3-oxopropionate (6.0 g), 4-[4-(dimethylamino)piperidin-1-yl] benzaldehyde (8.3 g) and ammonium acetate (18.0 g).

Starting Material Synthetic Example 91

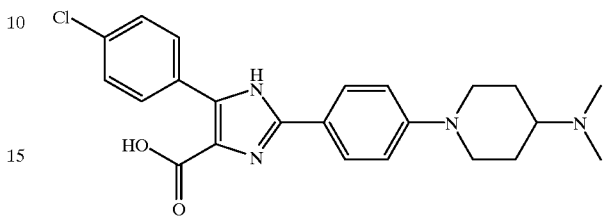

In the same manner as in Starting Material Synthetic Example 62, 5-(4-chlorophenyl)-2-[4-[4-(dimethylamino) piperidin-1-yl]phenyl]imidazole-4-carboxyic acid (1.7 g), melting point 210–213° C. (decomposition), was obtained from ethyl 5-(4-chlorophenyl)-2-[4-[4-(dimethylamino) piperidin-1-yl]phenyl]imidazole-4-carboxylate (2.5 g).

Starting Material Synthetic Example 92

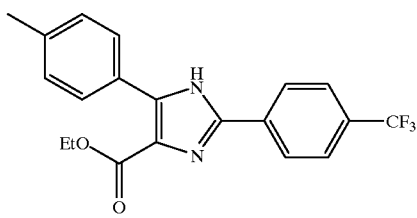

In the same manner as in Starting Material Synthetic Example 61, ethyl 5-(4-methylphenyl)-2-(4-trifluoromethylphenyl)imidazole-4-carboxylate (43.7 g), melting point 163–164° C., was obtained from ethyl 3-(4-methylphenyl)-2-hydroxyimino-3-oxopropionate (122 g), 4-trifluoromethylbenzaldehyde (136 g) and ammonium acetate (400 g).

Starting Material Synthetic Example 93

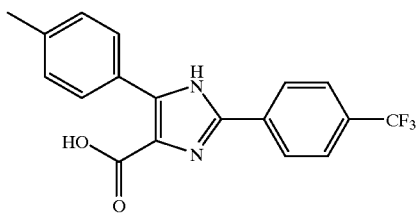

In the same manner as in Starting Material Synthetic Example 62, 5-(4-methylphenyl)-2-(4-trifluoromethylphenyl)imidazole-4-carboxyic acid (38.0 g), melting point 218–219° C. (decomposition), was obtained from ethyl 5-(4-methylphenyl)-2-(4-trifluoromethyl-phenyl) imidazole-4-carboxylate (43.7 g).

Starting Material Synthetic Example 94

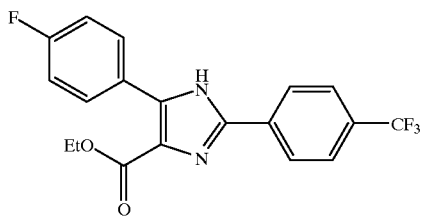

In the same manner as in Starting Material Synthetic Example 61, ethyl 5-(4-fluorophenyl)-2-(4-trifluoromethylphenyl)imidazole-4-carboxylate (12.0 g), melting point 185–188° C., was obtained from ethyl 3-(4-fluorophenyl)-2-hydroxyimino-3-oxopropionate (15.0 g), 4-trifluoromethylbenzaldehyde (16.3 g) and ammonium acetate (48.4 g).

Starting Material Synthetic Example 95

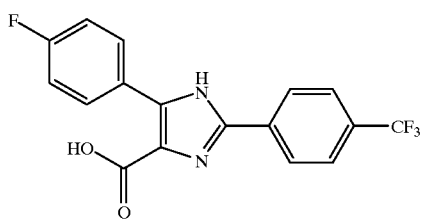

In the same manner as in Starting Material Synthetic Example 62, 5-(4-fluorophenyl)-2-(4-trifluoromethylphenyl)imidazole-4-carboxyic acid (10.0 g), melting point 159–160° C. (decomposition), was obtained from ethyl 5-(4-fluorophenyl)-2-(4-trifluoromethyl-phenyl)imidazole-4-carboxylate (11.0 g).

Starting Material Synthetic Example 96

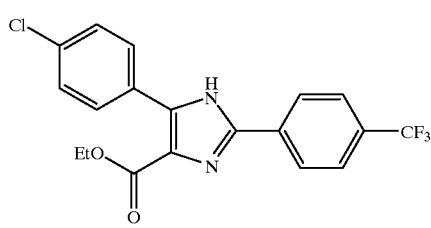

In the same manner as in Starting Material Synthetic Example 61, ethyl 5-(4-chlorophenyl)-2-(4-trifluoromethylphenyl)imidazole-4-carboxylate (9.7 g), melting point 171–173° C., was obtained from ethyl 3-(4-chlorophenyl)-2-hydroxyimino-3-oxopropionate (15.0 g), 4-trifluoromethylbenzaldehyde (15.3 g) and ammonium acetate (45.1 g).

Starting Material Synthetic Example 97

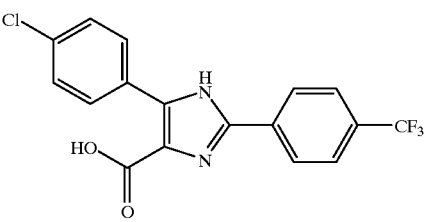

In the same manner as in Starting Material Synthetic Example 62, 5-(4-chlorophenyl)-2-(4-trifluoromethylphenyl)imidazole-4-carboxyic acid (8.9 g), melting point 178–180° C. (decomposition), was obtained from ethyl 5-(4-chlorophenyl)-2-(4-trifluoromethyl-phenyl)imidazole-4-carboxylate (9.0 g).

Starting Material Synthetic Example 98

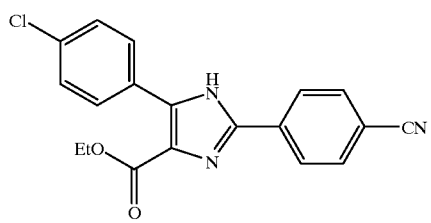

In the same manner as in Starting Material Synthetic Example 61, ethyl 5-(4-chlorophenyl)-2-(4-cyanophenyl)imidazole-4-carboxylate (3.6 g), melting point 235–237° C., was obtained from ethyl 3-(4-chlorophenyl)-2-hydroxyimino-3-oxopropionate (10.0 g), 4-cyanobenzaldehyde (7.7 g) and ammonium acetate (30.8 g).

Starting Material Synthetic Example 99

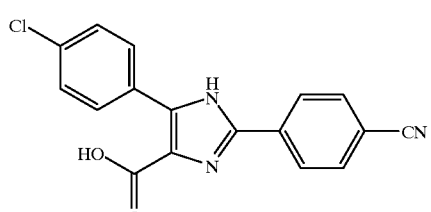

In the same manner as in Starting Material Synthetic Example 62, 5-(4-chlorophenyl)-2-(4-cyanophenyl)imidazole-4-carboxyic acid (3.1 g), melting point 187–188° C. (decomposition), was obtained from ethyl 5-(4-chlorophenyl)-2-(4-cyanophenyl)imidazole-4-carboxylate (3.0 g).

Starting Material Synthetic Example 100

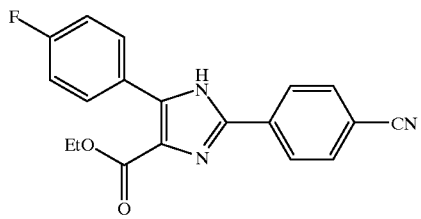

In the same manner as in Starting Material Synthetic Example 61, ethyl 5-(4-fluorophenyl)-2-(4-cyanophenyl) imidazole-4-carboxylate (3.1 g), melting point 208–211° C., was obtained from ethyl 3-(4-fluorophenyl)-2-hydroxyimino-3-oxopropionate (15.0 g), 4-cyanobenzaldehyde (12.3 g) and ammonium acetate (48.4 g).

Starting Material Synthetic Example 101

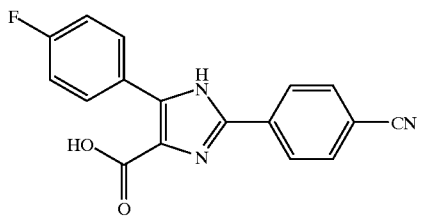

In the same manner as in Starting Material Synthetic Example 62, 2-(4-cyanophenyl)-5-(4-fluorophenyl) imidazole-4-carboxyic acid (2.1 g), melting point 193–194° C. (decomposition), was obtained from ethyl 5-(4-fluorophenyl)-2-(4-cyanophenyl)imidazole-4-carboxylate (3.0 g).

Starting Material Synthetic Example 102

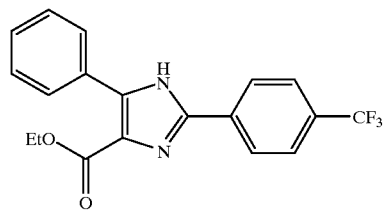

In the same manner as in Starting Material Synthetic Example 61, ethyl 5-phenyl-2-(4-trifluoromethylphenyl) imidazole-4-carboxylate (3.6 g), melting point 173–174° C., was obtained from ethyl 2-hydroxyimino-3-oxo-3-phenylpropionate (2.5 g), 4-trifluoro-methylbenzaldehyde (9.5 g) and ammonium acetate (28.2 g).

Starting Material Synthetic Example 103

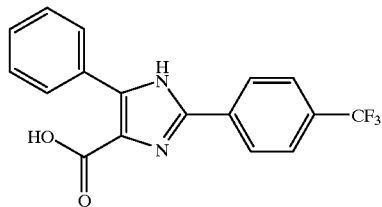

In the same manner as in Starting Material Synthetic Example 62, 5-phenyl-2-(4-trifluoromethylphenyl) imidazole-4-carboxyic acid (3.1 g), melting point 209–210° C. (decomposition), was obtained from ethyl 5-phenyl-2-(4-trifluoromethylphenyl)imidazole-4-carboxylate (3.5 g).

Starting Material Synthetic Example 104

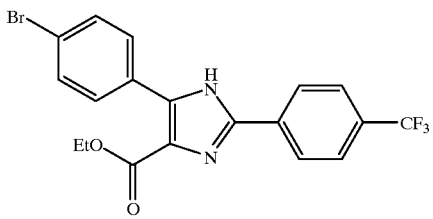

In the same manner as in Starting Material Synthetic Example 61, ethyl 5-(4-bromophenyl)-2-(4-trifluoromethylphenyl)imidazole-4-carboxylate (4.2 g), melting point 167–168° C., was obtained from ethyl 3-(4-bromophenyl)-2-hydroxyimino-3-oxopropionate (10.0 g), 4-trifluoromethylbenzaldehyde (8.7 g) and ammonium acetate (25.6 g).

Starting Material Synthetic Example 105

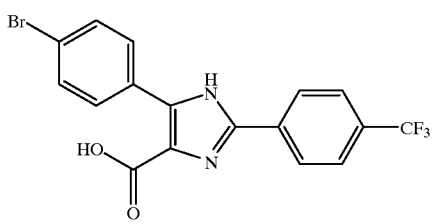

In the same manner as in Starting Material Synthetic Example 62, 5-(4-bromophenyl)-2-(4-trifluoromethylphenyl)imidazole-4-carboxyic acid (3.7 g), melting point 179–180° C. (decomposition), was obtained from ethyl 5-(4-bromophenyl)-2-(4-trifluoromethylphenyl)-imidazole-4-carboxylate (4.0 g).

Starting Material Synthetic Example 106

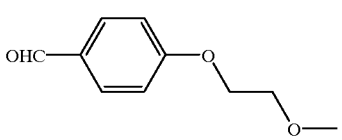

4-Hydroxybenzaldehyde (300 g) and 2-chloroethyl methyl ether (279 g) were dissolved in DMF (3 L) and potassium carbonate (408 g) was added. The mixture was stirred with heating at 60° C. for 16 hr. After the reaction, the reaction mixture was poured into water and liberated oil was extracted with ethyl acetate. The organic layer was washed with 1N aqueous sodium hydroxide solution and washed with saturated brine. The organic layer was dried over anhydrous magnesium sulfate. After drying, the residue was concentrated under reduced pressure to give 4-(2-methoxyethoxy)benzaldehyde as an oil (212 g).

$^1$H-NMR 270 MHz (CDCl$_3$, ppm) δ: 9.87(1H, s), 7.82 (2H, d), 7.02(2H, d), 4.18(2H, m), 3.77(2H, m), 3.44(3H, s).

Starting Material Synthetic Example 107

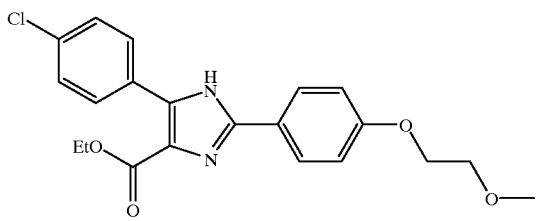

In the same manner as in Starting Material Synthetic Example 61, ethyl 5-(4-chlorophenyl)-2-[4-(2-methoxyethoxy)phenyl]-imidazole-4-carboxylate (62.1 g), melting point 157–158° C., was obtained from ethyl 3-(4-chlorophenyl)-2-hydroxyimino-3-oxopropionate (150 g), 4-(2-methoxyethoxy)benzaldehyde (165 g) and ammonium acetate (447 g).

Starting Material Synthetic Example 108

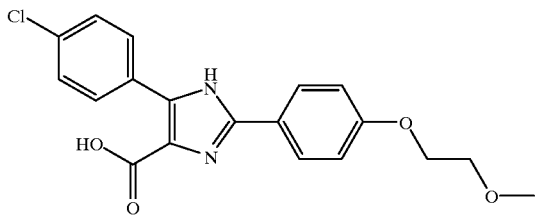

In the same manner as in Starting Material Synthetic Example 62, 5-(4-chlorophenyl)-2-[4-(2-methoxyethoxy)phenyl]imidazole-4-carboxyic acid (52 g), melting point 142–143° C. (decomposition), was obtained from ethyl 5-(4-chlorophenyl)-2-[4-(2-methoxyethoxy)-phenyl]imidazole-4-carboxylate (62 g).

Starting Material Synthetic Example 109

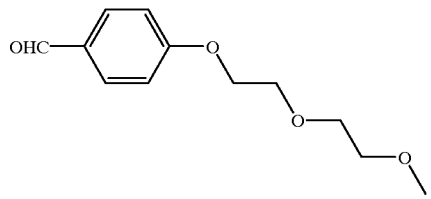

In the same manner as in Starting Material Synthetic Example 104, 4-[2-(2-methoxyethoxy)ethoxy]benzaldehyde (10 g) was obtained as an oil from 4-hydroxybenzaldehyde (10 g), 2-(2-chloroethoxy)ethyl methyl ether (9.0 g) and potassium carbonate (13.5 g).

$^1$H-NMR 270 MHz (CDCl$_3$, ppm) δ: 9.88(1H, s), 7.82 (2H, d), 7.01(2H, d), 4.22(2H, t), 3.89(2H, t), 3.54–3.78(7H, m).

Starting Material Synthetic Example 110

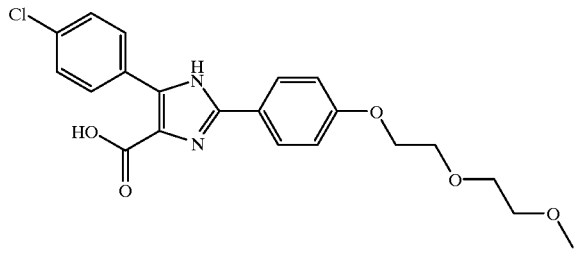

In the same manner as in Starting Material Synthetic Example 61, ethyl 5-(4-chlorophenyl)-2-{4-[2-(2-methoxyethoxy)ethoxy]-phenyl}imidazole-4-carboxylate (2.3 g), melting point 132–133° C., was obtained from ethyl 3-(4-chlorophenyl)-2-hydroxyimino-3-oxopropionate (8.8 g), 4-[2-(2-methoxyethoxy)ethoxy]benzaldehyde (10.2 g) and ammonium acetate (26.6 g).

Starting Material Synthetic Example 111

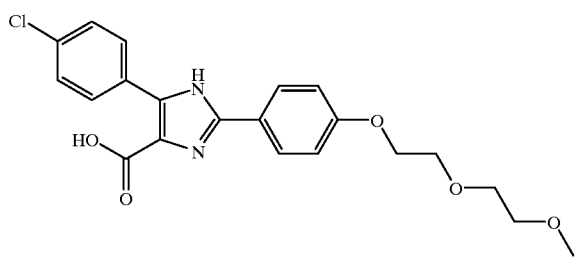

In the same manner as in Starting Material Synthetic Example 62, 5-(4-chlorophenyl)-2-{4-[2-(2-methoxyethoxy)ethoxy]-phenyl}imidazole-4-carboxyic acid (1.3 g), melting point 142-143° C. (decomposition), was obtained from ethyl 5-(4-chlorophenyl)-2-{4-[2-(2-methoxyethoxy)ethoxy]phenyl}imidazole-4-carboxylate (2.0 g).

Starting Material Synthetic Example 112

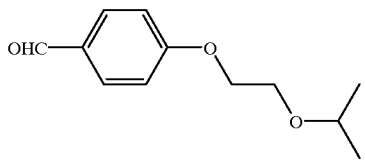

In the same manner as in Starting Material Synthetic Example 104, 4-(2-isopropoxyethoxy)benzaldehyde (8.3 g) was obtained from 4-hydroxybenzaldehyde (13.9 g), 2-chloroethyl isopropyl ether (14 g) and potassium carbonate (15.8 g).

$^1$H-NMR 270 MHz (CDCl$_3$, ppm) δ: 9.88(1H, s), 7.82 (2H, d), 7.02(2H, d), 4.19(2H, t), 3.80(2H, t), 3.62–3.82(1H, m), 1.20(6H, d).

Starting Material Synthetic Example 113

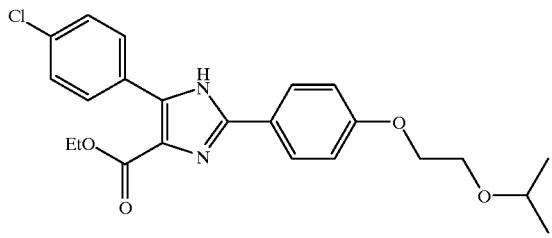

In the same manner as in Starting Material Synthetic Example 61, ethyl 5-(4-chlorophenyl)-2-[4-(2-isopropoxyethoxy)phenyl]-imidazole-4-carboxylate (3.58 g), melting point 155–158° C., was obtained from ethyl 3-(4-chlorophenyl)-2-hydroxyimino-3-oxopropionate (6.3 g), 4-(2-isopropoxyethoxy)benzaldehyde (8.3 g) and ammonium acetate (20.5 g).

Starting Material Synthetic Example 114

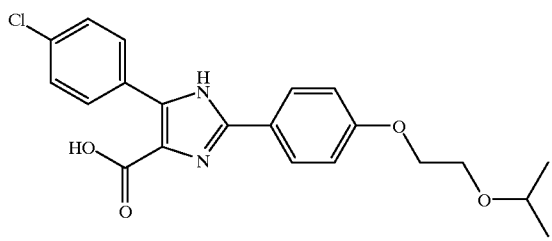

In the same manner as in Starting Material Synthetic Example 62, 5-(4-chlorophenyl)-2-[4-(2-isopropoxyethoxy)phenyl]imidazole-4-carboxyic acid (3.24 g), melting point 180° C. (decomposition), was obtained from ethyl 5-(4-chlorophenyl)-2-[4-(2-isopropoxyethoxy)-phenyl]imidazole-4-carboxylate (3.58 g).

Starting Material Synthetic Example 115

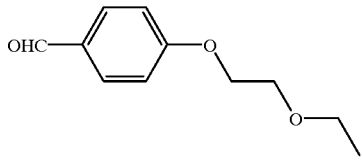

In the same manner as in Starting Material Synthetic Example 104, 4-(2-ethoxyethoxy)benzaldehyde (12.4 g) was obtained from 4-hydroxybenzaldehyde (24.4 g), 2-chloroethyl ethyl ether (21.7 g) and potassium carbonate (28 g).

$^1$H-NMR 270 MHz (CDCl$_3$, ppm) δ: 9.88(1H, s), 7.83 (2H, d), 7.03(2H, d), 4.21(2H, t), 3.82(2H, t), 3.57–3.65(2H, q), 1.25(6H, t).

Starting Material Synthetic Example 116

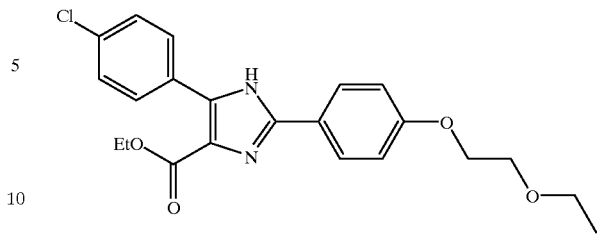

In the same manner as in Starting Material Synthetic Example 61, ethyl 5-(4-chlorophenyl)-2-[4-(2-ethoxyethoxy)phenyl]-imidazole-4-carboxylate (5.2 g), melting point 150–152° C., was obtained from ethyl 3-(4-chlorophenyl)-2-hydroxyimino-3-oxopropionate (10.9 g), 4-(2-ethoxyethoxy)benzaldehyde (12.4 g) and ammonium acetate (33 g).

Starting Material Synthetic Example 117

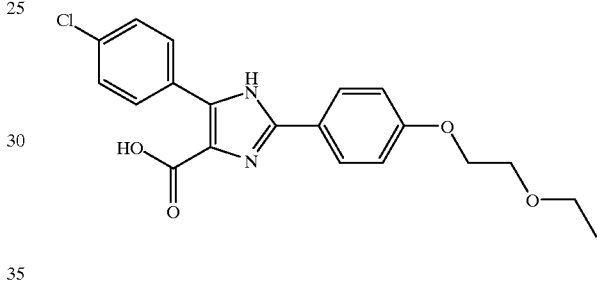

In the same manner as in Starting Material Synthetic Example 62, 5-(4-chlorophenyl)-2-[4-(2-ethoxyethoxy) phenyl]imidazole-4-carboxyic acid (5.0 g), melting point 145–150° C. (decomposition), was obtained from ethyl 5-(4-chlorophenyl)-2-[4-(2-ethoxyethoxy)-phenyl] imidazole-4-carboxylate (5.2 g).

Starting Material Synthetic Example 118

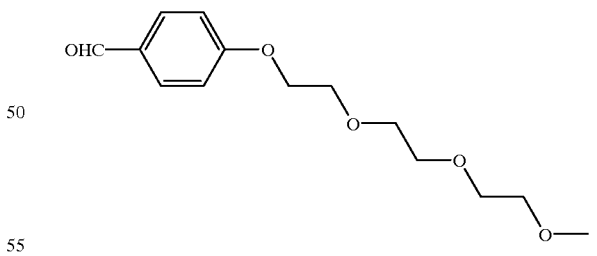

In the same manner as in Starting Material Synthetic Example 104, 4-{2-[2-(2-methoxyethoxy)ethoxy] ethoxy}benzaldehyde (18.7 g) was obtained from 4-hydroxybenzaldehyde (16.8 g), 2-[2-(2-chloroethoxy) ethoxy]ethyl methyl ether (25.24 g) and potassium carbonate (19 g).

$^1$H-NMR 270 MHz (CDCl$_3$, ppm) δ: 9.88(1H, s), 7.83 (2H, d), 7.02(2H, d), 4.22(2H, t), 3.89(2H, t), 3.54–3.78 (11H, m).

Starting Material Synthetic Example 119

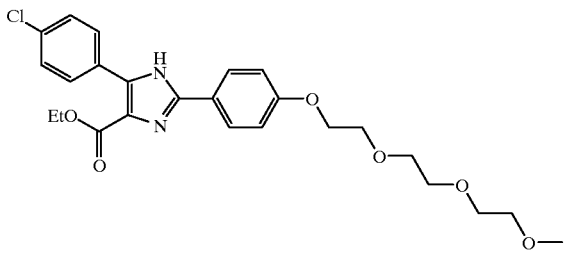

In the same manner as in Starting Material Synthetic Example 61, ethyl 5-(4-chlorophenyl)-2-(4-{2-[2-(2-methoxyethoxy)ethoxy]-ethoxy}phenyl)imidazole-4-carboxylate (6.3 g), melting point 90° C., was obtained from ethyl 3-(4-chlorophenyl)-2-hydroxyimino-3-oxopropionate (10.5 g), 4-{2-[2-(2-methoxyethoxy)ethoxy]ethoxy}-benzaldehyde (18.7 g) and ammonium acetate (31.6 g).

Starting Material Synthetic Example 120

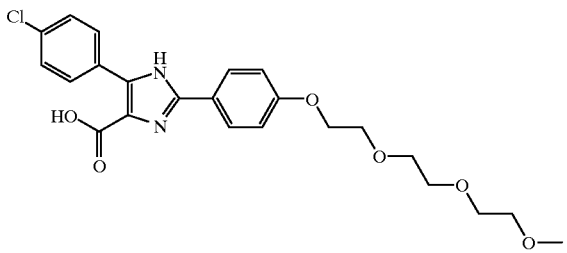

In the same manner as in Starting Material Synthetic Example 62, 5-(4-chlorophenyl)-2-(4-{2-[2-(2-methoxyethoxy)ethoxy]ethoxy}-phenyl)imidazole-4-carboxyic acid (5.7 g) was obtained from ethyl 5-(4-chlorophenyl)-2-(4-{2-[2-(2-methoxyethoxy)ethoxy]ethoxy}-phenyl)imidazole-4-carboxylate (6.3 g).

$^1$H-NMR 270 MHz (CDCl$_3$, ppm) δ: 10.7–11.4(2H, br), 7.80–7.98(4H, m), 7.12–7.39(2H, m), 6.70(2H, br), 3.24–3.92(15H, m).

Starting Material Synthetic Example 121

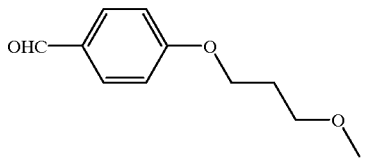

In the same manner as in Starting Material Synthetic Example 104, 4-(3-methoxypropoxy)benzaldehyde (4.79 g) was obtained from 4-hydroxybenzaldehyde (14.4 g), 3-chloropropylmethylether (12.8 g) and potassium carbonate (16.3 g).

$^1$H-NMR 270 MHz (CDCl$_3$, ppm) δ: 9.88(1H, s), 7.83 (2H, d), 7.01(2H, d), 4.15(2H, t), 3.56(2H, t), 3.36(3H, s), 2.08(2H, dt).

Starting Material Synthetic Example 122

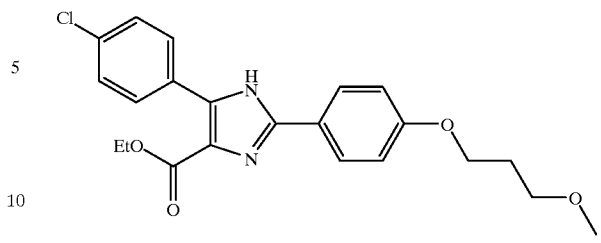

In the same manner as in Starting Material Synthetic Example 61, the objective ethyl 5-(4-chlorophenyl)-2-[4-(3-methoxypropoxy)phenyl]imidazole-4-carboxylate (2 g), melting point 179–180° C., was obtained from ethyl 3-(4-chlorophenyl)-2-hydroxyimino-3-oxopropionate (4.2 g), 4-(3-methoxypropoxy)-benzaldehyde (4.79 g) and ammonium acetate (12.7 g).

Starting Material Synthetic Example 123

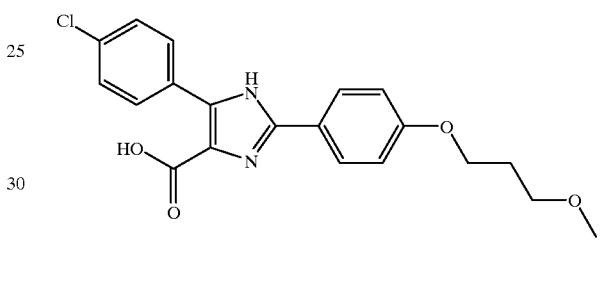

In the same manner as in Starting Material Synthetic Example 62, 5-(4-chlorophenyl)-2-[4-(3-methoxypropoxy) phenyl]imidazole-4-carboxyic acid (1.87 g), melting point 135–140° C. (decomposition), was obtained from ethyl 5-(4-chlorophenyl)-2-[4-(3-methoxypropoxy)-phenyl] imidazole-4-carboxylate (2 g).

Starting Material Synthetic Example 124

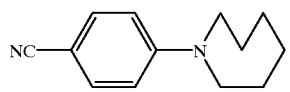

In the same manner as in Starting Material Synthetic Example 68, the objective 4-(homopiperidin-1-yl) benzonitrile (24.5 g), melting point 62° C., was obtained from 4-fluorobenzonitrile (50 g) and hexamethyleneimine (39.6 g).

Starting Material Synthetic Example 125

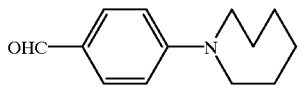

In the same manner as in Starting Material Synthetic Example 69, the objective 4-(homopiperidin-1-yl) benzaldehyde (45 g) was obtained as an oil from 4-(homopiperidin-1-yl)benzonitrile (54 g) and, without purification, used in the next Starting Material Synthetic Example 67.

Starting Material Synthetic Example 126

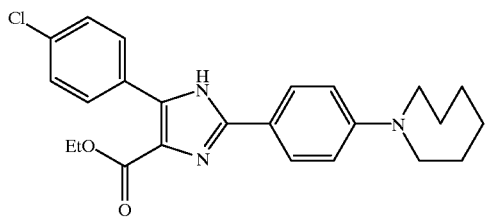

In the same manner as in Starting Material Synthetic Example 61, ethyl 5-(4-chlorophenyl)-2-[4-(homopiperidin-1-yl)phenyl]-imidazole-4-carboxylate (9.5 g), melting point 203–204° C., was obtained from ethyl 3-(4-chlorophenyl)-2-hydroxyimino-3-oxopropionate (37.7 g), unpurified 4-(homopiperidin-1-yl)benzaldehyde (45.0 g) obtained in Starting Material Synthetic Example 123 and ammonium acetate (113.6 g).

Starting Material Synthetic Example 127

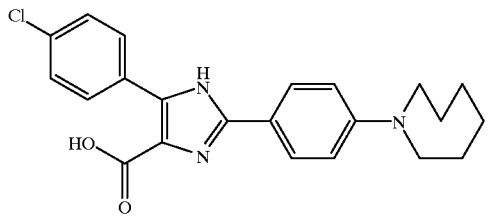

In the same manner as in Starting Material Synthetic Example 62, 5-(4-chlorophenyl)-2-[4-(homopiperidin-1-yl)phenyl]imidazole-4-carboxyic acid (2.5 g), melting point 208° C. (decomposition), was obtained from ethyl 5-(4-chlorophenyl)-2-[4-(homopiperidin-1-yl)phenyl]imidazole-4-carboxylate (9.0 g).

Starting Material Synthetic Example 128

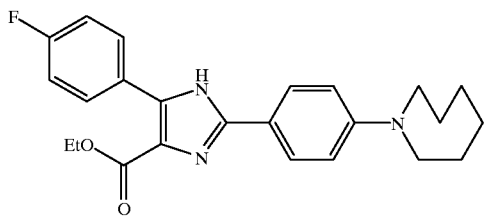

In the same manner as in Starting Material Synthetic Example 61, ethyl 5-(4-fluorophenyl)-2-[4-(homopiperidin-1-yl)phenyl]-imidazole-4-carboxylate is obtained from ethyl 3-(4-fluorophenyl)-2-hydroxyimino-3-oxopropionate, unpurified 4-(homopiperidin-1-yl)benzaldehyde obtained in Starting Material Synthetic Example 123 and ammonium acetate.

Starting Material Synthetic Example 129

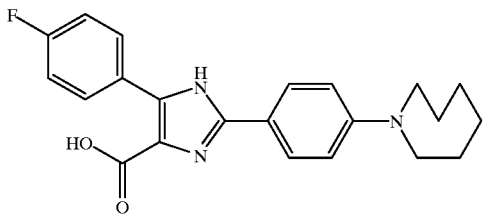

In the same manner as in Starting Material Synthetic Example 62, 5-(4-fluorophenyl)-2-[4-(homopiperidin-1-yl)phenyl]imidazole-4-carboxylic acid is obtained from ethyl 5-(4-fluorophenyl)-2-[4-(homopiperidin-1-yl)phenyl]imidazole-4-carboxylate.

Starting Material Synthetic Example 130

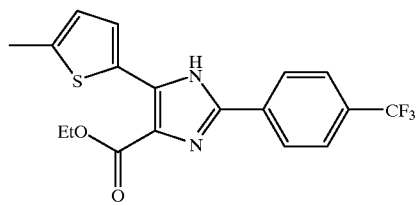

In the same manner as in Starting Material Synthetic Example 61, ethyl 5-(5-methylthiophen-2-yl)-2-(4-trifluoromethylphenyl)-imidazole-4-carboxylate (3.3 g), melting point 176–177° C., was obtained from ethyl 3-(5-methylthiophen-2-yl)-2-hydroxyimino-3-oxopropionate (15.3 g), 4-trifluoromethylbenzaldehyde (18.5 g) and ammonium acetate (48.9 g).

Starting Material Synthetic Example 131

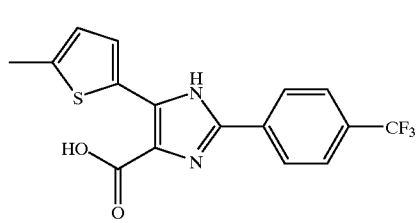

In the same manner as in Starting Material Synthetic Example 62, 5-(5-methylthiophen-2-yl)-2-(4-trifluoromethylphenyl)-imidazole-4-carboxyic acid (2.6 g), melting point 154° C. (decomposition), was obtained from ethyl 5-(5-methylthiophen-2-yl)-2-(4-trifluoromethylphenyl)imidazole-4-carboxylate (4.0 g).

Starting Material Synthetic Example 132

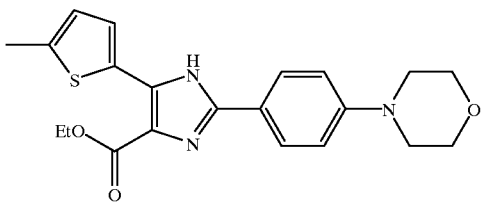

In the same manner as in Starting Material Synthetic Example 61, ethyl 5-(5-methylthiophen-2-yl)-2-(4-morpholinophenyl)-imidazole-4-carboxylate is obtained from ethyl 3-(5-methylthiophen-2-yl)-2-hydroxyimino-3-oxopropionate, 4-morpholinobenzaldehyde obtained in Starting Material Synthetic Example 60 and ammonium acetate.

Starting Material Synthetic Example 133

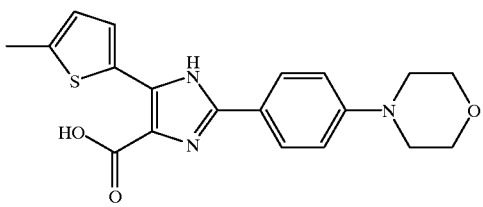

In the same manner as in Starting Material Synthetic Example 62, 5-(5-methylthiophen-2-yl)-2-(4-morpholinophenyl)imidazole-4-carboxylic acid is obtained from ethyl 5-(5-methylthiophen-2-yl)-2-(4-morpholinophenyl)imidazole-4-carboxylate.

Starting Material Synthetic Example 134

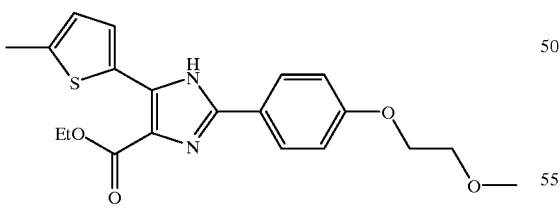

In the same manner as in Starting Material Synthetic Example 61, ethyl 2-[4-(2-methoxyethoxy)phenyl]-5-(5-methylthiophen-2-yl)-imidazole-4-carboxylate is obtained from ethyl 3-(5-methylthiophen-2-yl)-2-hydroxyimino-3-oxopropionate, 4-(2-methoxyethoxy)benzaldehyde obtained in Starting Material Synthetic Example 106 and ammonium acetate.

Starting Material Synthetic Example 135

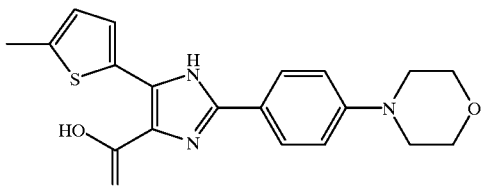

In the same manner as in Starting Material Synthetic Example 62, 2-[4-(2-methoxyethoxy)phenyl]-5-(5-methylthiophen-2-yl)-imidazole-4-carboxylic acid is obtained from ethyl 2-[4-(2-methoxyethoxy)phenyl]-5-(5-methylthiophen-2-yl)-imidazole-4-carboxylate.

Starting Material Synthetic Example 136

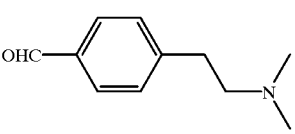

2-(4-Bromophenyl)-N,N-dimethylethylamine (6.8 g) was refluxed under heating with magnesium for 1 hr to prepare a Grignard reagent, which was reacted with DMF to give the objective 4-(2-dimethylaminoethyl)benzaldehyde as an oil (4.2 g).

$^1$H-NMR 270 MHz (CDCl$_3$, ppm) δ: 9.87(1H, s), 7.82 (2H, d), 7.02(2H, d), 4.18(2H, m), 3.77(2H, m), 3.44(3H, s)

Starting Material Synthetic Example 137

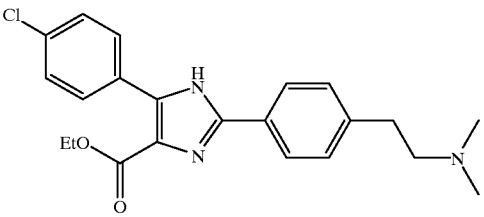

In the same manner as in Starting Material Synthetic Example 61, ethyl 5-(4-chlorophenyl)-2-[4-(2-dimethylaminoethyl)phenyl]-imidazole-4-carboxylate (0.6 g), melting point 128–129° C., was obtained from ethyl 3-(4-chlorophenyl)-2-hydroxyimino-3-oxopropionate (4.0 g), 4-(2-dimethylaminoethyl)benzaldehyde (4.2 g) and ammonium acetate (12.0 g).

Starting Material Synthetic Example 138

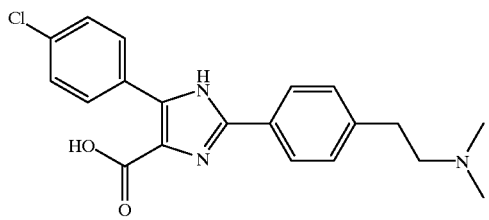

In the same manner as in Starting Material Synthetic Example 62, 5-(4-chlorophenyl)-2-[4-(2-dimethylaminoethyl)phenyl]-imidazole-4-carboxylic acid is obtained from ethyl 5-(4-chlorophenyl)-2-[4-(2-dimethylaminoethyl)phenyl]imidazole-4-carboxylate.

Starting Material Synthetic Example 139

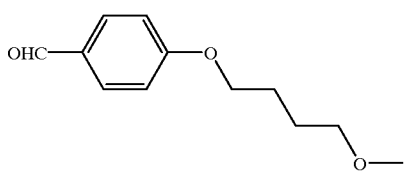

In the same manner as in Starting Material Synthetic Example 106, 4-(4-methoxybutoxy)benzaldehyde is obtained from 4-hydroxybenzaldehyde, 4-chlorobutyl methyl ether and potassium carbonate.

Starting Material Synthetic Example 140

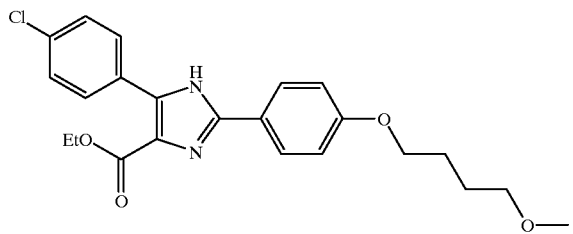

In the same manner as in Starting Material Synthetic Example 61, ethyl 5-(4-chlorophenyl)-2-[4-(4-methoxybutoxy)phenyl]-imidazole-4-carboxylate is obtained from ethyl 3-(4-chlorophenyl)-2-hydroxyimino-3-oxopropionate, 4-(4-methoxybutoxy)benzaldehyde and ammonium acetate.

Starting Material Synthetic Example 141

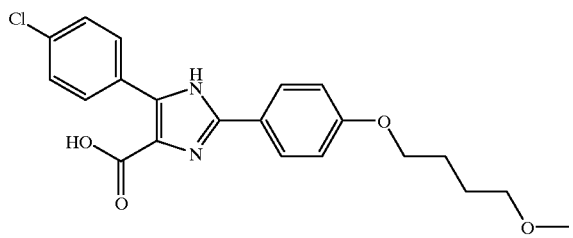

In the same manner as in Starting Material Synthetic Example 62, 5-(4-chlorophenyl)-2-[4-(4-methoxybutoxy) phenyl]imidazole-4-carboxylic acid is obtained from ethyl 5-(4-chlorophenyl)-2-[4-(4-methoxybutoxy)phenyl] imidazole-4-carboxylate.

Starting Material Synthetic Example 142

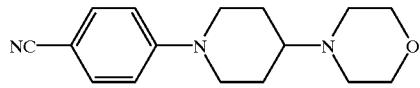

In the same manner as in Starting Material Synthetic Example 68, the objective 4-(4-morpholinopiperidin-1-yl) benzonitrile (23.1 g), melting point 123–128° C., was obtained from 4-fluorobenzonitrile (11.9 g) and 4-morpholinopiperidine (16.7 g).

Starting Material Synthetic Example 143

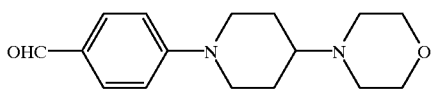

In the same manner as in Starting Material Synthetic Example 69, the objective 4-(4-morpholinopiperidin-1-yl) benzaldehyde (21 g), melting point 130° C., was obtained from 4-(4-morpholinopiperidin-1-yl)benzonitrile (23.1 g).

Starting Material Synthetic Example 144

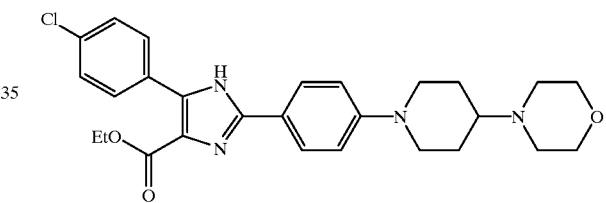

In the same manner as in Starting Material Synthetic Example 61, the objective ethyl 5-(4-chlorophenyl)-2-[4-(4-morpholinopiperidin-1-yl)phenyl]imidazole-4-carboxylate (6.2 g), melting point 228–231° C., was obtained from ethyl 3-(4-chlorophenyl)-2-hydroxyimino-3-oxopropionate (6.2 g), 4-(4-morpholinopiperidin-1-yl)benzaldehyde (10 g) and ammonium acetate (18.7 g).

Starting Material Synthetic Example 145

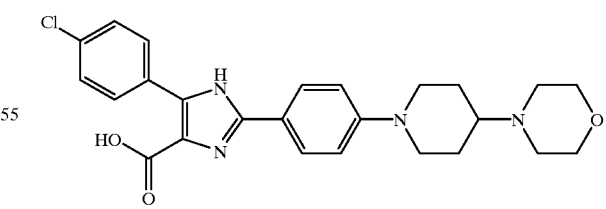

In the same manner as in Starting Material Synthetic Example 62, 5-(4-chlorophenyl)-2-[4-(4-morpholinopiperidin-1-yl)phenyl]imidazole-4-carboxyic acid (5.6 g), melting point 180–185° C. (decomposition), was obtained from ethyl 5-(4-chlorophenyl)-2-[4-(4-morpholinopiperidin-1-yl)phenyl]imidazole-4-carboxylate (6.2 g).

Starting Material Synthetic Example 146

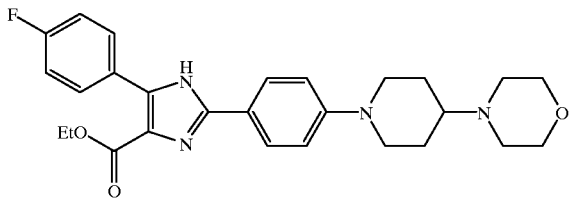

In the same manner as in Starting Material Synthetic Example 61, ethyl 5-(4-fluorophenyl)-2-[4-(4-morpholinopiperidin-1-yl)phenyl]imidazole-4-carboxylate is obtained from ethyl 3-(4-fluorophenyl)-2-hydroxyimino-3-oxopropionate, 4-(4-morpholinopiperidin-1-yl)benzaldehyde and ammonium acetate.

Starting Material Synthetic Example 147

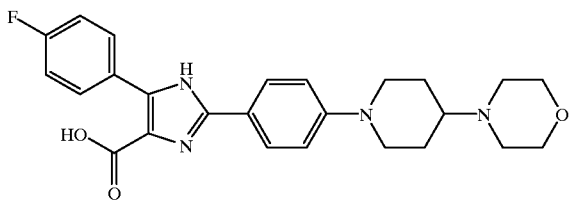

In the same manner as in Starting Material Synthetic Example 62, 5-(4-fluorophenyl)-2-[4-(4-morpholinopiperidin-1-yl)phenyl]-imidazole-4-carboxylic acid is obtained from ethyl 5-(4-fluorophenyl)-2-[4-(4-morpholinopiperidin-1-yl)phenyl]imidazole-4-carboxylate.

Starting Material Synthetic Example 148

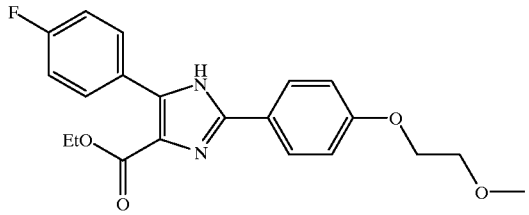

In the same manner as in Starting Material Synthetic Example 61, ethyl 5-(4-fluorophenyl)-2-[4-(2-methoxyethoxy)phenyl]-imidazole-4-carboxylate (7.2 g), meltingpoint 183-184° C., was obtained from ethyl 3-(4-fluorophenyl)-2-hydroxyimino-3-oxopropionate (15.0 g), 4-(2-methoxyethoxy)-benzaldehyde (16.9 g) obtained in Starting Material Synthetic Example 106 and ammonium acetate (48.3 g).

Starting Material Synthetic Example 149

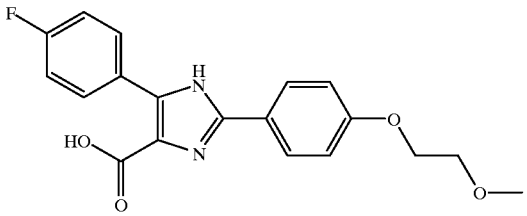

In the same manner as in Starting Material Synthetic Example 62, 5-(4-fluorophenyl)-2-[4-(2-methoxyethoxy)phenyl]imidazole-4-carboxyic acid (5.1g), melting point 138–140° C., was obtained fromethyl 5-(4-fluorophenyl)-2-[4-(2-methoxyethoxy)phenyl]imidazole-4-carboxylate (7.2 g).

Starting Material Synthetic Example 150

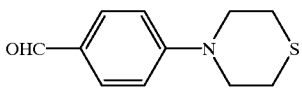

In the same manner as in Starting Material Synthetic Example 60, 4-(thiomorpholin-4-yl)benzaldehyde is obtained from N-phenylthiomorpholine and phosphorus oxychloride.

Starting Material Synthetic Example 151

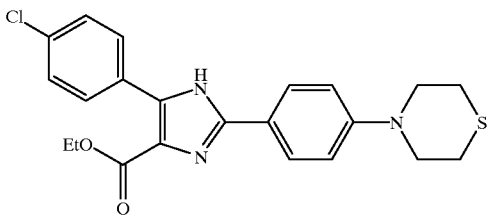

In the same manner as in Starting Material Synthetic Example 61, ethyl 5-(4-chlorophenyl)-2-[4-(thiomorpholin-4-yl)phenyl]-imidazole-4-carboxylate is obtained from ethyl 3-(4-chlorophenyl)-2-hydroxyimino-3-oxopropionate, 4-(thiomorpholin-4-yl)benzaldehyde and ammonium acetate.

Starting Material Synthetic Example 152

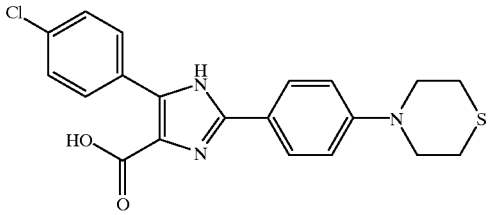

In the same manner as in Starting Material Synthetic Example 62, 5-(4-chlorophenyl)-2-[4-(thiomorpholin-4-yl)phenyl]imidazole-4-carboxylic acid is obtained from ethyl 5-(4-chlorophenyl)-2-[4-(thiomorpholin-4-yl)phenyl]imidazole-4-carboxylate.

Starting Material Synthetic Example 153

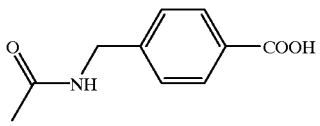

4-(Aminomethyl)benzoic acid (20.46 g) was dissolved in ethyl acetate (100 ml) and thereto were added 3N aqueous sodium hydroxide solution (100 ml) and then acetic anhydride (14 ml) at 5–7° C. The reaction mixture was stirred at room temperature for 1 hr and acidified with 10% hydrochloric acid. The mixture was extracted (100 ml×5) with ethyl acetate:ethanol (10:1). The extract was washed with saturated brine and dried over anhydrous sodium sulfate. The solvent was evaporated to give a pale-yellow solid (27.2 g). The obtained solid was crystallized from ethyl acetate:ethanol (1:1500 ml) to give the objective 4-acetamidomethylbenzoate (16.7 g) as white crystals, melting point 200–202° C.

Starting Material Synthetic Example 154

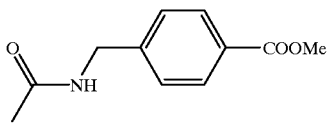

4-Acetamidomethylbenzoate (4.0 g) was dissolved in a 0.5% hydrogen chloride—methanol solution (100 ml). The reaction mixture was stirred at 40° C. for 3.5 hr, poured into ice water (300 ml) and extracted with ethyl acetate (100 ml×4). The extract was washed with saturated aqueous hydrogencarbonate solution and saturated brine and dried over anhydrous sodium sulfate. The solvent was evaporated to give a pale-yellow solid (4.3 g). The obtained solid was crystallized from ethyl acetate (50 ml) to give the objective methyl 4-acetamidomethylbenzoate (3.2 g) as pale-yellow crystals, melting point 110–111° C.

Starting Material Synthetic Example 155

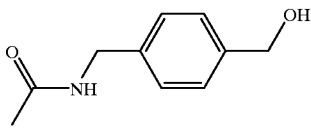

To a suspension of lithium aluminum hydride (570 mg) in THF (80 ml) was added a solution of methyl 4-acetamidomethylbenzoate (3.1 g) in THF (20 ml) under ice-cooling. The reaction mixture was stirred at room temperature for 1.5 hr. A saturated aqueous sodium sulfate solution (7 ml) was added at 10° C., and the mixture was stirred at room temperature for 1 hr. The precipitate was collected by filtration and the solvent was evaporated to give the objective N-(4-hydroxymethylphenylmethyl)acetamide (2.8 g) as a white solid.

$^1$H-NMR 270 MHz (DMSO-D$_6$, ppm) δ: 1.86(3H, s), 4.22(2H, d), 4.46(2H, s), 5.13(1H, br.s), 7.19(2H, d), 7.25 (2H, d), 8.30(1H, m).

Starting Material Synthetic Example 156

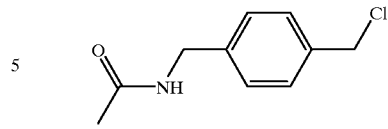

To a solution of N-(4-hydroxymethylphenylmethyl) acetamide (1.5 g) in chloroform (50 ml) was added thionyl chloride (0.73 ml) and the mixture was refluxed under heating for 1 hr. The solvent was evaporated and the obtained residue was crystallized from ethyl acetate to give the objective N-(4-chloromethylphenylmethyl)acetamide (1.8 g) as pale-yellow crystals, melting point 116–118° C.

Starting Material Synthetic Example 157

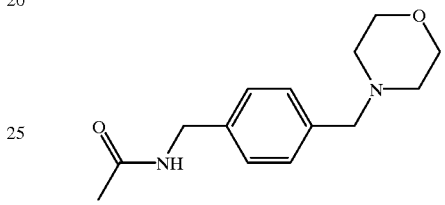

N-(4-Chloromethylphenylmethyl)acetamide (19.7 g) and orpholine (10.5 ml) were dissolved in DMF (190 ml), and potassium carbonate (13.8 g) was added. The mixture was stirred at 60° C. for 3 hr 20 min. The solvent was evaporated and toluene was added to the obtained residue. An insoluble solid was filtered off and the filtrate was concentrated under reduced pressure. The residue was subjected to silica gel column chromatography to give an oil (27 g). The obtained oil was dissolved in ethyl acetate (150 ml) and 14% hydrogen chloride ethanol solution was added under ice-cooling. The precipitated crystals were collected by filtration to give the objective N-(4-morpholinomethylphenylmethyl) acetamide hydrochloride (28.4 g), melting point 60° C.

Starting Material Synthetic Example 158

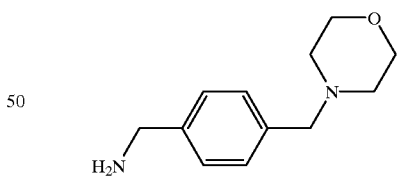

N-(4-Morpholinomethylphenylmethyl)acetamide hydrochloride (28.4 g) was dissolved in 4N hydrochloric acid (114 ml) and the mixture was refluxed under heating for 3 hr 15 min. The solvent was evaporated and ethyl acetate was added. The resulting crystals were collected by filtration. The obtained crystals were dissolved in water (40 ml) and potassium carbonate was added to saturation, and the mixture was extracted with chloroform. The extract was dried over anhydrous sodium sulfate and, after drying, the solvent was evaporated under reduced pressure to give the objective 4-(morpholinomethyl)phenylmethylamine (17.4 g), melting point 47–49° C.

Starting Material Synthetic Example 159

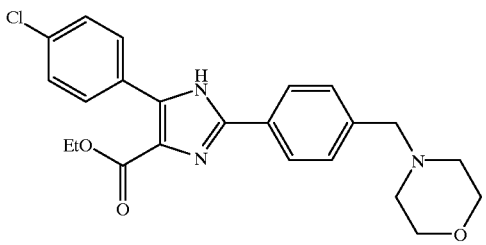

4-(Morpholinomethyl)phenylmethylamine (8 g) and ethyl 3-(4-chlorophenyl) -2-hydroxyimino-3-oxopropionate (8.26 g) were dissolved in pyridine (120 ml) and the mixture was refluxed under heating for 12 hr. The solvent was evaporated under reduced pressure and the obtained residue was subjected to silica gel column chromatography to give the objective ethyl 5-(4-chlorophenyl)-2-[4-(morpholinomethyl)phenyl]imidazole-4-carboxylate (8.46 g), melting point 183–185° C.

Starting Material Synthetic Example 160

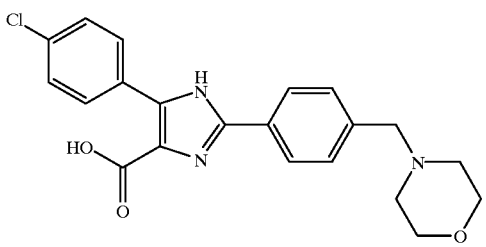

In the same manner as in Starting Material Synthetic Example 62, 5-(4-chlorophenyl)-2-[4-(morpholinomethyl)phenyl]imidazole-4-carboxyic acid (7.6 g), melting point 175–180° C. (decomposition), was obtained from ethyl 5-(4-chlorophenyl)-2-[4-(morpholinomethyl)-phenyl]imidazole-4-carboxylate (8.46 g).

Starting Material Synthetic Example 161

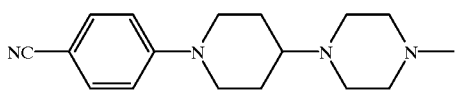

In the same manner as in Starting Material Synthetic Example 68, the objective 4-[4-(4-methylpiperazin-1-yl)piperidin-1yl]benzonitrile is obtained from 4-fluorobenzonitrile and 4-(4-methylpiperazin-1-yl)piperidine.

Starting Material Synthetic Example 162

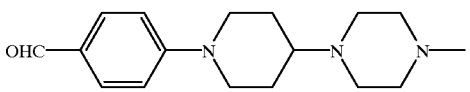

In the same manner as in Starting Material Synthetic Example 69, the objective 4-[4-(4-methylpiperazin-1-yl)piperidin-1-yl]benzaldehyde is obtained from 4-[4-(4-methylpiperazin-1-yl)piperidin-1-yl]benzonitrile.

Starting Material Synthetic Example 163

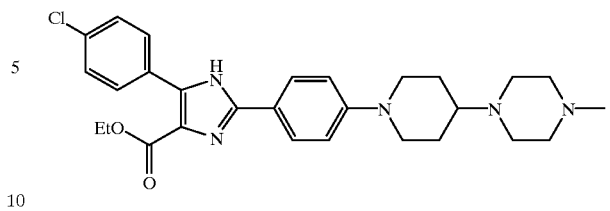

In the same manner as in Starting Material Synthetic Example 61, ethyl 5-(4-chlorophenyl)-2-{4-[4-(4-mfethylpiperazin-1-yl)piperidin-1-yl]phenyl}imidazole-4-carboxylate is obtained from ethyl 3-(4-chlorophenyl )-2-hydroxyimino-3-oxopropionate, 4-[4-(4-methylpiperazin-1-yl)piperidin-1-yl]benzaldehyde and ammonium acetate.

Starting Material Synthetic Example 164

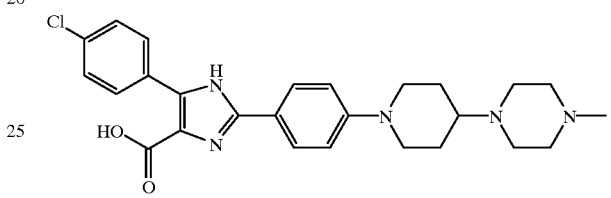

In the same manner as in Starting Material Synthetic Example 62, 5-(4-chlorophenyl)-2-{4-[4-(4-methylpiperazin-1-yl)piperidin-1-yl]phenyl}imidazole-4-carboxylic acid is obtained from ethyl 5-(4-chlorophenyl)-2-{4-[4-(4-methylpiperazin-1-yl)piperidin-1-yl]phenyl}imidazole-4-carboxylate.

Starting Material Synthetic Example 165

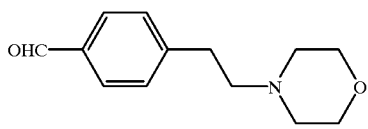

In the same manner as in Starting Material Synthetic Example 136, theobjective4-(2-morpholinoethyl)benzaldehyde is obtained from N-[2-(4-bromophenyl)ethyl]morpholine, magnesium and DMF.

Starting Material Synthetic Example 166

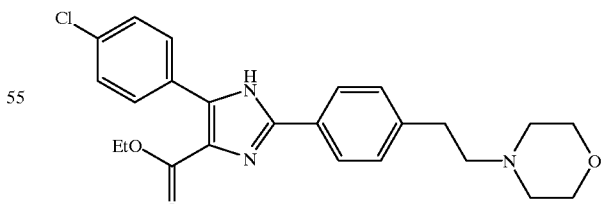

In the same manner as in Starting Material Synthetic Example 61, ethyl 5-(4-chlorophenyl)-2-[4-(2-morpholinoethyl)phenyl]-imidazole-4-carboxylate is obtained from ethyl 3-(4-chlorophenyl)-2-hydroxyimino-3-oxopropionate, 4-(2-morpholinoethyl)benzaldehyde and ammonium acetate.

Starting Material Synthetic Example 167

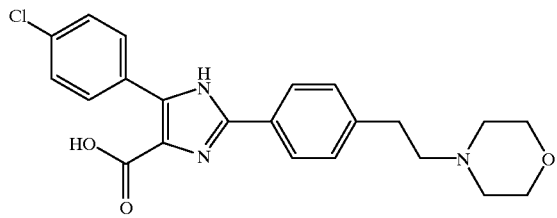

In the same manner as in Starting Material Synthetic Example 62, 5-(4-chlorophenyl)-2-[4-(2-morpholinoethyl)phenyl]imidazole-4-carboxylic acid is obtained from ethyl 5-(4-chlorophenyl)-2-[4-(2-morpholinoethyl)phenyl]imidazole-4-carboxylate.

Starting Material Synthetic Example 168

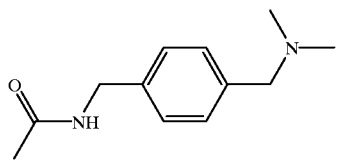

N-(4-Chloromethylphenylmethyl)acetamide (20.0 g) and dimethylamine hydrochloride (9.1 g) were dissolved in acetonitrile (190 ml), and potassium carbonate (28 g) was added. The mixture was refluxed under heating overnight. An insoluble solid was filtered off and the solvent was evaporated to give the objective N-(4-dimethylaminomethylphenylmethyl)acetamide (28.4 g) as an oil.

$^1$H-NMR 270 MHz (CDCl$_3$, ppm) δ: 1.99(3H, s), 2.02 (3H, s), 4.36(2H, s), 4.66(2H, s), 7.37(2H, d), 7.47(2H, d).

Starting Material Synthetic Example 169

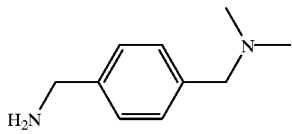

N-(4-Dimethylaminomethylphenylmethyl)acetamide (22 g) was dissolved in 4N hydrochloric acid (100 ml) and the mixture was refluxed under heating for 3 hr 40 min. The solvent was evaporated and ethyl acetate was added. The resulting crystals were collected by filtration. The obtained crystals were dissolved in water (40 ml) and potassium carbonate was added to saturation, and the mixture was extracted with chloroform. The extract was dried over anhydrous sodium sulfate and, after drying, the solvent was evaporated under reduced pressure to give the objective 4-(dimethylaminomethyl)phenylmethylamine (11.7 g), melting point 38–39° C.

Starting Material Synthetic Example 170

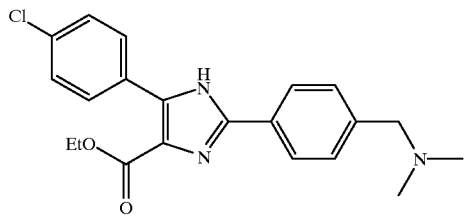

4-(Dimethylaminomethyl)phenylmethylamine (11.7 g) and ethyl 3-(4-chlorophenyl)-2-hydroxyimino-3-oxopropionate (15.1 g) were dissolved in pyridine (220 ml) and the solution was refluxed under heating for 12 hr. The solvent was concentrated under reduced pressure and the obtained residue was subjected to silica gel column chromatography to give the objective ethyl 5-(4-chlorophenyl)-2-[4-(dimethylaminomethyl)phenyl]imidazole-4-carboxylate (9.0 g), melting point 175–176° C.

Starting Material Synthetic Example 171

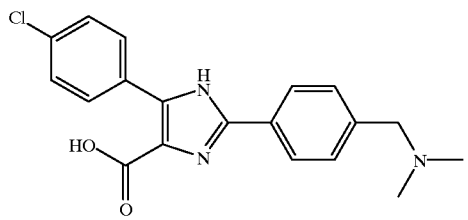

In the same manner as in Starting Material Synthetic Example 62, 5-(4-chlorophenyl)-2-[4-(dimethylaminomethyl)phenyl]imidazole-4-carboxyic acid (8.3 g), melting point 117–118° C., was obtained from ethyl 5-(4-chlorophenyl)-2-[4-(dimethylaminomethyl)phenyl]-imidazole-4-carboxylate (9.0 g).

Starting Material Synthetic Example 172

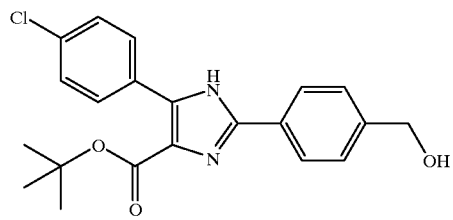

4-(Hydroxymethyl)phenylmethylamine and tert-butyl 3-(4-chlorophenyl)-2-hydroxyimino-3-oxopropionate are dissolved in pyridine, and the mixture is treated in the same manner as in Starting Material Synthetic Example 170 to give the objective tert-butyl 5-(4-chlorophenyl)-2-(4-hydroxymethylphenyl)imidazole-4-carboxylate.

Starting Material Synthetic Example 173

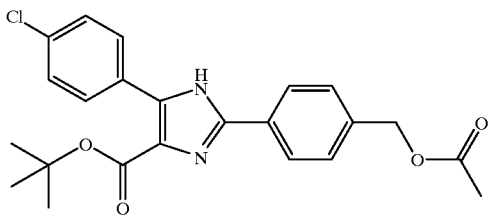

tert-Butyl 5-(4-chlorophenyl)-2-(4-hydroxymethylphenyl)-imidazole-4-carboxylate is dissolved in pyridine and reacted with acetic anhydride to give the objective tert-butyl 2-(4-acetoxymethylphenyl)-5-(4-chlorophenyl)imidazole-4-carboxylate.

Starting Material Synthetic Example 174

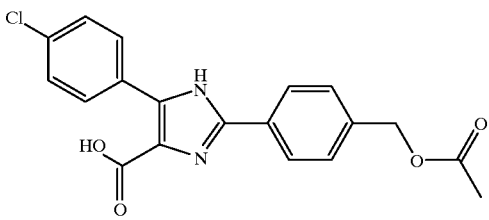

tert-Butyl 2-(4-acetoxymethylphenyl)-5-(4-chlorophenyl)-imidazole-4-carboxylate is dissolved in trifluoroacetic acid, and the solution is stirred at room temperature to give the objective 2-(4-acetoxymethylphenyl)-5-(4-chlorophenyl)imidazole-4-carboxylic acid.

Starting Material Synthetic Example 175

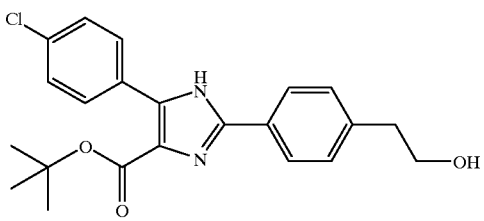

4-(2-Hydroxyethyl)phenylmethylamine and tert-butyl 3-(4-chlorophenyl)-2-hydroxyimino-3-oxopropionate are dissolved in pyridine, and the mixture is treated in the same manner as in Starting Material Synthetic Example 170 to give the objective tert-butyl 5-(4-chlorophenyl)-2-[4-(2-hydroxyethyl)phenyl]imidazole-4-carboxylate.

Starting Material Synthetic Example 176

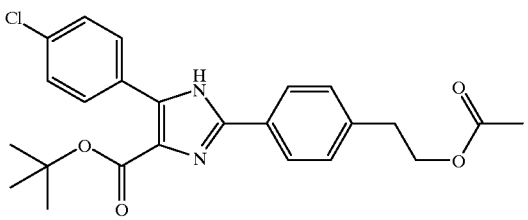

In the same manner as in Starting Material Synthetic Example 173, the objective tert-butyl 2-[4-(2-acetoxyethyl)phenyl]-5-(4-chlorophenyl)imidazole-4-carboxylate is obtained from tert-butyl 5-(4-chlorophenyl)-2-[4-(2-hydroxyethyl)phenyl]imidazole-4-carboxylate.

Starting Material Synthetic Example 177

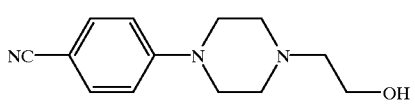

In the same manner as in Starting Material Synthetic Example 174, the objective 2-[4-(2-acetoxyethyl)phenyl]-5-(4-chlorophenyl) imidazole-4-carboxylic acid is obtained from tert-butyl 2-[4-(2-acetoxyethyl)phenyl]-5-(4-chlorophenyl)imidazole-4-carboxylate.

Starting Material Synthetic Example 178

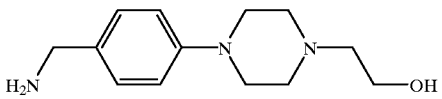

In the same manner as in Starting Material Synthetic Example 68, the objective 4-[4-(2-hydroxyethyl)piperazin-1-yl]benzonitrile is obtained from 4-fluorobenzonitrile and 1-(2-hydroxyethyl)-piperazine.

Starting Material Synthetic Example 179

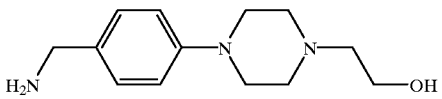

The objective 4-[4-(2-hydroxyethyl)piperazin-1-yl]phenyl-methylamine is obtained from 4-[4-(2-hydroxyethyl)piperazin-1-yl]benzonitrile by reduction with LiAlH$_4$.

Starting Material Synthetic Example 180

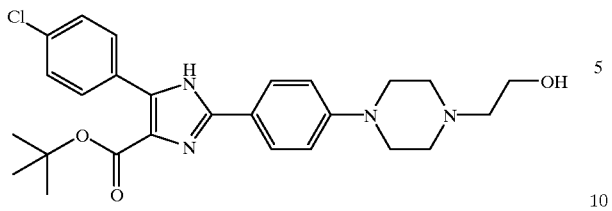

4-[4-(2-Hydroxyethyl)piperazin-1-yl]phenylmethylamine and tert-butyl 3-(4-chlorophenyl)-2-hydroxyimino-3-oxopropionate are dissolved in pyridine, and the solution is treated in the same manner as in Starting Material Synthetic Example 170 to give the objective tert-butyl 5-(4-chlorophenyl)-2-{4-[4-(2-hydroxyethyl)piperazin-1-yl]phenyl}imidazole-4-carboxylate.

Starting Material Synthetic Example 181

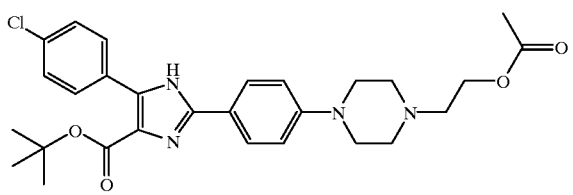

173, tert-butyl 2-{4-[4-(2-acetoxyethyl)piperazin-1-yl]phenyl}-5-(4-chlorophenyl)imidazole-4-carboxylate is obtained from tert-butyl 5-(4-chlorophenyl)-2-{4-[4-(2-hydroxyethyl)piperazin-1-yl]phenyl}imidazole-4-carboxylate.

Starting Material Synthetic Example 182

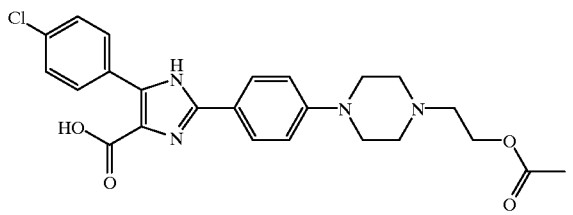

In the same manner as in Starting Material Synthetic Example 174, 2-{4-[4-(2-acetoxyethyl)piperazin-1-yl]phenyl}-5-(4-chlorophenyl)imidazole-4-carboxylic acid is obtained from tert-butyl 2-{4-[4-(2-acetoxyethyl)piperazin-1-yl]phenyl}-5-(4-chlorophenyl)imidazole-4-carboxylate.

Starting Material Synthetic Example 183

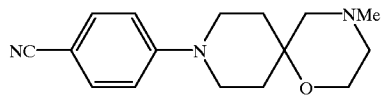

In the same manner as in Starting Material Synthetic Example 68, the objective 4-(4-methyl-1-oxa-4,9-diazaspiro[5,5]undecan-9-yl)benzonitrile (9.7 g), melting point 105–109° C., was obtained from 4-fluorobenzonitrile (10 g) and 4-methyl-1-oxa-4,9-diazaspiro[5,5]undecane (15.7 g).

Starting Material Synthetic Example 184

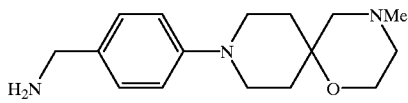

Lithium aluminum hydride (2 g) was suspended in THF (40 ml) and a solution of 4-(4-methyl-1-oxa-4,9-diazaspiro[5,5]undecan-9-yl)benzonitrile (12 g) in THF (100 ml) was added dropwise under ice-cooling. The mixture was stirred at room temperature for 2 hr 40 min and a saturated aqueous sodium sulfate solution was added portionwise under ice-cooling. The precipitated solid was filtrated and washed with chloroform. The chloroform layer was dried over anhydrous sodium sulfate and, after drying, the solvent was evaporated under reduced pressure to give the objective 4-(4-methyl-1-oxa-4,9-diazaspiro[5,5]undecan-9-yl)phenylmethylamine (13 g), which was used in the next Starting Material Synthetic Example 185 without purification.

Starting Material Synthetic Example 185

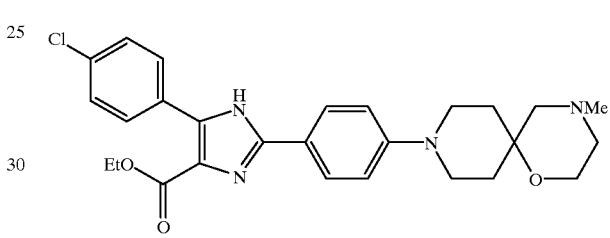

Unpurified 4-(4-methyl-1-oxa-4,9-diazaspiro[5,5]undecan-9-yl)phenylmethylamine (13 g) obtained in Starting Material Synthetic Example 184 and ethyl 3-(4-chlorophenyl)-2-hydroxyimino-3-oxopropionate (10.9 g) were dissolved in pyridine (130 ml) and the mixture was refluxed under heating for 17 hr. After the reaction, the solvent was evaporated under reduced pressure and the residue was subjected to silica gel column chromatography to give the objective ethyl 5-(4-chlorophenyl)-2-[4-(4-methyl-1-oxa-4,9-diazaspiro[5,5]-undecan-9-yl)phenyl]imidazole-4-carboxylate (6.57 g), melting point 235–236° C.

Starting Material Synthetic Example 186

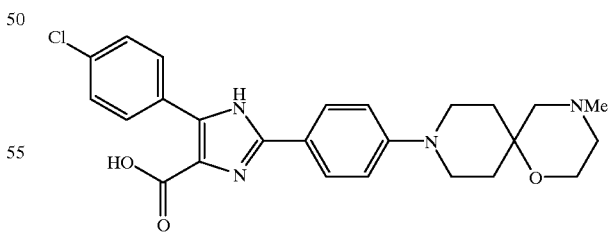

In the same manner as in Starting Material Synthetic Example 62, 5-(4-chlorophenyl)-2-[4-(4-methyl-1-oxa-4,9-diazaspiro[5,5]-undecan-9-yl)phenyl]imidazole-4-carboxyic acid (5 g), melting point 190–195° C. (decomposition), was obtained from ethyl 5-(4-chlorophenyl)-2-[4-(4-methyl-1-oxa-4,9-diazaspiro[5,5]undecan-9-yl)phenyl]imidazole-4-carboxylate (6.57 g).

Example 1

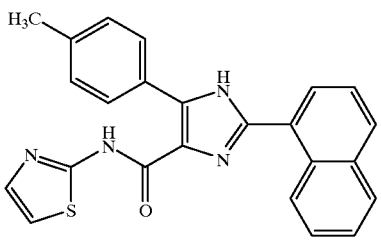

5-(4-Methylphenyl)-2-(1-naphthyl)imidazole-4-carboxylic acid (2.0 g) obtained in Starting Material Synthetic Example 2 was dissolved in dioxane (35 ml) and 1 M hydrochloric acid—ether solution (25 ml) was added, which was followed by stirring for 30 min. To the reaction mixture was added thionyl chloride (29 ml) and the mixture was refluxed under heating for 2.5 hr and concentrated under reduced pressure. To the residue were added pyridine (50 ml) and 2-aminothiazole (0.79 g) and the mixture was refluxed under heating for 5 hr. The mixture was cooled to room temperature and saturated aqueous hydrogen carbonate solution was added. The mixture was extracted with ethyl acetate. The ethyl acetate layer was washed with water, dried and concentrated. To the obtained residue was added ether, and the precipitated crystals were collected by filtration. The obtained crude crystals were recrystallized from ethyl acetate to give 5-(4-methylphenyl)-2-(1-naphthyl)-N-(2-thiazolyl)imidazole-4-carboxamide (1.2 g), melting point 228–229° C.

In addition, acid addition salts with hydrochloric acid, methanesulfonic acid, p-toluenesulfonic acid, hydrobromic acid and nitric acid were obtained. Hydrochloride: melting point 250° C. or above (decomposition)

$^1$H-NMR 400 MHz (DMSO-D$_6$, ppm) δ: 2.39(3H,s), 7.28(1H,d), 7.33(2H,d), 7.55(1H,t), 7.65(3H,m), 7.84(2H, d), 7.99(1H,d), 8.05(1H,d), 8.10(1H,d), 8.86(1H,d).
Methanesulfonate: melting point 252–254° C. (decomposition)
p-Toluenesulfonate: melting point 233–234° C. (decomposition)
Hydrobromide: melting point 275–277° C. (decomposition)
Nitrate: melting point 169–170° C. (decomposition)

Example 2

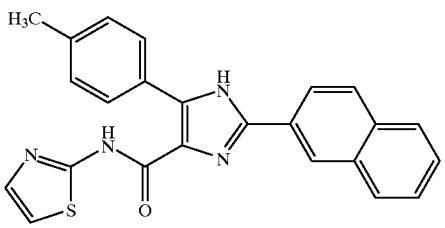

5-(4-Methylphenyl)-2-(2-naphthyl)imidazole-4-carboxylic acid (1.4 g) obtained in Starting Material Synthetic Example 17, 1 M hydrochloric acid—ether solution (25 ml), thionyl chloride (20 ml) and 2-aminothiazole (0.56 g) were reacted and treated in the same manner as in Example 1 to give 5-(4-methylphenyl)-2-(2-naphthyl)-N-(2-thiazolyl)imidazole-4-carboxamide (0.95 g), melting point 250° C. or above.

$^1$H-NMR 400 MHz (CDCl$_3$, ppm) δ: 2.44(3H,s), 7.02(1H, d), 7.33(1H,d), 7.55(2H,t), 7.85(2H,d), 7.89(1H,t), 7.96(2H, m), 8.21(1H,d), 8.54(1H,s).

Example 3

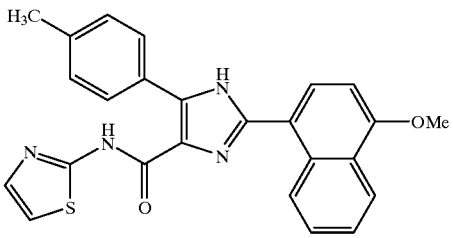

2-(4-Methoxy-1-naphthyl)-5-(4-methylphenyl) imidazole-4-carboxylic acid (2.0 g) obtained in Starting Material Synthetic Example 18, 1 M hydrochloric acid—ether solution (25 ml), thionyl chloride (25 ml) and 2-aminothiazole (0.73 g) were reacted and treated in the same manner as in Example 1 to give 2-(4-methoxy-1-naphthyl)-5-(4-methylphenyl)-N-(2-thiazolyl)imidazole-4-carboxamide (1.2 g), melting point 250° C. or above.

$^1$H-NMR 400 MHz (CDCl$_3$, ppm) δ: 2.39(3H,s), 4.05(3H, S), 7.13(1H,d), 7.25(1H,d), 7.33(2H,t), 7.51(1H,d), 7.60 (1H,t), 7.68(1H,t), 7.84(2H,d), 7.92(1H,d), 8.27(1H,d), 8.95 (1H,d).

Example 4

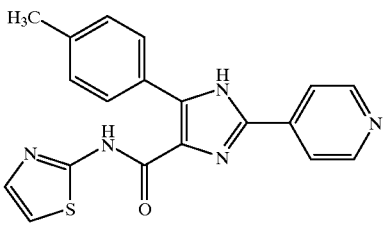

5-(4-Methylphenyl)-2-(4-pyridyl)imidazole-4-carboxylic acid (1.0 g) obtained by reacting and treating the compound obtained in Starting Material Synthetic Example 19 in the same manner as in Starting Material Synthetic Example 2, 1 M hydrochloric acid—ether solution (1.3 ml), thionyl chloride (3 ml) and 2-aminothiazole (0.36 g) were reacted and treated in the same manner as in Example 1 to give 5-(4-methylphenyl)-2-(4-pyridyl)-N-(2-thiazolyl) imidazole-4-carboxamide (0.88 g), melting point 250° C. or above.

$^1$H-NMR 400 MHz (CDCl$_3$, ppm) δ: 2.44(3H,s), 7.04(1H, d), 7.33(2H,d), 7.48(1H,d), 7.77(2H,d), 8.05(2H,dd), 8.65 (2H,dd)

Example 5

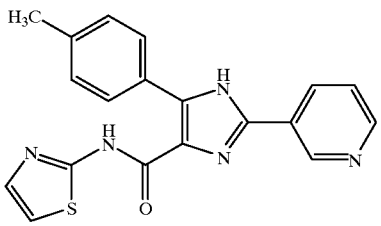

5-(4-Methylphenyl)-2-(3-pyridyl)imidazole-4-carboxylic acid (0.39 g) obtained in Starting Material Synthetic Example 20, 1 M hydrochloric acid—ether solution (0.52 ml), thionyl chloride (4.2 ml) and 2-aminothiazole (0.15 g) were reacted and treated in the same manner as in Example 1 to give 5-(4-methylphenyl)-2-(3-pyridyl)-N-(2-thiazolyl)imidazole-4-carboxamide (0.10 g), melting point 200° C. or above.

$^1$H-NMR 400 MHz (CDCl$_3$, ppm) δ: 2.42(3H,s), 6.99(1H,d), 7.30(2H,d), 7.47(1H,d), 7.51(1H,t), 7.77(2H,d), 8.49(1H,m), 9.11(1H,d).

Example 6

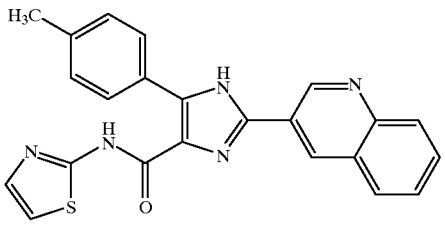

5-(4-Methylphenyl)-2-(3-quinolyl)imidazole-4-carboxylic acid (0.50 g) obtained in Starting Material Synthetic Example 21, 1 M hydrochloric acid—ether solution (5.0 ml), thionyl chloride (7.5 ml) and 2-aminothiazole (0.18 g) were reacted and treated in the same manner as in Example 1 to give 5-(4-methylphenyl)-2-(3-quinolyl)-N-(2-thiazolyl)imidazole-4-carboxamide (0.15 g), melting point 250° C. or above.

$^1$H-NMR 400 MHz (DMSO-D$_6$, ppm) δ: 2.40(3H,s), 7.26(1H,d), 7.36(2H,d), 7.54(1H,d), 7.69(1H,t), 7.82(2H,m), 9.07(1H,s), 9.79(1H,s), 11.49(1H,s), 13.50(1H,s).

Example 7

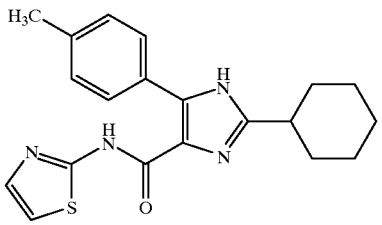

2-Cyclohexyl-5-(4-methylphenyl)imidazole-4-carboxylic acid (390 mg) obtained in Starting Material Synthetic Example 4 was suspended in dichloromethane (20 ml), and thionyl chloride (0.2 ml) and N,N-dimethylformamide (0.1 ml) were added. The mixture was refluxed under heating for 3.5 hr, and concentrated under reduced pressure. The residue was dissolved in dichloromethane (20 ml) and this solution was added dropwise to a solution of 2-aminothiazole (200 mg) in pyridine (20 ml). N,N-Dimethylaminopyridine (20 mg) was added and the mixture was stirred at room temperature for 18 hr. To the reaction mixture were added ethanol and water, and the mixture was concentrated under reduced pressure. The obtained residue was purified by silica gel column chromatography and crystallized from ethyl acetate—methanol to give 2-cyclohexyl-5-(4-methylphenyl)-N-(2-thiazolyl)imidazole-4-carboxamide (270 mg), melting point 199–200° C.

$^1$H-NMR 400 MHz(CDCl$_3$,ppm) δ:1.25–2.09(10H,m), 2.39(3H,s), 2.72(1H,m), 6.94(1H,d), 7.25(2H,d), 7.47(1H,d), 7.68(2H,d), 9.03(1H,brs), 10.6(1H,brs)

Example 8

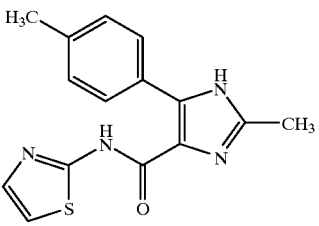

2-Methyl-5-(4-methylphenyl)imidazole-4-carboxylic acid (520 mg) obtained by reacting and treating the compound obtained in Starting Material Synthetic Example 22 in the same manner as in Starting Material Synthetic Example 2, thionyl chloride (1.0 ml) and 2-aminothiazole (210 mg) were reacted and treated in the same manner as in Example 1 to give 2-methyl-5-(4-methylphenyl)-N-(2-thiazolyl)imidazole-4-carboxamide (383 mg), melting point 275–276° C.

$^1$H-NMR 400 MHz(CDCl$_3$, ppm) δ: 1.25–2.09(10H,m), 2.39(3H,s), 2.72(1H,m), 6.94(1H,d), 7.25(2H,d), 7.47(1H,d), 7.68(2H,d), 9.03(1H,brs), 10.6(1H,brs).

Example 9

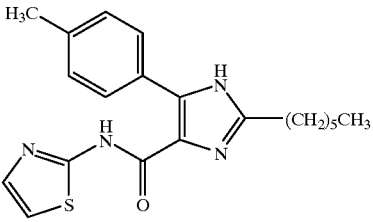

2-Hexyl-5-(4-methylphenyl)imidazole-4-carboxylic acid (900 mg) obtained in Starting Material Synthetic Example 23, thionyl chloride (2.0 ml) and 2-aminothiazole (300 mg) were reacted and treated in the same manner as in Example 1 to give 2-hexyl-5-(4-methylphenyl)-N-(2-thiazolyl)imidazole-4-carboxamide (700 mg).

This was converted to hydrochloride to give 2-hexyl-5-(4-methylphenyl)-N-(2-thiazolyl)imidazole-4-carboxamide hydrochloride (325 mg) as amorphous, melting point 124–130° C.

$^1$H-NMR 400 MHz (DMSO-D$_6$, ppm) δ: 0.86(3H,t), 1.30(6H,m), 1.77(2H,m), 2.37(3H,s), 6.93(2H,t), 7.25(1H,d), 7.34(2H,d), 7.51(1H,d), 7.71(2H,d).

Example 10

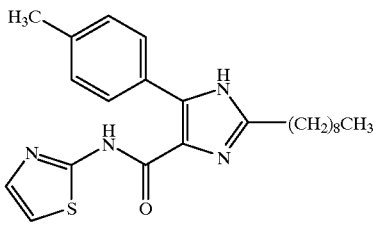

5-(4-Methylphenyl)-2-nonylimidazole-4-carboxylic acid (800 mg) obtained by reacting and treating the compound obtained in Starting Material Synthetic Example 24 in the same manner as in Starting Material Synthetic Example 2, thionyl chloride (1.0 ml), N,N-dimethylaminopyridine (20 mg) and 2-aminothiazole (230 mg) were reacted and treated in the same manner as in Example 1 to give 5-(4-methylphenyl)-2-nonyl-N-(2-thiazolyl)imidazole-4-carboxamide (400 mg). This was converted to hydrochloride to give 5-(4-methylphenyl)-2-nonyl-N-(2-thiazolyl) imidazole-4-carboxamide hydrochloride (240 mg) as amorphous, melting point 125–128° C.

$^1$H-NMR 400 MHz (DMSO-D$_6$, ppm) δ: 0.85(3H,t), 1.25–1.31(10H,m), 1.78(2H,m), 2.39(3H,s), 2.88(2H,t), 7.25(1H,d), 7.34(2H,t), 7.52(1H,d), 7.72(2H,d)

Example 11

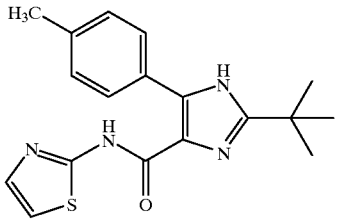

2-tert-Butyl-5-(4-methylphenyl)imidazole-4-carboxylic acid (500 mg) obtained by reacting and treating the compound obtained in Starting Material Synthetic Example 25 in the same manner as in Starting Material Synthetic Example 2, thionyl chloride (0.3 ml), N,N-dimethylaminopyridine (20 mg) and 2-aminothiazole (250 mg) were reacted and treated in the same manner as in Example 1 to give 2-tert-butyl-5-(4-methylphenyl)-N-(2-thiazolyl)imidazole-4-carboxamide (210 mg), melting point 218° C.

$^1$H-NMR 400 MHz (CDCl$_3$, ppm) δ: 1.42(9H,s), 2.39(3H, s), 6.95(1H,d), 7.27(2H,d), 7.47(1H,d), 7.68(2H,d), 9.01(1H,brs), 10.6(1H,brs)

Example 12

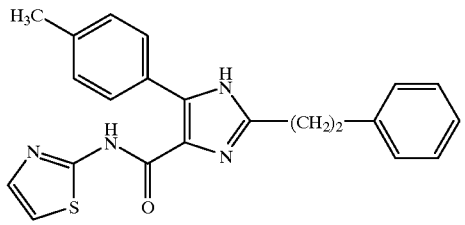

5-(4-Methylphenyl)-2-(2-phenylethyl)imidazole-4-carboxylic acid (800 mg) obtained by reacting and treating the compound obtained in Starting Material Synthetic Example 26 in the same manner as in Starting Material Synthetic Example 2, thionyl chloride (2.0 ml), N,N-dimethylaminopyridine (20 mg) and 2-aminothiazole (260 mg) were reacted and treated in the same manner as in Example 1 to give 5-(4-methylphenyl)-2-(2-phenylethyl)-N-(2-thiazolyl)imidazole-4-carboxamide (630 mg). This was converted to hydrochloride to give 5-(4-methylphenyl)-2-(2-phenylethyl)-N-(2-thiazolyl)imidazole-4-carboxamide hydrochloride (265 mg) as amorphous, melting point 198–201° C.

$^1$H-NMR 400 MHz (DMSO-D$_6$, ppm) δ: 2.39(3H,s), 3.16(4H,m), 7.21(8H,m), 7.51(1H,d), 7.72(2H,m).

Example 13

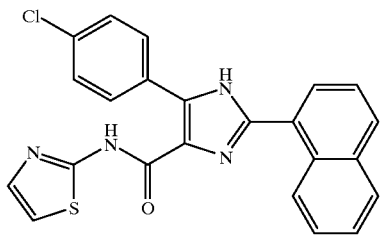

5-(4-Chlorophenyl)-2-(1-naphthyl)imidazole-4-carboxylic acid (3.0 g) obtained in Starting Material Synthetic Example 27, 1 M hydrochloric acid—ether solution (15 ml), thionyl chloride (20 ml) and 2-aminothiazole (1.0 g) were reacted and treated in the same manner as in Example 1 to give 5-(4-chlorophenyl)-2-(1-naphthyl)-N-(2-thiazolyl) imidazole-4-carboxamide (1.48 g), melting point 206-208° C., hydrochloride: melting point 250° C. or above.

$^1$H-NMR 400 MHz (DMSO-D$_6$, ppm) δ: 7.30(1H,dd), 7.55–7.69(6H,m), 7.98–8.11(5H,m), 8.90(1H,d).

Example 14

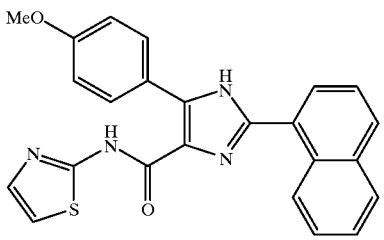

5-(4-Methoxyphenyl)-2-(1-naphthyl)imidazole-4-carboxylic acid (1.96 g) obtained in Starting Material Synthetic Example 28, 1 M hydrochloric acid—ether solution (10 ml), thionyl chloride (15 ml) and 2-aminothiazole (0.65 g) were reacted and treated in the same manner as in Example 1 to give 5-(4-methoxyphenyl)-2-(1-naphthyl)-N-(2-thiazolyl)imidazole-4-carboxamide (0.25 g), melting point 198–200° C.

Example 15

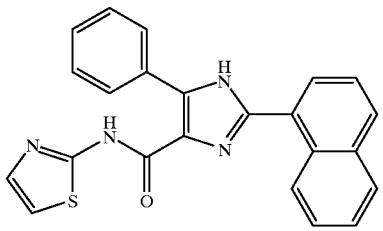

2-(1-Naphthyl)-5-phenylimidazole-4-carboxylic acid (3.00 g) obtained in Starting Material Synthetic Example 29, 1 M hydrochloric acid—ether solution (15 ml), thionyl chloride (20 ml) and 2-aminothiazole (1.00 g) were reacted and treated in the same manner as in Example 1 to give 2-(1-naphthyl)-5-phenyl-N-(2-thiazolyl)-imidazole-4-carboxamide (1.47 g), melting point 250° C. or above.

$^1$H-NMR 400 MHz (DMSO-D$_6$, ppm) δ: 7.26(d,1H), 7.45–7.71(7H,m), 7.93–8.09(5H,m), 8.97(1H,d).

Hydrochloride: melting point 250° C. or above.

1H-NMR 400 MHz (DMSO-D$_6$, ppm) δ: 7.30(1H, d), 7.46–7.69(7H,m), 7.93–8.12(5H,m), 8.88(1H,d).

Example 16

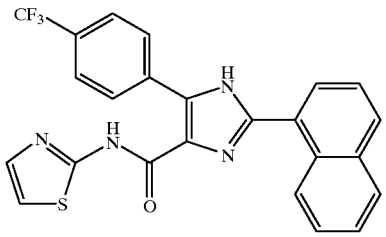

2-(1-Naphthyl)-5-(4-trifluoromethylphenyl)imidazole-4-carboxylic acid (2.50 g) obtained in Starting Material Synthetic Example 30, 1 M hydrochloric acid—ether solution (15 ml), thionyl chloride (20 ml) and 2-aminothiazole (1.00 g) were reacted and treated in the same manner as in Example 1 to give 2-(1-naphthyl)-5-(4-trifluoromethylphenyl)-N-(2-thiazolyl)imidazole-4-carboxamide (0.80 g), melting point 222–223° C.

Hydrochloride: melting point 250° C. or above.

$^1$H-NMR 400 MHz (DMSO-D$_6$, ppm) δ: 7.30(1H,d), 7.55(1H,d), 7.61–7.68(3H,m), 7.90(2H,d), 8.01–8.18(5H,m), 8.95(1H,d).

Example 17

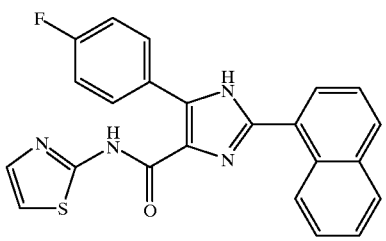

5-(4-Fluorophenyl)-2-(1-naphthyl)imidazole-4-carboxylic acid (2.30 g) obtained in Starting Material Synthetic Example 31, 1 M hydrochloric acid—ether solution (15 ml), thionyl chloride (20 ml) and 2-aminothiazole (1.00 g) were reacted and treated in the same manner as in Example 1 to give 5-(4-fluorophenyl)-2-(1-naphthyl)-N-(2-thiazolyl)imidazole-4-carboxamide (0.80 g), melting point 218–220° C.

Hydrochloride: melting point 250° C. or above.

$^1$H-NMR 400 MHz (DMSO-D$_6$, ppm) δ: 7.28(1H, d), 7.36–7.40(2H,m), 7.55(1H,d), 7.61–7.69(3H,m), 7.99–8.11 (5H,m), 8.91(1H,d).

Example 18

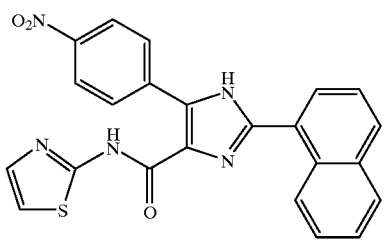

2-(1-Naphthyl)-5-(4-nitrophenyl)imidazole-4-carboxylic acid (3.0 g) obtained in Starting Material Synthetic Example 32, 1 M hydrochloric acid—ether solution (15 ml), thionyl chloride (20 ml) and 2-aminothiazole (1.00g) were reacted and treated in the same manner as in Example 1 to give 2-(1-naphthyl)-5-(4-nitrophenyl)-N-(2-thiazolyl)imidazole-4-carboxamide (1.06 g), melting point 237–238° C.

Hydrochloride: melting point 250° C. or above $^1$H-NMR 400 MHz (DMSO-D$_6$, ppm) δ: 7.29(1H,d), 7.55(1H,d), 7.63–7.68(3H,m), 8.01–8.12(3H,m), 8.25(2H, d), 8.37(2H,d), 8.97(1H,d).

Example 19

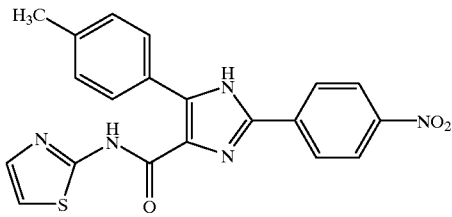

5-(4-Methylphenyl)-2-(4-nitrophenyl)imidazole-4-carboxylic acid (15.0 g) obtained in Starting Material Synthetic Example 33, 1 M hydrochloric acid—ether solution (75 ml), thionyl chloride (50 ml) and 2-aminothiazole (5.27 g) were reacted and treated in the same manner as in Example 1 to give 5-(4-methylphenyl)-2-(4-nitrophenyl)-N-(2-thiazolyl)imidazole-4-carboxamide (0.86 g), melting point 256–258° C.

Hydrochloride: melting point 250° C. or above.

$^1$H-NMR 400 MHz (DMSO-D$_6$, ppm) δ: 7.27(1H,d), 7.34(2H,d), 7.55(1H,d), 7.80(2H,d), 8.38(2H,d), 8.48(2H,d).

Example 20

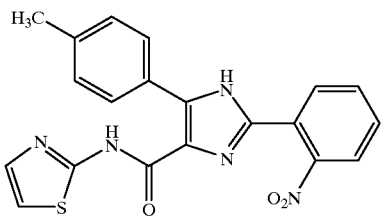

5-(4-Methylphenyl)-2-(2-nitrophenyl)imidazole-4-carboxylic acid (2.20 g) obtained in Starting Material Synthetic Example 34, 1 M hydrochloric acid—ether solution (15 ml), thionyl chloride (20 ml) and 2-aminothiazole (1.00 g) were reacted and treated in the samemanner as in Example 1 to give 5-(4-methylphenyl)-2-(2-nitrophenyl)-N-(2-thiazolyl)imidazole-4-carboxamide (0.50 g), melting point 203–204° C.

Example 21

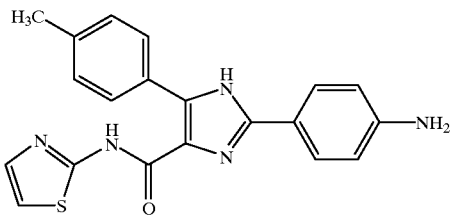

5-(4-Methylphenyl)-2-(4-nitrophenyl)-N-(2-thiazolyl)-imidazole-4-carboxamide (0.44 g) obtained in Example 19 was suspended in methanol and ice-cooled. To the suspension was added a solution of tin(II) chloride 6 hydrate (1.0 g) in 6 M hydrochloric acid solution (10 ml) and the mixture was refluxed under heating for 2.5 hr. Water was added and the mixture was neutralized with potassium carbonate and extracted with ethyl acetate. The organic layer was washed with water and, after drying, the solvent was evaporated under reduced pressure. The obtained residue was dissolved in ethyl acetate and 1 M hydrochloric acid—ether solution (5 ml) was added. The precipitated crystals were collected by filtration, and the obtained crude crystals were recrystallized from methanol to give 2-(4-aminophenyl)-5-(4-methylphenyl)-N-(2-thiazolyl)imidazole-4-carboxamide (0.28 g), melting point 244° C. (decomposition).

Example 22

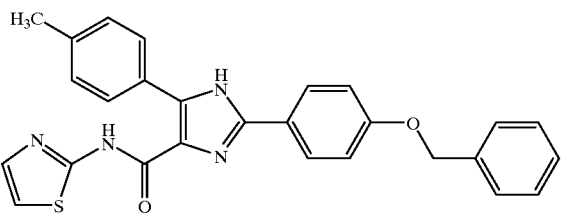

(1) Ethyl 2-hydroxyimino-3-(4-methylphenyl)-3-oxopropionate (44.9g), 4-benzyloxybenzaldehyde (61.0 g) and ammonium acetate (147 g) were added to acetic acid (400 ml) and themixturewas refluxed under heating for 17 hr. Water (1.5 L) was added and the mixture was extracted with ethyl acetate. The ethyl acetate layer was washed with water, saturated aqueous sodium hydrogencarbonate solution and saturated brine, and dried. The solvent was evaporated under reduced pressure and the obtained residue was recrystallized from ethyl acetate and ether to give ethyl 2-(4-benzyloxyphenyl)-5-(4-methylphenyl)-imidazole-4-carboxylate (36.9 g), melting point 168–170° C.

(2) Ethyl 2-(4-benzyloxyphenyl)-5-(4-methylphenyl) imidazole-4-carboxylate (36.0 g) was reacted and treated in the same manner as in Starting Material Synthetic Example 2 to give 2-(4-benzyloxyphenyl)-5-(4-methylphenyl) imidazole-4-carboxylic acid (31.3 g), melting point 168° C. (decomposition).

(3) 2-(4-Benzyloxyphenyl)-5-(4-methylphenyl)imidazole-4-carboxylic acid (7.80 g) was reacted and treated in the same manner as in Example 1 to give 2-(4-benzyloxyphenyl)-5-(4-methylphenyl)-N-(2-thiazolyl) imidazole-4-carboxamide (5.85 g), melting point 207–208° C. hydrochloride: melting point 206° C. (decomposition).

Example 23

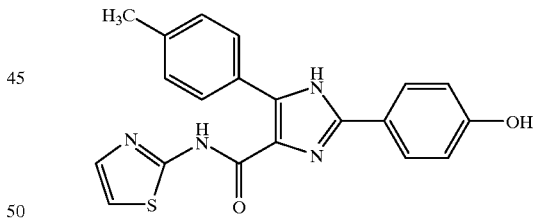

2-(4-Benzyloxyphenyl)-5-(4-methylphenyl)-N-(2-thiazolyl)-imidazole-4-carboxamide (5.10 g) obtained in Example 22(3) and thioanisole (6.4 ml) were dissolved in trifluoroacetic acid (100 ml) and the mixture was stirred for 6 hr. The reaction mixture was made alkaline with 2 M aqueous sodium hydroxide solution and then acidified with aqueouscitricacid. Themixturewasextractedwithethylacetate. The ethyl acetate layer was washed with saturated brine and, after drying, the solvent was evaporated. The obtained residue was purified by silica gel chromatography (hexane:ethyl acetate=6:4) and recrystallized from ethyl acetate and hexane to give 2-(4-hydroxyphenyl)-5-(4-methylphenyl)-N-(2-thiazolyl)imidazole-4-carboxamide (2.33 g), melting point 286–289° C. (decomposition).

Example 24

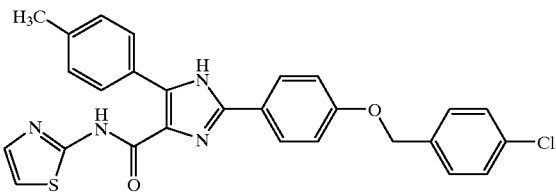

2-(4-Hydroxyphenyl)-5-(4-methylphenyl)-N-(2-thiazolyl)-imidazole-4-carboxamide (0.38 g) obtained in Example 23, 4-chlorobenzyl alcohol (0.14 g) and triphenylphosphine (0.26 g) were dissolved in tetrahydrofuran (25 ml) and diethyl azodicarboxylate (0.16 ml) was added. The mixture was stirred for 40 hr. Water was added and the mixture was extracted with ethyl acetate. The ethyl acetate layer was washed with saturated brine and dried. The solvent was evaporated and the obtained residue was purified by silica gel chromatography (hexane:ethyl acetate=7:3). The obtained residue was converted to hydrochloride to give 2-(4-(4-chlorophenylmethyloxy)-phenyl)-5-(4-methylphenyl)-N-(2-thiazolyl)imidazole-4-carboxamide hydrochloride (61 mg), melting point 203–205° C. (decomposition).

Example 25

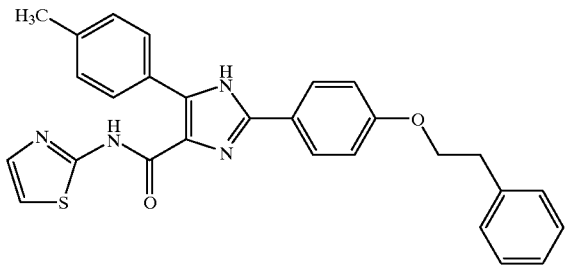

2-(4-Hydroxyphenyl)-5-(4-methylphenyl)-N-(2-thiazolyl)imidazole-4-carboxamide (0.52 g) obtained in Example 23, phenethyl alcohol (0.33 ml), triphenylphosphine (0.72 g) and diethyl azodicarboxylate (0.44 ml) were reacted and treated in the same manner as in Example 24 to give 5-(4-methylphenyl)-2-(4-(2-phenylethyloxy)phenyl)-N-(2-thiazolyl)imidazole-4-carboxamide hydrochloride (0.29 g), melting point 166–167° C. (decomposition).

Example 26

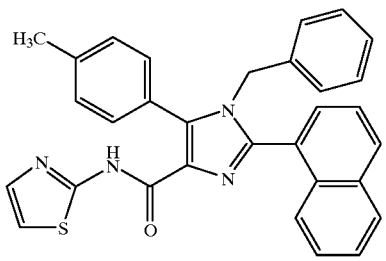

(1) Ethyl 5-(4-methylphenyl)-2-(1-naphthyl)imidazole-4-carboxylate (1.5 g) obtained in Starting Material Synthetic Example 1 was dissolved in N,N-dimethylformamide (13 ml) and 60% sodium hydride (0.19 g) was added. The mixture was stirred for 20 min. Benzyl bromide (0.55 ml) was added and the mixture was stirred for 3 hr. Water was added and the mixture was extracted with ethyl acetate. The ethyl acetate layer was washed with saturated brine and dried. The solvent was evaporated and the obtained residue was purified by silica gel chromatography (hexane:ethyl acetate=8:2) to give ethyl 1-benzyl-5-(4-methylphenyl)-2-(1-naphthyl)imidazole-4-carboxylate (0.73 g).

$^1$H-NMR 400 MHz (CDCl$_3$, ppm) δ: 1.27(3H,t), 2.39(3H,s), 4.30(2H,q), 4.85(2H,s), 6.44(2H,d), 6.97–7.07(3H,m), 7.21–7.28(4H,m), 7.41(1H,dd), 7.48–7.53(3H,m), 7.64–7.67(1H,m), 7.87–7.92(2H,m).

(2) Ethyl 1-benzyl-5-(4-methylphenyl)-2-(1-naphthyl)imidazole-4-carboxylate (0.65 g) was hydrolyzed in the same manner as in Starting Material Synthetic Example 2 and the obtained residue was reacted and treated in the same manner as in Example 1 to give 1-benzyl-5-(4-methylphenyl)-2-(1-naphthyl)-N-(2-thiazolyl)imidazole-4-carboxamide (0.51 g), melting point 231–232° C.

Hydrochloride: melting point 227–229° C. (decomposition).

Example 27

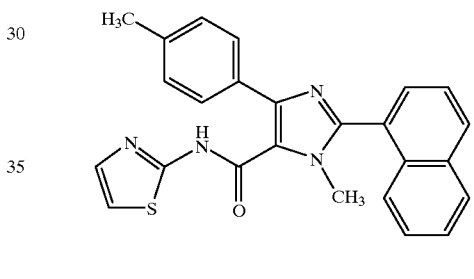

(1) Ethyl 5-(4-methylphenyl)-2-(1-naphthyl)imidazole-4-carboxylate (3.0 g) obtained in Starting Material Synthetic Example 1 and methyl iodide (0.58 ml) were reacted and treated in the same manner as in Example 26(1) to give ethyl 1-methyl-4-(4-methylphenyl)-2-(1-naphthyl)imidazole-5-carboxylate (1.68 g) and ethyl 1-methyl-5-(4-methylphenyl)-2-(1-naphthyl)imidazole-4-carboxylate (1.32 g). ethyl 1-methyl-4-(4-methylphenyl)-2-(1-naphthyl)imidazole-5-carboxylate: $^1$H-NMR 400 MHz (CDCl$_3$, ppm) δ: 1.29(3H,t), 2.39(3H,s), 3.69(3H,s), 4.32(2H,q), 7.21(2H,d), 7.49–7.59(3H,m), 7.64(1H,d), 7.67–7.71(3H,m), 7.91–7.94(1H,m), 7.99(1H,d) ethyl 1-methyl-5-(4-methylphenyl)-2-(1-naphthyl)imidazole-4-carboxylate: $^1$H-NMR 400 MHz (CDCl$_{31}$ ppm) δ: 1.28(3H,t), 2.44(3H,s), 3.23(3H,s), 4.30(2H,q), 7.30(2H,d), 7.38(2H,d), 7.48–7.56 (3H,m), 7.62–7.67(2H,m), 7.89–7.92(1H,m), 7.96(1H,d).

(2) Ethyl 1-methyl-4-(4-methylphenyl)-2-(1-naphthyl)imidazole-5-carboxylate (1.60 g) obtained in (1) was hydrolyzed in the same manner as in Starting Material Synthetic Example 2, and the obtained residue was reacted and treated in the same manner as in Example 1 to give 1-methyl-4-(4-methylphenyl)-2-(1-naphthyl)-N-(2-thiazolyl)imidazole-5-carboxamide (1.23 g), melting point 281–283° C. (decomposition).

Hydrochloride: melting point 265–266° C. (decomposition).

Example 28

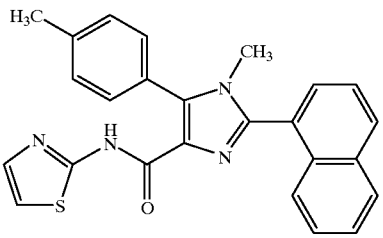

Ethyl 1-methyl-5-(4-methylphenyl)-2-(1-naphthyl)imidazole- 4-carboxylate (1.22 g) obtained in Example 27(1) was hydrolyzed in the same manner as in Starting Material Synthetic Example 2 and the obtained residue was reacted and treated in the same manner as in Example 1 to give 1-methyl-5-(4-methylphenyl)-2-(1-naphthyl)-N-(2-thiazolyl)imidazole-4-carboxamide (0.45 g), melting point 251–252° C.

Hydrochloride: $^1$H-NMR 400 MHz (DMSO-D$_6$, ppm) δ: 2.41(3H,s), 3.29(3H,s), 7.27(1H,d), 7.37(2H,d), 7.52(1H,d), 7.57(2h,d), 7.60–7.65(2H,m), 7.70(1H,dd), 7.83(1H,d), 7.90–7.93(1H,m), 8.08–8.10(1H,m), 8.18(1H,d).

Example 29

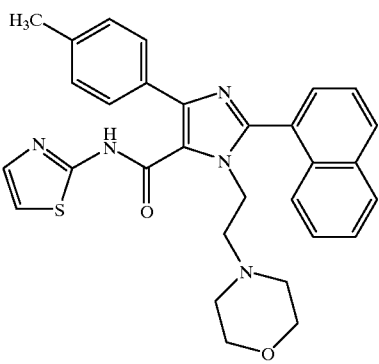

(1) Ethyl 5-(4-methylphenyl)-2-(1-naphthyl)imidazole-4-carboxylate (3.0 g) obtained in Starting Material Synthetic Example 1 and 4 -(2-chloroethyl)morpholine (1.39g) were reacted and treated in the same manner as in Example 26(1) to give ethyl 4-(4-methylphenyl)-1-(2-morpholinoethyl)-2-(1-naphthyl)imidazole-5-carboxylate (2.89 g) and ethyl 5-(4-methylphenyl)-1-(2-morpholinoethyl)-2-(1-naphthyl) imidazole-4-carboxylate (0.78 g). ethyl 4-(4-methylphenyl)-1-(2-morpholinoethyl)-2-(1-naphthyl)imidazole-5-carboxylate: $^1$H-NMR 400 MHz (CDCl$_3$, ppm) δ: 1.27(3H,t), 2.09(4H,t), 2.39(3H,s), 2.49(2H,t), 3.36(4H,t), 4.28(2H,t), 4.31(2H,q), 7.21(2H,d), 7.49–7.58(3H,m), 7.64–7.70(4H,m), 7.90–7.92(1H,m), 7.98(1H,d) ethyl 5-(4-methylphenyl)-1-(2-morpholinoethyl)-2-(1-naphthyl)imidazole-4-carboxylate: $^1$H-NMR 400 MHz (CDCl$_3$, ppm) δ: 1.26(3H,t), 1.78(4H,t), 2.04(2H,t), 2.43(3H,s), 3.30(4H,t), 3.80(2H,t), 4.29(2H,q), 7.32(2H,d), 7.40(2H,d), 7.51–7.57(3H,m), 7.68–7.70(2H,m),7.90–7.93(1H,m), 7.97(1H,d).

(2) Ethyl 4-(4-methylphenyl)-1-(2-morpholinoethyl)-2-(1 -naphthyl)imidazole-5-carboxylate (2.79 g) obtained in (1) was hydrolyzed in the same manner as in Starting Material Synthetic Example 2 and the obtained residue was reacted and treated in the same manner as in Example 1 to give 4-(4-methylphenyl)-1-(2-morpholinoethyl)-2-(1-naphthyl)-N-(2-thiazolyl)imidazole-5-carboxamide. This compound was reacted and treated in the same manner as in Example 1 to give 4-(4-methylphenyl)-1-(2-morpholinoethyl)-2-(1-naphthyl)-N-(2-thiazolyl)imidazole-5-carboxamide dihydrochloride (0.40 g).

$^1$H-NMR 400 MHz (DMSO-D$_6$, ppm) δ: 2.35(3H,s), 2.92(2H,br.s), 3.08(2H,br.s), 3.42(2H,br.s), 3.66(2H,br.s), 3.75(2H,br.s), 4.65(2H,br.s), 7.28–7.30(3H,m), 7.55–7.78 (7H,m), 8.09(1H,br.d), 8.13–8.15(1H,m), 8.28(1H,d).

Example 30

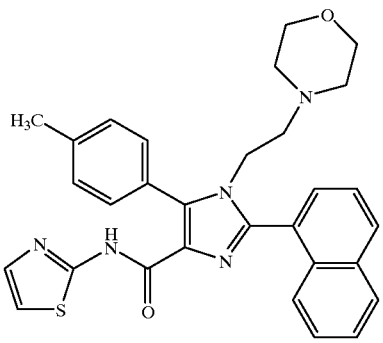

Ethyl 5-(4-methylphenyl)-1-(2-morpholinoethyl)-2-(1-naphthyl)imidazole-4-carboxylate (0.71 g) obtained in Example 29(1) was reacted and treated in the same manner as in Starting Material Synthetic Example 2 and the obtained residue was reacted and treated in the same manner as in Example 1 to give 5-(4-methylphenyl)-1-(2-morpholinoethyl)-2-(1-naphthyl)-N-(2-thiazolyl)imidazole-4-carboxamide (0.40 g), melting point 226–227° C. Hydrochloride: $^1$H-NMR 400 MHz (DMSO-D$_6$, ppm) δ: 2.43(3H, s), 2.49(2H,br.s), 2.68(2H,br.s), 2.81(2H,br.s), 3.48(2H,br.s), 3.60(2H,br,s), 4.21(2H,t), 7.23(1H,d), 7.40(2H,d), 7.48(1H, d), 7.61–7.69(4H,m), 7.71(1H,dd), 7.89(2H,d), 8.08–8.11 (1H,m), 8.19(1H,d).

Example 31

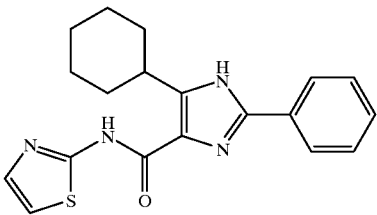

tert-Butyl 5-cyclohexyl-2-phenylimidazole-4-carboxylate (1.0 g) obtained in Starting Material Synthetic Example 5 was dissolved in trifluoroacetic acid (15 ml) and the mixture was stirred at room temperature for 4 days. Trifluoroacetic acid was evaporated under reduced pressure and the obtained residue was crystallized from ethyl acetate to give 2-phenyl-5-(4-cyclohexyl) imidazole-4-carboxylic acid (trifluoroacetate 1.4 g). Dioxane (30 ml) and thionyl chloride (1.0 ml) were added and the mixture was refluxed under heating for 0. 5 hr. The solvent was evaporated under reduced pressure and to the obtained residue were added pyridine (40 ml) and 2-aminothiazole (0.33 g), and the mixture was refluxed under heating for 1 hr. The solvent was evaporated under reduced pressure and to the residue was added a saturated aqueous sodium hydrogencarbonate solution. The mixture was extracted with chloroform. The organic layer was washed with water and, after drying, the solvent was evaporated. The obtained residue was dissolved in ethyl acetate and 1 M hydrochloric acid—ether solution (3 ml) was added. The precipitated crystals were collected by filtration and the obtained crude crystals were recrystallized from methanol—ethyl acetate to give 5-cyclohexyl-2-phenyl-N-(2-thiazolyl) imidazole-4-carboxamide dihydrochloride (0.16 g), melting point 212–215° C. (decomposition).

1H-NMR 400 MHZ (CD$_3$OD, ppm) δ: 1.40–2.00(10H, m), 3.92(1H,t), 7.15(1H,d), 7.48(1H,d), 7.60–7.72(3H,m), 8.00(2H,dd)

Example 32

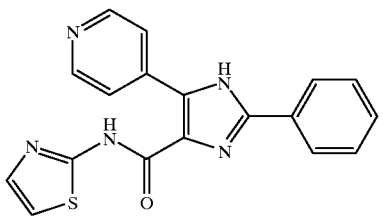

tert-Butyl 2-phenyl-5-(4-pyridyl)imidazole-4-carboxylate (3.0 g) obtained in Starting Material Synthetic Example 6, trifluoroacetic acid (30 ml), thionyl chloride (0.4 ml) and 2-aminothiazole (0.43 g) were reacted and treated in the same manner as in Example 31 to give 2-phenyl-5-(4-pyridyl)-N-(2-thiazolyl)imidazole-4-carboxamide dihydrochloride (0.13 g), melting point 280° C. or above.

$^1$H-NMR 400 MHz (CD$_3$OD, ppm) δ: 7.41(1H,d), 7.45–7.63(3H,m), 7.70(1H,d), 8.10–8.25(2H,m), 8.80(2H, d), 8.94(2H,d)

Example 33

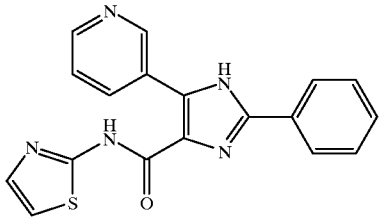

tert-Butyl 2-phenyl-5-(3-pyridyl) imidazole-4-carboxylate (2.2 g) obtained in Starting Material Synthetic Example 7, trifluoroacetic acid (30 ml), thionyl chloride (18 ml) and 2-aminothiazole (0.61 g) were reacted and treated in the same manner as in Example 31 to give 2-phenyl-5-(3-pyridyl)-N-(2-thiazolyl)imidazole-4-carboxamide dihydrochloride (0.35 g), melting point 279–280° C. (decomposition).

$^1$H-NMR 400 MHz (CD$_3$OD, ppm) δ: 7.39(1H,d), 7.55–7.67(3H,m), 7.67(1H,d), 8.12–8.22(2H,m), 8.26(1H, dd), 8.95(1H,d), 9.18(1H,dt), 9.16(1H,d)

Example 34

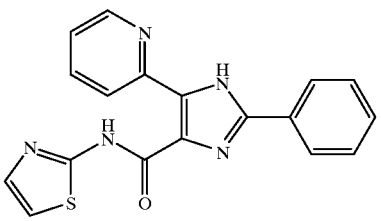

tert-Butyl 2-phenyl-5-(2-pyridyl)imidazole-4-carboxylate (1.2 g) obtained in Starting Material Synthetic Example 8, trifluoroacetic acid (30 ml), thionyl chloride (0.4 ml) and 2-aminothiazole (0.35 g) were reacted and treated in the same manner as in Example 31 to give 2-phenyl-5-(2-pyridyl)-N-(2-thiazolyl)imidazole-4-carboxamide dihydrochloride (0.46 g), melting point 283-284° C. (decomposition).

$^1$H-NMR 400 MHz (CD$_3$OD, ppm) δ: 7.22(1H,d), 7.38–7.53(3H,m), 7.55(1H,d), 7.82(1H,t), 7.99–8.10(2H,m), 8.46(1H,t), 8.73(1H,d), 8.97(1H,d).

Example 35

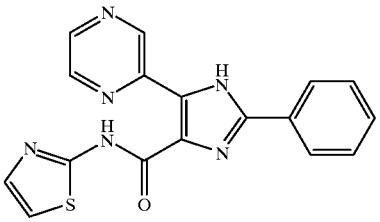

tert-Butyl 2-phenyl-5-(2-pyrazinyl)imidazole-4-carboxylate (0.9 g) obtained in Starting Material Synthetic Example 9, trifluoroacetic acid (30 ml), thionyl chloride (0.2 ml) and 2-aminothiazole (0.20 g) were reacted and treated in the same manner as in Example 31 to give 2-phenyl-5-(2-pyrazinyl)-N-(2-thiazolyl)imidazole-4-carboxamide hydrochloride (0.10 g), melting point 266–268° C. (decomposition).

$^1$H-NMR 400 MHz (CD$_3$OD, ppm) δ: 7.40(1H,d), 7.49–7.62(3H,m), 7.71(1H,d), 8.05–8.19(2H,m), 8.76(1H, d), 8.95(1H,s), 9.78(1H,s).

Example 36

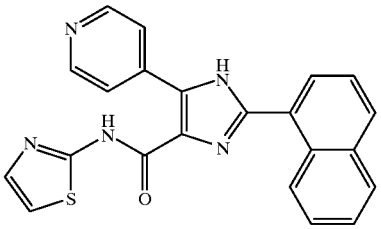

tert-Butyl 2-(1-naphthyl)-5-(4-pyridyl)imidazole-4-carboxylate (2.3 g) obtained in Starting Material Synthetic Example 10, trifluoroacetic acid (20 ml), thionyl chloride (1.5 ml) and 2-aminothiazole (0.45 g) were reacted and treated in the same manner as in Example 31 to give 2-(1-naphthyl)-5-(4-pyridyl)-N-(2-thiazolyl)imidazole-4-carboxamide dihydrochloride (0.05 g), melting point 217–222° C. (decomposition).

¹H-NMR 400 MHz (CD₃OD, ppm) δ: 7.35(1H,d), 7.55–7.73(4H,m), 7.97(1H,d), 8.03(1H,d), 8.13(1H,d), 8.63 (1H,d), 8.85(2H,d), 8.95(2H,d).

Example 37

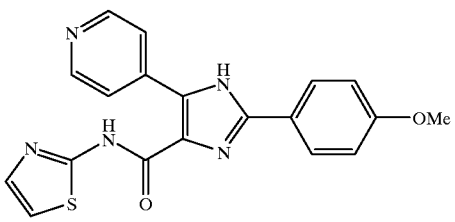

tert-Butyl 2-(4-methoxyphenyl)-5-(4-pyridyl)imidazole-4-carboxylate (1.3 g) obtained in Starting Material Synthetic Example 11, trifluoroacetic acid (20 ml), thionyl chloride (1.5 ml) and 2-aminothiazole (0.45 g) were reacted and treated in the same manner as in Example 31 to give 2-(4-methoxyphenyl)-5-(4-pyridyl)-N-(2-thiazolyl)imidazole-4-carboxamide hydrochloride (0.40 g), melting point 251–253° C. (decomposition).

¹H-NMR 400 MHz (CD₃OD, ppm) δ: 7.09(2H,d), 7.21 (1H,d), 7.54(1H,d), 8.09(2H,d), 8.80(2H,d), 8.85(2H,d)

Example 38

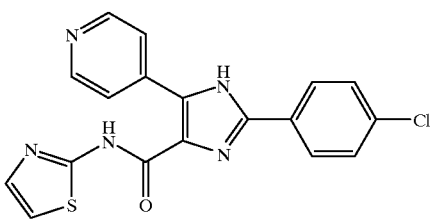

tert-Butyl 2-(4-chlorophenyl)-5-(4-pyridyl)imidazole-4-carboxylate (1.2 g) obtained in Starting Material Synthetic Example 12, trifluoroacetic acid (20 ml), thionyl chloride (2.0 ml) and 2-aminothiazole (0.34 g) were reacted and treated in the same manner as in Example 31 to give 2-(4-chlorophenyl)-5-(4-pyridyl)-N-(2-thiazolyl)imidazole-4-carboxamide dihydrochloride (0.13 g), melting point 270° C. or above.

¹H-NMR 400 MBz (CD₃OD, ppm) Γ: 7.42 (1H, d), 7.60(2H, d), 7.71(1H,d), 8.20(2H,d), 8.81(2H,d), 8.94(2H,d)

Example 39

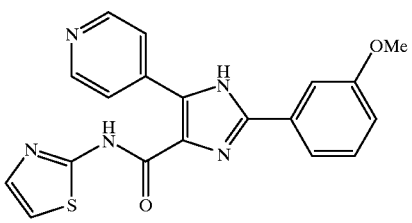

tert-Butyl 2-(3-methoxyphenyl)-5-(4-pyridyl)imidazole-4-carboxylate (1.4 g) obtained in Starting Material Synthetic Example 13, trifluoroacetic acid (30 ml), thionyl chloride (0.5 ml) and 2-aminothiazole (0.34 g) were reacted and treated in the same manner as in Example 31 to give 2-(3-methoxyphenyl)-5-(4-pyridyl)-N-(2-thiazolyl)imidazole-4-carboxamide hydrochloride (0.27 g), melting point 271–273° C. (decomposition).

¹H-NMR 400 MHz (CD₃OD, ppm) δ: 7.09(1H,d), 7.22 (1H,d), 7.47(1H,t), 7.54(1H,d), 7.66–7.77(2H,m), 8.80(2H, d), 8.86(2H,d).

Example 40

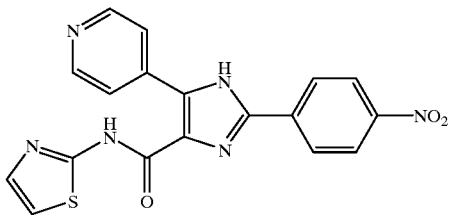

tert-Butyl 2-(4-nitrophenyl)-5-(4-pyridyl)imidazole-4-carboxylate (0.65 g) obtained in Starting Material Synthetic Example 14, trifluoroacetic acid (10 ml), thionyl chloride (0.5 ml) and 2-aminothiazole (0.34 g) were reacted and treated in the same manner as in Example 31 to give 2-(4-nitrophenyl)-5-(4-pyridyl)-N-(2-thiazolyl)imidazole-4-carboxamide dihydrochloride (0.06 g), melting point 280° C. or above.

¹H-NMR 400 MHz (DMSO-D₆, ppm) δ: 7.34(1H,d), 7.60(1H,d), 8.43(2H,d), 8.55(2H,d), 8.66(2H,d), 8.98(2H,d).

Example 41

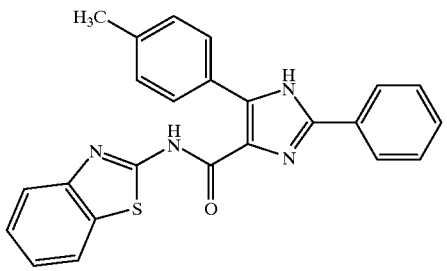

5-(4-Methylphenyl)-2-phenylimidazole-4-carboxylic acid (0.5 g) and 2-aminobenzothiazole (0.35 g) were reacted and treated in the same manner as in Example 1 to give N-(benzothiazol-2-yl)-5-(4-methylphenyl)-2-phenylimidazole-4-carboxamide (0.05 g), melting point 269–270° C.

Example 42

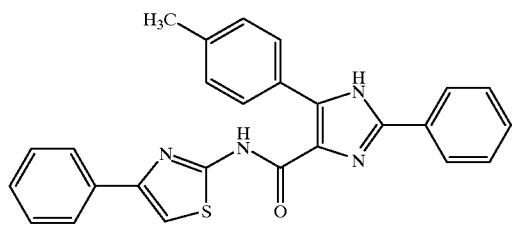

5-(4-Methylphenyl)-2-phenylimidazole-4-carboxylic acid (0.5 g) and 2-amino-4-phenylthiazole (0.55 g) were reacted and treated in the same manner as in Example 1 to give 5-(4-methylphenyl)-2-phenyl-N-(4-phenylthiazol-2-yl)imidazole-4-carboxamide (0.06 g), melting point 274–276° C.

Example 43

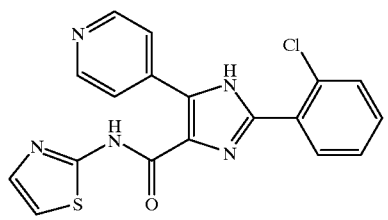

tert-Butyl 2-(2-chlorophenyl)-5-(4-pyridyl)imidazole-4-carboxylate obtained in Starting Material Synthetic Example 15 and 2-aminothiazole are reacted and treated in the same manner as in Example 31 to give 2-(2-chlorophenyl)-5-(4-pyridyl)-N-(2-thiazolyl)-imidazole-4-carboxamide hydrochloride.

Example 44

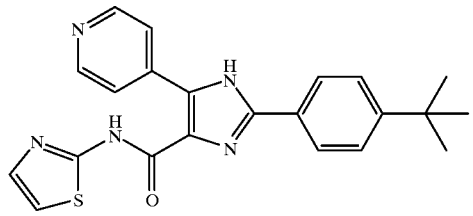

tert-Butyl 2-(4-tert-butylphenyl)-5-(4-pyridyl)imidazole-4-carboxylate hydrochloride obtained in Starting Material Synthetic Example 16 and 2-aminothiazole are reacted and treated in the same manner as in Example 31 to give 2-(4-tert-butylphenyl)-5-(4-pyridyl)-N-(2-thiazolyl)imidazole-4-carboxamide hydrochloride.

Example 45

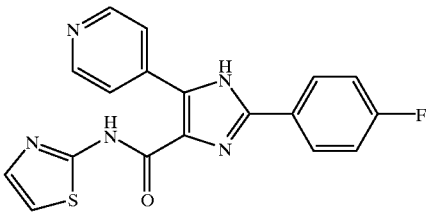

tert-Butyl 2-(4-fluorophenyl)-5-(4-pyridyl)imidazole-4-carboxylate obtained in Starting Material Synthetic Example 35 and 2-aminothiazole are reacted and treated in the same manner as in Example 31 to give 2-(4-fluorophenyl)-5-(4-pyridyl)-N-(2-thiazolyl)-imidazole-4-carboxamide hydrochloride.

Example 46

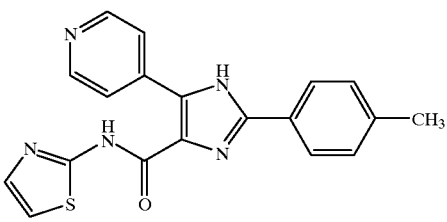

tert-Butyl 2-(4-methylphenyl)-5-(4-pyridyl)imidazole-4-carboxylate obtained in Starting Material Synthetic Example 36 and 2-aminothiazole are reacted and treated in the same manner as in Example 31 to give 2-(4-methylphenyl)-5-(4-pyridyl)-N-(2-thiazolyl)-imidazole-4-carboxamide hydrochloride.

Example 47

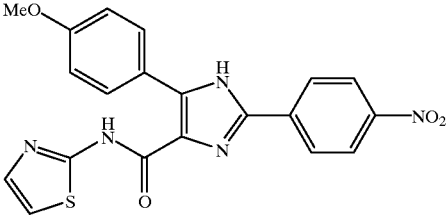

5-(4-Methoxyphenyl)-2-(4-nitrophenyl)imidazole-4-carboxylic acid (4.9 g) obtained in Starting Material Synthetic Example 37, 1 M hydrochloric acid—ether solution (30 ml), thionyl chloride (50 ml) and 2-aminothiazole (1.5 g) were reacted and treated in the same manner as in Example 1 to give 5-(4-methoxyphenyl)-2-(4-nitrophenyl)-N-(2-thiazolyl)imidazole-4-carboxamide (0.93 g). This was converted to hydrochloride to give 5-(4-methoxyphenyl)-2-(4-nitrophenyl)-N-(2-thiazolyl)imidazole-4-carboxamide hydrochloride (0.27 g), melting point 274–276° C. (decomposition).

Example 48

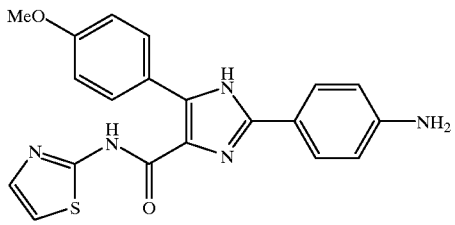

5-(4-Methoxyphenyl)-2-(4-nitrophenyl)-N-(2-thiazolyl)-imidazole-4-carboxamide (0.52 g) obtained in Example 47 and tin(II) chloride 6 hydrate (1.2 g) were reacted and treated in the same manner as in Example 59 to give 2-(4-aminophenyl)-5-(4-methoxyphenyl)-N-(2-thiazolyl) imidazole-4-carboxamide (0.17 g), melting point 257–258° C. (decomposition).

Example 49

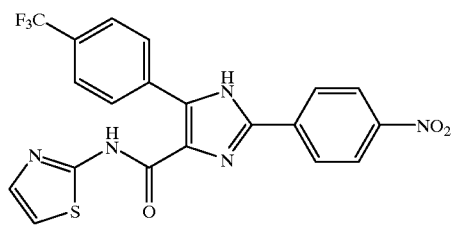

2-(4-Nitrophenyl)-5-(4-trifluoromethylphenyl)imidazole-4-carboxylic acid (4.0 g) obtained in Starting Material Synthetic Example 38, 1 M hydrochloric acid—ether solution (20 ml), thionyl chloride (40 ml) and 2-aminothiazole (1.1 g) were reacted and treated in the same manner as in Example 1 to give 2-(4-nitrophenyl)-5-(4-trifluoromethylphenyl)-N-(2-thiazolyl)imidazole-4-carboxamide (2.36 g). This was converted to hydrochloride to give 2-(4-nitrophenyl)-5-(4-trifluoromethylphenyl)-N-(2-thiazolyl)imidazole-4-carboxamide hydrochloride (1.65 g), melting point 250° C. or above.

$^1$H-NMR 400 MHz (DMSO-D$_6$, ppm) δ: 8.48(2H,d), 8.40(2H,d), 8.13(2H,d), 7.90(2H,d), 7.56(1H,d), 7.28(1H,d).

Example 50

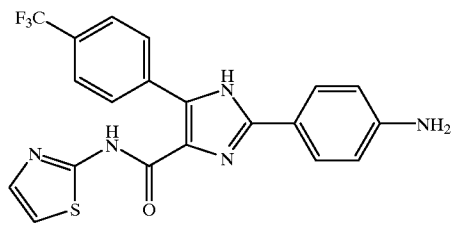

2-(4-Nitrophenyl)-5-(4-trifluoromethylphenyl)-N-(2-thiazolyl)-imidazole-4-carboxamide (0.42 g) obtained in Example 49 was hydrogenated in methanol using palladium. The catalyst was filtered off and the residue was concentrated to give 2-(4-aminophenyl)-5-(4-trifluoromethylphenyl)-N-(2-thiazolyl)imidazole-4-carboxamide (0.25 g), melting point 175–177° C.

Example 51

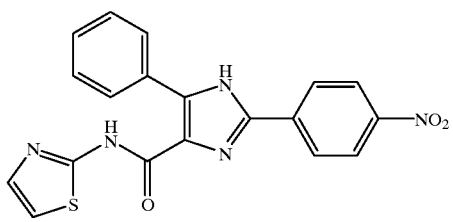

2-(4-Nitrophenyl)-5-phenylimidazole-4-carboxylic acid (5.0 g) obtained in Starting Material Synthetic Example 39, 1 M hydrochloric acid—ether solution (30 ml), thionyl chloride (50 ml) and 2-aminothiazole (1.7 g) were reacted and treated in the same manner as in Example 1 to give 2-(4-nitrophenyl)-5-phenyl-N-(2-thiazolyl)-imidazole-4-carboxamide (3.84 g). This was converted to hydrochloride to give 2-(4-nitrophenyl)-5-phenyl-N-(2-thiazolyl)-imidazole-4-carboxamide hydrochloride (0.51 g), melting point 250° C. or above.

1H-NMR 400 MHz (DMSO-D$_{61}$ ppm) δ: 8.49(2H,d), 8.49(2H,d), 7.89(2H,d), 7.55–7.48(4H,m), 7.27(1H,d)

Example 52

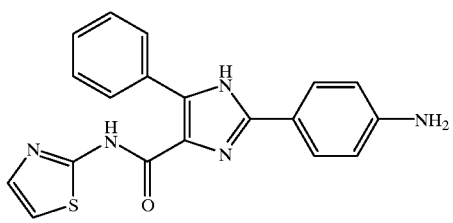

2-(4-Nitrophenyl)-5-phenyl-N-(2-thiazolyl)imidazole-4-carboxamide (0.52 g) obtained in Example 51 and tin(II) chloride 6 hydrate (1.2 g) were reacted and treated in the same manner as in Example 59 to give 2-(4-aminophenyl)-5-phenyl-N-(2-thiazolyl)imidazole-4-carboxamide (0.17 g), melting point 257–258° C. (decomposition).

Example 53

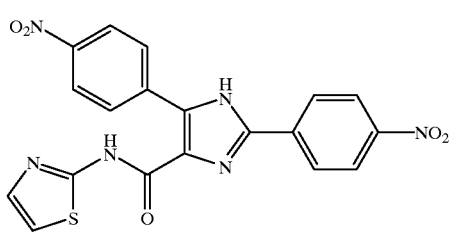

2,5-bis (4-Nitrophenyl) imidazole-4-carboxylic acid obtained in Starting Material Synthetic Example 40, 1 M hydrochloric acid—ether solution, thionyl chloride and 2-aminothiazole are reacted and treated in the same manner as in Example 1 to give 2,5-bis(4-nitrophenyl)-N-(2-thiazolyl)imidazole-4-carboxamide.

Example 54

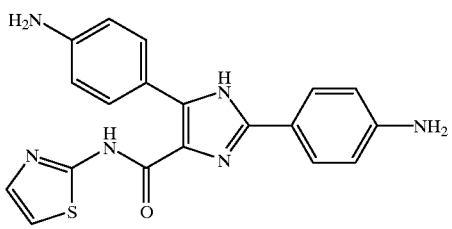

2,5-bis(4-Nitrophenyl)-N-(2-thiazolyl)imidazole-4-carboxamide obtained in Example 53 is suspended in methanol and ice-cooled. To the suspension is added a solution of tin(II) chloride 6 hydrate in 6 M hydrochloric acid solution and the mixture is reacted and treated in the same manner as in Example 48 to give 2,5-bis(4-aminophenyl)-N-(2-thiazolyl)imidazole-4-carboxamide.

Example 55

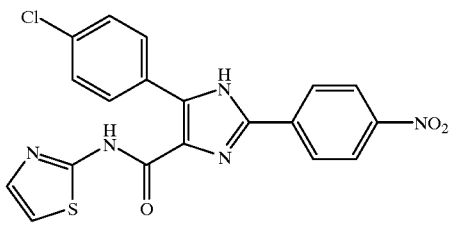

5-(4-Chlorophenyl)-2-(4-nitrophenyl)imidazole-4-carboxylic acid obtained in Starting Material Synthetic Example 41, 1 M hydrochloric acid—ether solution, thionyl chloride and 2-aminothiazole are reacted and treated in the same manner as in Example 1 to give 5-(4-chlorophenyl)-2-(4-nitrophenyl)-N-(2-thiazolyl)imidazole-4-carboxamide.

Example 56

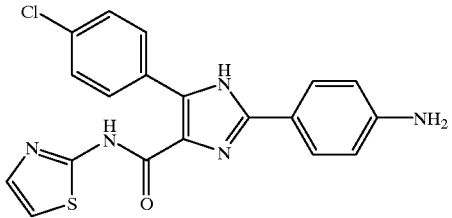

5-(4-Chlorophenyl)-2-(4-nitrophenyl)-N-(2-thiazolyl)-imidazole-4-carboxamide obtained in Example 55 is suspended in methanol and ice-cooled. To the suspension was added a solution of tin(II) chloride 6 hydrate in 6 M hydrochloric acid and the mixture is reacted and treated in the same manner as in Example 48 to give 2-(4-aminophenyl)-5-(4-chlorophenyl)-N-(2-thiazolyl) imidazole-4-carboxamide.

Example 57

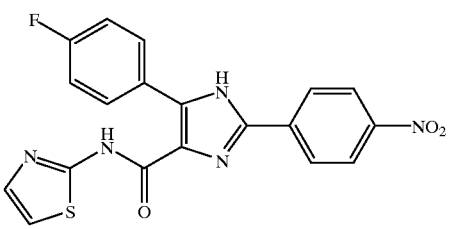

5-(4-Fluorophenyl)-2-(4-nitrophenyl)imidazole-4-carboxylic acid obtained in Starting Material Synthetic Example 42, 1 M hydrochloric acid—ether solution, thionyl chloride and 2-aminothiazole are reacted and treated in the same manner as in Example 1 to give 5-(4-fluorophenyl)-2-(4-nitrophenyl)-N-(2-thiazolyl)-imidazole-4-carboxamide.

Example 58

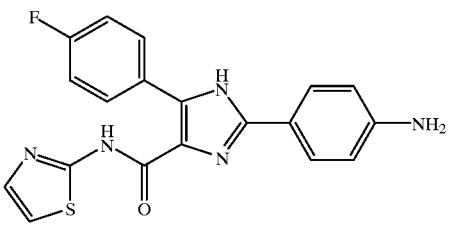

5-(4-Fluorophenyl)-2-(4-nitrophenyl)-N-(2-thiazolyl)-imidazole-4-carboxamide obtained in Example 57 is suspended in methanol and ice-cooled. To the suspension is added a solution of tin(II) chloride 6 hydrate in 6 M hydrochloric acid solution and the mixture is reacted and treated in the same manner as in Example 48 to give 2-(4-aminophenyl)-5-(4-fluorophenyl)-N-(2-thiazolyl)-imidazole-4-carboxamide.

Example 59

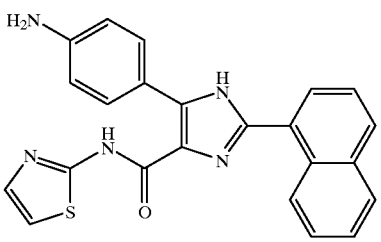

2-(1-Naphthyl)-5-(4-nitrophenyl)-N-(2-thiazolyl) imidazole-4-carboxamide (1.22 g) obtained in Example 18 was suspended in methanol and ice-cooled. To the suspension was added a solution of tin(II) chloride 6 hydrate (3.0 g) in 6 M hydrochloric acid (30 ml) and the mixture was refluxed under heating for 1.5 hr. The precipitated white crystals were collected by filtration and the crystals were dissolved in ethyl acetate. The ethyl acetate layer was washed with saturated aqueous sodium hydrogencarbonate solution and water, and dried. To the ethyl acetate layer was added 1 M hydrochloric acid—ether and the precipitated crystals were collected by filtration. The obtained crude crystals were recrystallized from methanol to give 5-(4-aminophenyl)-2-(1-naphthyl)-N-(2-thiazolyl)imidazole-4-carboxamide (0.28 g).

Hydrochloride: melting point 242° C. (decomposition)

Example 60

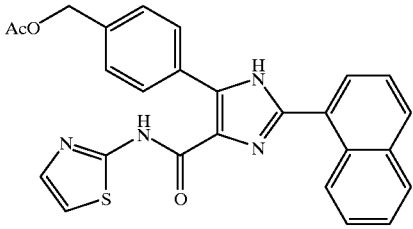

(1) tert-Butyl 3-(4-acetoxymethylphenyl)-2-hydroxyimino-3-oxopropionate (19.2 g) and 1-naphthylmethylamine (11.3 g) were reacted and treated in the same manner as in Starting Material Synthetic Example 1 to give tert-butyl 5-(4-acetoxymethylphenyl)-2-(1-naphthyl)-imidazole-4-carboxylate (10.5 g), melting point 162–164° C. (2) tert-Butyl 5-(4-acetoxymethylphenyl)-2-(1-naphthyl)imidazole-4-carboxylate (10.5 g) was reacted and treated in the same manner as in Example 31 to give 5-(4-acetoxymethylphenyl)-2-(1-naphthyl)-N-(2-thiazolyl) imidazole-4-carboxamide (6.62 g), melting point 197–199° C.

Hydrochloride: melting point 225–227° C. (decomposition).

Example 61

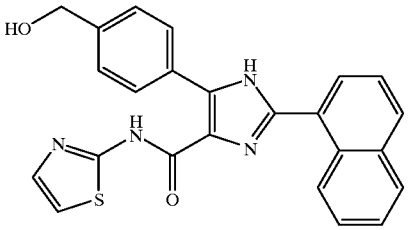

5-(4-Acetoxymethylphenyl)-2-(1-naphthyl)-N-(2-thiazolyl)-imidazole-4-carboxamide (2.98 g) obtained in Example 60(2) was dissolved in acetone (250 ml) and 0.25 M aqueous sodium hydroxide solution (56 ml) was added under ice-cooling. The mixture was stirred at room temperature for 2 hr. Acetone was evaporated under reduced pressure and the residue was acidified with aqueous citric acid solution and extracted with ethyl acetate. The ethyl acetate layer was washed with water and the solvent was evaporated. The obtained residue was recrystallized from ethyl acetate to give 5-(4-hydroxymethylphenyl)-2-(1-naphthyl)-N-(2-thiazolyl)imidazole-4-carboxamide (2.08 g), melting point 226–228° C.

Hydrochloride: melting point 278–281° C. (decomposition).

Example 62

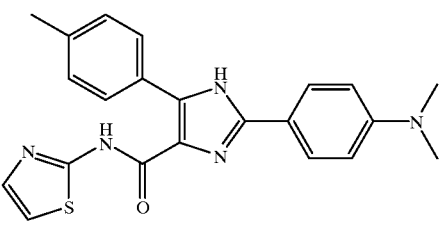

A suspension of 2-(4-aminophenyl)-5-(4-methylphenyl)-N-(2-thiazolyl)imidazole-4-carboxamide (0.13 g) obtained in Example 21 and sodium borohydride (1.5 g) in tetrahydrofuran was added dropwise to a 3N solution of sulfuric acid (3 ml) and 37% formaldehyde (3 ml) in tetrahydrofuran under ice-cooling. The mixture was stirred at room temperature for about 30 min and water was added. The mixture was made alkaline with potassium hydroxide. The aqueous layer was extracted twice with ethyl acetate and the ethyl acetate layer was washed with saturated brine, dried and concentrated. The white precipitate was recrystallized from ethyl acetate to give 2-(4-dimethylamino-phenyl)-5-(4-methylphenyl)-N-(2-thiazolyl)imidazole-4-carboxamide (50 mg), melting point 265–267° C. (decomposition).

Example 63

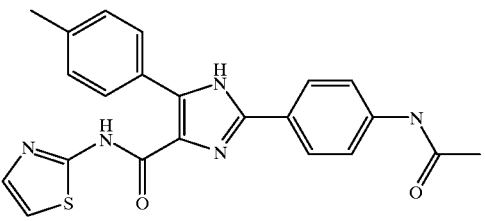

2-(4-Aminophenyl)-5-(4-methylphenyl)-N-(2-thiazolyl)-imidazole-4-carboxamide (0.30 g) obtained in Example 21 was dissolved in pyridine (20 ml) and acetyl chloride (0.8 ml) was added dropwise under ice-cooling. The mixture was stirred at room temperature for 2 hr. The reaction mixture was concentrated to give white crystals, which were recrystallized from ethyl acetate to give 2-(4-acetamidophenyl)-5-(methylphenyl)-N-(2-thiazolyl)imidazole-4-carboxamide (0.17 g), melting point 269–271° C.

Example 64

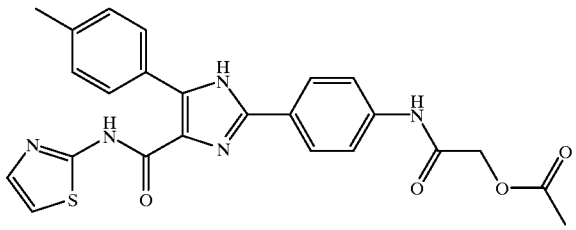

2-(4-Aminophenyl)-5-(4-methylphenyl)-N-(2-thiazolyl)-imidazole-4-carboxamide (0.30 g) obtained in Example 21 was dissolved in pyridine (20 ml) and acetoxyacetyl chloride (0.1 ml) was added dropwise under ice-cooling. The mixture was stirred at room temperature for 4 hr. The reaction mixture was concentrated and the residue was purified by silica gel chromatography using, as a mobile phase, chloroform/ethyl acetate=20:1. Theresidue was recrystallized from ethyl acetate to give 4-[5-(4-methylphenyl)-4-(2-thiazolylcarbamoyl)imidazol-2-yl]phenylcarbamoylmethyl acetate (0.13 g), melting point 250° C. or above.

$^1$H-NMR 400 MHz (DMSO-D$_6$, ppm) δ: 13.1(1H,s), 11.2(1H,s), 10.3(1H,s), 8.14(2H,d), 7.79(2H,d), 7.71(2H,d), 7.51(1H.d), 7.32(2H.d), 7.24(1H,d), 4.67(2H,d), 2.39(3H,s), 2.13(3H,s)

Example 65

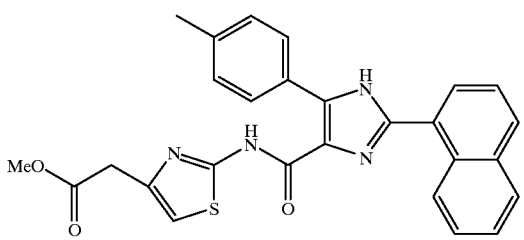

5-(4-Methylphenyl)-2-(1-naphthyl)imidazole-4-carboxylic acid (0.5 g) obtained in Starting Material Synthetic Example 2, 1 M hydrochloric acid—ether solution (5 ml), thionyl chloride (10 ml) and methyl 2-amino-4-thiazoleacetate (0.3 g) were reacted and treated in the same manner as in Example 1 to give methyl 2-[5-(4-methylphenyl)-2-(l-naphthyl)imidazole-4-carboxamido]-4-thiazoleacetate (0.16 g), melting point 147–149° C. (decomposition).

Example 66

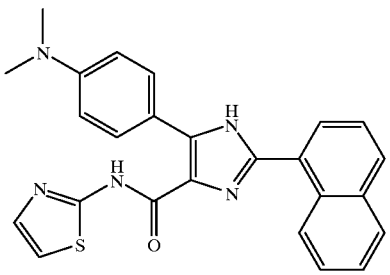

5-(4-Aminophenyl)-2-(1-naphthyl)-N-(thiazolyl) imidazole-4-carboxamide (0.42 g) obtained in Example 59, sodium borohydride (1.5 g), 3N sulfuric acid (3 ml) and 37% formaldehyde (3 ml) were treated in the same manner as in Example 62 to give 5-(4-dimethylaminophenyl)-2-(1-naphthyl)-N-(2-thiazolyl)imidazole-4-carboxamide (0.16 g), melting point 242–243° C. (decomposition).

Example 67

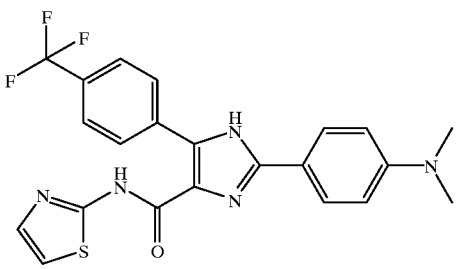

2-(4-Aminophenyl)-5-(4-trifluoromethylphenyl)-N-(2-thiazolyl) imidazole-4-carboxamide (0.2 g),sodium borohydride(1.5 g), 3N sulfuric acid (3 ml) and 37% formaldehyde (3 ml) were treated in the same manner as in Example 62 to give 2-(4-dimethylamino-phenyl)-5-(4-trifluoromethylphenyl)-N-(2-thiazolyl)imidazole-4-carboxamide (0.20 g), melting point 260–261° C. (decomposition).

Hydrochloride: melting point 227–229° C. (decomposition).

Example 68

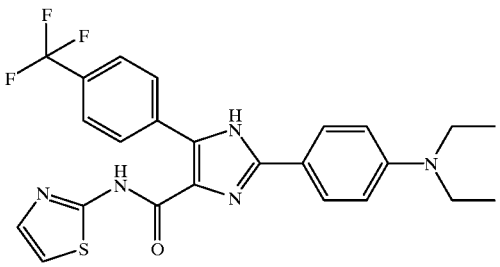

2-(4-Aminophenyl)-5-(4-trifluoromethylphenyl)-N-(2-thiazolyl)imidazole-4-carboxamide (0.7 g) obtained in Example 50, sodium borohydride (1.5 g), 3N sulfuric acid (3 ml) and acetaldehyde (1 ml) were treated in the same manner as in Example 62 to give 2-(4-diethylaminophenyl)-5-(4-trifluoromethylphenyl)-N-(2-thiazolyl)imidazole-4-carboxamide (0.6 g). This was converted to hydrochloride to give 2-(4-diethylaminophenyl)-5-(4-trifluoromethylphenyl)-N-(2-thiazolyl)imidazole-4-carboxamide.

Hydrochloride (0.58 g): melting point 253–255° C. (decomposition).

Example 69

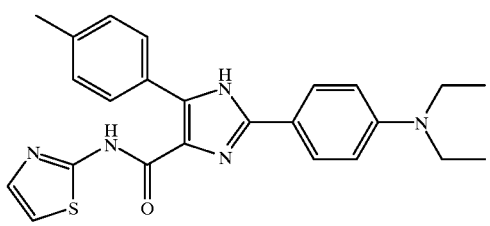

2-(4-Aminophenyl)-5-(4-methylphenyl)-N-(2-thiazolyl)-imidazole-4-carboxamide (0.3 g) obtained in Example 21, sodium borohydride (0.5 g), 3N sulfuric acid (3 ml) and acetaldehyde (0.3 ml) were treated in the same manner as in Example 62 to give 2-(4-diethylaminophenyl)-5-(4-methylphenyl)-N-(2-thiazolyl)imidazole-4-carboxamide (0.17 g), melting point 98–99° C. (decomposition).

Example 70

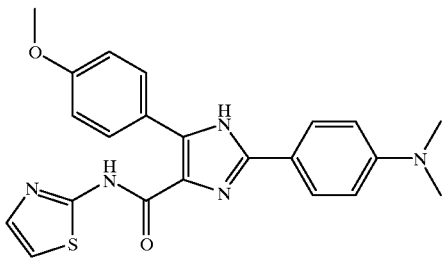

2-(4-Aminophenyl)-5-(4-methoxyphenyl)-N-(2-thiazolyl)-imidazole-4-carboxamide (0.5 g) obtained in Example 48, sodium borohydride (1.5 g), 3N sulfuric acid (3 ml) and 37%formaldehyde (3 ml) were treated in the same manner as in Example 62 to give 2-(4-dimethylaminophenyl)-5-(4-methoxyphenyl)-N-(2-thiazolyl)imidazole-4-carboxamide (0.27 g). This was converted to hydrochloride to give 2-(4-dimethylaminophenyl)-5-(4-methoxyphenyl)-N-(2-thiazolyl)-imidazole-4-carboxamide. Hydrochloride (0.3 g): melting point 228–230° C. (decomposition).

Example 71

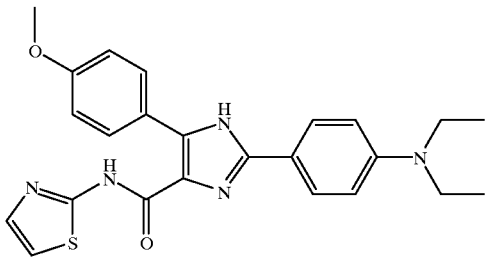

2-(4-Aminophenyl)-5-(4-methoxyphenyl)-N-(2-thiazolyl)-imidazole-4-carboxamide (1.5 g) obtained in Example 48, sodium borohydride (3.0 g), 3N sulfuric acid (3 ml) and acetaldehyde (2 ml) were treated in the same manner as in Example 62 to give 2-(4-diethylaminophenyl)-5-(4-methoxyphenyl)-N-(2-thiazolyl)imidazole-4-carboxamide (0.85 g). This was converted to hydrochloride to give 2-(4-diethylaminophenyl)-5-(4-methoxyphenyl)-N-(2-thiazolyl)-imidazole-4-carboxamide. Hydrochloride (0.78 g): melting point 217–220° C. (decomposition).

Example 72

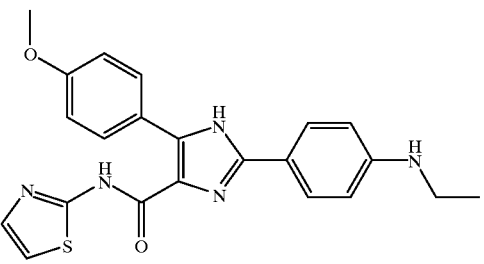

2-(4-Aminophenyl)-5-(4-methoxyphenyl)-N-(2-thiazolyl)-imidazole-4-carboxamide (1.0 g) obtained in Example 48 was dissolved in a mixed solvent of tetrahydrofuran and methanol, and added to a solution of 4N sulfuric acid (0.2 ml) and acetaldehyde (0.2 ml) in tetrahydrofuran. To the solution was added sodium borohydride (0.13 g) and the mixture was stirred at room temperature for 2 hr. To the reaction mixture was added a saturated aqueous sodium hydrogencarbonate solution and the mixture was extracted with ethyl acetate. The ethyl acetate phase was washed with saturated brine, dried and concentrated. The residue was purified by silica gel chromatography using, as a mobile phase, chloroform/ethyl acetate=100:1 to give 2-(4-ethylaminophenyl)-5-(4-methoxyphenyl)-N-(2-thiazolyl)imidazole-4-carboxamide (1.2 g). This was converted to hydrochloride to give 2-(4-ethylaminophenyl)-5-(4-methoxy-phenyl)-N-(2-thiazolyl)imidazole-4-carboxamide hydrochloride (0.48 g), melting point 250° C. or above.

$^1$H-NMR 400 MHz (DMSO-D$_6$, ppm) δ: 8.16(2H,d), 7.81(2H,d), 7.57(1H,d), 7.30(1H,d), 7.11(2H,d), 6.97(2H,d), 3.85(3H,s), 3.21(2H,q), 1.22(3H,t)

Example 73

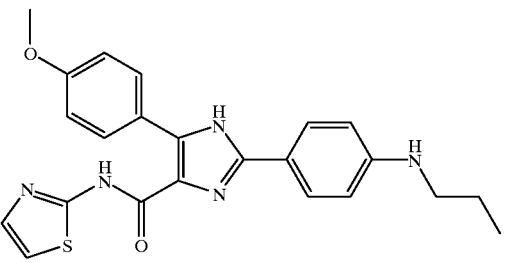

2-(4-Aminophenyl)-5-(4-methoxyphenyl)-N-(2-thiazolyl)-imidazole-4-carboxamide (1.0 g) obtained in Example 48, sodium borohydride (0.13 g), 4N sulfuric acid (0.2 ml) and propyl aldehyde (0.2 ml) were treated in the same manner as in Example 72 to give 5-(4-methoxyphenyl)-2-(4-propylaminophenyl)-N-(2-thiazolyl)-imidazole-4-carboxamide (1.1 g). This was converted to hydrochloride to give 5-(4-methoxyphenyl)-2-(4-propylaminophenyl)-N-(2-thiazolyl)imidazole-4-carboxamide hydrochloride (0.28 g), melting point 250° C. or above.

$^1$H-NMR 270 MHz (DMSO-D$_6$, ppm) δ: 8.13(2H,d), 7.79(2H,d), 7.57(1H,d), 7.30(1H,d), 7.12(2H,d), 6.88(2H,d), 3.85(3H,s), 3.15(2H,t), 2.51(2H,m), 0.96(3H,t).

Example 74

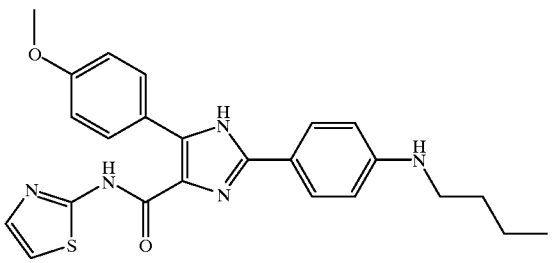

2-(4-Aminophenyl)-5-(4-methoxyphenyl)-N-(2-thiazolyl)-imidazole-4-carboxamide (1.0 g) obtained in Example 48, sodium borohydride (0.13 g), 4N sulfuric acid (0.2 ml) and butyraldehyde (0.3 ml) were treated in the same manner as in Example 72 to give 2-(4-butylaminophenyl)-5-(4-methoxyphenyl)-N-(2-thiazolyl)imidazole-4-carboxamide (1.1 g). This was converted to hydrochloride to give 2-(4-butylaminophenyl)-5-(4-methoxyphenyl)-N-(2-thiazolyl)-imidazole-4-carboxamide hydrochloride (0.20 g), melting point 250° C. or above.

$^1$H-NMR 270 MHz (DMSO-D$_6$, ppm) δ: 8.12(2H,d), 7.80(2H,d), 7.56(1H,d), 7.30(1H,d), 7.11(2H,d), 6.87(2H,d), 3.85(3H,s), 3.15(2H,t), 1.59(2H,m), 1.40(2H,m), 0.92(3H,t)

Example 75

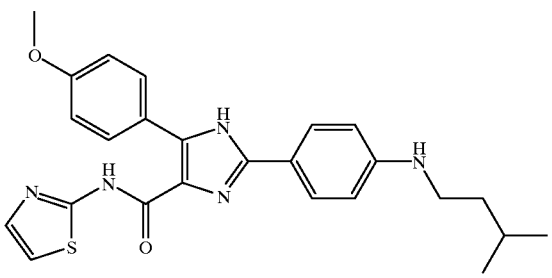

2-(4-Aminophenyl)-5-(4-methoxyphenyl)-N-(2-thiazolyl)-imidazole-4-carboxamide (0.8 g) obtained in Example 48, sodium borohydride (0.13 g), 2.5N sulfuric acid (0.4 ml) and isopentyl aldehyde (0.3 ml) were treated in the same manner as in Example 72 to give 2-(4-isopentylaminophenyl)-5-(4-methoxyphenyl)-N-(2-thiazolyl)imidazole-4-carboxamide (0.3 g), melting point 235–239° C.

Example 76

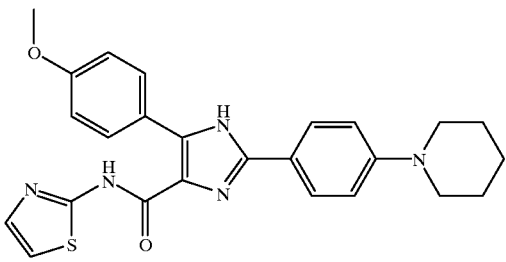

2-(4-Aminophenyl)-5-(4-methoxyphenyl)-N-(2-thiazolyl)-imidazole-4-carboxamide (2.0 g) obtained in Example 48, sodium borohydride (0.8 g), 3N sulfuric acid (4 ml) and 25% glutaraldehyde (4 ml) were treated in the same manner as in Example 62 to give 5-(4-methoxyphenyl)-2-(4-piperidinophenyl)-N-(2-thiazolyl)imidazole-4-carboxamide (1.53 g). This was converted to hydrochloride to give 5-(4-methoxyphenyl)-2-(4-piperidinophenyl)-N-(2-thiazolyl)-imidazole-4-carboxamide hydrochloride (0.25 g), melting point 250° C. or above.

$^1$H-NMR 270 MHz (DMSO-D$_6$, ppm) δ: 8.34(2H,d), 7.87(2H,d), 7.61(1H,d), 7.33(1H,d), 7.11(2H,d), 6.87(2H,d), 3.85(3H,s), 3.52(4H,br), 1.90(4H,br), 1.67(2H,br).

Example 77

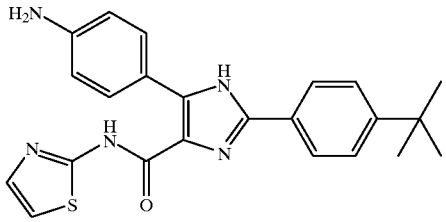

2-(4-tert-Butylphenyl)-5-(4-nitrophenyl)-N-(2-thiazolyl)-imidazole-4-carboxamide (16.3 g) was dissolved in a mixed solvent of dioxane and methanol and hydrogenated with Raney nickel. The catalyst was filtered off and the residue was concentrated and crystallized from ethyl acetate and isopropyl ether to give 5-(4-aminophenyl)-2-(4-tert-butylphenyl)-N-(2-thiazolyl)imidazole-4-carboxamide (7.13 g). 1.0 g therefrom was converted to hydrochloride to give 5-(4-aminophenyl)-2-(4-tert-butylphenyl)-N-(2-thiazolyl)imidazole-4-carboxamide hydrochloride (0.48 g), melting point 270–272° C. (decomposition).

Example 78

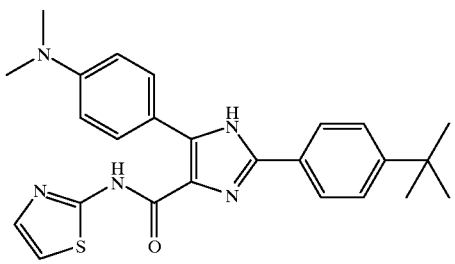

5-(4-Aminophenyl)-2-(4-tert-butylphenyl)-N-(2-thiazolyl)-imidazole-4-carboxamide (2.0 g) obtained in Example 77 was dissolved in methanol and 37% formaldehyde (3.6 ml) was added. Thereto was added sodium cyanoborohydride (3.0 g) under ice-cooling and the mixture was stirred at room temperature overnight. After the reaction, the reaction mixture was concentrated and the residue was purified by 5 silica gel chromatography using, as a mobile phase, chloroform/ethyl acetate=100:1. After purification, the compound was converted to hydrochloride to give 2-(4-tert-butylphenyl)-5-(4-dimethylamino-phenyl)-N-(2-thiazolyl)imidazole-4-carboxamide hydrochloride (0.47 g), melting point 228–230° C. (decomposition).

Example 79

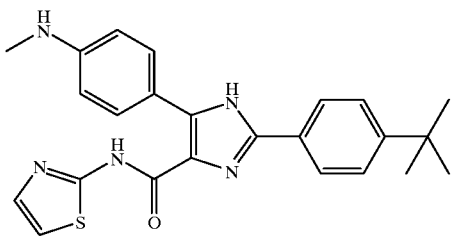

5-(4-Aminophenyl)-2-(4-tert-butylphenyl)-N-(2-thiazolyl)-imidazole-4-carboxamide (0.5 g) obtained in Example 77 was refluxed in triethyl orthoformate overnight and concentrated. Thereto were added ethanol and tetrahydrofuran, and sodium borohydride (0.4 g) was added. The mixture was refluxed under heating for 2 hr. After refluxing, water was added and the mixture was extracted with ethyl acetate. The ethyl acetate phase was washed with saturated brine and dried. After drying, the residue was concentrated to give 2-(4-tert-butylphenyl)-5-(4-methylaminophenyl)-N-(2-thiazolyl)-imidazole-4-carboxamide (0.5 g). This was converted to hydrochloride to give 2-(4-tert-butylphenyl)-5-(4-methylaminophenyl)-N-(2-thiazolyl) imidazole-4-carboxamide hydrochloride (0.24 g), melting point 257–259° C. (decomposition).

Example 80

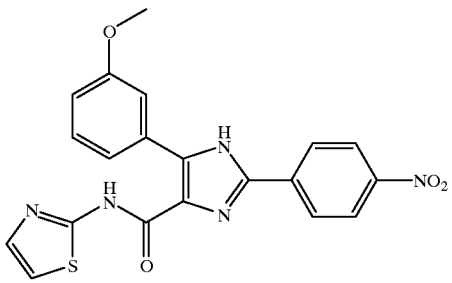

5-(3-Methoxyphenyl)-2-(4-nitrophenyl)imidazole-4-carboxylic acid (5.0 g) obtained in Starting Material Synthetic Example 44, 1 M hydrochloric acid—ether solution (20 ml), thionyl chloride (10 ml) and 2-aminothiazole (1.5 g) were reacted and treated in the same manner as in Example 1 to give 5-(3-methoxyphenyl)-2-(4-nitrophenyl)-N-(2-thiazolyl)imidazole-4-carboxamide. This was converted to hydrochloride to give 5-(3-methoxyphenyl)-2-(4-nitrophenyl)-N-(2-thiazolyl)imidazole-4-carboxamide hydrochloride (0.73 g), melting point 257–260° C. (decomposition).

Example 81

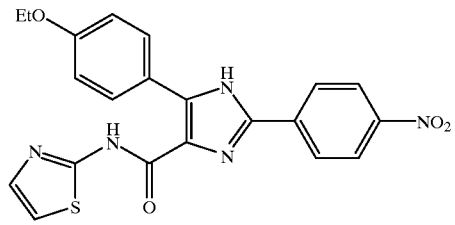

5-(4-Ethoxyphenyl)-2-(4-nitrophenyl)imidazole-4-carboxylic acid (5.0 g) obtained in Starting Material Synthetic Example 46, 1 M hydrochloric acid—ether solution (20 ml), thionyl chloride (10 ml) and 2-aminothiazole (1.5 g) were reacted and treated in the same manner as in Example 1 to give 5-(4-ethoxyphenyl)-2-(4-nitrophenyl)-N-(2-thiazolyl)imidazole-4-carboxamide. This was converted to hydrochloride to give 5-(4-ethoxyphenyl)-2-(4-nitrophenyl)-N-(2-thiazolyl)imidazole-4-carboxamide hydrochloride (0.14 g), melting point 267–270° C. (decomposition).

Example 82

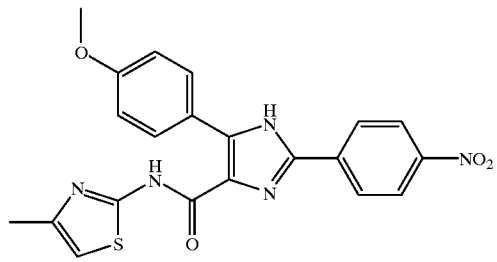

5-(4-Methoxyphenyl)-2-(4-nitrophenyl)imidazole-4-carboxylic acid (1.0 g) obtained in Starting Material Synthetic Example 37, 1 M hydrochloric acid—ether solution (5 ml), thionyl chloride (2 ml) and 2-amino-4-methylthiazole (0.3 g) were reacted and treated in the same manner as in Example 1 to give 5-(4-methoxyphenyl)-2-(4-nitrophenyl)-N-(4-methyl-2-thiazolyl)imidazole-4-carboxamide. This was converted to hydrochloride to give 5-(4-methoxyphenyl)-2(4-nitrophenyl)-N-(4-methyl-2-thiazolyl) imidazole-4-carboxamide hydrochloride (0.31 g), melting point 210–212° C. (decomposition).

Example 83

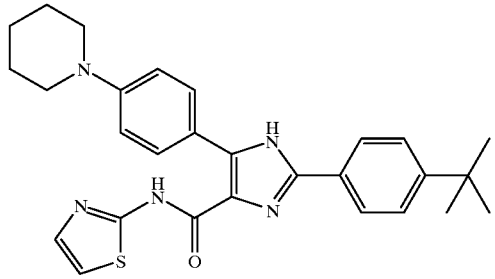

5-(4-Aminophenyl)-2-(4-tert-butylphenyl)-N-(2-thiazolyl)-imidazole-4-carboxamide (1.0 g) obtained in Example 77 was dissolved in tetrahydrofuran (55 ml), methanol (55 ml) and KH$_2$PO$_4$-Na$_2$HPO$_4$ buffer (pH 6.5, 70 ml), and 25% glutaraldehyde aqueous solution (1.22 g) and sodium cyanoborohydride (1.32 g) were added under ice-cooling. The mixture was stirred at room temperature for 17 days. Water (100 ml) was added and the mixture was extracted with ethyl acetate. The organic layer was washed with saturated aqueous hydrogencarbonate solution and saturated brine, and dried over anhydrous magnesium sulfate. The solvent was evaporated under reduced pressure and the residue was subjected to silica gel column chromatography to give the objective 2-(4-tert-butylphenyl)-5-(4-piperidinophenyl)-N-(2-thiazolyl)-imidazole-4-carboxamide (0.12 g), melting point 250–252° C. (decomposition).

Example 84

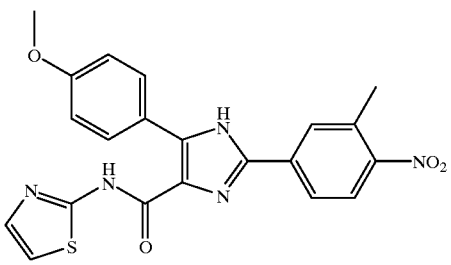

5-(4-Methoxyphenyl)-2-(3-methyl-4-nitrophenyl) imidazole-4-carboxylic acid (20.9 g) obtained in Starting Material Synthetic Example 48, 1 M hydrochloric acid—ether solution (38 ml), thionyl chloride (48.2 ml) and 2-aminothiazole (6.56 g) were reacted and treated in the same manner as in Example 1 to give 5-(4-methoxyphenyl)-2-(3-methyl-4-nitrophenyl)-N-(2-thiazolyl)-imidazole-4-carboxamide (12.5 g). 1.09 g therefrom was converted to hydrochloride to give 5-(4-methoxyphenyl)-2-(3-methyl-4-nitrophenyl)-N-(2-thiazolyl)imidazole-4-carboxamide hydrochloride (0.68 g), melting point 250° C. or above.

$^1$H-NMR 270 MHz (DMSO-D$_6$, ppm) δ: 8.39(1H,s), 8.28(1H,d), 8.13(1H,d), 7.90(1H,d), 7.65(1H,d), 7.34(1H,d), 7.09(1H,d), 5.22(2H,br), 3.84(3H,s), 2.62(3H,s).

Example 85

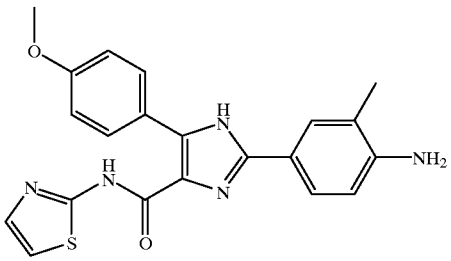

5-(4-Methoxyphenyl)-2-(3-methyl-4-nitrophenyl)-N-(2-thiazolyl)imidazole-4-carboxamide (1.5 g) obtained in Example 84 was dissolved in 50% aqueous ethanol solution (60 ml) and dioxane (50 ml), and iron powder (0.6 g) was added. Conc. hydrochloric acid (0.06 ml) was added under refluxing and the mixture was refluxed for 1 hr. A saturated aqueous hydrogencarbonate solution was added and the mixture was neutralized. An insoluble matter was filtered off and the filtrate was concentrated under reduced pressure. Water was added to the residue and the mixture was extracted with ethyl acetate and dried over anhydrous magnesium sulfate. After drying, the solvent was evaporated under reduced pressure. The obtained crystals (0.79 g) were dissolved in methanol (24 ml) and dioxane (35 ml) and 1 M hydrochloric acid—ether solution (5.85 ml) was added. The mixture was stirred at room temperature for 1 hr. The solvent was evaporated under reduced pressure and the obtained crystals were recrystallized from ethanol to give the objective 2-(4-amino-3-methylphenyl)-5-(4-methoxyphenyl)-N-(2-thiazolyl)imidazole-4-carboxamide. Hydrochloride (0.43 g): melting point 250° C. or above $^1$H-NMR 270 MHz (DMSO-D$_6$, ppm) δ: 8.13(1H,s), 8.06(1H,d), 7.84(1H,d), 7.59(1H,d), 7.31(1H,d), 7.23(1H,d), 7.10(1H,d), 5.50(4H,br), 3.85(3H,s), 2.50(3H,s)

Example 86

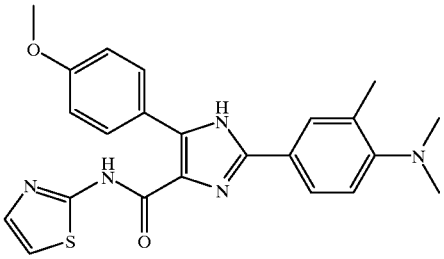

To a solution of tetrahydrofuran (7 ml), 2.5N sulfuric acid (8.3 ml) and 37% formalin (7 ml) were added 2-(4-amino-3-methylphenyl)-5-(4-methoxyphenyl)-N-(2-thiazolyl) imidazole-4-carboxamide (1.2 g) obtained in Example 85 and tetrahydrofuran (45 ml) with stirring under ice-cooling. The mixture was stirred for 5 min. Sodium borohydride (3.5 g) was added portionwise and the mixture was stirred at room temperature for 2.5 hr. The mixture was neutralized with 5% aqueous potassium carbonate solution and the solvent was evaporated under reduced pressure. Water was added to the obtained residue and the mixture was extracted with ethyl acetate. The organic layer was dried over anhydrous magnesium sulfate and, after drying, the solvent was evaporated under reduced pressure. The residue was subjected to silica gel column chromatography to give the objective 2-(4-dimethylamino-3-methylphenyl)-5-(4-methoxyphenyl)-N-(2-thiazolyl)imidazole-4-carboxamide. This was converted to hydrochloride to give 2-(4-dimethylamino-3-methylphenyl)-5-(4-methoxyphenyl)-N-(2-thiazolyl)imidazole-4-carboxamide. Hydrochloride (0.40 g): melting point 245–250° C. (decomposition).

Example 87

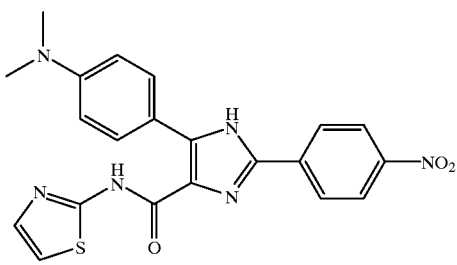

Ethyl 5-(4-dimethylaminophenyl)-2-(4-nitrophenyl)imidazole-4-carboxylate (1.2 g) obtained in Starting Material Synthetic Example 49 was reacted and treated in the same manner as in Starting Material Synthetic Example 2 and then Example 1 to give 5-(4-dimethylamino-phenyl)-2-(4-nitrophenyl)-N-(2-thiazolyl)imidazole-4-carboxamide (230 mg), melting point 250–251° C.

Example 88

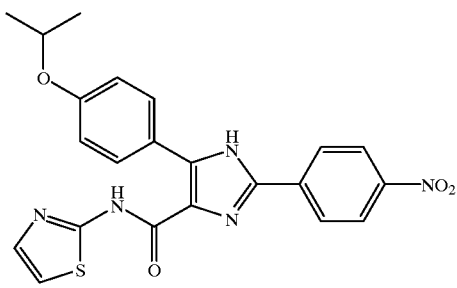

Ethyl 5-(4-isopropoxyphenyl)-2-(4-nitrophenyl)imidazole-4-carboxylate (1.4 g) obtained in Starting Material Synthetic Example 50 was reacted and treated in the same manner as in Starting Material Synthetic Example 2 and then Example 1 to give 5-(4-isopropoxy-phenyl)-2-(4-nitrophenyl)-N-(2-thiazolyl)imidazole-4-carboxamide (550 mg), melting point 267–270° C.

Example 89

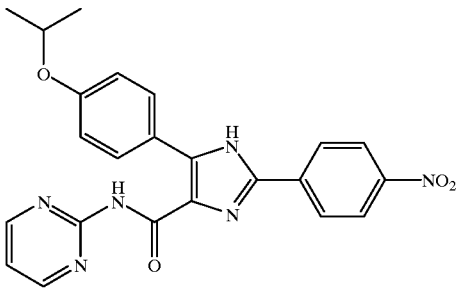

Ethyl 5-(4-isopropoxyphenyl)-2-(4-nitrophenyl)imidazole-4-carboxylate (1.4 g) obtained in Starting Material Synthetic Example 50 was reacted and treated in the same manner as in Starting Material Synthetic Example 2. The obtained carboxylic acid and 2-aminopyrimidine (200 mg) were reacted and treated in the same manner as in Example 1 to give 5-(4-isopropoxyphenyl)-2-(4-nitrophenyl)-N-(2-pyrimidinyl)imidazole-4-carboxamide hydrochloride (590 mg), melting point 275° C. or above.

Example 90

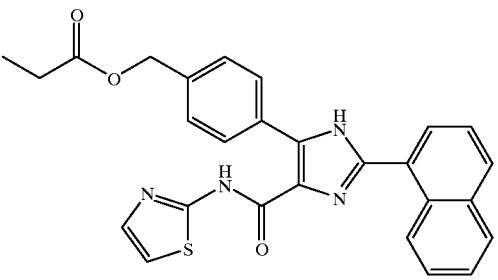

5-(4-Hydroxymethylphenyl)-2-(1-naphthyl)-N-(2-thiazolyl)-imidazole-4-carboxamide (300 mg) obtained in Example 61 was dissolved in pyridine (5 ml) and propionic anhydride (5 ml), and the mixture was left standingfor 12 hr. Thereaction mixture was poured into icewater and extracted with ethyl acetate. The ethyl acetate layer was washed with water and, after drying, concentrated. The obtained residue was recrystallized from ethyl acetate to give 2-(1-naphthyl)-5-(4-propionyloxymethylphenyl)-N-(2-thiazolyl)imidazole-4-carboxamide (150 mg), melting point 281–283° C.

Example 91

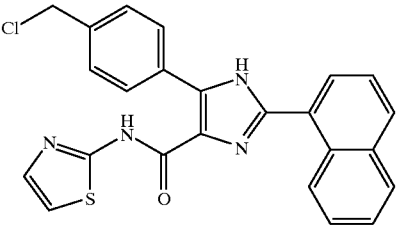

5-(4-Hydroxymethylphenyl)-2-(1-naphthyl)-N-(2-thiazolyl)-imidazole-4-carboxamide (1.0 g) obtained in Example 61 was dissolved in tetrahydrofuran (200 ml), and triphenylphosphine (1.24 g) and N-chlorosuccinimide (633 mg) were added. The mixture was stirred for 15 min and triphenylphosphine (1.24 g) and N-chlorosuccinimide (633 mg) were added. The mixture was stirred for 30 min. The reaction mixture was poured into ice water and extracted with ethyl acetate. The ethyl acetate layer was washed with water and, after drying, concentrated. The obtained residue was suspended in acetone (30 ml) and 1 M hydrochloric acid—ether solution (3 ml) was added. The solvent was evaporated and ethyl acetate was added to the obtained residue. The resulting crystals were collected by filtration to give 5-(4-chloromethylphenyl)-2-(1-naphthyl)-N-(2-thiazolyl)imidazole-4-carboxamide hydrochloride (580 mg), melting point 280° C. or above.

$^1$H-NMR 400 MHz (DMSO-D$_6$, ppm) δ: 4.85(2H,s), 7.31(1H,d), 7.56(1H,d), 7.58–7.69(5H,m), 7.95(2H,d), 8.01(1H,d), 8.05(1H,d), 8.11(1H,d), 8.90(1H,d).

Example 92

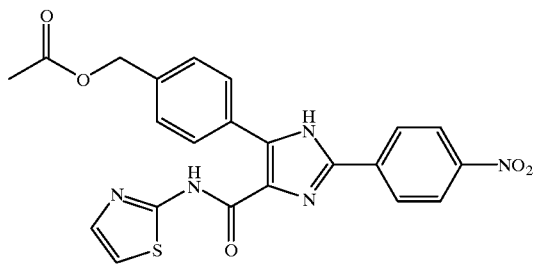

tert-Butyl 5-(4-acetoxymethylphenyl)-2-(4-nitrophenyl)-imidazole-4-carboxylate (5.27 g) obtained in Starting Material Synthetic Example 51 was reacted and treated in the same manner as in Example 31 to give 5-(4-acetoxymethylphenyl)-2-(4-nitrophenyl)-N-(2-thiazolyl) imidazole-4-carboxamide (5.75 g), melting point 265–266° C. (decomposition).

Hydrochloride: melting point 257–261° C. (decomposition).

Example 93

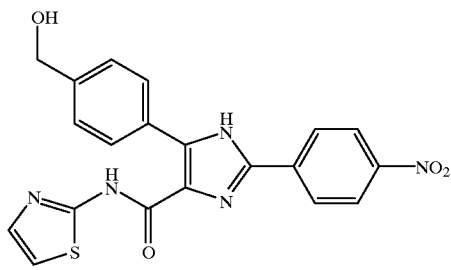

5-(4-Acetoxymethylphenyl)-2-(4-nitrophenyl)-N-(2-thiazolyl)imidazole-4-carboxamide (4.93 g) obtained in Example 92 was reacted and treated in the same manner as in Example 61 to give 5-(4-hydroxymethylphenyl)-2-(4-nitrophenyl)-N-(2-thiazolyl)-imidazole-4-carboxamide (4.45 g), melting point 249–252° C.

Example 94

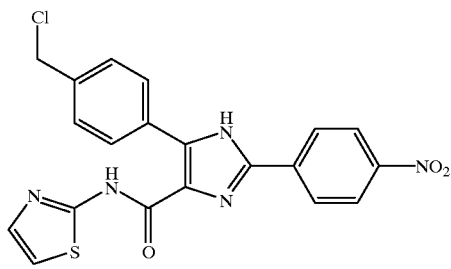

5-(4-Hydroxymethylphenyl)-2-(4-nitrophenyl)-N-(2-thiazolyl)imidazole-4-carboxamide (2.67 g) obtained in Example 93 was dissolved in tetrahydrofuran (300 ml) and triphenylphosphine (3.33 g) and N-chlorosuccinimide (1.70 g) were added. The mixture was stirred for 15 min and triphenylphosphine (3.33 g) and N-chlorosuccinimide (1.70 g) were added. The mixture was stirred for 30 min. The reaction mixture was poured into ice water and extracted with ethyl acetate. The ethyl acetate layer was washed with water and, after drying, concentrated. The obtained residue was recrystallized from ethyl acetate to give 5-(4-chloromethylphenyl)-2-(4-nitrophenyl)-N-(2-thiazolyl) imidazole-4-carboxamide (2.60 g), melting point 280° C. or above.

$^1$H-NMR 400 MHz (DMSO-D$_6$, ppm) δ: 4.85(2H,s), 7.28(1H,d), 7.56(1H,d), 7.59(2H,d), 7.90(2H,d), 8.40(2H,d), 8.48(2H,d).

Example 95

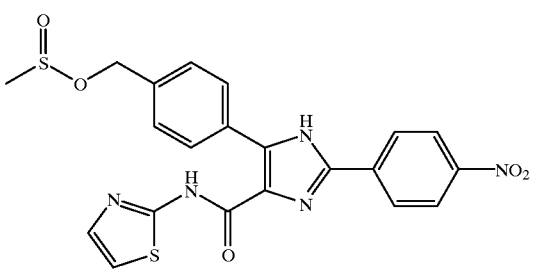

5-(4-Chloromethylphenyl)-2-(4-nitrophenyl)-N-(2-thiazolyl)-imidazole-4-carboxamide (700 mg) obtained in Example 94 and sodium methanesulfinate (325 mg) were dissolved in dimethylformamide (30 ml) and the mixture was stirred at 80° C. for 1 hr. The mixture was poured into water (100 ml) and extracted with ethyl acetate. The ethyl acetate layer was washed with water and, after drying, the solvent was evaporated. The obtained residue was suspended in acetone (30 ml) and 1 M hydrochloric acid—ether solution (3 ml) was added. The solvent was evaporated and the obtained residue was recrystallized from acetone to give 5-(4-methanesulfinyloxymethylphenyl)-2-(4-nitrophenyl)-N-(2-thiazolyl) imidazole-4-carboxamide hydrochloride (736 mg), melting point 278–282° C. (decomposition).

Example 96

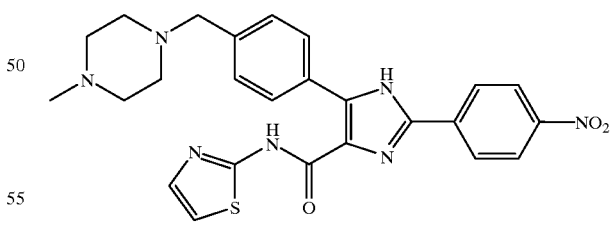

5-(4-Chloromethylphenyl)-2-(4-nitrophenyl)-N-(2-thiazolyl)-imidazole-4-carboxamide (900 mg) obtained in Example 94 and 1-methylpiperazine (309 mg) were reacted and treated in the same manner as in Example 95 to give 5-(4-(4-methylpiperazin-1-ylmethyl)-phenyl)-2-(4-nitrophenyl)-N-(2-thiazolyl)imidazole-4-carboxamide trihydrochloride (742 mg), melting point 248–252° C. (decomposition).

Example 97

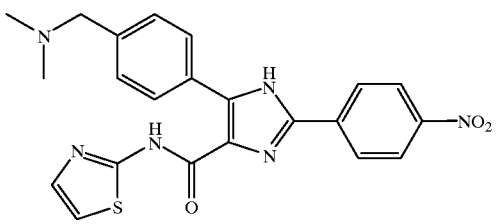

5-(4-Chloromethylphenyl)-2-(4-nitrophenyl)-N-(2-thiazolyl)-imidazole-4-carboxamide (900 mg) obtained in Example 94 and 50% aqueous dimethylamine solution (5 ml) were reacted and treated in the same manner as in Example 95 to give 5-(4-dimethylaminomethylphenyl)-2-(4-nitrophenyl)-N-(2-thiazolyl)imidazole-4-carboxamide dihydrochloride (645 mg), melting point 273–279° C. (decomposition).

Example 98

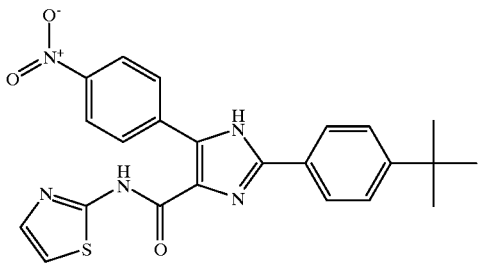

2-(4-tert-Butylphenyl)-5-(4-nitrophenyl)imidazole-4-carboxylic acid (18.4 g) obtained in Starting Material Synthetic Example 53, 1 M hydrochloric acid—ether solution (92 ml), thionyl chloride (110 ml) and 2-aminothiazole (5.8 g) were reacted and treated in the same manner as in Example 1 to give 2-(4-tert-butylphenyl)-5-(4-nitrophenyl)-N-(2-thiazolyl)imidazole-4-carboxamide (17.3 g).

Hydrochloride: melting point 240° C. or above.
$^1$H-NMR 270 MHz (DMSO-D$_6$, ppm) δ: 1.34(9H,s), 7.31(1H,d), 7.57–7.60(3H,m), 8.17(2H,d), 8.21(2H,d), 8.37(2H,d).

Example 99

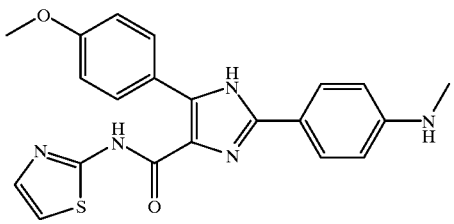

To 2-(4-aminophenyl)-5-(4-methoxyphenyl)-N-(2-thiazolyl)-imidazole-4-carboxamide (1.35 g) obtained in Example 48 were added ethyl orthoformate (40 ml) and trifluoroacetic acid (0.5 ml) and the mixture was refluxed under heating for one day. The reaction mixture was concentrated and to the residue were added tetrahydrofuran (40 ml) and ethyl alcohol (25 ml). Sodium borohydride (1.2 g) was added to the mixture with stirring. The mixture was stirred at room temperature for 1 hr and refluxed under heating for 2 hr. The reaction mixture was extracted with ethyl acetate, dried and concentrated. The obtained crude product was purified by silica gel column chromatography to give 5-(4-methoxyphenyl)-2-(4-methylaminophenyl)-N-(2-thiazolyl)-imidazole-4-carboxamide (0.6 g). This compound was dissolved in ethyl acetate and ether—hydrochloric acid was added to allow precipitation of the crystals of hydrochloride. The precipitated crystals were collected by filtration and recrystallized from methyl alcohol to give 5-(4-methoxyphenyl)-2-(4-methylaminophenyl)-N-(2-thiazolyl)-imidazole-4-carboxamide hydrochloride dihydrate (240 mg), melting point 193–197° C.

Example 100

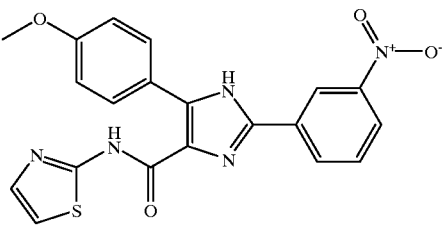

5-(4-ehxphnl-3-nitrophenyl )imidazole-4-carboxylic aci (1.3g), 1M hydrohloicacid—ether solution (50 ml), thionyl chloide(27.2 ml) and 2-aminothiazole (3.7 g) were reacted and treated in the same manner as in Example 1 to give 5-(4-methoxyphenyl)-2-(3-nitrophenyl)-N-(2-thiazolyl) imidazole-4-carboxamide hydrochloride monohydrate (8.9 g), melting point 205–207° C.

Example 101

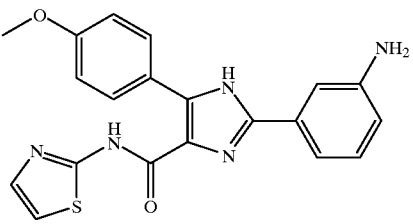

5-(4-Methoxyphenyl)-2-(3-nitrophenyl)-N-(2-thiazolyl)-imidazole-4-carboxamide hydrochloride monohydrate (1.0 g) was suspended in a mixed solvent of methanol (100 ml) and dioxane (100 ml), and 10% palladium carbon (containing water 50%, 0.5 g) was added to carryoutcatalyticreductionatnormalpressure. Thereactionmixture was filtered and concentrated. The obtained crude crystals were recrystallized from methanol to give 2-(3-aminophenyl)-5-(4-methoxyphenyl)-N-(2-thiazolyl)imidazole-4-carboxamide hydrochloride 3/2 hydrate (110 mg), melting point 245° C. (decomposition).

Example 102

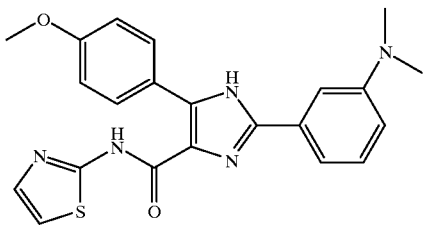

2-(3-Aminophenyl)-5-(4-methoxyphenyl)-N-(2-thiazolyl)-imidazole-4-carboxamide hydrochloride 3/2 hydrate (1.5 g) was dissolved in tetrahydrofuran (40 ml), 37% formalin (9 ml) and 3N sulfuric acid (9 ml), and sodium borohydride (4.5 g) was added portionwise with stirring under ice-cooling. The mixture was stirred at room temperature for 1 hr, extracted with ethyl acetate, dried and concentrated. The obtained product was purified by silica gel column chromatography and dissolved in dioxane. Hydrochloric acid/ether solution was added and the mixture was concentrated under reduced pressure. The obtained crude crystals were recrystallized from methanol to give 2-(3-dimethylaminophenyl)-5-(4-methoxyphenyl)-N-(2-thiazolyl)imidazole-4-carboxamide dihydrochloride 3/2 hydrate (0.7 g), melting point 230° C. (decomposition).

Example 103

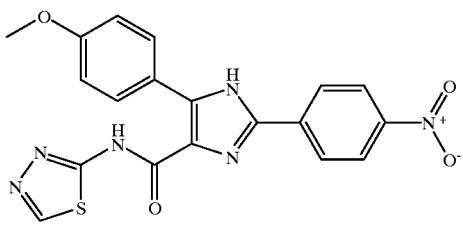

5-(4-Methoxyphenyl)-2-(4-nitrophenyl)imidazole-4-carboxylic acid, 1 M hydrochloric acid—ether solution, thionyl chloride and 2-amino-1,3,4-thiadiazole are reacted and treated in the same manner as in Example 1 to give 5-(4-methoxyphenyl)-2-(4-nitrophenyl)-N-(1,3,4-thiadiazol-2-yl)imidazole-4-carboxamide.

Example 104

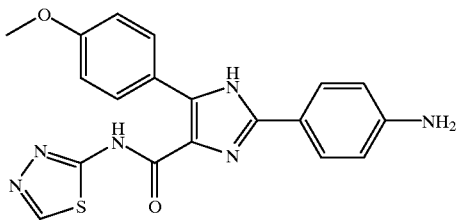

5-(4-Methoxyphenyl)-2-(4-nitrophenyl)-N-(1,3,4-thiadiazol-2-yl) imidazole-4-carboxamide is reacted and treated in the same manner as in Example 85 to give 2-(4-aminophenyl)-5-(4-methoxyphenyl)-N-(1,3,4-thiadiazol-2-yl)imidazole-4-carboxamide.

Example 105

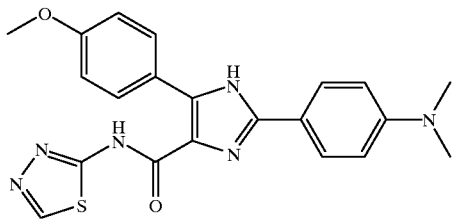

2-(4-Aminophenyl)-5-(4-methoxyphenyl)-N-(1,3,4-thiadiazol-2-yl)imidazole-4-carboxamide is reacted and treated in the samemanner as in Example 102 to give 2-(4-dimethylaminophenyl)-5-(4-methoxyphenyl)-N-(1,3,4-thiadiazol-2-yl)imidazole-4-carboxamide.

Example 106

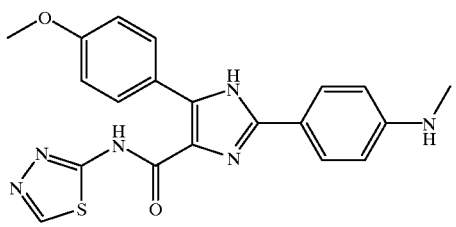

2-(4-Aminophenyl)-5-(4-methoxyphenyl)-N-(1,3,4-thiadiazol-2-yl) imidazole-4-carboxamide is reacted and treated in the same manner as in Example 99 to give 5-(4-methoxyphenyl)-2-(4-methylaminophenyl)-N-(1,3,4-thiadiazol-2-yl)imidazole-4-carboxamide.

Example 107

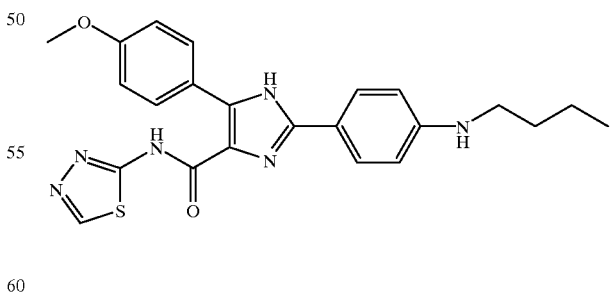

2-(4-Aminophenyl)-5-(4-methoxyphenyl)-N-(1,3,4-thiadiazol-2-yl) imidazole-4-carboxamide is reacted and treated in the same manner as in Example 74 to give 2-(4-butylaminophenyl)-5-(4-methoxyphenyl)-N-(1,3,4-thiadiazol-2-yl)imidazole-4-carboxamide.

Example 108

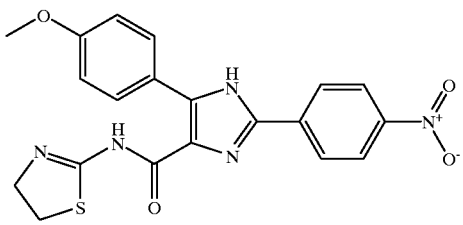

2-(4-Nitrophenyl)-5-(4-methoxyphenyl)imidazole-4-carboxylic acid, 1 M hydrochloric acid—ether solution, thionyl chloride and 2-aminothiazoline were reacted and treated in the same manner as in Example 1 to give 5-(4-methoxyphenyl)-2-(4-nitrophenyl)-N-(2-thiazolinyl) imidazole-4-carboxamide.

Hydrochloride: melting point 260° C. or above.

$^1$H-NMR 270 MHz (DMSO-D$_6$, ppm) δ: 3.54(2H,t), 3.85(3H,s), 4.04(2H,t), 7.11(2H,d), 7.87(2H,d), 8.40(2H,d), 8.50(2H,d)

Example 109

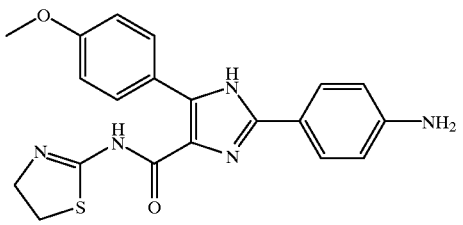

5-(4-Methoxyphenyl)-2-(4-nitrophenyl)-N-(2-thiazolinyl)-imidazole-4-carboxamide is reacted and treated in the same manner as in Example 85 to give 2-(4-aminophenyl)-5-(4-methoxyphenyl)-N-(2-thiazolinyl) imidazole-4-carboxamide.

Example 110

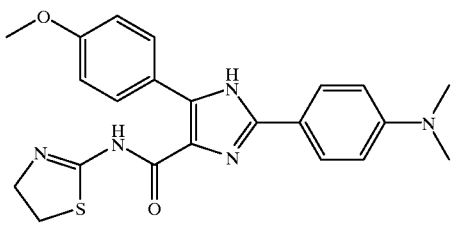

2-(4-Aminophenyl)-5-(4-methoxyphenyl)-N-(2-thiazolinyl)-imidazole-4-carboxamide is reacted and treated in the same manner as in Example 102 to give 2-(4-dimethylaminophenyl)-5-(4-methoxyphenyl)-N-(2-thiazolinyl)imidazole-4-carboxamide.

Example 111

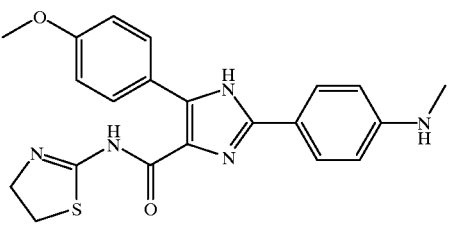

2-(4-Aminophenyl)-5-(4-methoxyphenyl)-N-(2-thiazolinyl)-imidazole-4-carboxamide is reacted and treated in the same manner as in Example 99 to give 5-(4-methoxyphenyl)-2-(4-methylaminophenyl)-N-(2-thiazolinyl)imidazole-4-carboxamide.

Example 112

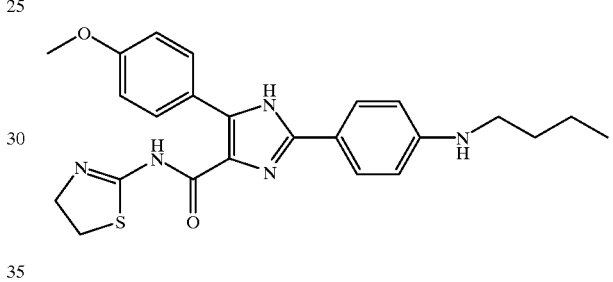

2-(4-Aminophenyl)-5-(4-methoxyphenyl)-N-(2-thiazolinyl)-imidazole-4-carboxamide is reacted and treated in the same manner as in Example 74 to give 2-(4-butylaminophenyl)-5-(4-methoxyphenyl)-N-(2-thiazolinyl) imidazole-4-carboxamide.

Example 113

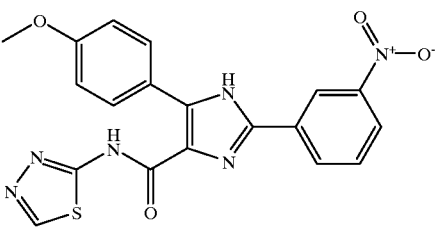

5-(4-Methoxyphenyl)-2-(3-nitrophenyl)imidazole-4-carboxylic acid, 1 M hydrochloric acid—ether solution, thionyl chloride and 2-amino-1,3,4-thiadiazole are reacted and treated in the same manner as in Example 1 to give 5-(4-methoxyphenyl)-2-(3-nitrophenyl)-N-(1,3,4-thiadiazol-2-yl)imidazole-4-carboxamide.

Example 114

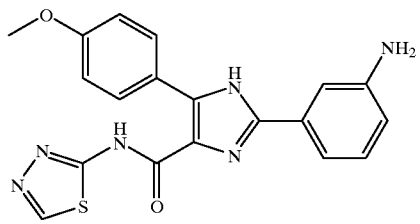

5-(4-Methoxyphenyl)-2-(3-nitrophenyl)-N-(1,3,4-thiadiazole-2-yl) imidazole-4-carboxamide is reacted and treated in the same manner as in Example 85 to give 2-(3-aminophenyl)-5-(4-methoxyphenyl)-N-(1,3,4-thiadiazol-2-yl)imidazole-4-carboxamide.

Example 115

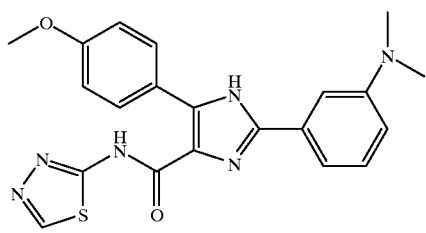

2-(3-Aminophenyl)-5-(4-methoxyphenyl)-N-(1,3,4-thiadiazol-2-yl) imidazole-4-carboxamide is reacted and treated in the same manner as in Example 102 to give 2-(3-dimethylaminophenyl)-5-(4-methoxyphenyl)-N-(1,3,4-thiadiazol-2-yl)imidazole-4-carboxamide.

Example 116

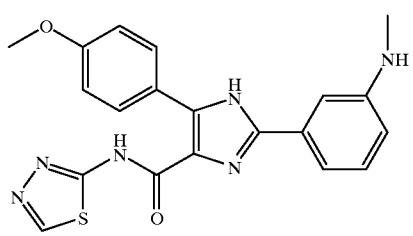

2-(3-Aminophenyl)-5-(4-methoxyphenyl)-N-(1,3,4-thiadiazol-2-yl) imidazole-4-carboxamide is reacted and treated in the same manner as in Example 99 to give 5-(4-methoxyphenyl)-2-(3-methylaminophenyl)-N-(1,3,4-thiadiazol-2-yl)imidazole-4-carboxamide.

Example 117

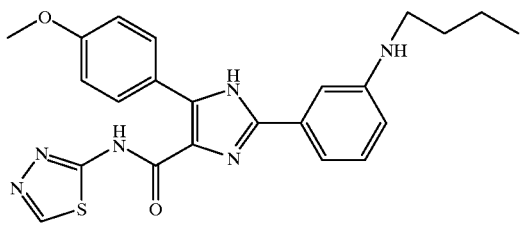

2-(3-Aminophenyl)-5-(4-methoxyphenyl)-N-(1,3,4-thiadiazol-2-yl) imidazole-4-carboxamide is reacted and treated in the same manner as in Example 74 to give 2-(3-butylaminophenyl)-5-(4-methoxyphenyl)-N-(1,3,4-thiadiazol-2-yl)imidazole-4-carboxamide.

Example 118

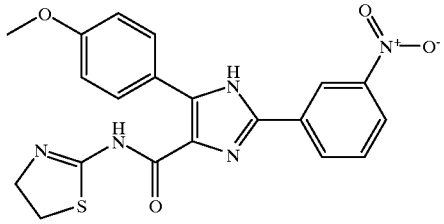

5-(4-Methoxyphenyl)-2-(3-nitrophenyl)imidazole-4-carboxylic acid, 1 M hydrochloric acid—ether solution, thionyl chloride and 2-aminothiazoline are reacted and treated in the same manner as in Example 1 to give 5-(4-methoxyphenyl)-2-(3-nitrophenyl)-N-(2-thiazolinyl) imidazole-4-carboxamide.

Example 119

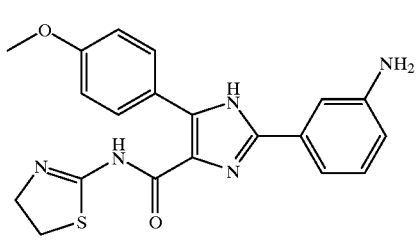

5-(4-Methoxyphenyl)-2-(3-nitrophenyl)-N-(2-thiazolinyl)-imidazole-4-carboxamide is reacted and treated in the same manner as in Example 85 to give 2-(3-aminophenyl)-5-(4-methoxyphenyl)-N-(2-thiazolinyl) imidazole-4-carboxamide.

Example 120

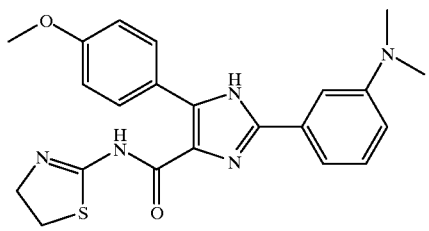

2-(3-Aminophenyl)-5-(4-methoxyphenyl)-N-(2-thiazolinyl)-imidazole-4-carboxamide is reacted and treated in the same manner as in Example 102 to give 2-(3-dimethylaminophenyl)-5-(4-methoxyphenyl)-N-(2-thiazolinyl)imidazole-4-carboxamide.

Example 121

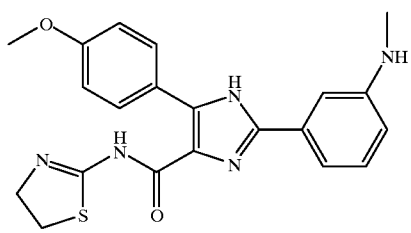

2-(3-Aminophenyl)-5-(4-methoxyphenyl)-N-(2-thiazolinyl)-imidazole-4-carboxamide is reacted and treated in the same manner as in Example 99 to give 5-(4-methoxyphenyl)-2-(3-methylaminophenyl)-N-(2-thiazolinyl)imidazole-4-carboxamide.

Example 122

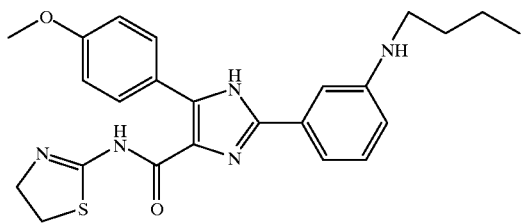

2-(3-Aminophenyl)-5-(4-methoxyphenyl)-N-(2-thiazolinyl)-imidazole-4-carboxamide is reacted and treated in the same manner as in Example 74 to give 2-(3-butylaminophenyl)-5-(4-methoxyphenyl)-N-(2-thiazolinyl) imidazole-4-carboxamide.

Example 123

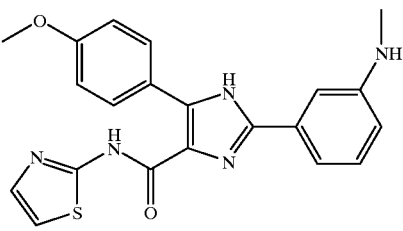

2-(3-Aminophenyl)-5-(4-methoxyphenyl)-N-(2-thiazolyl)-imidazole-4-carboxamide is reacted and treated in the same manner as in Example 99 to give 5-(4-methoxyphenyl)-2-(3-methylaminophenyl)-N-(2-thiazolyl) imidazole-4-carboxamide.

Example 124

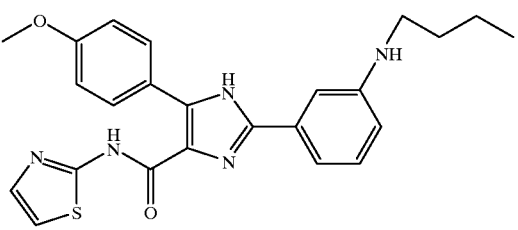

2-(3-Aminophenyl)-5-(4-methoxyphenyl)-N-(2-thiazolyl)-imidazole-4-carboxamide is reacted and treated in the same manner as in Example 74 to give 2-(3-butylaminophenyl)-5-(4-methoxyphenyl)-N-(2-thiazolyl) imidazole-4-carboxamide.

Example 125

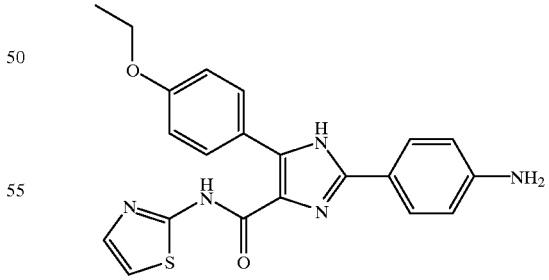

5-(4-Ethoxyphenyl)-2-(4-nitrophenyl)-N-(2-thiazolyl)-imidazole-4-carboxamide obtained in Example 81 is treated in the same manner as in Example 85 to give the objective 2-(4-aminophenyl)-5-(4-ethoxyphenyl)-N-(2-thiazolyl) imidazole-4-carboxamide.

Example 126

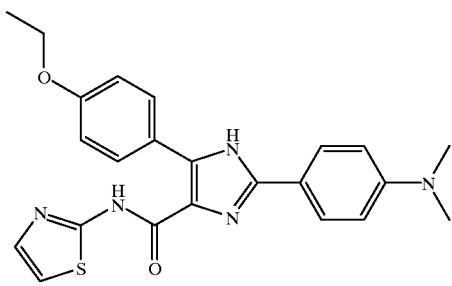

2-(4-Aminophenyl)-5-(4-ethoxyphenyl)-N-(2-thiazolyl)-imidazole-4-carboxamide obtained in Example 125 is treated in the same manner as in Example 102 to give the objective 2-(4-dimethylaminophenyl)-5-(4-ethoxyphenyl)-N-(2-thiazolyl)imidazole-4-carboxamide.

Example 127

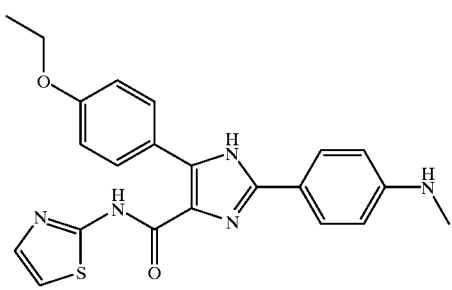

2-(4-Aminophenyl)-5-(4-ethoxyphenyl)-N-(2-thiazolyl)-imidazole-4-carboxamide obtained in Example 125 is treated in the same manner as in Example 99 to give the objective 5-(4-ethoxyphenyl)-2-(4-methylaminophenyl)-N-(2-thiazolyl)imidazole-4-carboxamide.

Example 128

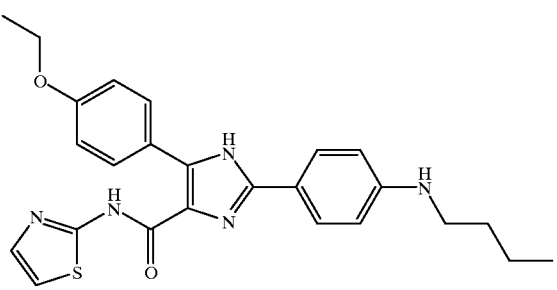

2-(4-Aminophenyl)-5-(4-ethoxyphenyl)-N-(2-thiazolyl)-imidazole-4-carboxamide obtained in Example 125 is treated in the same manner as in Example 74 to give the objective 2-(4-butylaminophenyl)-5-(4-ethoxyphenyl)-N-(2-thiazolyl)imidazole-4-carboxamide.

Example 129

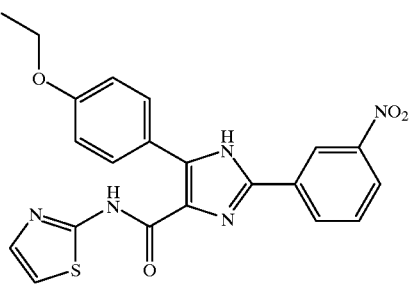

5-(4-Ethoxyphenyl)-2-(3-nitrophenyl)imidazole-4-carboxylic acid obtained in Starting Material Synthetic Example 56 is treated in the same manner as in Example 1 to give the objective 5-(4-ethoxyphenyl)-2-(3-nitrophenyl)-N-(2-thiazolyl)imidazole-4-carboxamide.

Example 130

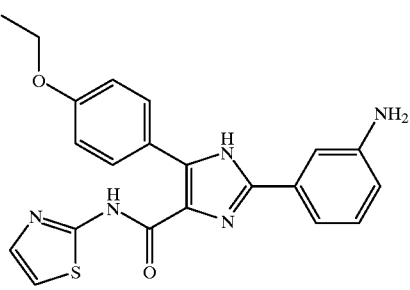

5-(4-Ethoxyphenyl)-2-(3-nitrophenyl)-N-(2-thiazolyl)-imidazole-4-carboxamide obtained in Example 129 is treated in the same manner as in Example 85 to give the objective 2-(3-aminophenyl)-5-(4-ethoxyphenyl)-N-(2-thiazolyl)imidazole-4-carboxamide.

Example 131

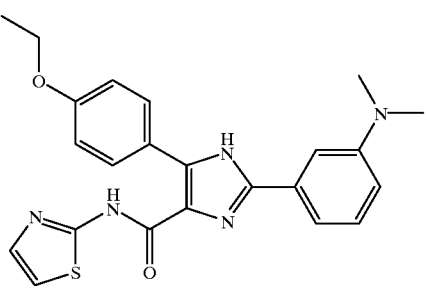

2-(3-Aminophenyl)-5-(4-ethoxyphenyl)-N-(2-thiazolyl)-imidazole-4-carboxamide obtained in Example 130 is treated in the same manner as in Example 102 to give the objective 2-(3-dimethylamino-phenyl)-5-(4-ethoxyphenyl)-N-(2-thiazolyl)imidazole-4-carboxamide.

Example 132

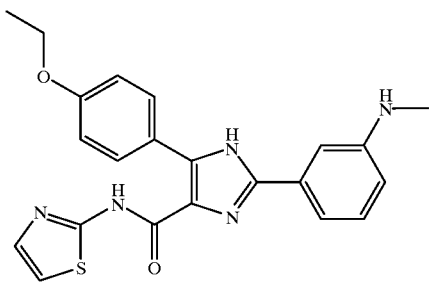

2-(3-Aminophenyl)-5-(4-ethoxyphenyl)-N-(2-thiazolyl)-imidazole-4-carboxamide obtained in Example 130 is treated in the same manner as in Example 99 to give the objective 5-(4-ethoxyphenyl)-2-(3-methylaminophenyl)-N-(2-thiazolyl)imidazole-4-carboxamide.

Example 133

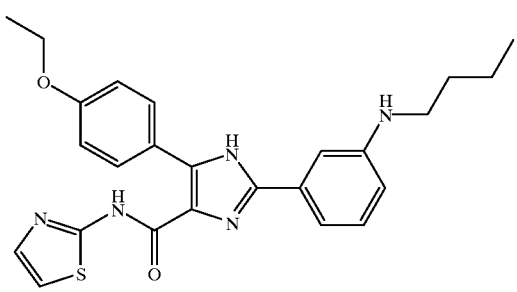

2-(3-Aminophenyl)-5-(4-ethoxyphenyl)-N-(2-thiazolyl)-imidazole-4-carboxamide obtained in Example 130 is treated in the same manner as in Example 74 to give the objective 2-(3-butylamino-phenyl)-5-(4-ethoxyphenyl)-N-(2-thiazolyl)imidazole-4-carboxamide.

Example 134

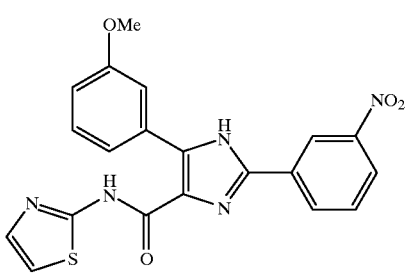

5-(3-Methoxyphenyl)-2-(3-nitrophenyl)imidazole-4-carboxylic acid obtained in Starting Material Synthetic Example 57 is treated in the same manner as in Example 1 to give the objective 5-(3-methoxyphenyl)-2-(3-nitrophenyl)-N-(2-thiazolyl)imidazole-4-carboxamide.

Example 135

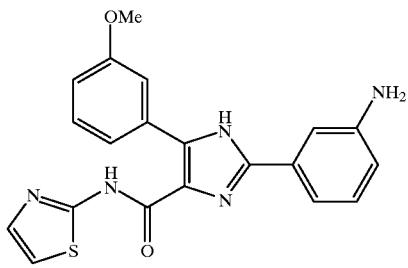

5-(3-Methoxyphenyl)-2-(3-nitrophenyl)-N-(2-thiazolyl)-imidazole-4-carboxamide obtained in Example 134 is treated in the same manner as in Example 85 to give the objective 2-(3-aminophenyl)-5-(3-methoxyphenyl)-N-(2-thiazolyl)imidazole-4-carboxamide.

Example 136

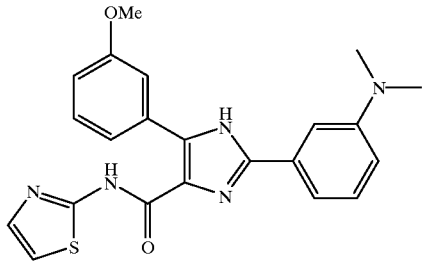

2-(3-Aminophenyl)-5-(3-methoxyphenyl)-N-(2-thiazolyl)-imidazole-4-carboxamide obtained in Example 135 is treated in the same manner as in Example 102 to give the objective 2-(3-dimethylamino-phenyl)-5-(3-methoxyphenyl)-N-(2-thiazolyl)imidazole-4-carboxamide.

Example 137

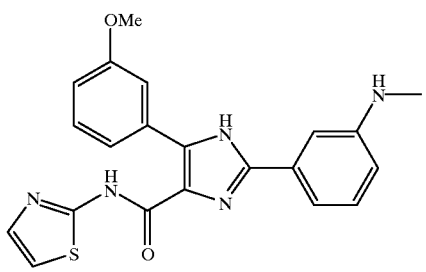

2-(3-Aminophenyl)-5-(3-methoxyphenyl)-N-(2-thiazolyl)-imidazole-4-carboxamide obtained in Example 135 is treated in the same manner as in Example 99 to give the objective 5-(3-methoxyphenyl)-2-(3-methylaminophenyl)-N-(2-thiazolyl)imidazole-4-carboxamide.

Example 138

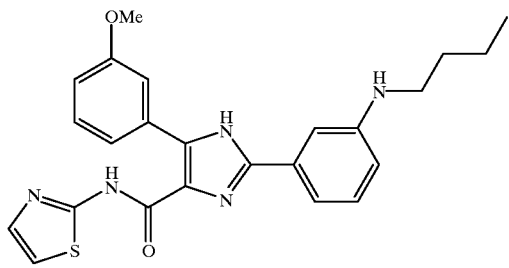

2-(3-Aminophenyl)-5-(3-methoxyphenyl)-N-(2-thiazolyl)-imidazole-4-carboxamide obtained in Example 135 is treated in the same manner as in Example 74 to give the objective 2-(3-butylaminophenyl)-5-(3-methoxyphenyl)-N-(2-thiazolyl)imidazole-4-carboxamide.

Example 139

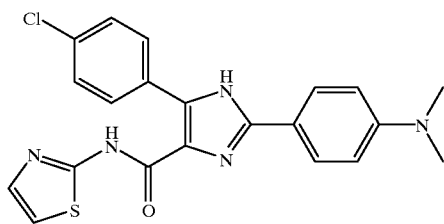

2-(4-Aminophenyl)-5-(4-chlorophenyl)-N-(2-thiazolyl)-imidazole-4-carboxamide is treated in the same manner as in Example 102 to give 5-(4-chlorophenyl)-2-(4-dimethylaminophenyl)-N-(2-thiazolyl)imidazole-4-carboxamide.

Example 140

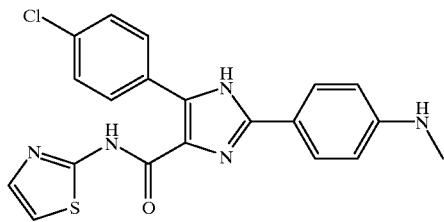

2-(4-Aminophenyl)-5-(4-chlorophenyl)-N-(2-thiazolyl)-imidazole-4-carboxamide is treated in the same manner as in Example 99 to give 5-(4-chlorophenyl)-2-(4-methylaminophenyl)-N-(2-thiazolyl)imidazole-4-carboxamide.

Example 141

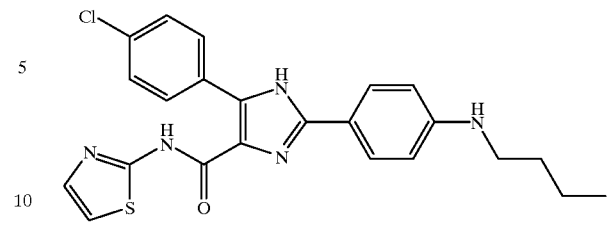

2-(4-Aminophenyl)-5-(4-chlorophenyl)-N-(2-thiazolyl)-imidazole-4-carboxamide is treated in the same manner as in Example 74 to give 2-(4-butylaminophenyl)-5-(4-chlorophenyl)-N-(2-thiazolyl)imidazole-4-carboxamide.

Example 142

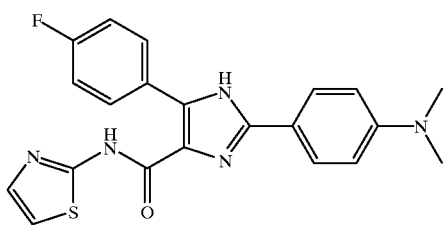

2-(4-Aminophenyl)-5-(4-fluorophenyl)-N-(2-thiazolyl)-imidazole-4-carboxamide is treated in the same manner as in Example 102 to give 2-(4-dimethylaminophenyl)-5-(4-fluorophenyl)-N-(2-thiazolyl)imidazole-4-carboxamide.

Example 143

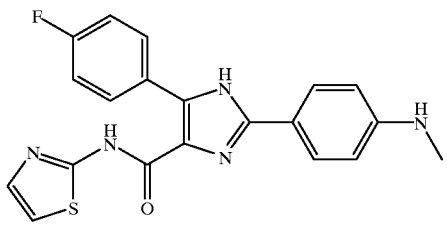

2-(4-Aminophenyl)-5-(4-fluorophenyl)-N-(2-thiazolyl)-imidazole-4-carboxamide is treated in the same manner as in Example 99 to give 5-(4-fluorophenyl)-2-(4-methylaminophenyl)-N-(2-thiazolyl)imidazole-4-carboxamide.

Example 144

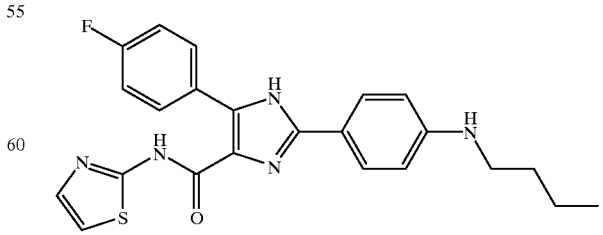

2-(4-Aminophenyl)-5-(4-fluorophenyl)-N-(2-thiazolyl)-imidazole-4-carboxamide is treated in the same manner as in Example 74 to give 2-(4-butylaminophenyl)-5-(4-fluorophenyl)-N-(2-thiazolyl)imidazole-4-carboxamide.

Example 145

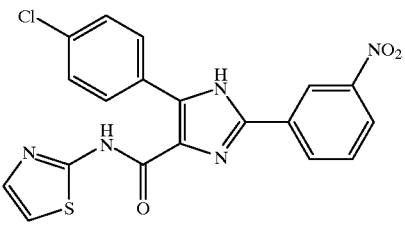

5-(4-Chlorophenyl)-2-(3-nitrophenyl)imidazole-4-carboxylic acid is treated in the same manner as in Example 1 to give 5-(4-chlorophenyl)-2-(3-nitrophenyl)-N-(2-thiazolyl)imidazole-4-carboxamide.

Example 146

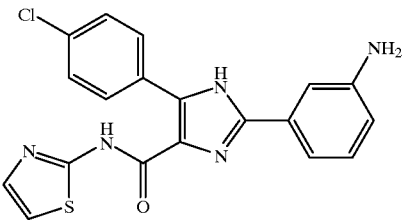

5-(4-Chlorophenyl)-2-(3-nitrophenyl)-N-(2-thiazolyl)-imidazole-4-carboxamide is treated in the same manner as in Example 85 to give 2-(3-aminophenyl)-5-(4-chlorophenyl)-N-(2-thiazolyl)-imidazole-4-carboxamide.

Example 147

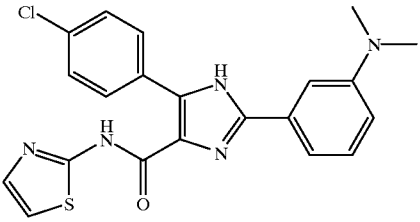

2-(3-Aminophenyl)-5-(4-chlorophenyl)-N-(2-thiazolyl)-imidazole-4-carboxamide is treated in the same manner as in Example 102 to give 5-(4-chlorophenyl)-2-(3-dimethylaminophenyl)-N-(2-thiazolyl)imidazole-4-carboxamide.

Example 148

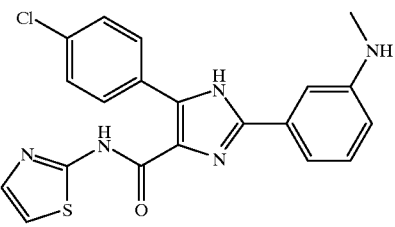

(3-Aminophenyl)-5-(4-chlorophenyl)-N-(2-thiazolyl)-imidazole-4-carboxamide is treated in the same manner as in Example 99 to give 5-(4-chlorophenyl)-2-(3-methylaminophenyl)-N-(2-thiazolyl)iimidazole-4-carboxamide.

Example 149

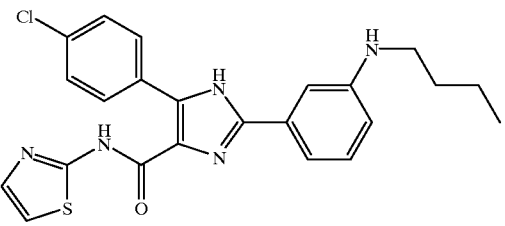

2-(3-Aminophenyl)-5-(4-chlorophenyl)-N-(2-thiazolyl)-imidazole-4-carboxamide is treated in the same manner as in Example 74 to give 2-(3-butylaminophenyl)-5-(4-chlorophenyl)-N-(2-thiazolyl)imidazole-4-carboxamide.

Example 150

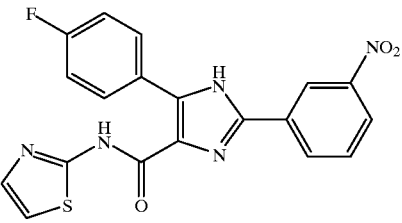

5-(4-Fluorophenyl)-2-(3-nitrophenyl)imidazole-4-carboxylic acid is treated in the same manner as in Example 1 to give 5-(4-fluorophenyl)-2-(3-nitrophenyl)-N-(2-thiazolyl)imidazole-4-carboxamide.

Example 151

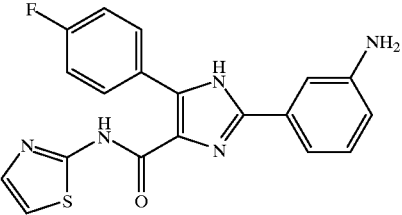

5-(4-Fluorophenyl)-2-(3-nitrophenyl)-N-(2-thiazolyl)-imidazole-4-carboxamide is treated in the same manner as in Example 85 to give 2-(3-aminophenyl)-5-(4-fluorophenyl)-N-(2-thiazolyl)-imidazole-4-carboxamide.

Example 152

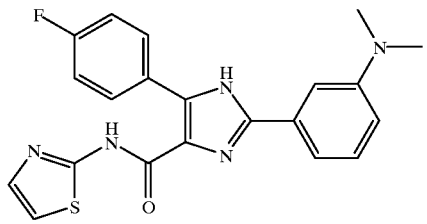

2-(3-Aminophenyl)-5-(4-fluorophenyl)-N-(2-thiazolyl)-imidazole-4-carboxamide is treated in the same manner as in Example 102 to give 5-(4-fluorophenyl)-2-(3-dimethylaminophenyl)-N-(2-thiazolyl)imidazole-4-carboxamide.

Example 153

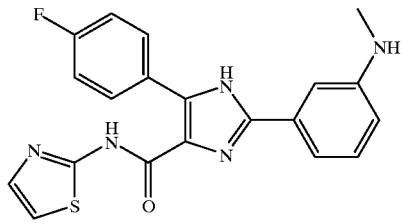

2-(3-Aminophenyl)-5-(4-fluorophenyl)-N-(2-thiazolyl)-imidazole-4-carboxamide is treated in the same manner as in Example 99 to give 5-(4-fluorophenyl)-2-(3-methylaminophenyl)-N-(2-thiazolyl)imidazole-4-carboxamide.

Example 154

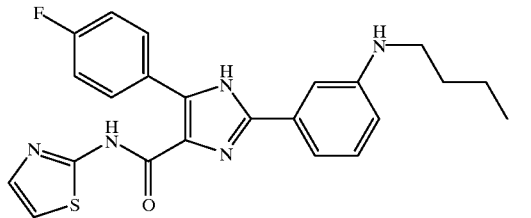

2-(3-Aminophenyl)-5-(4-fluorophenyl)-N-(2-thiazolyl)-imidazole-4-carboxamide is treated in the same manner as in Example 74 to give 2-(3-butylaminophenyl)-5-(4-fluorophenyl)-N-(2-thiazolyl)imidazole-4-carboxamide.

Example 155

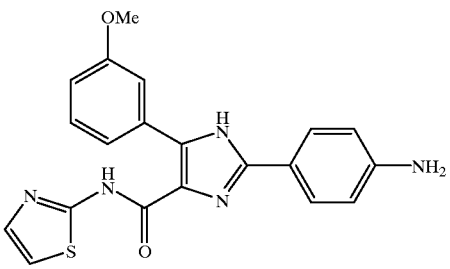

5-(3-Methoxyphenyl)-2-(4-nitrophenyl)-N-(2-thiazolyl)-imidazole-4-carboxamide (1.8 g) obtained in Example 80 was treated in the same manner as in Example 85 to give the objective 2-(4-aminophenyl)-5-(3-methoxyphenyl)-N-(2-thiazolyl)imidazole-4-carboxamide (1.3 g), melting point 262–263° C.

Example 156

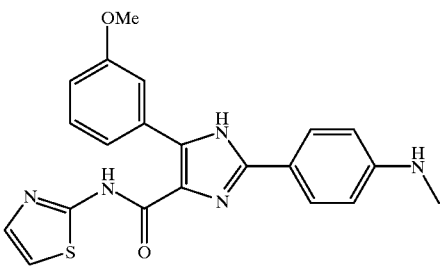

2-(4-Aminophenyl)-5-(3-methoxyphenyl)-N-(2-thiazolyl)-imidazole-4-carboxamide (0.4 g) obtained in Example 155 was treated in the same manner as in Example 99 to give the objective 5-(3-methoxyphenyl)-2-(4-methylaminophenyl)-N-(2-thiazolyl)imidazole-4-carboxamide (0.32 g), melting point 248–251° C. (hydrochloride).

Example 157

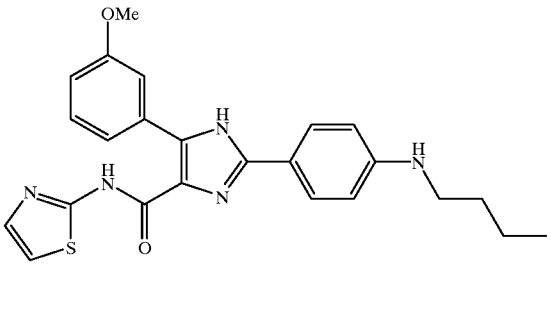

2-(4-Aminophenyl)-5-(3-methoxyphenyl)-N-(2-thiazolyl)-imidazole-4-carboxamide (0.8 g) obtained in Example 155 was treated in the same manner as in Example 74 to give the objective 2-(4-butylaminophenyl)-5-(3-methoxyphenyl)-N-(2-thiazolyl)imidazole-4-carboxamide (0.38 g), melting point 228–231° C. (hydrochloride).

Example 158

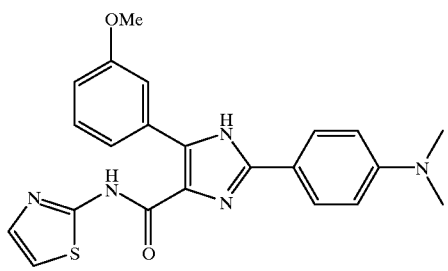

2-(4-Aminophenyl)-5-(3-methoxyphenyl)-N-(2-thiazolyl)-imidazole-4-carboxamide obtained in Example 155 is treated in the same manner as in Example 102 to give the objective 2-(4-dimethylamino-phenyl)-5-(3-methoxyphenyl)-N-(2-thiazolyl)imidazole-4-carboxamide.

Example 159

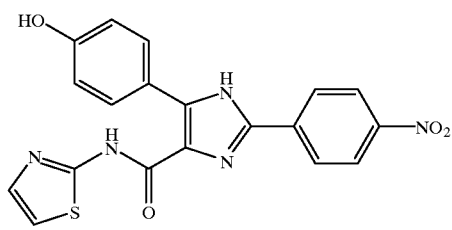

5-(4-Methoxyphenyl)-2-(4-nitrophenyl)-N-(2-thiazolyl)-imidazole-4-carboxamide (2.1 g) obtained in Example 47 was dissolved in dichloromethane (210 ml) and boron tribromide (3 ml) was added. The mixture was stirred for one day. The reaction mixture was poured into cold water and the precipitated crystals were collected by filtration to give 5-(4-hydroxyphenyl)-2-(4-nitrophenyl)-N-(2-thiazolyl)-imidazole-4-carboxamide (1.7 g).

Hydrochloride: melting point 250° C. or above.

$^1$H-NMR 270 MHz (DMSO-$d_6$, ppm) δ: 6.90(2H,d), 7.28(1H,d), 7.56(1H,d), 7.75(2H,d), 8.38(2H,d), 8.47(2H,d)

Example 160

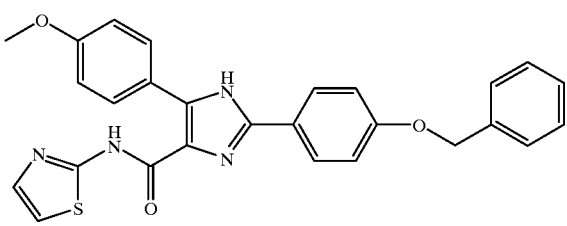

Ethyl $^2$-hydroxyimino-3-(4-methoxyphenyl)-3-oxopropionate, 4-benzyloxybenzaldehyde and ammonium acetate are reacted and treated in the same manner as in Example 22 to give ethyl 2-(4-benzyloxyphenyl)-5-(4-methoxyphenyl)imidazole-4-carboxylate. Ethyl 2-(4-benzyloxyphenyl)-5-(4-methoxyphenyl)imidazole-4-carboxylate is reacted and treated in the same manner as in Starting Material Synthetic Example 2 to give 2-(4-benzyloxyphenyl)-5-(4-methoxyphenyl)imidazole-4-carboxylic acid. 2-(4-Benzyloxyphenyl)-5-(4-methoxyphenyl)imidazole-4-carboxylic acid is reacted and treated in the same manner as in Example 1 to give 2-(4-benzyloxyphenyl)-5-(4-methoxyphenyl)-N-(2-thiazolyl)imidazole-4-carboxamide.

Example 161

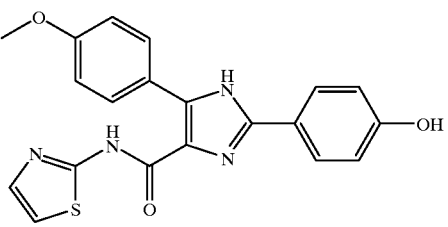

2-(4-Benzyloxyphenyl)-5-(4-methoxyphenyl)-N-(2-thiazolyl)-imidazole-4-carboxamide is reacted and treated in the same manner as in Example 23 to give 2-(4-hydroxyphenyl)-5-(4-methoxyphenyl)-N-(2-thiazolyl) imidazole-4-carboxamide.

Example 162

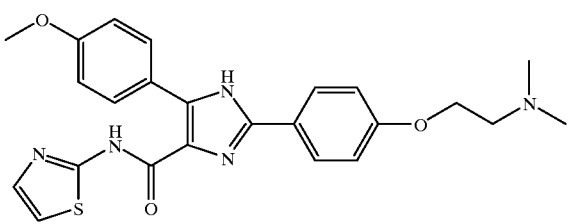

2-(4-Hydroxyphenyl)-5-(4-methoxyphenyl)-N-(2-thiazolyl)-imidazole-4-carboxamide, 2-dimethylaminoethanol, triphenylphosphine and diethyl azodicarboxylate are reacted and treated in the same manner as in Example 24 to give 2-(4-(2-dimethylaminoethyloxy)phenyl)-5-(4-methoxyphenyl)-N-(2-thiazolyl)imidazole-4-carboxamide.

Example 163

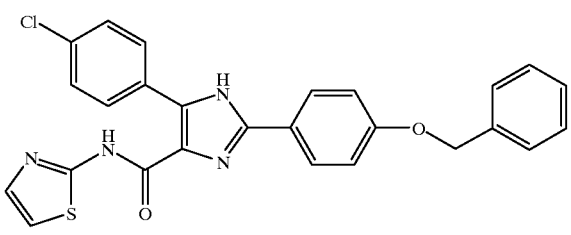

Ethyl 3-(4-chlorophenyl)-2-hydroxyimino-3-oxopropionate, 4-benzyloxybenzaldehyde and ammonium acetate are reacted and treated in the same manner as in Example 22 to give ethyl 2-(4-benzyloxyphenyl)-5-(4-chlorophenyl)imidazole-4-carboxylate. Ethyl 2-(4-benzyloxyphenyl)-5-(4-chlorophenyl)imidazole-4-carboxylate is reacted and treated in the same manner as in Starting Material Synthetic Example 2 to give 2-(4-benzyloxyphenyl)-5-(4-chlorophenyl)-imidazole-4-carboxylic acid. 2-(4-Benzyloxyphenyl)-5-(4-chlorophenyl)imidazole-4-carboxylic acid is reacted and treated in the same manner as in Example 1 to give 2-(4-benzyloxyphenyl)-5-(4-chlorophenyl)-N-(2-thiazolyl) imidazole-4-carboxamide.

Example 164

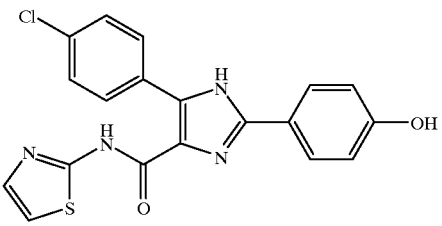

2-(4-Benzyloxyphenyl)-5-(4-chlorophenyl)-N-(2-thiazolyl)-imidazole- 4-carboxamide is reacted and treated in the same manner as in Example 23 to give 5-(4-chlorophenyl)-2-(4-hydroxyphenyl)-N-(2-thiazolyl) imidazole-4-carboxamide.

Example 165

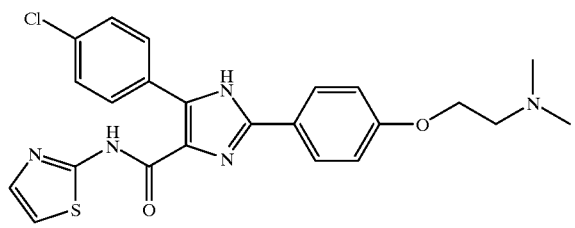

5-(4-Chlorophenyl)-2-(4-hydroxyphenyl)-N-(2-thiazolyl)-imidazole-4-carboxamide, 2-dimethylaminoethanol, triphenylphosphine and diethyl azodicarboxylate are reacted and treated in the same manner as in Example 24 to give 5-(4-chlorophenyl)-2-(4-(2-dimethylamino-ethyloxy)phenyl)-N-(2-thiazolyl)imidazole-4-carboxamide.

Example 166

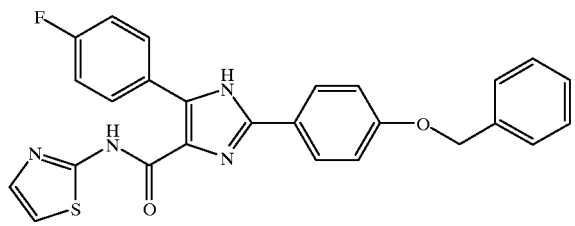

Ethyl 3-(4-fluorophenyl)-2-hydroxyimino-3-oxopropionate, 4-benzyloxybenzaldehyde and ammonium acetate are reacted and treated in the same manner as in Example 22 to give ethyl 2-(4-benzyloxy-phenyl)-5-(4-fluorophenyl)imidazole-4-carboxylate. Ethyl 2-(4-benzyloxyphenyl)-5-(4-fluorophenyl)imidazole-4-carboxylate is reacted and treated in the same manner as in Starting Material Synthetic Example 2 to give 2-(4-benzyloxyphenyl)-5-(4-fluorophenyl)-imidazole-4-carboxylic acid. 2-(4-Benzyloxyphenyl)-5-(4-fluorophenyl) imidazole-4-carboxylic acid is reacted and treated in the same manner as in Example 1 to give 2-(4-benzyloxyphenyl)-5-(4-fluorophenyl)-N-(2-thiazolyl) imidazole-4-carboxamide.

Example 167

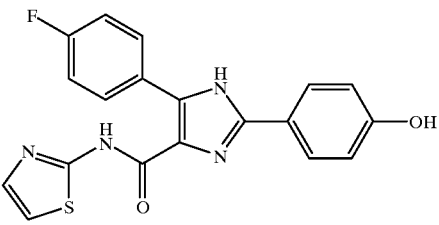

2-(4-Benzyloxyphenyl)-5-(4-fluorophenyl)-N-(2-thiazolyl)-imidazole-4-carboxamide is reacted and treated in the same manner as in Example 23 to give 5-(4-fluorophenyl)-2-(4-hydroxyphenyl)-N-(2-thiazolyl) imidazole-4-carboxamide.

Example 168

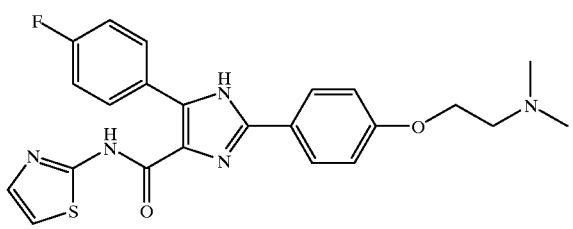

5-(4-Fluorophenyl)-2-(4-hydroxyphenyl)-N-(2-thiazolyl)-imidazole-4-carboxamide, 2-dimethylaminoethanol, triphenylphosphine and diethyl azodicarboxylate are reacted and treated in the same manner as in Example 24 to give 5-(4-fluorophenyl)-2-(4-(2-dimethylaminoethyloxy)phenyl)-N-(2-thiazolyl)imidazole-4-carboxamide.

Example 169

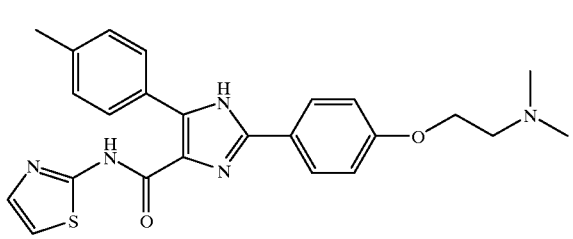

2-(4-Hydroxyphenyl)-5-(4-methylphenyl)-N-(2-thiazolyl)imidazole-4-carboxamide, 2-dimethylaminoethanol, triphenylphosphine and diethyl azodicarboxylate are reacted and treated in the same manner as in Example 24 to give 2-(4-(2-dimethylaminoethyloxy) phenyl)-5-(4-methylphenyl)-N-(2-thiazolyl)imidazole-4-carboxamide.

Example 170

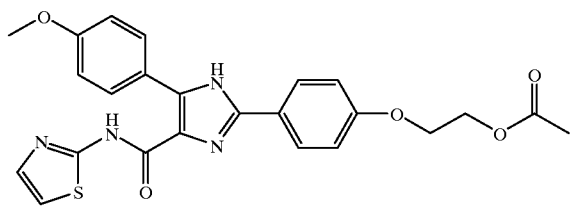

2-(4-Hydroxyphenyl)-5-(4-methoxyphenyl)-N-(2-thiazolyl)-imidazole-4-carboxamide, 2-hydroxyethyl acetate, triphenylphosphine and diethyl azodicarboxylate are reacted and treated in the same manner as in Example 24 to give 2-(4-(2-acetoxyethyloxy)phenyl)-5-(4-methoxyphenyl)-N-(2-thiazolyl)imidazole-4-carboxamide.

Example 171

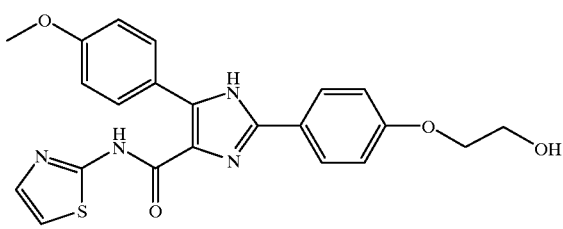

2-(4-(2-Acetoxyethyloxy)phenyl)-5-(4-methoxyphenyl)-N-(2-thiazolyl)imidazole-4-carboxamide is hydrolyzed with sodium hydroxide to give 2-(4-(2-hydroxyethyloxy)phenyl)-5-(4-methoxyphenyl)-N-(2-thiazolyl)imidazole-4-carboxamide.

Example 172

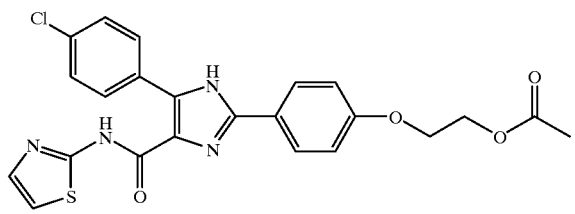

5-(4-Chlorophenyl)-2-(4-hydroxyphenyl)-N-(2-thiazolyl)-imidazole-4-carboxamide, 2-hydroxyethyl acetate, triphenylphosphine and diethyl azodicarboxylate are reacted and treated in the same manner as in Example 24 to give 2-(4-(2-acetoxyethyloxy)phenyl)-5-(4-chlorophenyl)-N-(2-thiazolyl)imidazole-4-carboxamide.

Example 173

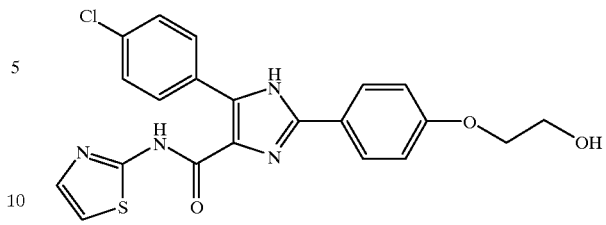

2-(4-(2-Acetoxyethyloxy)phenyl)-5-(4-chlorophenyl)-N-(2-thiazolyl)imidazole-4-carboxamide is hydrolyzed with sodium hydroxide to give 5-(4-chlorophenyl)-2-(4-(2-hydroxyethyloxy)-phenyl)-N-(2-thiazolyl)imidazole-4-carboxamide.

Example 174

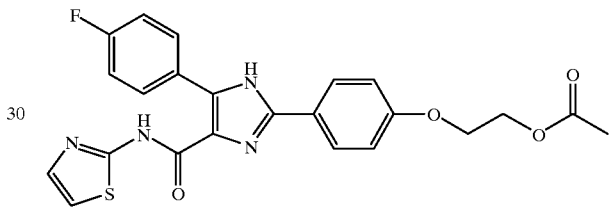

5-(4-Fluorophenyl)-2-(4-hydroxyphenyl)-N-(2-thiazolyl)-imidazole-4-carboxamide, 2-hydroxyethyl acetate, triphenylphosphine and diethylazodicarboxylate are reacted and treated in the same manner as in Example 24 to give 2-(4-(2-acetoxyethyloxy)phenyl)-5-(4-fluorophenyl)-N-(2-thiazolyl)imidazole-4-carboxamide.

Example 175

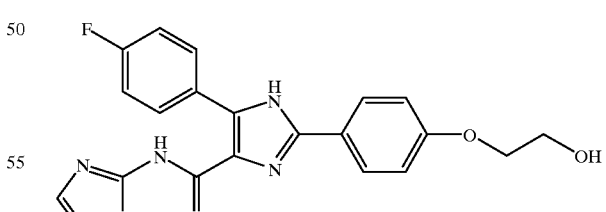

2-(4-(2-Acetoxyethyloxy)phenyl)-5-(4-fluorophenyl)-N-(2-thiazolyl)imidazole-4-carboxamide is hydrolyzed with sodium hydroxide to give 5-(4-fluorophenyl)-2-(4-(2-hydroxyethyloxy)-phenyl)-N-(2-thiazolyl)imidazole-4-carboxamide.

Example 176

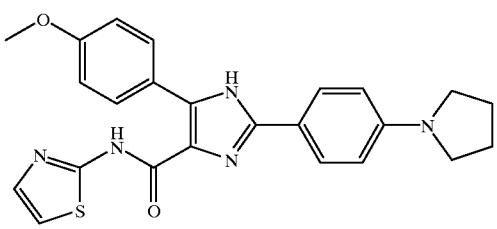

Ethyl 2-hydroxyimino-3-(4-methoxyphenyl)-3-oxopropionate, 4-(1-pyrrolidinyl)benzylamine is reacted and treated in the same manner as in Starting Material Synthetic Example 1 to give ethyl 5-(4-methoxyphenyl)-2-(4-(1-pyrrolidinyl)phenyl)imidazole-4-carboxylate. Ethyl 5-(4-methoxyphenyl)-2-(4-(1-pyrrolidinyl)-phenyl)imidazole-4-carboxylate is reacted and treated in the same manner as in Starting Material Synthetic Example 2 to give 5-(4-methoxyphenyl)-2-(4-(1-pyrrolidinyl)phenyl)imidazole-4-carboxylic acid. 5-(4-Methoxyphenyl)-2-(4-(1-pyrrolidinyl)phenyl)imidazole-4-carboxylicacid isreactedandtreatedinthesamemanneras in Example 1 to give 5-(4-methoxyphenyl)-2-(4-(1-pyrrolidinyl)phenyl)-N-(2-thiazolyl)imidazole-4-carboxamide.

Example 178

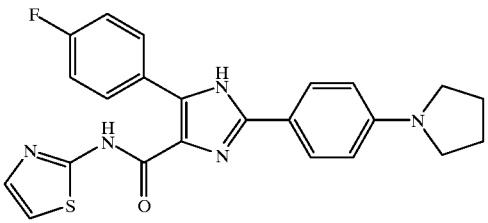

Ethyl 3-(4-fluorophenyl)-2-hydroxyimino-3-oxopropionate and 4-(1-pyrrolidinyl)benzylamine are reacted and treated in the same manner as in Starting Material Synthetic Example 1 to give ethyl 5-(4-fluorophenyl)-2-(4-(1-pyrrolidinyl)phenyl)imidazole-4-carboxylate. Ethyl 5-(4-fluorophenyl)-2-(4-(1-pyrrolidinyl)-phenyl)imidazole-4-carboxylate is reacted and treated in the same manner as in Starting Material Synthetic Example 2 to give 5-(4-fluorophenyl)-2-(4-(1-pyrrolidinyl)phenyl)imidazole-4-carboxylic acid. 5-(4-Fluorophenyl)-2-(4-(1-pyrrolidinyl)phenyl)imidazole-4-carboxylic acid is reacted and treated in the same manner as in Example 1 to give 5-(4-fluorophenyl)-2-(4-(1-pyrrolidinyl)phenyl)-N-(2-thiazolyl)imidazole-4-carboxamide.

Example 177

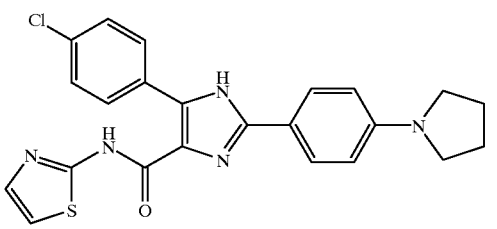

Ethyl 3-(4-chlorophenyl)-2-hydroxyimino-3-oxopropionate and 4-(1-pyrrolidinyl)benzylamine are reacted and treated in the same manner as in Starting Material Synthetic Example 1 to give ethyl 5-(4-chlorophenyl)-2-(4-(1-pyrrolidinyl)phenyl)imidazole-4-carboxylate. Ethyl 5-(4-chlorophenyl)-2-(4-(1-pyrrolidinyl)-phenyl)imidazole-4-carboxylate is reacted and treated in the same manner as in Starting Material Synthetic Example 2 to give 5-(4-chlorophenyl)-2-(4-(1-pyrrolidinyl)phenyl)imidazole-4-carboxylic acid. 5-(4-Chlorophenyl)-2-(4-(1-pyrrolidinyl)phenyl)imidazole-4-carboxylic acid is reacted and treated in the same manner as in Example 1 to give 5-(4-chlorophenyl)-2-(4-(1-pyrrolidinyl)phenyl)-N-(2-thiazolyl)imidazole-4-carboxamide.

Example 179

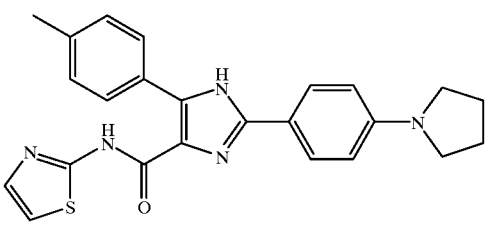

Ethyl 2-hydroxyimino-3-(4-methylphenyl)-3-oxopropionate and 4-(1-pyrrolidinyl)benzylamine are reacted and treated in the same manner as in Starting Material Synthetic Example 1 to give ethyl 5-(4-methylphenyl)-2-(4-(1-pyrrolidinyl)phenyl)imidazole-4-carboxylate. Ethyl 5-(4-methylphenyl)-2-(4-(1-pyrrolidinyl)-phenyl)imidazole-4-carboxylate is reacted and treated in the same manner as in Starting Material Synthetic Example 2 to give 5-(4-methylphenyl)-2-(4-(1-pyrrolidinyl)phenyl)imidazole-4-carboxylic acid. 5-(4-Methylphenyl)-2-(4-(1-pyrrolidinyl)phenyl)imidazole-4-carboxylic acid is reacted and treated in the same manner as in Example 1 to give 5-(4-methylphenyl)-2-(4-(1-pyrrolidinyl)phenyl)-N-(2-thiazolyl)imidazole-4-carboxamide.

Example 180

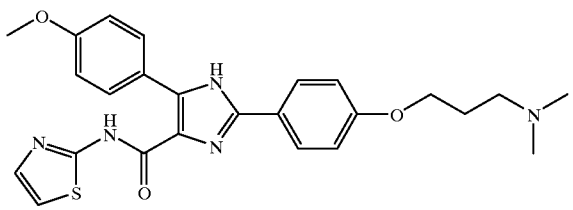

2-(4-Hydroxyphenyl)-5-(4-methoxyphenyl)-N-(2-thiazolyl)-imidazole-4-carboxamide, 3-dimethylaminopropanol, triphenyl-phosphine and diethyl azodicarboxylate are reacted and treated in the same manner as in Example 24 to give 2-(4-(3-dimethylamino-propyloxy)phenyl)-5-(4-methoxyphenyl)-N-(2-thiazolyl)imidazole-4-carboxamide.

Example 181

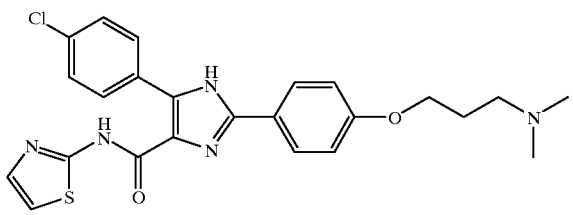

5-(4-Chlorophenyl)-2-(4-hydroxyphenyl)-N-(2-thiazolyl)-imidazole-4-carboxamide, 3-dimethylaminopropanol, triphenyl-phosphine and diethyl azodicarboxylate are reacted and treated in the same manner as in Example 24 to give 5-(4-chlorophenyl)-2-(4-(3-dimethylaminopropyloxy)phenyl)-N-(2-thiazolyl)imidazole-4-carboxamide.

Example 182

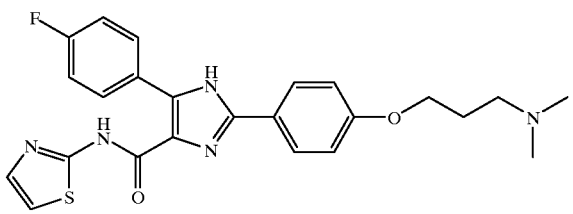

5-(4-Fluorophenyl)-2-(4-hydroxyphenyl)-N-(2-thiazolyl)-imidazole-4-carboxamide, 3-dimethylaminopropanol, triphenyl-phosphine and diethyl azodicarboxylate are reacted and treated in the same manner as in Example 24 to give 5-(4-fluorophenyl)-2-(4-(3-dimethylaminopropyloxy)phenyl)-N-(2-thiazolyl)imidazole-4 -carboxamide.

Example 183

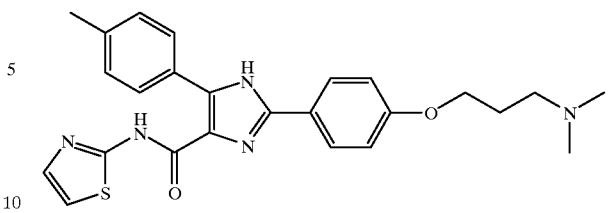

2-(4-Hydroxyphenyl)-5-(4-methylphenyl)-N-(2-thiazolyl)-imidazole-4-carboxamide, 3-dimethylaminopropanol, triphenyl-phosphine and diethyl azodicarboxylate are reacted and treated in the same manner as in Example 24 to give 2-(4-(3-dimethylamino-propyloxy)phenyl)-5-(4-methylphenyl)-N-(2-thiazolyl)imidazole-4-carboxamide.

Example 184

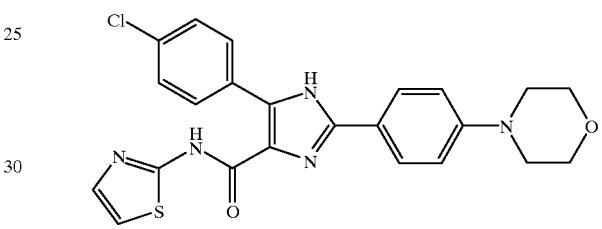

5-(4-Chlorophenyl)-2-(4-morpholinophenyl)imidazole-4-carboxylic acid (49.4 g) obtained in Starting Material Synthetic Example 62 was suspended in tetrahydrofuran (1000 ml) and 2N hydrogen chloride—ether solution (154 ml) was added. The mixture was stirred for 30 min. To the suspension were added DMF (15 ml) and thionyl chloride (94 ml), and the mixture was refluxed under heating for 2 hr and concentrated under reduced pressure. To the residue were added pyridine (1500 ml) and 2-aminothiazole (12.9 g) and the mixture was refluxed under heating for 1 hr 45 min. After the reaction, the solvent was concentrated under reduced pressure, neutralized with saturated aqueous hydrogencarbonate solution and extracted with chloroform. The organic layer was dried over anhydrous magnesium sulfate and concentrated under reduced pressure. The residue was subjected to silica gel column chromatography. The obtained crude crystals were recrystallized from tetrahydrofuran to give 5-(4-chlorophenyl)-2-(4-morpholinophenyl)-N-(2-thiazolyl)imidazole-4-carboxamide (21.8 g), melting point 260° C. or above.

1H-NMR 270 MHz (DMSO-$d_6$, ppm) δ: 12.98(1H, s), 11.26(1H, s), 8.03(2H, d), 7.94(2H, d), 7.54–7.61(3H, m), 7.26(1H, d), 7.05(2H, d), 3.76(4H, t), 3.21(4H, t).

In addition, an acid addition salt with hydrochloric acid was obtained.

Monohydrochloride: melting point 255–258° C.

$^1$H-NMR 270 MHz (DMSO-$d_6$, ppm) δ: 8.60–10.60(2H, br), 8.20(2H, d), 7.92(2H, d), 7.58–7.63(3H, m), 7.31(1H, d), 7.15(2H, d), 3.77(4H, t), 3.31(4H, t)

Example 185

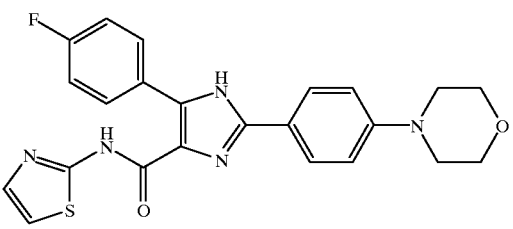

In the same manner as in Example 184, 5-(4-fluorophenyl)-2-(4-morpholinophenyl)-N-(2-thiazolyl)imidazole-4-carboxamide (0.17 g), melting point 250° C. or above, was obtained from 5-(4-fluorophenyl)-2-(4-morpholinophenyl)imidazole-4-carboxylic acid (1.2 g) obtained in Starting Material Synthetic Example 64, 1N hydrogen chloride—ether solution (7.8 ml), DMF (0.3 ml), thionyl chloride (2.4 ml) and 2-aminothiazole (0.33 g).

$^1$H-NMR 270 MHz (DMSO-$d_6$, ppm) δ: 12.96(1H, s), 11.19(1H, s), 7.93–8.05(4H, m), 7.54(1H, d), 7.37(1H, t), 7.26(1H, d), 7.06(2H, d), 3.76(4H, t), 3.22(4H, t).

Example 186

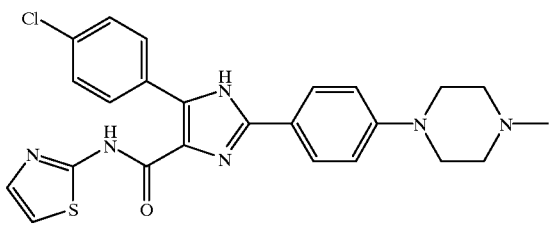

5-(4-Chlorophenyl)-2-[4-(4-methylpiperazin-1-yl)phenyl]-imidazole-4-carboxylic acid (2 g) obtained in Starting Material Synthetic Example 67, 1N hydrogen chloride—ether solution (18.1 ml), DMF (0.3 ml), thionyl chloride (3.7 ml) and 2-aminothiazole (0.50 g) were reacted and treated in the same manner as in Example 184 to give 5-(4-chlorophenyl)-2-[4-(4-methylpiperazin-1-yl)phenyl]-N-(2-thiazolyl)imidazole-4-carboxamide (0.59 g), melting point 250° C. or above.

$^1$H-NMR 270 MHz($D_2O$, ppm) δ: 7.93–8.01(4H,m), 7.53–7.59(3H,m), 7.26(1H, d), 7.04(2H, d), 3.23–3.33(4H, br), 2.44–2.50(4H, br), 2.23(3H, S)

Example 187

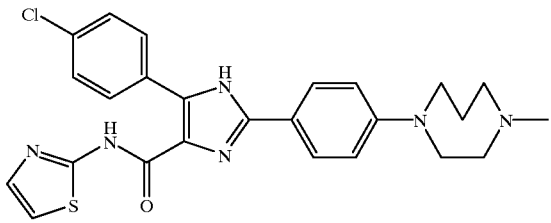

5-(4-Chlorophenyl)-2-[4-(4-methylhomopiperazin-1-yl)phenyl]imidazole-4-carboxylic acid (2 g) obtained in Starting Material Synthetic Example 71, 1N hydrogen chloride—ether solution (17.5 ml), DMF (0.3 ml), thionyl chloride (3.55 ml) and 2-aminothiazole (0.49 g) were reacted and treated in the same manner as in Example 184 to give 5-(4-chlorophenyl)-2-[4-(4-methylhomopiperazin-1-yl)phenyl]-N-(2-thiazolyl)imidazole-4-carboxamide (0.47g), melting point 225–230° C. (decomposition).

Example 188

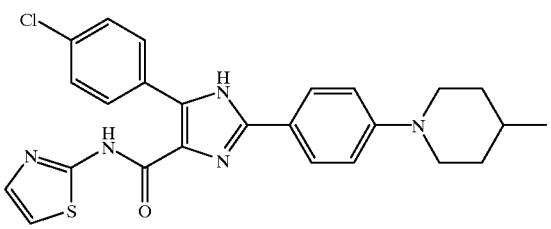

5-(4-Chlorophenyl)-2-[4-(4-methylpiperidin-1-yl)phenyl]-imidazole-4-carboxylic acid (2.2 g) obtained in Starting Material Synthetic Example 75, iN hydrogen chloride—ether solution (13.9 ml), DMF (0.3 ml), thionyl chloride (4.1 ml) and 2-aminothiazole (0.56 g) were reacted and treated in the same manner as in Example 184 to give 5-(4-chlorophenyl)-2-[4-(4-methylpiperidin-1-yl)phenyl]-N-(2-thiazolyl)imidazole-4-carboxamide (1.04 g), melting point 250° C. or above.

$^1$H-NMR 270 MHz (DMSO-$d_6$, ppm) δ: 12.93(1H, s), 11.19(1H, s), 7.93–8.00(4H, m), 7.53–7.66(3H, m), 7.26(1H, d), 7.02(2H, d), 3.81(2H, d), 2.73(2H, dd), 1.49–1.72(3H, m), 1.14–1.28(2H, m), 0.94(3H, d)

Example 189

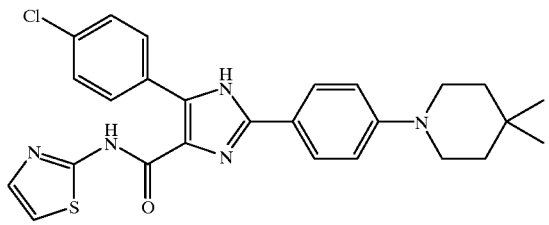

5-(4-Chlorophenyl)-2-[4-(4,4-dimethylpiperidin-1-yl)phenyl]imidazole-4-carboxylic acid (2 g) obtained in Starting Material Synthetic Example 79, 1N hydrogen chloride—ether solution (11.7 ml), DMF (0.7 ml), thionyl chloride (3.6 ml) and 2-aminothiazole (0.49 g) were reacted and treated in the same manner as in Example 184 to give 5-(4-chlorophenyl)-2-[4-(4,4-dimethylpiperidin-1-yl)phenyl]-N-(2-thiazolyl)imidazole-4-carboxamide (0.63 g), melting point 150–154° C.

Example 190

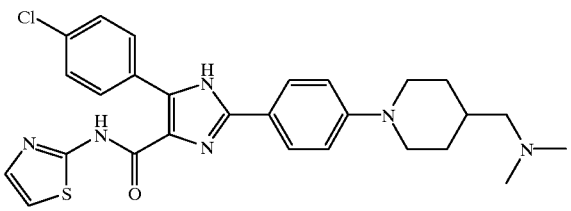

5-(4-Chlorophenyl)-2-{4-[4-(dimethylaminomethyl) piperidin-1-yl]phenyl}imidazole-4-carboxylic acid (4.7 g) obtained in Starting Material Synthetic Example 83, iN hydrogen chloride—ether solution (38.5 ml), DMF (1.4 ml), thionyl chloride (7.8 ml) and 2-aminothiazole (1.07 g) were reacted and treated in the same manner as in Example 184 to give 5-(4-chlorophenyl)-2-{4-[4-(dimethylaminomethyl) piperidin-1-yl]phenyl}-N-(2-thiazolyl)imidazole-4-carboxamide (1.08 g), melting point 246–248° C.

In addition, an acid addition salt of fumaric acid was obtained. ½ Fumarate: melting point 235–240° C. (decomposition).

Example 191

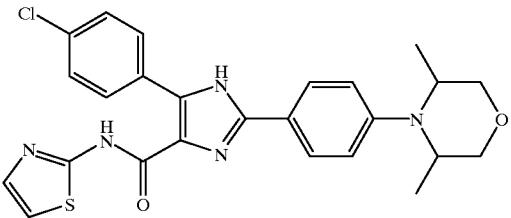

5-(4-Chlorophenyl)-2-[4-(3,5-dimethylmorpholin-4-yl)phenyl]imidazole-4-carboxylic acid (3 g) obtained in Starting Material Synthetic Example 87, 1N hydrogen chloride—ether solution (8.7 ml), DMF (0.6 ml), thionyl chloride (5.3 ml) and 2-aminothiazole (0.73 g) were reacted and treated in the same manner as in Example 184 to give 5-(4-chlorophenyl)-2-[4-(3,5-dimethylmorpholin-4-yl)phenyl]-N-(2-thiazolyl)imidazole-4-carboxamide (0.8 g), melting point 250° C. or above.

$^1$H-NMR 270 MHz (DMSO-$d_6$, ppm) δ: 12.96(1H, s), 11.23(1H, s), 8.01(2H, d), 7.94(2H, d), 7.58(2H, d), 7.54 (1H, d), 7.26(2H, d), 7.05(2H, d), 3.67–3.74(4H, m), 2.32 (2H, t), 1.18(6H, d).

In addition, hydrochloric acid was added to give monohydrochloride, melting point 233–238° C. (decomposition).

Example 192

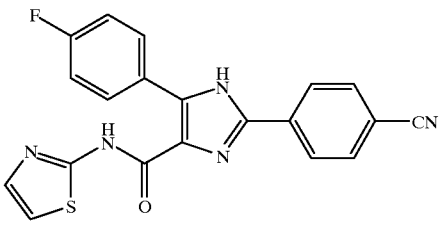

2-(4-Cyanophenyl)-5-(4-fluorophenyl)imidazole-4-carboxylic acid (2.0 g) obtained in Starting Material Synthetic Example 101, 1N hydrogen chloride—ether solution (8.5 ml), DMF (0.2 ml), thionyl chloride (3.2 ml) and 2-aminothiazole (0.7 g) were reacted and treated in the same manner as in Example 184 to give 2-(4-cyanophenyl)-5-(4-fluorophenyl)-N-(2-thiazolyl)imidazole-4-carboxamide. By the addition of hydrochloric acid, an acid addition salt (0.5 g) of hydrochloric acid was obtained. Monohydrochloride: melting point 250° C. or above $^1$H-NMR 270 MHz (DMSO-$d_6$, ppm) δ: 8.46(2H, d), 8.02–7.97(5H,m), 7.66(1H, d), 7.37–7.34(4H, m)

Example 193

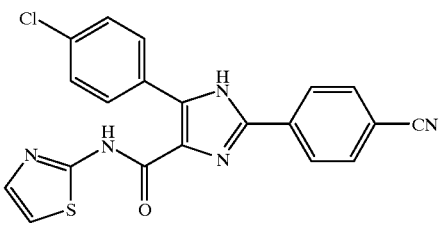

5-(4-Chlorophenyl)-2-(4-cyanophenyl)imidazole-4-carboxylic 10 acid (3.0 g) obtained in Starting Material Synthetic Example 99, 1N hydrogen chloride—ether solution (12 ml), DMF (0.3 ml), thionyl chloride (10 ml) and 2-aminothiazole (0.9 g) were reacted and treated in the same manner as in Example 184 to give 5-(4-chlorophenyl)-2-(4-cyanophenyl)-N-(2-thiazolyl)imidazole-4-carboxamide (0.7 g). By the addition of hydrochloric acid, an acid addition salt of hydrochloric acid was obtained.

Monohydrochloride: melting point 250° C. or above.

$^1$H-NMR 270 MHz (DMSO-$d_6$, ppm) δ: 8.45(2H, d), 7.98(2H, d), 7.97(2H, d), 7.65(1H, d), 7.58(2H, d).

Example 194

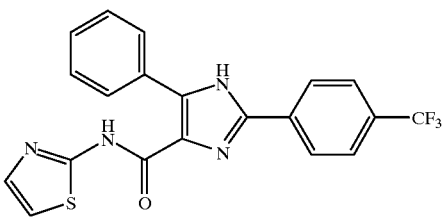

5-Phenyl-2-(4-trifluoromethylphenyl)imidazole-4-carboxylic acid (2.5 g) obtained in Starting Material Synthetic Example 103, 1N hydrogen chloride—ether solution (12 ml), DMF (0.3 ml), thionyl chloride (5.5 ml) and 2-aminothiazole (0.7 g) were reacted and treated in the same manner as in Example 184 to give 5-phenyl-N-(2-thiazolyl)-2-(4-trifluoromethylphenyl)-imidazole-4-carboxamide (0.3 g). By the addition of hydrochloric acid, an acid addition salt of hydrochloric acid was obtained.

Monohydrochloride: melting point 250° C. or above $^1$H-NMR 270 MHz (DMSO-$d_6$, ppm) δ: 8.47(2H, d), 7.93–7.90(4H, m), 7.64(1H, d), 7.53(2H, d), 7.34(1H, d)

Example 195

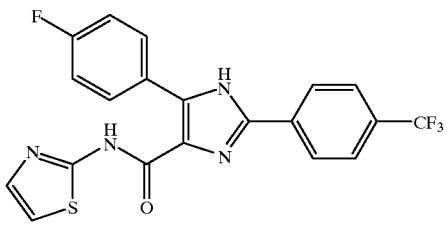

5-(4-Fluorophenyl)-2-(4-trifluoromethylphenyl) imidazole-4-carboxylic acid (3.0 g) obtained in Starting Material Synthetic Example 95 was suspended in methylene chloride (60 ml). To the suspension were added 2-aminothiazole (0.9 g) and triethylamine (2.4 ml). A solution of 2-chloro-1,3-dimethylimidazolinium chloride (2.1 q) dissolved in methylene chloride (20 ml) was added dropwise under ice-cooling and the mixture was stirred at room temperature for 2 hr. After the reaction, a saturated aqueous hydrogencarbonate solution was added and the organic layer was extracted with ethyl acetate. The organic layer was dried and the residue was subjected to silica gel chromatography to give 5-(4-fluorophenyl)-N-(2-thiazolyl)-2-(4-trifluoromethyl-phenyl) imidazole-4-carboxamide. By the addition of hydrochloric acid, an acid addition salt (1.2 g) of hydrochloric acid was obtained. Monohydrochloride: melting point 250° C. or above $^1$H-NMR 270 MHz (DMSO-$d_6$, ppm) δ: 8.48(2H, d), 8.03–7.98(4H, m), 7.67(1H, d), 7.41–7.34(3H, m).

Example 196

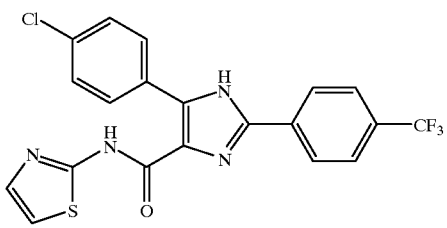

5-(4-Chlorophenyl)-2-(4-trifluoromethylphenyl) imidazole-4-carboxylic acid (3.0 g) obtained in Starting Material Synthetic Example 97, 2-aminothiazole (0.8 g), triethylamine (2.3 ml) and 2-chloro-1,3-dimethylimidazolinium chloride (2.2 g) were reacted and treated in the same manner as in Example 195 to give 5-(4-chlorophenyl)-N-(2-thiazolyl)-2-(4-trifluoromethylphenyl)imidazole-4-carboxamide. By the addition of hydrochloric acid, an acid addition salt (0.3 g) of hydrochloric acid was obtained.

Monohydrochloride: melting point 250° C. or above.

$^1$H-NMR 270 MHz (DMSO-$d_6$, ppm) δ: 8.47(2H, d), 7.99–7.88(4H, m), 7.65–7.55(3H, m), 7.34(1H, d).

Example 197

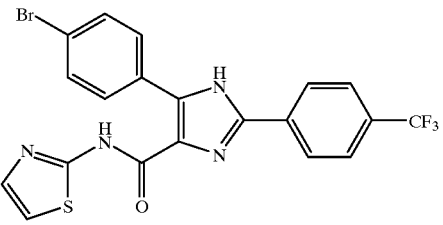

5-(4-Bromophenyl)-2-(4-trifluoromethylphenyl) imidazole-4-carboxylic acid (3.0 g) obtained in Starting Material Synthetic Example 105, lNhydrogenchloride-ethersolution (15 ml), DMF (0.3 ml), thionyl chloride (5.3 ml) and 2-aminothiazole (0.7 g) were reacted and treated in the same manner as in Example 184 to give 5-(4-bromophenyl)-N-(2-thiazolyl)-2-(4-trifluoromethylphenyl) imidazole-4-carboxamide. By the addition of hydrochloric acid, an acid addition salt (0.4 g) of hydrochloric acid was obtained.

Monohydrochloride: melting point 256–257° C.

Example 198

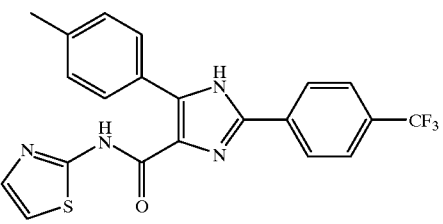

5-(4-Methylphenyl)-2-(4-trifluoromethylphenyl) imidazole-4-carboxylic acid (2.0 g) obtained in Starting Material Synthetic Example 152, 1N hydrogen chloride-ethersolution(12 ml), DMF (0.2 ml), thionyl chloride (2.9 ml) and 2-aminothiazole (0.6 g) were reacted and treated in the same manner as in Example 184 to give 5-(4-methylphenyl)-N-(2-thiazolyl)-2-(4-trifluoromethylphenyl) iimidazole-4-carboxamide. By the addition of hydrochloric acid, an acid addition salt (0.4 g) of hydrochloric acid was obtained.

Monohydrochloride: melting point 250° C. or above $^1$H-NMR 270 MHz (DMSO-$d_6$, ppm) δ: 8.47(2H, d), 7.90(2H, d), 7.82(2H, d), 7.64(1H, d), 7.35–7.32(3H, m), 2.40(3H, s).

Example 199

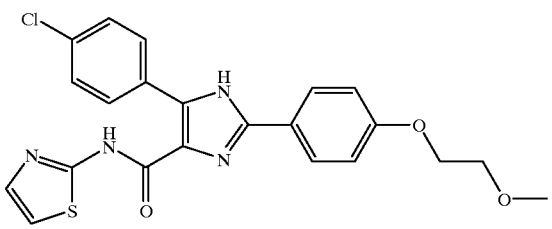

5-(4-Chlorophenyl)-2-[4-(2-methoxyethoxy)phenyl]imidazole-4-carboxylic acid (45.5 g) obtained in Starting Material Synthetic Example 108, 1N hydrogen chloride—ether solution (130 ml), a catalytic amount of DMF, thionyl chloride (70 ml) and 2-aminothiazole (12 g) were reacted and treated in the same manner as in Example 184 to give 5-(4-chlorophenyl)-2-[4-(2-methoxyethoxy)phenyl]-N-(2-thiazolyl)-imidazole-4-carboxamide (30.2 g), melting point 147–148° C.

By the addition of hydrochloric acid, an acid addition salt (31.0 g) of hydrochloric acid was obtained.

Monohydrochloride: melting point 238–240° C.

Example 200

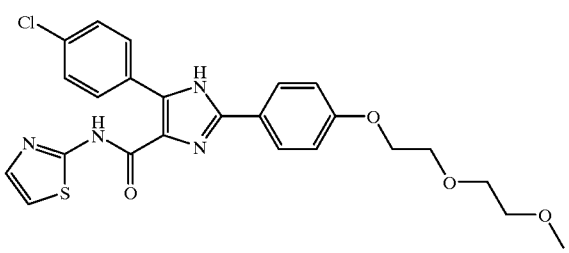

5-(4-Chlorophenyl)-2-{4-[2-(2-methoxyethoxy)ethoxy]-phenyl}imidazole-4-carboxylic acid (1.3 g) obtained in Starting Material Synthetic Example 111, 1N hydrogen chloride—ether solution (4.5 ml), DMF (0.1 ml), thionyl chloride (1.6 ml) and 2-aminothiazole (12 g) were reacted and treated in the same manner as in Example 184 to give 5-(4-chlorophenyl)-2-{4-[2-(2-methoxyethoxy)ethoxy]-phenyl}-N-(2-thiazolyl)imidazole-4-carboxamide. By the addition of hydrochloric acid, an acid addition salt (0.4 g) of hydrochloric acid was obtained.

Monohydrochloride: melting point 205–206° C.

Example 201

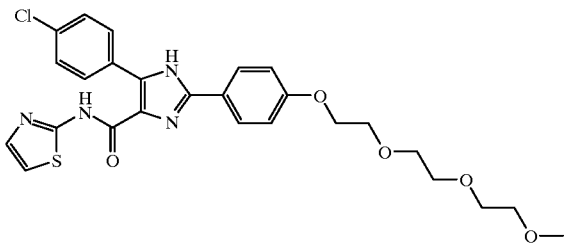

5-(4-Chlorophenyl)-2-(4-{2-[2-(2-methoxyethoxy)ethoxy]-ethoxy}phenyl)imidazole-4-carboxylic acid (3.5 g) obtained in Starting Material Synthetic Example 120, 2N hydrogen chloride—ether solution (4.56 ml), DMF (0.6 ml), thionyl chloride (5.5 ml) and 2-aminothiazole (0.76 g) were reacted and treated in the same manner as in Example 184 to give 5-(4-chlorophenyl)-2-(4-{2-[2-(2-methoxyethoxy)ethoxy]ethoxy}phenyl)-N-(2-thiazolyl)imidazole-4-carboxamide (1.3 g), melting point 120-122° C.

By the addition of hydrochloric acid, an acid addition salt of hydrochloric acid was obtained.

Monohydrochloride: melting point 75–80° C.

Example 202

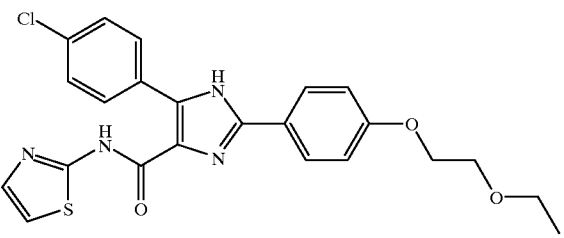

5-(4-Chlorophenyl)-2-[4-(2-ethoxyethoxy)phenyl]imidazole-4-carboxylic acid (3 g) obtained in Starting Material Synthetic Example 117, 2N hydrogen chloride—ether solution (4.7 ml), DMF (0.6 ml), thionyl chloride (5.6 ml) and 2-aminothiazole (0.78 g) were reacted and treated in the same manner as in Example 184 to give 5-(4-chlorophenyl)-2-[4-(2-ethoxyethoxy)phenyl]-N-(2-thiazolyl)-imidazole-4-carboxamide (0.94 g), melting point 115° C.

By the addition of hydrochloric acid, monohydrochloride was obtained: melting point 195–200° C.

Example 203

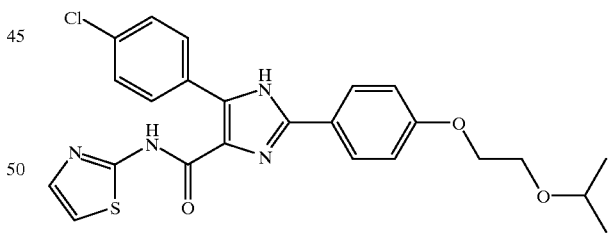

5-(4-Chlorophenyl)-2-[4-(2-isopropoxyethoxy)phenyl]-imidazole-4-carboxylic acid (2 g) obtained in Starting Material Synthetic Example 114, 2N hydrogen chloride—ether solution (3 ml), DMF (0.4 ml), thionyl chloride (3.64 ml) and 2-aminothiazole (0.5 g) were reacted and treated in the same manner as in Example 184 to give 5-(4-chlorophenyl)-2-[4-(2-isopropoxyethoxy)phenyl]-N-(2-thiazolyl)imidazole-4-carboxamide (0.62 g), melting point 121–125° C.

By the addition of hydrochloric acid, monohydrochloride was obtained: melting point 195–198° C.

Example 204

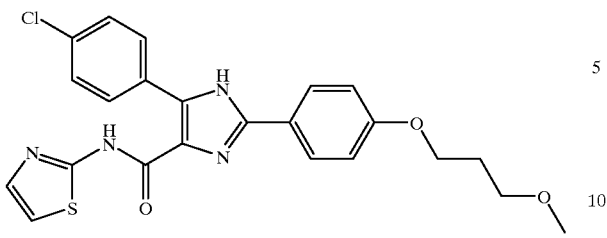

5-(4-Chlorophenyl)-2-[4-(3-methoxypropoxy)phenyl]imidazole-4-carboxylic acid (1.87 g) obtained in Starting Material Synthetic Example 123, 2N hydrogen chloride—ether solution (2.9 ml), DMF (0.2 ml), thionyl chloride (3.53 ml) and 2-aminothiazole (0.48 g) were reacted and treated in the same manner as in Example 184 to give 5-(4-chlorophenyl)-2-{4-(3-methoxypropoxy)phenyl}-N-(2-thiazolyl)-imidazole-4-carboxamide (0.84 g), melting point 173–177° C.

By the addition of hydrochloric acid, monohydrochloride was obtained: melting point 230–234° C.

Example 205

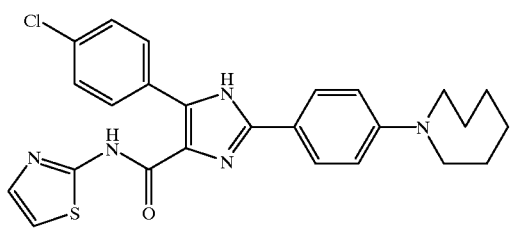

5-(4-Chlorophenyl)-2-[4-(homopiperidin-1-yl)phenyl]-imidazole-4-carboxylic acid (2.0 g) obtained in Starting Material Synthetic Example 127, 1N hydrogen chloride—ether solution (10 ml), DMF (0.2 ml), thionyl chloride (2.5 ml) and 2-aminothiazole (0.5 g) were reacted and treated in the same manner as in Example 184 to give 5-(4-chlorophenyl)-2-[4-(homopiperidin-1-yl)phenyl]-N-(2-thiazolyl)imidazole-4-carboxamide (0.47 g), melting point 246–247° C.

Example 206

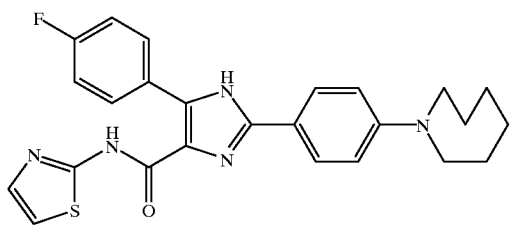

5-(4-Fluorophenyl)-2-[4-(homopiperidin-1-yl)phenyl]-imidazole-4-carboxylic acid obtained in Starting Material Synthetic Example 129, 2N hydrogen chloride—ether solution, DMF, thionyl chloride and 2-aminothiazole are reacted and treated in the same manner as in Example 184 to give 5-(4-fluorophenyl)-2-[4-(homopiperidin-1-yl)phenyl]-N-(2-thiazolyl)imidazole-4-carboxamide.

Example 207

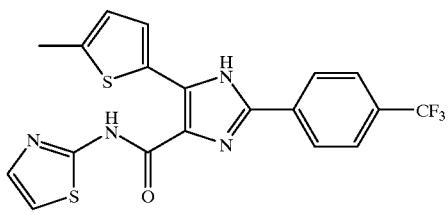

5-(5-Methylthiophen-2-yl)-2-(4-trifluoromethylphenyl)-imidazole-4-carboxylic acid (1.0 g) obtained in Starting Material Synthetic Example 131, 2-aminothiazole (0.3 g), triethylamine (0.8 ml) and 2-chloro-1,3-dimethylimidazolium chloride (0.7 g) were reacted and treated in the same manner as in Example 196 to give 5-(5-methylthiophen-2-yl)-N-(2-thiazolyl)-2-(4-trifluoromethylphenyl)-imidazole-4-carboxamide (0.4 g), melting point 235–237° C.

Example 208

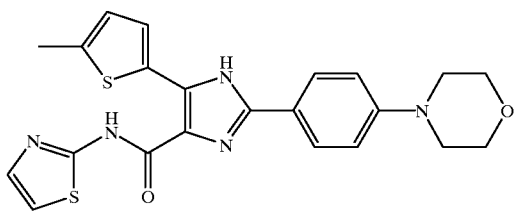

5-(5-Methylthiophen-2-yl)-2-(4-morpholinophenyl)imidazole-4-carboxylic acid obtained in Starting Material Synthetic Example 133, 2N hydrogen chloride—ether solution, DMF, thionyl chloride and 2-aminothiazole are reacted and treated in the same manner as in Example 184 to give 5-(5-methylthiophen-2-yl)-2-(4-morpholinophenyl)-N-(2-thiazolyl)imidazole-4-carboxamide.

Example 209

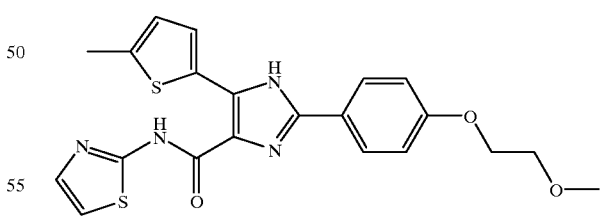

2-[4-(2-Methoxyethoxy)phenyl]-5-(5-methylthiophen-2-yl)-imidazole-4-carboxylic acid obtained in Starting Material Synthetic Example 135, 2N hydrogen chloride—ether solution, DMF, thionyl chloride and 2-aminothiazole are reacted and treated in the same manner as in Example 184 to give 2-[4-(2-methoxyethoxy)phenyl]-5-(5-methylthiophen-2-yl)-N-(2-thiazolyl)imidazole-4-carboxamide.

Example 210

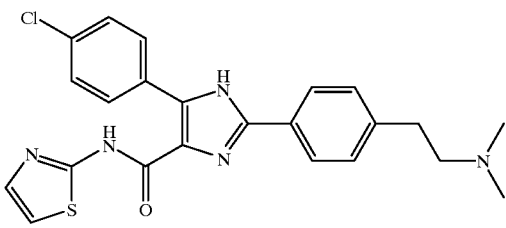

5-(4-Chlorophenyl)-2-[4-(2-dimethylaminoethyl)phenyl]-imidazole-4-carboxylic acid obtained in Starting Material Synthetic Example 138, 2N hydrogen chloride—ether solution, DMF, thionyl chloride and 2-aminothiazole are reacted and treated in the same manner as in Example 184 to give 5-(4-chlorophenyl)-2-[4-(2-dimethylaminoethyl)phenyl]-N-(2-thiazolyl)imidazole-4-carboxamide.

Example 211

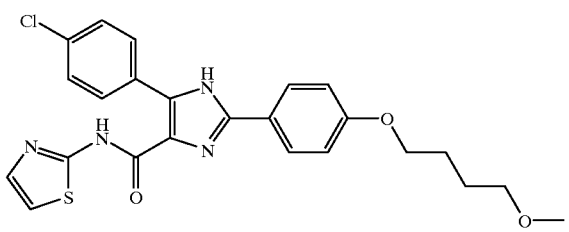

5-(4-Chlorophenyl)-2-[4-(4-methoxybutoxy)phenyl] imidazole-4-carboxylic acid obtained in Starting Material Synthetic Example 141, 2N hydrogen chloride—ether solution, DMF, thionyl chloride and 2-aminothiazole are reacted and treated in the same manner as in Example 184 to give 5-(4-chlorophenyl)-2-[4-(4-methoxybutoxy)phenyl]-N-(2-thiazolyl)imidazole-4-carboxamide.

Example 212

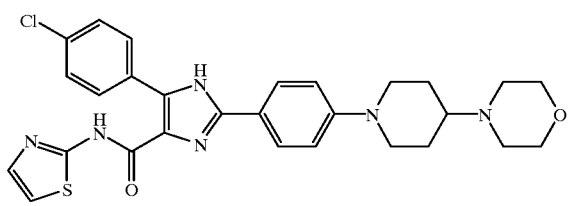

5-(4-Chlorophenyl)-2-[4-(4-morpholinopiperidin-1-yl)phenyl]imidazole-4-carboxylic acid (1.66 g) obtained in Starting Material Synthetic Example 145, 2N hydrogen chloride—ether solution (6.4 ml), DMF (0.3 ml), thionyl chloride (2.59 ml) and 2-aminothiazole (0.36 g) were reacted and treated in the same manner as in Example 184 to give the objective 5-(4-chlorophenyl)-2-[4-(4-morpholino-piperidin-1-yl)phenyl]-N-(2-thiazolyl)imidazole-4-carboxamide (0.46 g), melting point 165–170° C.

Example 213

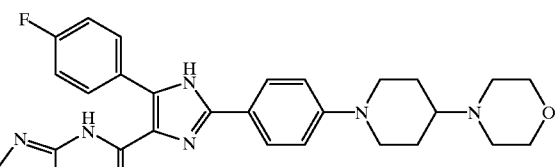

5-(4-Fluorophenyl)-2-[4-(4-morpholinopiperidin-1-yl)phenyl]imidazole-4-carboxylic acid obtained in Starting Material Synthetic Example 147, 2N hydrogen chloride—ether solution, DMF, thionyl chloride and 2-aminothiazole are reacted and treated in the same manner as in Example 184 to give 5-(4-fluorophenyl)-2-[4-(4-morpholinopiperidin-1-yl)phenyl]-N-(2-thiazolyl)imidazole-4-carboxamide.

Example 214

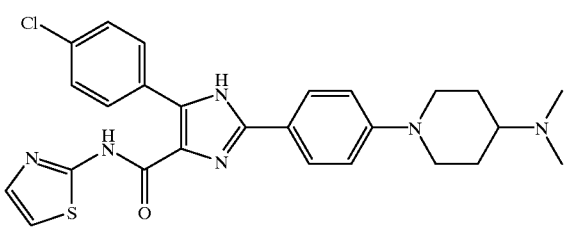

5-(4-Chlorophenyl)-2-[4-[4-(dimethylamino)piperidin-1-yl]phenyl]imidazole-4-carboxylic acid obtained in Starting Material Synthetic Example 91, 2N hydrogen chloride—ether solution, DMF, thionyl chloride and 2-aminothiazole are reacted and treated in the same manner as in Example 184 to give 5-(4-chlorophenyl)-2-[4-[4-(dimethylamino)piperidin-1-yl]phenyl]-N-(2-thiazolyl)imidazole-4-carboxamide.

Example 215

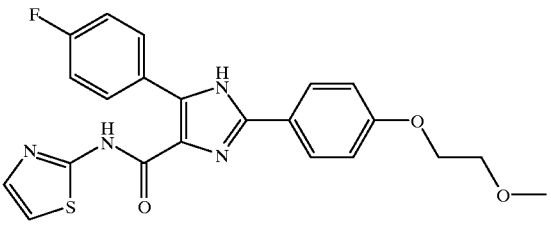

5-(4-Fluorophenyl)-2-[4-(2-methoxyethoxy)phenyl] imidazole-4-carboxylic acid obtained in Starting Material Synthetic Example 149, 2N hydrogen chloride—ether solution, DMF, thionyl chloride and 2-aminothiazole are reacted and treated in the same manner as in Example 184 to give 5-(4-fluorophenyl)-2-[4-(2-methoxyethoxy)phenyl]-N-(2-thiazolyl)imidazole-4-carboxamide.

Example 216

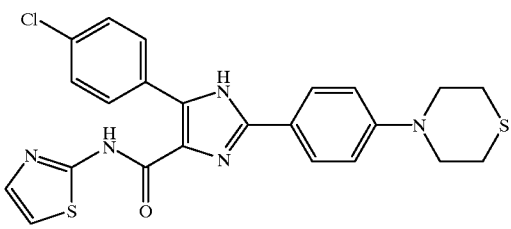

5-(4-Chlorophenyl)-2-[4-(thiomorpholin-4-yl)phenyl]-imidazole-4-carboxylic acid obtained in Starting Material Synthetic Example 152, 2N hydrogen chloride—ether solution, DMF, thionyl chloride and 2-aminothiazole are reacted and treated in the same manner as in Example 184 to give 5-(4-chlorophenyl)-N-(2-thiazolyl)-2-[4-(thiomorpholin-4-yl)phenyl]imidazole-4-carboxamide.

Example 217

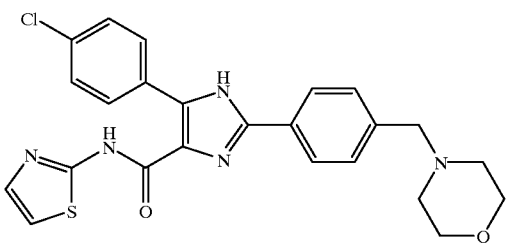

5-(4-Chlorophenyl)-2-[4-(morpholinomethyl)phenyl]imidazole-4-carboxylic acid (2.5 g) obtained in Starting Material Synthetic Example 160, 2N hydrogen chloride—ether solution (7.5 ml), DMF (0.3 ml), thionyl chloride (4.6 ml) and 2-aminothiazole (0.63 g) were reacted and treated in the same manner as in Example 184 to give 5-(4-chlorophenyl)-2-[4-(morpholinomethyl)phenyl]-N-(2-thiazolyl)-imidazole-4-carboxamide (1.87 g), melting point 253–255° C.

By the addition of hydrochloric acid, dihydrochloride was obtained: melting point 260° C. or above.

1H-NMR 270 MHz (DMSO-$d_6$, ppm) δ: 11.69(1H, br.s), 8.34(2H, d), 7.98(2H, d), 7.82(2H, d), 7.59–7.62(3H, m), 7.32(1H, d), 4.40(2H, br.s), 3.83–3.97(4H, m), 3.14–3.28 (4H, m)

Example 218

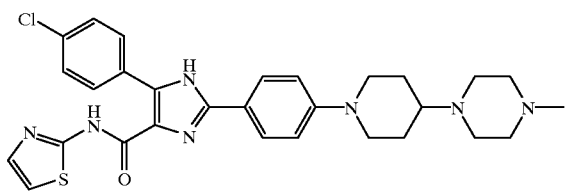

5-(4-Chlorophenyl)-2-{4-[4-(4-methylpiperazin-1-yl)piperidin-1-yl]phenyl}imidazole-4-carboxylic acid obtained in Starting Material Synthetic Example 164, 2N hydrogen chloride—ether solution, DMF, thionyl chloride and 2-aminothiazole are reacted and treated in the same manner as in Example 184 to give 5-(4-chlorophenyl)-2-{4-[(4-methylpiperazin-1-yl)piperidin-1-yl]phenyl}-N-(2-thiazolyl)imidazole-4-carboxamide.

Example 219

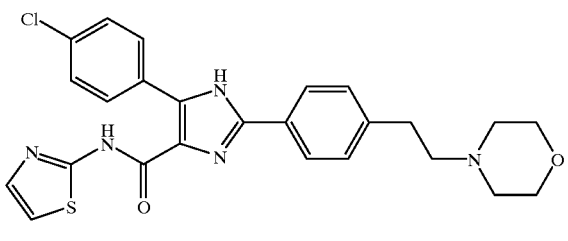

5-(4-Chlorophenyl)-2-[4-(2-morpholinoethyl)phenyl]-imidazole-4-carboxylic acid obtained in Starting Material Synthetic Example 167, 2N hydrogen chloride—ether solution, DMF, thionyl chloride and 2-aminothiazole are reacted and treated in the same manner as in Example 184 to give 5-(4-chlorophenyl)-2-[4-(2-morpholinoethyl)phenyl]-N-(2-thiazolyl)imidazole-4-carboxamide.

Example 220

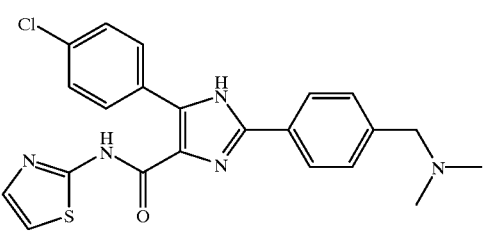

5-(4-Chlorophenyl)-2-[4-(dimethylaminomethyl)-phenyl]-imidazole-4-carboxylic acid (2.0 g) obtained in Starting Material Synthetic Example 171, 2N hydrogen chloride—ether solution (10 ml), DMF (0.2 ml), thionyl chloride (2.7 ml) and 2-aminothiazole (0.6 g) were reacted and treated in the same manner as in Example 184 to give 5-(4-chlorophenyl)-2-[4-(dimethylaminomethyl)phenyl]-N-(2-thiazolyl)imidazole-4-carboxamide (0.4 g), melting point 143-145° C.

Example 221

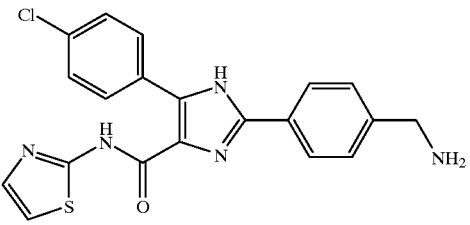

5-(4-Chlorophenyl)-2-(4-cyanophenyl)-N-(2-thiazolyl)-imidazole-4-carboxamide obtained in Example 193 is reduced with LiAlH$_4$ to give 2-(4-aminomethylphenyl)-5-(4-chlorophenyl)-N-(2-thiazolyl)imidazole-4-carboxamide.

Example 222

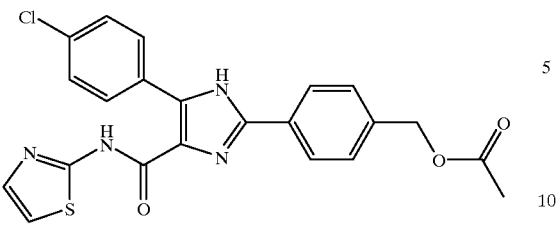

2-(4-Acetoxymethylphenyl)-5-(4-chlorophenyl) imidazole-4-carboxylic acid obtained in Starting Material Synthetic Example 174, 2N hydrogen chloride—ether solution, DMF, thionyl chloride and 2-aminothiazole are reacted and treated in the same manner as in Example 184 to give 2-(4-acetoxymethylphenyl)-5-(4-chlorophenyl)-N-(2-thiazolyl)imidazole-4-carboxamide.

Example 223

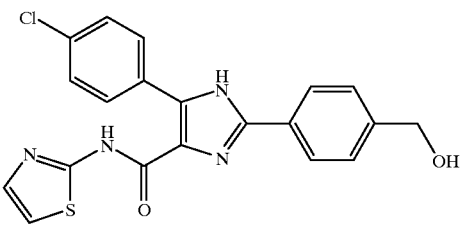

2-(4-Acetoxymethylphenyl)-5-(4-chlorophenyl)-N-(2-thiazolyl)imidazole-4-carboxamide obtained in Example 222 is hydrolyzed with aqueous sodium hydroxide solution to give the objective 5-(4-chlorophenyl)-2-(4-hydroxymethylphenyl)-N-(2-thiazolyl)-imidazole-4-carboxamide.

Example 224

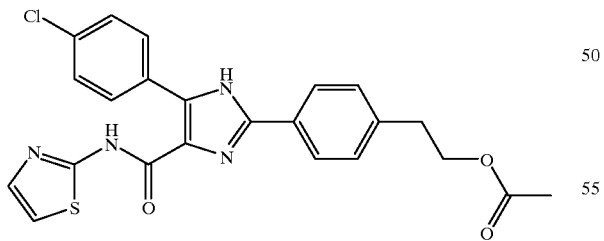

2-[4-(2-Acetoxyethyl)phenyl]-5-(4-chlorophenyl) imidazole-4-carboxylic acid obtained in Starting Material Synthetic Example 177, 2N hydrogen chloride—ether solution, DMF, thionyl chloride and 2-aminothiazole are reacted and treated in the same manner as in Example 184 to give 2-[4-(2-acetoxyethyl)phenyl]-5-(4-chlorophenyl)-N-(2-thiazolyl)imidazole-4-carboxamide.

Example 225

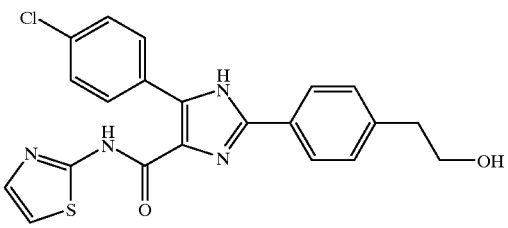

In the same manner as in Example 223, the objective 5-(4-chlorophenyl)-2-[4-(2-hydroxyethyl)phenyl]-N-(2-thiazolyl)-imidazole-4-carboxamide is obtained from 2-[4-(2-acetoxyethyl)-phenyl]-5-(4-chlorophenyl)-N-(2-thiazolyl)imidazole-4-carboxamide obtained in Example 224.

Example 226

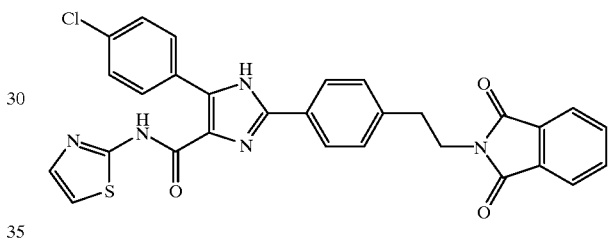

5-(4-Chlorophenyl)-2-[4-(2-hydroxyethyl)phenyl]-N-(2-thiazolyl)imidazole-4-carboxamide obtained in Example 225, phthalimide, diethyl azodicarboxylate and triphenylphosphine are subjected to Mitsunobu reaction to give the objective 5-(4-chlorophenyl)-2-{4-[2-(phthalimid-1-yl)ethyl]phenyl}-N-(2-thiazolyl)imidazole-4-carboxamide.

Example 227

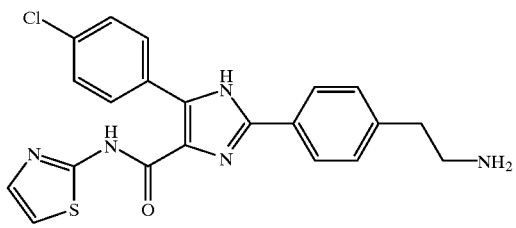

5-(4-Chlorophenyl)-2-{4-[2-(phthalimid-1-yl)ethyl]phenyl}-N-(2-thiazolyl)imidazole-4-carboxamide obtained in Example 226 is reacted with hydrazine monohydrate to give the objective 2-[4-(2-aminoethyl)phenyl]-5-(4-chlorophenyl)-N-(2-thiazolyl)imidazole-4-carboxamide.

Example 228

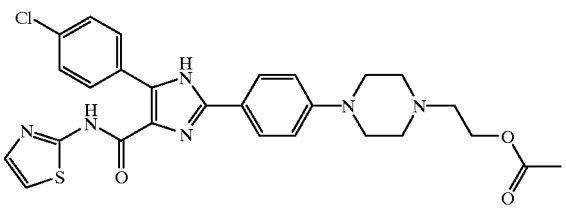

2-{4-[4-(2-Acetoxyethyl)piperazin-1-yl]phenyl}-5-(4-chlorophenyl)imidazole-4-carboxylic acid obtained in Starting Material Synthetic Example 182, 2N hydrogen chloride—ether solution, DMF, thionyl chloride and 2-aminothiazole are reacted and treated in the same manner as in Example 184 to give 2-{4-[4-(2-acetoxyethyl)piperazin-1-yl]phenyl}-5-(4-chlorophenyl)-N-(2-thiazolyl)imidazole-4-carboxamide.

Example 229

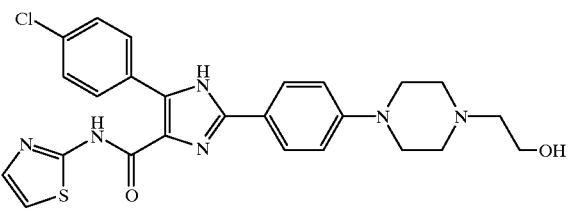

In the same manner as in Example 223, the objective 5-(4-chlorophenyl)-2-{4-[4-(2-hydroxyethyl)piperazin-1-yl]phenyl}-N-(2-thiazolyl)imidazole-4-carboxamide is obtained from 2-{4-[4-(2-acetoxyethyl)piperazin-1-yl]phenyl}-5-(4-chlorophenyl)-N-(2-thiazolyl)imidazole-4-carboxamide obtained in Example 228.

Example 230

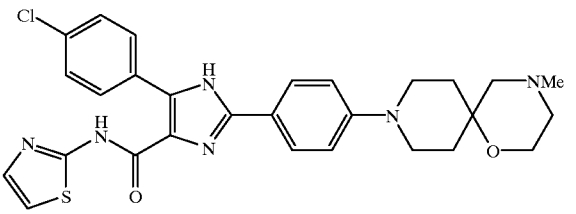

In the same manner as in Example 184, 5-(4-chlorophenyl)-2-[4-(4-methyl-1-oxa-4,9-diazaspiro[5,5]undecan-9-yl)phenyl]-N-(2-thiazolyl)imidazole-4-carboxamide (1.6 g), melting point 205-210° C., was obtained from 5-(4-chlorophenyl)-2-[4-(4-methyl-1-oxa-4,9-diazaspiro[5,5]undecan-9-yl)phenyl]imidazole-4-carboxylic acid (4.65 g) obtained in Starting Material Synthetic Example 186, 2N hydrogen chloride—ether solution (17.3 ml), DMF (0.62 ml), thionyl chloride (7.3 ml) and 2-aminothiazole (1 g).

The effect of the present invention is described in detail in the following by referring to Experimental Examples.

Experimental Example 1

Effect on IL-4 and IL-5 Production by Mouse Th2 Cell Line

1. Test Method
1) Preparation of Test Substance
A test substance was dissolved in dimethyl sulfoxide to the concentration of 10 mM and diluted with the following medium to the final concentration of $10^{-5}$–$10^{-7}$ M.
2) Th2 Cell Line
As the Th2 cell line, D10.G4.1 was used. The D10.G4.1 recognizes a conalbumin as an antigen, I-$A^K$ restrictively.
3) Medium
An RPMI1640 medium supplemented with inactivated fetal bovine serum (10%) and 2-mercaptoethanol (50 µM) was used.
4) Preparation of Antigen-Presenting Cell
Male C3H/HeN mice (6–12 weeks of age) were exsanguinated and the spleen was aseptically removed to prepare asplenic cell suspension. Mitomycin C was added to the final concentration of 40 µg/ml and the mixture was incubated at 37° C. for 30 min. Then, the splenic cells were washed twice with the medium and used as the antigen-presenting cells.
5) Measurement of IL-4 and IL-5 Amounts Produced by Th2 Cell Line Th2 cell line ($2\times10^4$), the antigen-presenting cells ($1\times10^5$), conalbumin (100 µg/ml) and a test substance were added per well of a 96 well microplate and incubated in a $CO_2$ incubator for 2 days. After incubation, the supernatant (100 µl) was recovered from each well. The concentration of IL-4 and IL-5 in the supernatant was assayed by the sandwich ELISA method.
2. Results
The effect on IL-4 and IL-5 production is shown in Table 1. The representative compound of the present invention inhibited IL-4 production at a concentration ($IC_{50}$) of about 1 µM and IL-5 production at a concentration ($IC_{50}$) of about 0.5 µM.

TABLE 1

Inhibitory effect on IL-4 and IL-5 production by Th2 clone

| | Inhibition ($IC_{50}$, µM) | |
|---|---|---|
| | IL-4 | IL-5 |
| compound of Example 1 | 0.91 | 0.33 |
| compound of Example 47 | 2.98 | 0.69 |
| compound of Example 70 | 3.77 | 0.44 |
| compound of Example 79 | 0.71 | 0.16 |

Experimental Example 2

Effect on Ovalbumin (OA)-Induced Biphasic Ear Edema Mouse Model

1. Test Method
1) Preparation of Test Substance
A test substance was suspended in 0.5% hydroxypropylmethylcellulose (HPMC) solution at 0.1 ml per 10 g body weight and used.
2) Test Protocol
Physiological saline (0.5 ml) containing OA (10 µg) and aluminum hydroxide gel (1 mg) was intraperitoneally administered to 7-week-old male BALB/c mice to actively sensitize them. After sensitization, OA (5 µg) was intradermally administered to the auricle on day 14 for antigen challenge. The thickness of the auricle before the antigen challenge, and 1 and 24 hours after the antigen challenge was measured with a dial thickness gauge and changes in the thickness of the auricle were calculated from the following formula.

Increase in thickness of the auricle
=thickness of the auricle after intradermal administration of antigen−thickness of the auricle before intradermal administration of antigen The test substance was orally administered for 3 consecutive days from 2 days before antigen challenge to the day of antigen challenge.

2. Results

The effect of the compound of Example 1 on the late phase (24 hr after antigen challenge) swelling of the auricle is shown in FIG. 1. The compound of Example 1, given at a dose of 10 mg/kg, significantly inhibited the late phase swelling mainly caused by T cell and eosinophil.

Experimental Example 3

Effect on Eosinophil Peroxidase (EPO) Activity in the Auricle of OA-Induced Biphasic Ear Edema Mouse Model 1. Test Method 1) Preparation of Test Substance A test substance was suspended in 0.5% hydroxypropylmethylcellulose (HPMC) solution at 0.1 ml per 10 g body weight and used.

2) Test Protocol

Physiological saline (0.5 ml) containing OA (10 $\mu$g) and aluminum hydroxide gel (1 mg) was intraperitoneally administered to 7-week-old male BALB/c mice to actively sensitize them. OA (5 $\mu$g) was intradermally administered to the auricle on day 14 for antigen challenge. The test substance was orally administered for 3 consecutive days from 2 days before antigen challenge to the day of antigen challenge. The mice were exsanguinated at 12 hours after antigen challenge and the auricle was removed. The excised auricle was slit and homogenized in 50 mM Tris—HCl buffer (pH 8.0, 1 ml) containing 0.5% hexadecyltrimethylammonium bromide. The homogenized suspension was centrifuged at 3000 rpm for 15 min and the supernatant was recovered. The EPO activity of the supernatant was assayed using o-phenylenediamine (OPD) as a substrate.

2. Results

Figure 2:
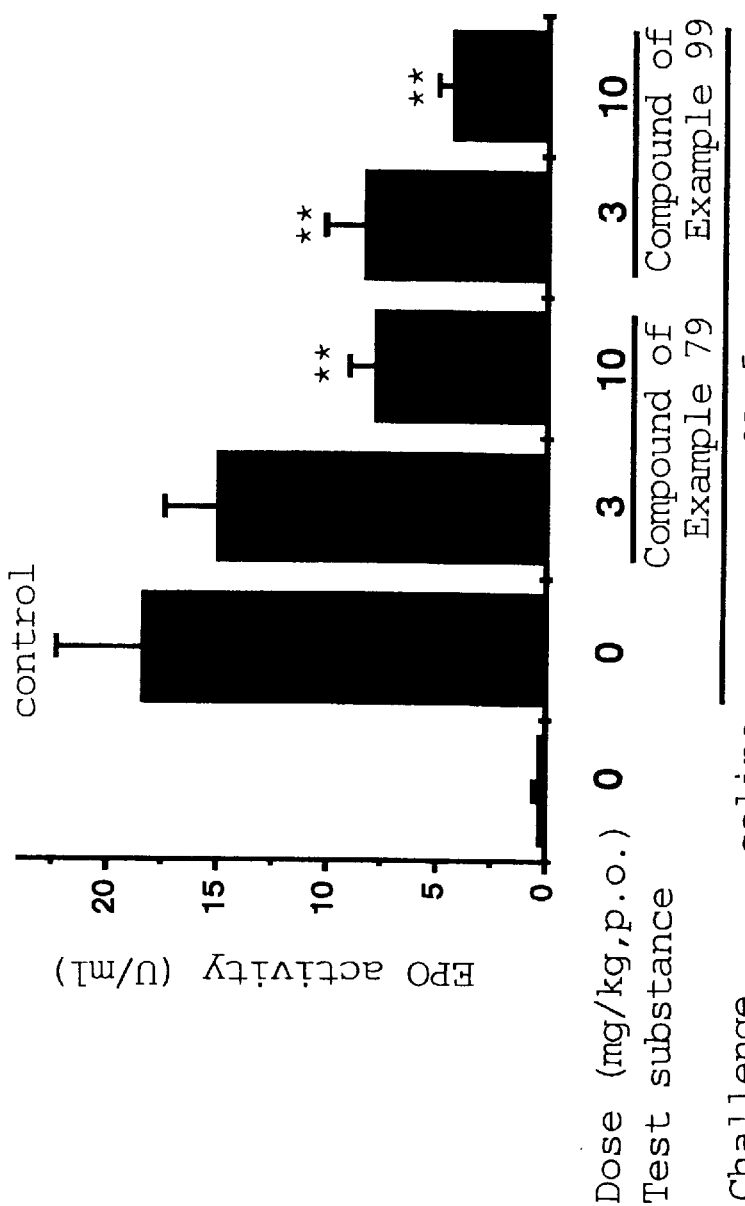
FIG. 2 is a graph showing the effect of the compounds of Examples 79 and 99 on an increase in the eosinophil peroxidase (EPO) activity in ovalbumin (OA)-induced mouse biphasic ear edema model in Experimental Example 3, wherein each value shows mean+standard error (n=13–16). Thesignificantdifference testwas performed by Dunnett's multiple comparison test, wherein ** shows P<0.01, indicating significant difference from control.

The effect of the compounds of Example 79 and Example 99 on the increase in the EPO activity in the auricle is shown in FIG. 2. The compounds of Example 79 and Example 99, given at a dose exceeding 10 mg/kg and a dose of 3 mg/kg, respectively, significantly inhibited an increase in the EPO activity in the auricle.

Experimental Example 4

OA-Induced Airway Inflammation Mouse Model

1. Test Method

1) Preparation of Test Substance

A test substance was suspended in 0.5% hydroxypropylmethylcellulose (HPMC) solution at 0.1 ml per 10 g body weight and used.

2) Test Protocol

Physiological saline (0.5 ml) containingOA (10 ig) and aluminum hydroxide gel (1 mg) was intraperitoneally administered to 7-week-old male BALB/c mice to actively sensitize them. On days 25, 29 and 33, physiological saline (50 $\mu$l) containing OA (1 $\mu$g) was administered into the airway. At 24hr after the last administration into the airway, bronchoalveolar lavage was performed to recover a bronchoalveolar lavage fluid (BALF). The total number of leukocytes in BALF was counted with an automatic hemocytometer. A cytospin specimen of BALF was prepared, Diff-Quick stained and the proportion of eosinophil was calculated with a microscopy. The number of eosinophils in BALF was calculated from the total leukocyte count and the proportion of eosinophil.

The test substance was orally administered for 10 consecutive days from day 24 to day 33.

Experimental Example 5

OA-Induced Nose Allergy Mouse Model

1. Test Method

1) Preparation of Test Substance

A test substance was suspended in 0.5% hydroxypropylmethylcellulose (HPMC) solution at 0.1 ml per 10 g body weight and used.

2) Test Protocol

Physiological saline (0.5 ml) containing OA (10 $\mu$g) and aluminum hydroxide gel (1 mg) was intraperitoneally administered to 7-week-old male BALB/c mice on day 1 and day 15 to actively sensitize them. Starting from day 22, a nose drop [2 mg/ml OA solution (20 $\mu$l)] was given to the mice every other day (total 8 times). After the final nose drop administration on day 36, the occurrence of sternutation was counted for 10 min. At 24 hr after the final nose drop administration, the airway of the mice was incised under deep anesthesia and a catheter was inserted into the nasal cavity. The nasal cavity was washed with 3 ml of 0.5% BSA-containing phosphate buffer. The total number of leukocytes in the lavage fluid was counted with an automatic hemocytometer. A cytospin specimen of the nasal cavity lavage fluid was prepared, Diff-Quick stained and the proportion of eosinophil was calculated with a microscopy. The number of eosinophils in the nasal cavity lavage fluid was calculated from the total leukocyte count and the proportion of eosinophil.

The test substance was orally administered for 8 consecutive days from day 29 to day 36.

Experimental Example 6

Effect on IL-4 and IL-5 Production by Mouse Th2 Cell Line

1. Test Method

1) Preparation of Test Substance

A test substance was dissolved in dimethyl sulfoxide (Wako Pure Chemical Industries, Ltd.) to the concentration of 10 mmol/L and diluted with an RPMI1640 medium (Nacalai Tesque) to the final concentration of $10^5$–$10^7$ mol/L.

2) Th2 Cell Line

As the Th2 cell line, D10.G4.1 (obtained from ATCC) was used. The D10.G4.1 recognizes a conalbumin as an antigen, I-$A^K$ restrictively.

3) Medium

An RPMI1640 medium supplemented with inactivated fetal bovine serum (10%, Gibco BRL) and 2-mercaptoethanol (Wako Pure Chemical Industries, Ltd., 50 $\mu$mol/L) was used.

4) Preparation of Antigen-Presenting Cell

Male C3H/HeN mice (6–12 weeks of age, CHARLES RIVER JAPAN INC.) were exsanguinated and the spleen was aseptically removed to prepare a splenic cell suspension. Mitomycin C (Sigma) was added to the final concentration of 40 $\mu$g/ml and the mixture was incubated at 37° C. for 30 min. Then, the splenic cells were washed twice with the medium and used as the antigen-presenting cells.

5) Measurement of IL-4 and IL-5 Amounts Produced by Th2 Cell Line

Th2 cell line ($2\times10^4$), the antigen-presenting cells ($1\times10^5$), conalbumin (100 $\mu$g/ml, Sigma, Lot 67H7145) and a test substance were added per well of a 96 well microplate (Sumitomo Bakelite Company, Limited.) and incubated in a $CO_2$ incubator (SANYO) for 2 days. After incubation, the supernatant (100 $\mu$l) was recovered from each well. The concentration of IL-4 and IL-5 in the supernatant was assayed by the sandwich ELISA method (anti-mouse IL-4 antibody, biotin-labeled anti-mouse IL-4 antibody, anti-mouse IL-5 antibody, biotin-labeled anti-mouse IL-5 antibody and POD-labeled streptavidin were purchased from Pharmingen, peroxydase coloring kit 0 was purchased from Sumitomo Bakelite Company, Limited.).

2. Results

The effect on IL-4 and IL-5 production is shown in Table 2. The representative compound encompassed in the present invention inhibited IL-4 production and IL-5 production at a concentration ($IC_{50}$) of about 1 μmol/L.

TABLE 2

Inhibitory effect on IL-4 and IL-5 production by Th2 clone

| | Inhibition ($IC_{50}$, μmol/L) | |
|---|---|---|
| | IL-4 | IL-5 |
| compound of Example 184 | 0.46 | 0.92 |
| compound of Example 185 | 0.94 | 0.96 |
| compound of Example 199 | 0.53 | 1.62 |
| compound of Example 195 | 1.15 | 0.87 |

Experimental Example 7

Effect on Ovalbumin (OA)-Induced Biphasic Ear Edema Mouse Model

1. Test Method

1) Preparation of Test Substance

A test substance was suspended in 0.5% hydroxypropylmethylcellulose (HPMC) solution at 0.1 ml per 10 g body weight and used.

2) Test Protocol

Physiological saline (0.5 ml, OTSUKA PHARMACEUTICAL FACTORY, INC.) containing OA (ovalbumin, 10 g, Sigma, Lot 37H7010) and aluminum hydroxide gel (1 mg, LSL Co., Ltd., Lot 7450222) was intraperitoneally administered to 7-week-old male BALB/c mice (CHARLES RIVER JAPAN INC.) to actively sensitize them. After sensitization, OA (5 μg) was intradermally administered to the auricle on day 14 for antigen challenge. The thickness of the auricle before the antigen challenge, and 1 and 24 hours after the antigen challenge was measured with a dial thickness gauge (Peacock, G-1A), and changes in the thickness of the auricle were calculated from the following formula.

Increase in thickness of the auricle

=(thickness of the auricle after intradermal administration of antigen)−(thickness of the auricle before intradermal administration of antigen).

The test substance was orally administered (0.3 mg/kg, 1 mg/kg and 3 mg/kg of each test substance) twice a day for 3 consecutive days from 2 days before antigen challenge to the day of antigen challenge.

2. Results

Figure 3:
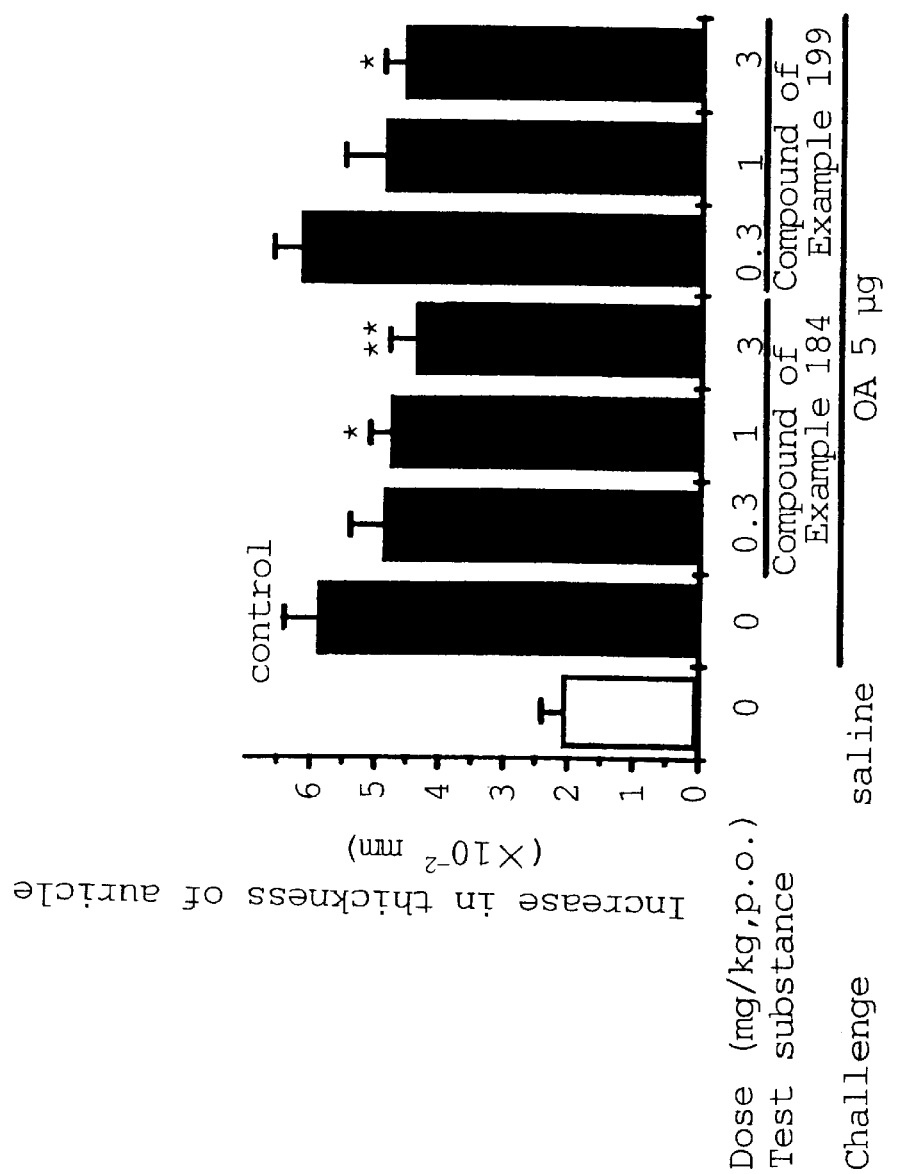
FIG. 3 shows the effect on the late phase (24 hr after antigen challenge) of the compounds of Examples 184 and 199 against swelling of the auricle in ovalbumin (OA)-induced mouse biphasic ear edema model in Experimental Example 7, wherein each value shows meanistandard error (n=12–16). Thesignificantdifference test was performedby-Dunnett's multiple comparison test, wherein * shows P<0.5 and ** shows P<0.01, indicating significant difference from control.

The effect of the compounds of Examples 184 and 199 on the late phase (24 hr after antigen challenge) swelling of the auricle is shown in FIG. 3. Each value shows mean+standard error (n=12–16). The significant difference was examined by Dunnett's multiple comparison test, wherein * shows P<0.5 and ** shows P<0.01, whereby a significant difference from the control was found.

The compounds of Examples 184 and 199, given at a dose exceeding 1 mg/kg and at a dose of 3 mg/kg, respectively, inhibited the late phase swelling mainly caused by T cell and eosinophil.

Experimental Example 8

OA-Induced Airway Tract Inflammation Mouse Model

1. Test Method 1) Preparation of Test Substance

A test substance was suspended in 0.5% hydroxypropylmethylcellulose (HPMC) solution at 0.1 ml per 10 g body weight and used.

2) Test Protocol

Physiological saline (0.5 ml) containing OA (10 μg) and aluminum hydroxide gel (1 mg) was intraperitoneally administered to 7-week-old male BALB/c mice to actively sensitize them. On days 25, 29 and 33, physiological saline (50 μl) containing OA (1 μg) was administered into the airway. At 24hr after the last administration into the airway, bronchoalveolar lavage was performed to recover a bronchoalveolar lavage fluid (BALF). The total number of leukocytes in BALF was counted with an automatic hemocytometer (NIHON KOHDEN). A cytospin (Shandon, Cytospin 3) specimen of BALF was prepared, Diff-Quick (International Reagent Corporation) stained and the proportion of eosinophil was calculated with a microscopy. The number of eosinophils in BALF was calculated from the total leukocyte count and the proportion of eosinophil.

The test substance was orally administered for 10 consecutive days from day 24 to day 33.

2. Results

Figure 4:
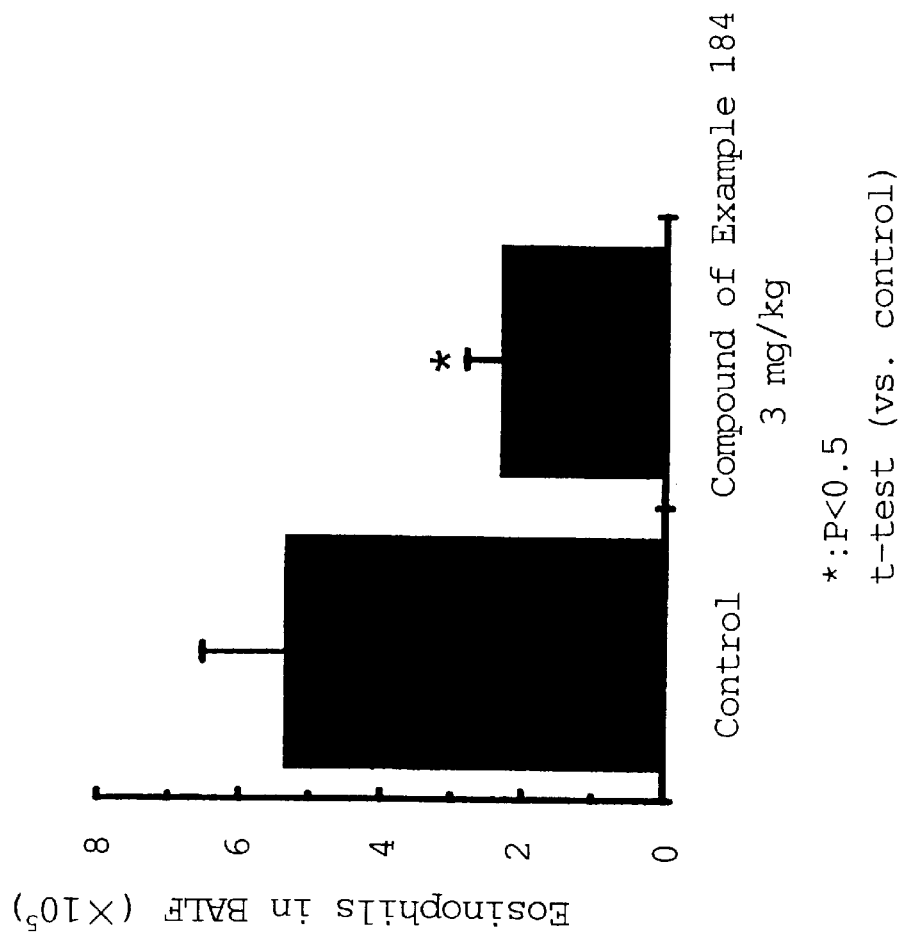
FIG. 4 shows the effect of the compound of Example 184 on the number of eosinophils in BALF from OA-induced respiratory tract inflammation model in Experimental Example 8, wherein each value shows meanlstandard error (n=9–10). The significant difference test was performed by t-test, wherein * shows P<0.5, indicating significant difference from control.

The effect of the compound of Example 184 on the number of eosinophils in BALF is shown in FIG. 4. Each value shows mean±standard error (n=9-10). The significant difference was examined by t-test, wherein * shows P<0.5, whereby a significant difference from the control was found. The compound of Example 184 given at a dose of 3 mg/kg significantly inhibited increase in the number of eosinophils in BALF.

Experimental Example 9

OA-Induced Nose Allergy Mouse Model

1. Test Method

1) Preparation of Test Substance

A test substance was suspended in 0.5% hydroxypropylmethylcellulose (HPMC) solution at 0.1 ml per 10 g body weight and used.

2) Test Protocol

Physiological saline (0.5 ml) containing OA (10 μg) and aluminum hydroxide gel (1 mg) was intraperitoneally administered to 7-week-old male BALB/c mice on day 1 and day 15 to actively sensitize them. Starting from day 22, a nose drop [2 mg/ml OA solution (20 μl)] was given to the mice every other day (total 8 times). After the final nose drop administration on day 36, the occurrence of sternutation was counted for 10 min. At 24 hr after the final nose drop administration, the airway of the mice was incised under deep anesthesia and a catheter was inserted into the nasal cavity. The nasal cavity was washed with 3 ml of 0.5% BSA (bovine serum albumin, Wako Pure Chemical Industries, Ltd.)-containing phosphate buffer. The total number of leukocytes in the lavage fluid was counted with an automatic hemocytometer. A cytospin specimen of the nasal cavity lavage fluid was prepared, Diff-Quick stained and the proportion of eosinophil was calculated with a microscopy. The number of eosinophils in the nasal cavity lavage fluid was calculated from the total leukocyte count and the proportion of eosinophil. The test substance was orally administered for 8 consecutive days from day 29 to day 36.

Experimental Example 10
Effect of Concurrent use with External Steroidal Agent
1. Test Method
1) Preparation of Test Substance A test substance was suspended in 0.5% hydroxypropylmethylcellulose (HPMC) solution at 0.1 ml per 10 g body weight and used. Hydrocortisone butyrate (medium class external steroidal agent, Sigma, Lot 40H0863) and betamethasone valerate (strong class external steroidal agent, Sigma, Lot 93H0330) were each dissolved in 50% ethanol (Wako Pure Chemical Industries, Ltd.) solution to the concentrations of 0.01 µg/10 µL, 0.03 µg/10 µL and 0.1 µg/10 µL.

2) Test Protocol

An OA-induced biphasic ear edema mouse model was prepared in the same manner as in Experimental Example 7. A test substance was orally administered (10 mg/kg) once a day for 3 consecutive days from 2 days before antigen challenge to the day of antigen challenge. The external steroidal agent was applied (10 µL) once a day to both auricles for 3 consecutive days.

The group, to which the solvent alone of each test substance was administered, was taken as a positive control group, and the group subjected to challenging with physiological saline instead of the antigen solution containing OA was taken as a negative control group.

2. Results

Figure 5:
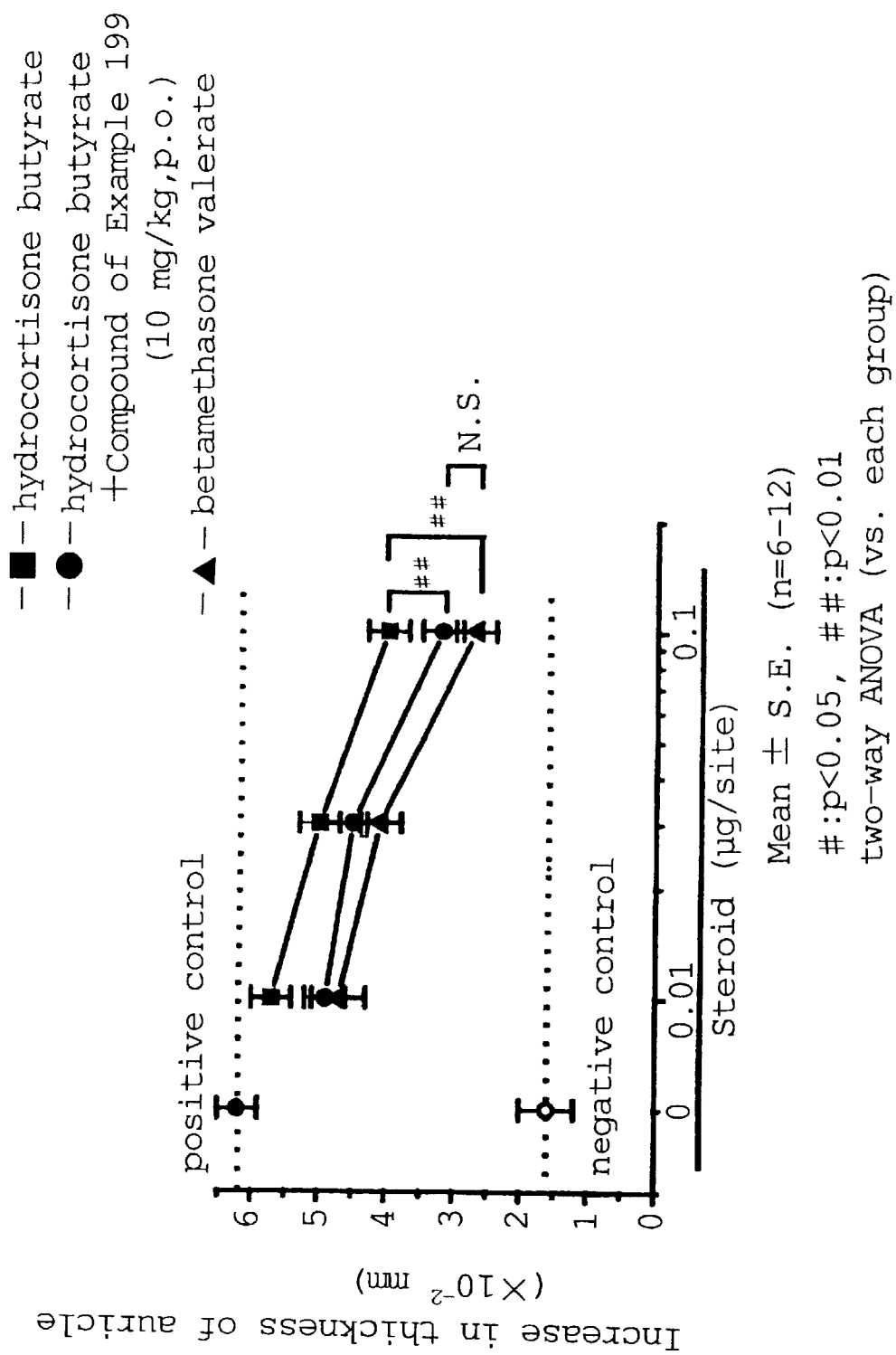
FIG. 5 shows the effect on the late phase (24 hr after antigen challenge) against swelling of the auricle in OA-induced mouse biphasic ear edema model in Experimental Example 10, wherein ■ is a hydrocortisone butyrate application group, ● is a hydrocortisone butyrate (applied)—compound of Example 199 (10 mg/kg, p.o.) concurrent administration group, ▲ is a betamethasone valerate application group and each value shows meanistandard error (n=6–12). The significant difference test was performed by two-way ANOVA (vs. each group), wherein # shows P<0.05 and ## shows P<0.01, indicating presence of a significant difference between groups.

The effect on the late phase (24 hr after antigen challenge) swelling of the auricle is shown in FIG. 5. Each value shows mean±standard error (n=6–12). The significant difference was examined by two-way ANOVA.

In FIG. 5, ## shows P<0.01 indicating the presence of a significant difference between groups. The concurrent use of the compound of Example 199 (oral administration) with the application of hydrocortisone butyrate (medium class external steroidal agent) exhibited synergistic effect which was of the same level as of a single application of betamethasone valerate (strong class external steroidal agent).

REFERENCES

1) Life Sci., 64:PL139–PL144, 1999
2) Jpn. J. Pharmacol., 75:129–134, 1997
3) Allergy, 45:1127–1132, 1996
4) Nippon Jibiinkoka Gakkai Kaiho, 99:454–463, 1996

INDUSTRIAL APPLICABILITY

The imidazole derivative and a pharmaceutically acceptable salt thereof of the present invention inhibit IL-4 and IL-5 production by Th2 cells and are effective for the prophylaxis and treatment of allergic diseases such as atopic dermatitis, bronchial asthma, allergic rhinitis and the like.

This application is based on application Nos. 359671/1997, 174074/1999 and 045165/2000 filed in Japan, the contents of which are incorporated hereinto by reference.

What is claimed is:

1. An imidazole derivative of the formula (I)

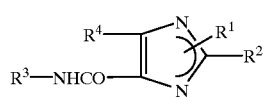

(I)

wherein
  $R^1$ is hydrogen, optionally substituted alkyl or optionally substituted aralkyl;
  $R^2$ is hydrogen or optionally substituted phenyl;
  $R^3$ is thiadiazolyl, pyrimidinyl, benzothiazolyl or thiazolyl optionally substituted by phenyl; and
  $R^4$ is optionally substituted phenyl;
  provided that when $R^1$ is hydrogen, $R^2$ is phenyl or phenyl substituted by halogen atom, lower alkyl or lower alkoxy, and $R^4$ is phenyl or phenyl substituted by halogen atom, lower alkyl or lower alkoxy, $R^3$ is benzothiazolyl or thiazolyl substituted by phenyl,
or a pharmaceutically acceptable salt thereof.

2. An imidazole derivative of the formula (I)

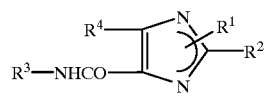

(I)

wherein
  $R^1$ is hydrogen, optionally substituted alkyl or optionally substituted aralkyl;
  $R^2$ is hydrogen or optionally substituted phenyl;
  $R^3$ is thiadiazolyl, pyrirnidinyl, benzothiazolyl or thiazolyl optionally substituted by phenyl; and
  $R^4$ is optionally substituted phenyl;
  provided that when $R^1$ is hydrogen and $R^2$ is phenyl or phenyl substituted by halogen atom, lower alkyl or lower alkoxy, $R^4$ is a group other than phenyl and phenyl substituted by halogen atom, lower alkyl or lower alkoxy,
or a pharmaceutically acceptable salt thereof.

3. The imidazole derivative of claim 1, wherein, in the formula (I),
  $R^1$ is hydrogen;
  $R^2$ is phenyl substituted by one of nitro, amino, monoalkylamino, dialkylamino, acylamino, dialkylaminoalkylamino, acyloxyalkylcarbonylamino, dialkylaminoalkoxy, acyloxyalkoxy, hydroxyalkoxy and saturated 5- or 6-membered heteromonocyclic group having 1 or 2 nitrogen atoms and optionally substituted by lower alkyl having 1 to 6 carbon atoms and optionally having an oxygen atom;
  $R^3$ is thiadiazolyl, pyrimidinyl, benzothiazolyl or thiazolyl optionally substituted by phenyl; and
  $R^4$ is optionally substituted phenyl,
or a pharmaceutically acceptable salt thereof.

4. The imidazole derivative of claim 1, which is a member selected from the group consisting of
5-(4-methoxyphenyl)-2-(4-ntrophenyl)-N-(2-thiazolyl) imidazole-4-carboxamide,
5-(4-methoxyphenyl)-2-(4-methylaminophenyl)-N-(2-thiazolyl)-imidazole-4-carboxamide,
2-(4-butylaminophenyl)-5-(4-methoxyphenyl)-N-(2-thiazolyl)-imidazole-4-carboxamide,
2-(3-dimethylaminophenyl)-5-(4-methoxyphenyl)-N-(2-thiazolyl)-imidazole-4-carboxamide,
2-(4-butylaminophenyl)-5-(4-chlorophenyl)-N-(2-thiazolyl)-imidazole-4-carboxamide,
5-(4-chlorophenyl)-2-(4-methylaminophenyl)-N-(2-thiazolyl)-imidazole-4-carboxamide,
5-(4-chlorophenyl)-2-(4-nitrophenyl)-N-(2-thiazolyl) imidazole-4-carboxamide,
5-(4-chlorophenyl)-2-(4-(-pyrrolidinyl)phenyl)-N-(2-thiazolyl)-imidazole-4-carboxamide, 5-(4-chlorophenyl)-2-(4-(2-dimethylaminoethyloxy) phenyl)-N-(2-thiazolyl)imdazole-4-carboxamde,
5-(4-chlorophenyl)-2-(4-(3-dimethylaminopropyloxy) phenyl)-N-(2-thiazolyl)imidazole-4-carboxamide and
5-(4-chlorophenyl)-2-(4-(2-hydroxyethyloxy)phenyl)-N-(2-thiazolyl)lmidazole-4-carboxamide,
or a pharmaceutically acceptable salt thereof.

5. A pharmaceutical composition comprising a therapeutically effective amount of the imidazole derivative of any of claims 1–3 or 4 or a pharmaceutically acceptable salt thereof, and a pharmaceutically acceptable additive.

6. A method for selectively inhibiting interleukin-4 and interleukin-5 production, comprising administering an effective amount of the imidazole derivative of any of claims 1–3 or 4 or a pharmaceutically acceptable salt thereof to a patient.

7. A method for the prophylaxis or treatment of allergy, comprising administering an effective amount of the imidazole derivative of any of claims 1–3or 4 or a pharmaceutically acceptable salt thereof to a patient.

8. An imidazole derivative of the following formula (XII)

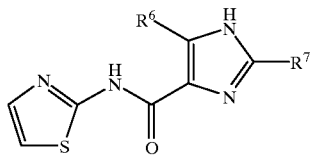

(XII)

wherein
$R^6$ is optionally substituted phenyl,
$R^7$ is phenyl substituted by one substituent or the same or different 2 substituents selected from the group consisting of cyano, substituted alkyl, an optionally substituted spiro ring comprising the same or different two saturated 6- or 7-membered heteromonocyclic groups having 1 to 3 nitrogen atoms and optionally having an oxygen atom or sulfur atom, and a group of the formula (XIII)

$$(O—(CH_2)_1)_m—O—(CH_2)_nCH_3 \qquad (XIII)$$

wherein 1 and m are each an integer of 1 to 4, n is an integer of 0 to 3, and alkyl chain is optionally substituted,
or a pharmaceutically acceptable salt thereof.

9. The imidazole derivative of claim 8, wherein, in the formula (XII), $R^6$ is phenyl substituted by a member selected from the group consisting of halogen atom and methyl, and
$R^7$ is phenyl substituted by a substituent selected from the group consisting of substituted alkyl and a group of the formula (XIV)

$$O—(CH_2)_1—O—(CH_2)_nCH_3 \qquad (XIV)$$

wherein 1 is an integer of 1 to 4, n is an integer of 0 to 3, and alkyl chain is optionally substituted,
or a pharmaceutically acceptable salt thereof.

10. The imidazole derivative of claim 8, wherein, in the formula (XII), $R^6$ is phenyl substituted by a member selected from the group consisting of halogen atom and methyl, and
$R^7$ is phenyl substituted by a substituent selected from the group consisting of trifluoromethyl and a group of the formula (XIV)

$$O—(CH_2)_1—O—(CH_2)_nCH_3 \qquad (XIV)$$

wherein 1 is an integer of 1 to 4, and n is an integer of 0 to 3,
or a pharmaceutically acceptable salt thereof.

11. The imidazole derivative of claim 8, wherein, in the formula (XII),
$R^6$ is phenyl substituted by a member selected from the group consisting of halogen atom and methyl, and
$R^7$ is phenyl substituted by an optionally substituted spiro ring consisting of the same or different two saturated 6- or 7-membered heteromonocyclic groups having 1 to 3 nitrogen atoms and optionally having oxygen atom or sulfur atom,
or a pharmaceutically acceptable salt thereof.

12. The imidazole derivative of claim 8, which is a member selected from the group consisting of
5-(4-chlorophenyl)-2-[4-(2-methoxyethoxy)phenyl]-N-(2-thiazolyl)-imidazole-4-carboxarnide,
5-(4-fluorophenyl)-2-[4-(2-methoxyethoxy)phenyl]-N-(2-thiazolyi)-imidazole-4-carboxamide,
5-(4-methyl phenyl)-N-(2-thiazolyl)-2-(4-trifluoromethylphenyl)-imidazole-4-carboxamide,
5-(4-fluorophenyl)-N-(2-thiazolyl)-2-(4-trifluoromethylphenyl)-imidazole-4-carboxamide, and
5-(4-chlorophenyl)-N-(2-thiazolyl)-2-(4-trifluoromethylphenyl)-imidazole-4-carboxamide,
or a pharmaceutically acceptable salt thereof.

13. The imidazole derivative of claim 11, which is 5-(4-chlorophenyl)-2-[4-(4-methyl-1-oxa-4,9-diazaspiro[5,5] undecan-9-yl)phenyl]-N-(2-thiazolyl)imidazole-4-carboxamide, or a pharmaceutically acceptable salt thereof.

14. A pharmaceutical composition comprising a therapeutically effective amount of the imidazole derivative of any of claims 8 to 13 or a pharmaceutically acceptable salt thereof, and a pharmaceutically acceptable additive.

15. A method for selectively inhibiting interleukin-4 and interleukin-5 production, comprising administering an effective amount of the imidazole derivative of any of claims 8 to 13 or a pharmaceutically acceptable salt thereof to a patient.

16. A method for the prophylaxis or treatment of allergy, comprising administering an effective amount of the imidazole derivative of any of claims 8 to 13 or a pharmaceutically acceptable salt thereof to a patient.

17. The method of claim 16, capable of potentiating the anti-allergic action by the concurrent use with a steroidal agent.

* * * * *